(12) United States Patent
Richards et al.

(10) Patent No.: US 9,092,401 B2
(45) Date of Patent: Jul. 28, 2015

(54) SYSTEM AND METHODS FOR DETECTING GENETIC VARIATION

(71) Applicant: Counsyl, Inc., South San Francisco, CA (US)

(72) Inventors: Hunter Richards, San Francisco, CA (US); Eric Evans, San Bruno, CA (US); Balaji Srinivasan, South San Francisco, CA (US); Subramaniam Srinivasan, Plainview, NY (US); Abhik Shah, San Francisco, CA (US); A. Scott Patterson, San Francisco, CA (US); Clement Chu, San Francisco, CA (US)

(73) Assignee: Counsyl, Inc., South San Francisco, CA (US)

( * ) Notice: Subject to any disclaimer, the term of this patent is extended or adjusted under 35 U.S.C. 154(b) by 0 days.

(21) Appl. No.: 13/665,671

(22) Filed: Oct. 31, 2012

(65) Prior Publication Data

US 2014/0121116 A1    May 1, 2014

(51) Int. Cl.
| C40B 30/00 | (2006.01) |
| G06F 19/22 | (2011.01) |
| G06F 19/18 | (2011.01) |
| C12Q 1/68  | (2006.01) |

(52) U.S. Cl.
CPC .............. *G06F 19/22* (2013.01); *C12Q 1/6874* (2013.01); *C40B 30/00* (2013.01); *G06F 19/18* (2013.01)

(58) Field of Classification Search
None
See application file for complete search history.

(56) References Cited

U.S. PATENT DOCUMENTS

| | | |
|---|---|---|
| 5,171,534 A | 12/1992 | Smith et al. |
| 5,234,809 A | 8/1993 | Boom et al. |
| 5,476,930 A | 12/1995 | Letsinger et al. |
| 5,705,628 A | 1/1998 | Hawkins |
| 5,780,613 A | 7/1998 | Letsinger et al. |
| 6,056,661 A | 5/2000 | Schmidt |
| 6,060,288 A | 5/2000 | Adams et al. |
| 6,210,891 B1 | 4/2001 | Nyren et al. |
| 6,306,597 B1 | 10/2001 | Macevicz |
| 6,558,907 B2 | 5/2003 | Koroulis et al. |
| 6,833,246 B2 | 12/2004 | Balasubramanian |
| 6,917,726 B2 | 7/2005 | Levene et al. |
| 7,001,724 B1 | 2/2006 | Greenfield |
| 7,033,764 B2 | 4/2006 | Korlach et al. |
| 7,052,847 B2 | 5/2006 | Korlach et al. |
| 7,056,676 B2 | 6/2006 | Korlach et al. |
| 7,057,026 B2 | 6/2006 | Barnes et al. |
| 7,170,050 B2 | 1/2007 | Turner et al. |
| 7,361,466 B2 | 4/2008 | Korlach et al. |
| 7,416,844 B2 | 8/2008 | Korlach et al. |
| 7,985,565 B2 | 7/2011 | Mayer et al. |
| 8,209,130 B1 | 6/2012 | Kennedy et al. |
| 2002/0076735 A1 | 6/2002 | Williams et al. |
| 2003/0235834 A1* | 12/2003 | Dunlop et al. ................ 435/6 |
| 2005/0079510 A1 | 4/2005 | Berka et al. |
| 2007/0037182 A1 | 2/2007 | Gaskin et al. |
| 2007/0128624 A1 | 6/2007 | Gormley et al. |
| 2007/0134128 A1 | 6/2007 | Korlach |
| 2008/0009420 A1 | 1/2008 | Schroth et al. |
| 2009/0203531 A1 | 8/2009 | Kurn |
| 2009/0233802 A1 | 9/2009 | Bignell et al. |
| 2009/0299645 A1 | 12/2009 | Colby et al. |
| 2010/0015626 A1 | 1/2010 | Oliphant et al. |
| 2010/0022406 A1 | 1/2010 | Srinivasan et al. |
| 2011/0009276 A1 | 1/2011 | Vermaas et al. |
| 2011/0059865 A1 | 3/2011 | Smith et al. |
| 2011/0223601 A1 | 9/2011 | Rigatti et al. |
| 2011/0270533 A1 | 11/2011 | Zhang et al. |
| 2011/0319290 A1 | 12/2011 | Raymond et al. |
| 2012/0053074 A1 | 3/2012 | Smith |
| 2012/0157322 A1 | 6/2012 | Myllykangas et al. |
| 2012/0184449 A1 | 7/2012 | Hixson et al. |

FOREIGN PATENT DOCUMENTS

| | | |
|---|---|---|
| EP | 2298930 A1 | 3/2011 |
| WO | WO 98/44151 A1 | 10/1998 |
| WO | WO 00/18957 A1 | 4/2000 |
| WO | WO 2004/018497 A2 | 3/2004 |
| WO | WO 2004/018497 A3 | 6/2004 |
| WO | WO 2005/065814 A1 | 7/2005 |
| WO | WO 2007/010251 A2 | 1/2007 |
| WO | WO 2007/010251 A3 | 8/2007 |
| WO | WO 2007/123744 A2 | 11/2007 |
| WO | WO 2007/135368 A2 | 11/2007 |
| WO | WO 2008/002502 A2 | 1/2008 |
| WO | WO 2007/135368 A3 | 3/2008 |

OTHER PUBLICATIONS

Myllykangas et al. (2011) "Efficient targeted resequencing of human germline and cancer genomes by oligonucleotide-selective sequencing" Nature Biotechnology 29(11):1024-1027—document includes Online Methods and Supplementary Information.*

(Continued)

*Primary Examiner* — Tracy Vivlemore
*Assistant Examiner* — Karen S Weiler
(74) *Attorney, Agent, or Firm* — FisherBroyles, LLP; Victoria L. Boyd

(57) ABSTRACT

The invention provides methods, apparatuses, and compositions for high-throughput amplification sequencing of specific target sequences in one or more samples. In some aspects, barcode-tagged polynucleotides are sequenced simultaneously and sample sources are identified on the basis of barcode sequences. In some aspects, sequencing data are used to determine one or more genotypes at one or more loci comprising a causal genetic variant. In some aspects, systems and methods of detecting genetic variation are provided.

103 Claims, 56 Drawing Sheets

(56) References Cited

FOREIGN PATENT DOCUMENTS

| WO | WO 2008/002502 A3 | 7/2008 | |
|---|---|---|---|
| WO | WO 2007/123744 A3 | 11/2008 | |
| WO | WO 2009139929 A2 * | 11/2009 | ............... F41H 1/02 |
| WO | WO 2010/151842 A2 | 12/2010 | |
| WO | WO 2010/151842 A3 | 3/2011 | |

OTHER PUBLICATIONS

Homer et al. (2010) "Improved variant discovery through local re-alignment of short-read next-generation sequencing data using SRMA" Genome Biology 11(10):R99.*
Ng et al. (2009) "Targeted capture and massively parallel sequencing of 12 human exomes" Nature 461:272-276.*
Li et al (2008) "Mapping short DNA sequencing reads and calling variants using mapping quality scores" Genome Res 18:1851-1858.*
U.S. Appl. No. 13/551,584, filed Jul. 17, 2012, Richards et al.
U.S. Appl. No. 13/551,587, filed Jul. 17, 2012, Richards et al.
U.S. Appl. No. 13/551,590, filed Jul. 17, 2012, Richards et al.
Bauchet et al. Measuring European population stratification with microarray genotype data. *Am J Hum Genet*. 2007;80(5):948-56.
Bhangale, et al. Automating resequencing-based detection of insertion-deletion polymorphisms. Nat Genet. Dec. 2006;38(12):1457-62. Epub Nov. 19, 2006.
Delcher, et al. Alignment of whole genomes. Nucleic Acids Res. Jun. 1, 1999;27(11):2369-76.
Halder et al. A panel of ancestry informative markers for estimating individual biogeographical ancestry and admixture from four continents: utility and applications. *Hum Mutat*. 2008;29(5):648-58.
Hopp, et al. A short polypeptide marker sequence useful for recombinant protein identification and purification. BioTechnology. 1988; 6:1204-1210.
KENT. BLAT—the BLAST-like alignment tool. Genome Res. Apr. 2002;12(4):656-64.
Kurtz, et al. Versatile and open software for comparing large genomes. Genome Biol. 2004;5(2):R12. Epub Jan. 30, 2004.
Langmead, et al. Ultrafast and memory-efficient alignment of short DNA sequences to the human genome. Genome Biol. 2009;10(3):R25. doi: 10.1186/gb-2009-10-3-r25. Epub Mar. 4, 2009.
Larkin, et al. Clustal W and Clustal X version 2.0. Bioinformatics. Nov. 1, 2007;23(21):2947-8. Epub Sep. 10, 2007.
Li, et al. The Sequence Alignment/Map format and SAMtools. Bioinformatics. Aug. 15, 2009;25(16):2078-9. doi: 10.1093/bioinformatics/btp352. Epub Jun. 8, 2009.
Lipman. Rapid and sensitive protein similarity searches. Science. Mar. 22, 1985;227(4693):1435-41.
Lutz-Freyermuth, et al. Quantitative determination that one of two potential RNA-binding domains of the a protein component of the U1 small nuclear ribonucleoprotein complex binds with high affinity to stem-loop II of U1 RNA. Proc Natl Acad Sci U S A. Aug. 1990;87(16):6393-7.
Martin, et al. GAP domains responsible for ras p21-dependent inhibition of muscarinic atrial K+ channel currents. Science. Jan. 10, 1992;255(5041):192-4.
Merrifield. Solid-phase peptide synthesis. 3. An improved synthesis of bradykinin. Biochemistry. Sep. 1964;3:1385-90.
Mills, et al. Natural genetic variation caused by small insertions and deletions in the human genome. Genome Res. Jun. 2011;21(6):830-9. doi: 10.1101/gr.115907.110. Epub Apr. 1, 2011.
Ning, et al. SSAHA: a fast search method for large DNA databases. Genome Res. Oct. 2001;11(10):1725-9.
Paschou et al. PCA-correlated SNPs for structure identification in worldwide human populations. *PLoS Genet*. 2007;3(9):1672-86.
Pearson, et al. Improved tools for biological sequence comparison. Proc Natl Acad Sci U S A. Apr. 1988;85(8):2444-8.
Pirrung, et al. Novel Reagents and Procedures for Immobilization of DNA on Glass Microchips for Primer Extension. Langmuir. 2000; 16(5):2185-2191.
Price et al. Discerning the ancestry of European Americans in genetic association studies. *PLoS Genet*. 2008;4(1):e236.
Seldin et al. Application of ancestry informative markers to association studies in European Americans. *PLoS Genet*. 2008;4(1):e5.
Sievers, et al. Fast, scalable generation of high-quality protein multiple sequence alignments using Clustal Omega. Mol Syst Biol. Oct. 11, 2011;7:539. doi: 10.1038/msb.2011.75.
Skinner, et al. Use of the Glu-Glu-Phe C-terminal epitope for rapid purification of the catalytic domain of normal and mutant ras GTPase-activating proteins. J Biol Chem. Aug. 5, 1991;266(22):14163-6.
Slater, et al. Automated generation of heuristics for biological sequence comparison. BMC Bioinformatics. Feb. 15, 2005;6:31.
The 1000 Genomes Project Consortium, et al. A map of human genome variation from population-scale sequencing. Nature. Oct. 28, 2010;467(7319):1061-73. doi: 10.1038/nature09534.
Tian et al. Analysis and application of European genetic substructure using 300 K SNP information. *PLoS Genet*. 2008;4(1):e4.
Zhao, et al. Immobilization of oligodeoxyribonucleotides with multiple anchors to microchips. Nucleic Acids Res. Feb. 15, 2001;29(4):955-9.
Barker, et al. The identification of *Mycobacterium marinum* genes differentially expressed in macrophage phagosomes using promoter fusions to green fluorescent protein. Mol Microbiol. Sep. 1998;29(5):1167-77.
Mei, et al. Genome-wide detection of allelic imbalance using human SNPs and high-density DNA arrays. Genome Res. Aug. 2000;10(8):1126-37.
Office action dated Feb. 6, 2013 for U.S. Appl. No. 13/551,590.
Office action dated Feb. 19, 2013 for U.S. Appl. No. 13/551,587.
Office action dated Mar. 15, 2013 for U.S. Appl. No. 13/551,584.
Raymond, et al. Simple, quantitative primer-extension PCR assay for direct monitoring of microRNAs and short-interfering RNAs. RNA. Nov. 2005;11(11):1737-44.
Sommer, et al. Minimal homology requirements for PCR primers. Nucleic Acids Res. Aug. 25, 1989;17(16):6749.
You, et al. BatchPrimer3: a high throughput web application for PCR and sequencing primer design. BMC Bioinformatics. May 29, 2008;9:253. doi: 10.1186/1471-2105-9-253.
U.S. Appl. No. 14/102,462, filed Dec. 10, 2013, Richards et al.
International search report and written opinion dated Dec. 2, 2013 for PCT Application No. US2013/050965.

* cited by examiner

Figure 3

| Disease | Gene | Variant Name |
|---|---|---|
| 21-Hydroxylase Deficiency | CYP21A2 | F306+t |
| 21-Hydroxylase Deficiency | CYP21A2 | F306+t |
| 21-Hydroxylase Deficiency | CYP21A3 | g.655A/C>G |
| 21-Hydroxylase Deficiency | CYP21A4 | g.655A/C>G |
| 21-Hydroxylase Deficiency | CYP21A6 | G110del8nt |
| 21-Hydroxylase Deficiency | CYP21A5 | G110del8nt |
| 21-Hydroxylase Deficiency | CYP21A7 | I172N, rs34607927 |
| 21-Hydroxylase Deficiency | CYP21A2 | I236N |
| 21-Hydroxylase Deficiency | CYP21A2 | M239K, rs6476 |
| 21-Hydroxylase Deficiency | CYP21A2 | P30L |
| 21-Hydroxylase Deficiency | CYP21A2 | P453S |
| 21-Hydroxylase Deficiency | CYP21A2 | Q318X |
| 21-Hydroxylase Deficiency | CYP21A2 | R356W |
| 21-Hydroxylase Deficiency | CYP21A2 | V237E, rs12530380 |
| 21-Hydroxylase Deficiency | CYP21A2 | V281L, rs6471 |
| ABCC8-Related Hyperinsulinism | ABCC8 | 3992-9G>A |
| ABCC8-Related Hyperinsulinism | ABCC8 | delF1388 |
| ABCC8-Related Hyperinsulinism | ABCC8 | delF1388 |
| ABCC8-Related Hyperinsulinism | ABCC8 | V187D |
| Achondroplasia | FGFR3 | G375C |
| Achondroplasia | FGFR3 | G380R, rs28931614 |
| Achromatopsia | CNGB3 | c.1148delC |
| Achromatopsia | CNGB3 | c.1148delC |
| Achromatopsia | CNGB3 | c.819-826del8 |
| Achromatopsia | CNGB3 | c.819-826del8 |
| Achromatopsia | CNGB3 | c.886-896del11insT |
| Achromatopsia | CNGB3 | c.886-896del11insT |
| Achromatopsia | CNGB3 | c.991-3T>G |
| Achromatopsia | CNGB3 | p.Arg403Gln |
| Achromatopsia | CNGB3 | p.Glu336X |
| Adenosine Monophosphate Deaminase 1 | AMPD1 | P48L |
| Adenosine Monophosphate Deaminase 1 | AMPD1 | Q12X, rs17602729 |
| Agenesis of Corpus Callosum with Neuronopathy | SLC12A6 | c.2436delG |
| Agenesis of Corpus Callosum with Neuronopathy | SLC12A6 | c.2436delG |
| Alkaptonuria | HGD | c.174delA |
| Alkaptonuria | HGD | c.174delA |
| Alkaptonuria | HGD | c.457_458insG |
| Alkaptonuria | HGD | c.457_458insG |
| Alkaptonuria | HGD | G161R |
| Alkaptonuria | HGD | G270R |
| Alkaptonuria | HGD | IVS1-1G>A |

Figure 3 cont.

| Disease | Gene | Variant Name |
|---|---|---|
| Alkaptonuria | HGD | IVS5+1G>A |
| Alkaptonuria | HGD | Met368Val |
| Alkaptonuria | HGD | P230S |
| Alkaptonuria | HGD | S47L |
| Alkaptonuria | HGD | V300G |
| Alpha-1-Antitrypsin Deficiency | SERPINA1 | Arg101His, rs709932 |
| Alpha-1-Antitrypsin Deficiency | SERPINA1 | Glu264Val |
| Alpha-1-Antitrypsin Deficiency | SERPINA1 | Glu342Lys, rs28929474 |
| Alpha-1-Antitrypsin Deficiency | SERPINA1 | Glu376Asp, rs1303 |
| Alpha-Mannosidosis | MAN2B1 | IVS14+1G>C |
| Alpha-Mannosidosis | MAN2B1 | p.L809P |
| Alpha-Mannosidosis | MAN2B1 | p.R750W |
| Alpha-Sarcoglycanopathy | SGCA | R77C, rs28933693 |
| Alpha-Thalassemia | HBA2 | H19D |
| Alpha-Thalassemia | HBA1 | HbQ |
| Alpha-Thalassemia | HBA1,HBA2 | 3.7 kb (type I) deletion alpha-2 |
| Alpha-Thalassemia | HBA1,HBA2 | 3.7 kb (type I) deletion alpha-2 |
| Alpha-Thalassemia | HBA1,HBA2 | HbVar database id # 1086, --(SEA); deletion of ~20 kb including both alpha-globin genes alpha-Thal-1 |
| Alpha-Thalassemia | HBA1,HBA2 | HbVar database id # 1086, --(SEA); deletion of ~20 kb including both alpha-globin genes alpha-Thal-1 |
| Alpha-Thalassemia | HBA1,HBA2 | HbVar database id # 1087, --(MED-I); deletion of ~17.5 kb including both alpha-globin genes alpha-Thal-1 |
| Alpha-Thalassemia | HBA1,HBA2 | HbVar database id # 1087, --(MED-I); deletion of ~17.5 kb including both alpha-globin genes alpha-Thal-1 |
| Alpha-Thalassemia | HBA1,HBA2 | HbVar database id # 1088, -(alpha)20.5; this 20.5 kb deletion involves alpha2 and the 5' end of alpha1; alpha-Thal-1 |
| Alpha-Thalassemia | HBA1,HBA2 | HbVar database id # 1088, -(alpha)20.5; this 20.5 kb deletion involves alpha2 and the 5' end of alpha1; alpha-Thal-1 |
| Alpha-Thalassemia | HBA1,HBA2 | HbVar database id # 1094, --(FIL); a deletion of 30-34 kb involving the alpha1, alpha2, and zeta genes alpha-Thal-1 |
| Alpha-Thalassemia | HBA1,HBA2 | HbVar database id # 1094, --(FIL); a deletion of 30-34 kb involving the alpha1, alpha2, and zeta genes alpha-Thal-1 |

Figure 3 cont.

| Disease | Gene | Variant Name |
|---|---|---|
| Alpha-Thalassemia | HBA1,HBA2 | HbVar database id # 1095, --(THAI); a deletion of 34-38 kb involving the alpha1, alpha2, and zeta genes alpha-Thal-1 |
| Alpha-Thalassemia | HBA1,HBA2 | HbVar database id # 1095, --(THAI); a deletion of 34-38 kb involving the alpha1, alpha2, and zeta genes alpha-Thal-1 |
| Alpha-Thalassemia | HBA1,HBA2 | HbVar database id # 1097, --(MED-II); a deletion of 26.5 kb involving the two alpha and zeta genes alpha-Thal-1 |
| Alpha-Thalassemia | HBA1,HBA2 | HbVar database id # 1097, --(MED-II); a deletion of 26.5 kb involving the two alpha and zeta genes alpha-Thal-1 |
| Alpha-Thalassemia | HBA2 | HbVar database id # 187 |
| Alpha-Thalassemia | HBA2 | HbVar database id # 2598, IVS I-5 (G>A) |
| Alpha-Thalassemia | HBA1,HBA2 | HbVar database id # 703 |
| Alpha-Thalassemia | HBA1,HBA2 | HbVar database id # 704 |
| Alpha-Thalassemia | HBA1,HBA2 | HbVar database id # 705, Hb Koya Dora |
| Alpha-Thalassemia | HBA1,HBA2 | HbVar database id # 707, rs41412046 |
| Alpha-Thalassemia | HBA1 | HbVar database id # 87 |
| Alpha-Thalassemia | HBA1,HBA2 | HbVar database id # 969, Poly A (A->G); AATAAA->AATGAA beta+ |
| Alpha-Thalassemia | HBA1,HBA2 | HbVar database id # 971, Poly A (A->G); AATAAA->AATAAG beta+ |
| Alpha-Thalassemia | HBA2 | M1T |
| Alpha-Thalassemia | HBA1 | W14X |
| Angiotensin II Receptor, Type 1 | AGTR1 | A1166C |
| Apolipoprotein E Genotyping | APOE | p.C112R, rs429358 |
| Apolipoprotein E Genotyping | APOE | p.R158C, rs7412 |
| Argininosuccinicaciduria | ASL | R385C |
| ARSACS | SACS | 5254C>T |
| ARSACS | SACS | 6594delT |
| ARSACS | SACS | 6594delT |
| Aspartylglycosaminuria | AGA | c.199_200delGA |
| Aspartylglycosaminuria | AGA | c.199_200delGA |
| Aspartylglycosaminuria | AGA | C163S |
| Ataxia with Vitamin E Deficiency | TTPA | 744delA |
| Ataxia with Vitamin E Deficiency | TTPA | 744delA |
| Ataxia-Telangiectasia | ATM | R35X |

Figure 3 cont.

| Disease | Gene | Variant Name |
|---|---|---|
| Autoimmune Polyendocrinopathy Syndrome Type 1 | AIRE | c.1163_1164insA |
| Autoimmune Polyendocrinopathy Syndrome Type 1 | AIRE | c.1163_1164insA |
| Autoimmune Polyendocrinopathy Syndrome Type 1 | AIRE | c.769C>T |
| Autoimmune Polyendocrinopathy Syndrome Type 1 | AIRE | c.967_979del |
| Autoimmune Polyendocrinopathy Syndrome Type 1 | AIRE | c.967_979del |
| Autoimmune Polyendocrinopathy Syndrome Type 1 | AIRE | Y85C |
| Bardet-Biedl Syndrome | BBS1 | M390R |
| Bardet-Biedl Syndrome | BBS10 | p.C91LfsX4 |
| Bardet-Biedl Syndrome | BBS10 | p.C91LfsX4 |
| Best Vitelliform Macular Dystrophy | BEST1 | c.G383C |
| Beta-Sarcoglycanopathy | SGCB | S114F |
| Beta-Thalassemia | HBB | -28 (A->G) beta+ |
| Beta-Thalassemia | HBB | -29 (A->G) beta+ |
| Beta-Thalassemia | HBB | -29A>G |
| Beta-Thalassemia | HBB | -30 (T->A) beta+ |
| Beta-Thalassemia | HBB | -87 (C->G) beta+ |
| Beta-Thalassemia | HBB | -88C>T |
| Beta-Thalassemia | HBB | CAP+1 (A->C) beta+ |
| Beta-Thalassemia | HBB | Codon 15 (G->A); TGG(Trp)->TAG(stop codon) beta0, rs34716011 |
| Beta-Thalassemia | HBB | Codon 15 (G->A); TGG(Trp)->TAG(stop codon) beta0, rs34716011 |
| Beta-Thalassemia | HBB | Codon 16 (-C); GGC(Gly)->GG- beta0 |
| Beta-Thalassemia | HBB | Codon 16 (-C); GGC(Gly)->GG- beta0 |
| Beta-Thalassemia | HBB | Codon 17 (A->T); AAG(Lys)->TAG(stop codon) beta0 |
| Beta-Thalassemia | HBB | Codon 24 (T->A); GGT(Gly)->GGA(Gly) beta+ |
| Beta-Thalassemia | HBB | Codon 39 (C->T); CAG(Gln)->TAG(stop codon) beta0 |
| Beta-Thalassemia | HBB | Codon 5 (-CT); CCT(Pro)->C-- beta0 |
| Beta-Thalassemia | HBB | Codon 5 (-CT); CCT(Pro)->C-- beta0 |
| Beta-Thalassemia | HBB | Codon 6 (-A); GAG(Glu)->G-G beta0 |

Figure 3 cont.

| Disease | Gene | Variant Name |
|---|---|---|
| Beta-Thalassemia | HBB | Codon 6 (-A); GAG(Glu)->G-G beta0 |
| Beta-Thalassemia | HBB | Codon 8 (-AA); AAG(Lys)->--G beta0 |
| Beta-Thalassemia | HBB | Codon 8 (-AA); AAG(Lys)->--G beta0 |
| Beta-Thalassemia | HBB | Codons 41/42 (-TTCT); TTCTTT(Phe-Phe)->----TT beta0 |
| Beta-Thalassemia | HBB | Codons 41/42 (-TTCT); TTCTTT(Phe-Phe)->----TT beta0 |
| Beta-Thalassemia | HBB | Codons 71/72 (+A); TTT AGT(Phe Ser)->TTT A AGT; beta0 |
| Beta-Thalassemia | HBB | Codons 71/72 (+A); TTT AGT(Phe Ser)->TTT A AGT; beta0 |
| Beta-Thalassemia | HBB | Codons 8/9 (+G); AAG TCT(Lys;Ser)->AAG G TCT beta0 |
| Beta-Thalassemia | HBB | Codons 8/9 (+G); AAG TCT(Lys;Ser)->AAG G TCT beta0 |
| Beta-Thalassemia | HBB | HbVar database id # 889, IVS-II-654 (C->T); AAGGCAATA->AAG^GTAATA beta+(severe) |
| Beta-Thalassemia | HBB | HbVar database id # 890, IVS-II-705 (T->G); GATGTAAGA->GAG^GTAAGA beta+ |
| Beta-Thalassemia | HBB | HbVar database id # 891, IVS-II-745 (C->G); CAGCTACCAT->CAG^GTACCAT beta+ |
| Beta-Thalassemia | HBB | HbVar database id # 979, 619 bp deletion beta0 |
| Beta-Thalassemia | HBB | 619 bp deletion beta0 |
| Beta-Thalassemia | HBB | IVS-I-1 (G->A); AG^GTTGGT->AGATTGGT beta0 |
| Beta-Thalassemia | HBB | IVS-I-1 (G->T); AG^GTTGGT->AGTTTGGT beta0 |
| Beta-Thalassemia | HBB | IVS-I-110 (G->A) beta+; the mutation is 21 nucleotides 5' to the acceptor splice site AG^GC |
| Beta-Thalassemia | HBB | IVS-I-5 (G->C) beta+(severe) |
| Beta-Thalassemia | HBB | IVS-II-1 (G->A); beta0 |
| Beta-Thalassemia | HBB | IVS-II-844 (C->G); beta+ |
| Beta-Thalassemia | HBB | IVS1+6T>C |
| Beta-Thalassemia | HBB | IVS11-849A>C |
| Beta-Thalassemia | HBB | IVS11-849A>G |
| Biotinidase Deficiency | BTD | A171T, rs13073139 |
| Biotinidase Deficiency | BTD | D252G, rs28934601 |
| Biotinidase Deficiency | BTD | D444H, rs13078881 |
| Biotinidase Deficiency | BTD | F403V |
| Biotinidase Deficiency | BTD | G98:d7i3 |
| Biotinidase Deficiency | BTD | G98:d7i3 |
| Biotinidase Deficiency | BTD | Q456H |
| Biotinidase Deficiency | BTD | R157H |
| Biotinidase Deficiency | BTD | R538C |
| Blau Syndrome | NOD2 | E383K |

Figure 3 cont.

| Disease | Gene | Variant Name |
|---|---|---|
| Blau Syndrome | NOD2 | L469F |
| Blau Syndrome | NOD2 | R334Q |
| Blau Syndrome | NOD2 | R334W |
| Bloom Syndrome | BLM | 2407insT |
| Bloom Syndrome | BLM | 2407insT |
| Bloom Syndrome | BLM | 736delATCTGAinsTAGATTC (2281del6/ins7) |
| Bloom Syndrome | BLM | 736delATCTGAinsTAGATTC (2281del6/ins7) |
| BRCA1 Hereditary Breast/Ovarian Cancer | BRCA1 | 185delAG |
| BRCA1 Hereditary Breast/Ovarian Cancer | BRCA1 | 185delAG |
| BRCA1 Hereditary Breast/Ovarian Cancer | BRCA1 | 5382insC |
| BRCA1 Hereditary Breast/Ovarian Cancer | BRCA1 | 5382insC |
| BRCA1 Hereditary Breast/Ovarian Cancer | BRCA1 | Tyr978X |
| BRCA2 Hereditary Breast/Ovarian Cancer | BRCA2 | 6174delT |
| BRCA2 Hereditary Breast/Ovarian Cancer | BRCA2 | 6174delT |
| BRCA2 Hereditary Breast/Ovarian Cancer | BRCA2 | 8765delAG |
| BRCA2 Hereditary Breast/Ovarian Cancer | BRCA2 | 8765delAG |
| Canavan Disease | ASPA | A305E (914C>A), rs28940574 |
| Canavan Disease | ASPA | E285A (854A>C), rs28940279 |
| Canavan Disease | ASPA | IVS2-2A>G (433-2A>G) |
| Canavan Disease | ASPA | Y231X (693C>A) |
| Carnitine Palmitoyltransferase IA Deficiency | CPT1A | G710E |
| Carnitine Palmitoyltransferase IA Deficiency | CPT1A | P479L |
| Carnitine Palmitoyltransferase II Deficiency | CPT2 | G549D |
| Carnitine Palmitoyltransferase II Deficiency | CPT2 | L178F 534 ins/25 bp del |
| Carnitine Palmitoyltransferase II Deficiency | CPT2 | L178F 534 ins/25 bp del |
| Carnitine Palmitoyltransferase II Deficiency | CPT2 | P227L |
| Carnitine Palmitoyltransferase II Deficiency | CPT2 | P50H |

Figure 3 cont.

| Disease | Gene | Variant Name |
|---|---|---|
| Carnitine Palmitoyltransferase II Deficiency | CPT2 | P604S |
| Carnitine Palmitoyltransferase II Deficiency | CPT2 | Q413fs |
| Carnitine Palmitoyltransferase II Deficiency | CPT2 | Q413fs |
| Carnitine Palmitoyltransferase II Deficiency | CPT2 | Q550R |
| Carnitine Palmitoyltransferase II Deficiency | CPT2 | R124X |
| Carnitine Palmitoyltransferase II Deficiency | CPT2 | R503C |
| Carnitine Palmitoyltransferase II Deficiency | CPT2 | R631C |
| Carnitine Palmitoyltransferase II Deficiency | CPT2 | S113L |
| Carnitine Palmitoyltransferase II Deficiency | CPT2 | s38fs |
| Carnitine Palmitoyltransferase II Deficiency | CPT2 | s38fs |
| Carnitine Palmitoyltransferase II Deficiency | CPT2 | Y628S, rs28936673 |
| Cartilage-Hair Hypoplasia | RMRP | g.262G>T |
| Cartilage-Hair Hypoplasia | RMPR | g.70A>G |
| CFTR-Related Disorders | CFTR | 1811+1.6kbA->G |
| CFTR-Related Disorders | CFTR | 2183AA>G |
| CFTR-Related Disorders | CFTR | 2183AA>G |
| CFTR-Related Disorders | CFTR | 3849+10kbC>T |
| CFTR-Related Disorders | CFTR | A455E |
| CFTR-Related Disorders | CFTR | A559T |
| CFTR-Related Disorders | CFTR | C524X |
| CFTR-Related Disorders | CFTR | 574delA, 574delA |
| CFTR-Related Disorders | CFTR | 574delA, 574delA |
| CFTR-Related Disorders | CFTR | 2108delA, 2108delA |
| CFTR-Related Disorders | CFTR | 2108delA, 2108delA |
| CFTR-Related Disorders | CFTR | 3171delC, 3171delC |
| CFTR-Related Disorders | CFTR | 3171delC, 3171delC |
| CFTR-Related Disorders | CFTR | 621+1G->T |
| CFTR-Related Disorders | CFTR | 2105-2117del13insAGAAA |
| CFTR-Related Disorders | CFTR | 2105-2117del13insAGAAA |
| CFTR-Related Disorders | CFTR | 711+1G->T |
| CFTR-Related Disorders | CFTR | 711+5G->A |

Figure 3 cont.

| Disease | Gene | Variant Name |
|---|---|---|
| CFTR-Related Disorders | CFTR | 712-1G->T |
| CFTR-Related Disorders | CFTR | 1288insTA, 1288insTA |
| CFTR-Related Disorders | CFTR | 1288insTA, 1288insTA |
| CFTR-Related Disorders | CFTR | 936delTA |
| CFTR-Related Disorders | CFTR | 936delTA |
| CFTR-Related Disorders | CFTR | [delta]F311 |
| CFTR-Related Disorders | CFTR | [delta]F311 |
| CFTR-Related Disorders | CFTR | 1078delT, 1078delT |
| CFTR-Related Disorders | CFTR | 1078delT, 1078delT |
| CFTR-Related Disorders | CFTR | 1161delC, 1161delC |
| CFTR-Related Disorders | CFTR | 1161delC, 1161delC |
| CFTR-Related Disorders | CFTR | 1609delCA, 1609delCA |
| CFTR-Related Disorders | CFTR | 1609delCA, 1609delCA |
| CFTR-Related Disorders | CFTR | [delta]I507 |
| CFTR-Related Disorders | CFTR | [delta]I507 |
| CFTR-Related Disorders | CFTR | rs332, [delta]F508 |
| CFTR-Related Disorders | CFTR | rs332, [delta]F508 |
| CFTR-Related Disorders | CFTR | 1677delTA, 1677delTA |
| CFTR-Related Disorders | CFTR | 1677delTA, 1677delTA |
| CFTR-Related Disorders | CFTR | 1717-1G->A |
| CFTR-Related Disorders | CFTR | 1812-1G->A |
| CFTR-Related Disorders | CFTR | 1898+1G->A |
| CFTR-Related Disorders | CFTR | 1898+1G->T |
| CFTR-Related Disorders | CFTR | 1898+5G->T |
| CFTR-Related Disorders | CFTR | 1949del84, 1949del84 |
| CFTR-Related Disorders | CFTR | 1949del84, 1949del84 |
| CFTR-Related Disorders | CFTR | 2043delG, 2043delG |
| CFTR-Related Disorders | CFTR | 2043delG, 2043delG |
| CFTR-Related Disorders | CFTR | 2055del9->A |
| CFTR-Related Disorders | CFTR | 2055del9->A |
| CFTR-Related Disorders | CFTR | 2143delT, 2143delT |
| CFTR-Related Disorders | CFTR | 2143delT, 2143delT |
| CFTR-Related Disorders | CFTR | 2184delA, 2184delA |
| CFTR-Related Disorders | CFTR | 2184delA, 2184delA |
| CFTR-Related Disorders | CFTR | 2184insA, 2184insA |
| CFTR-Related Disorders | CFTR | 2184insA, 2184insA |
| CFTR-Related Disorders | CFTR | 2307insA, 2307insA |
| CFTR-Related Disorders | CFTR | 2307insA, 2307insA |
| CFTR-Related Disorders | CFTR | 296+12T->C |
| CFTR-Related Disorders | CFTR | 2789+5G->A |
| CFTR-Related Disorders | CFTR | 2869insG, 2869insG |
| CFTR-Related Disorders | CFTR | 2869insG, 2869insG |
| CFTR-Related Disorders | CFTR | 3120G->A |
| CFTR-Related Disorders | CFTR | 3120+1G->A |
| CFTR-Related Disorders | CFTR | 3272-26A->G |
| CFTR-Related Disorders | CFTR | 3659delC, 3659delC |
| CFTR-Related Disorders | CFTR | 3659delC, 3659delC |
| CFTR-Related Disorders | CFTR | 3667del4, 3667del4 |
| CFTR-Related Disorders | CFTR | 3667del4, 3667del4 |

Figure 3 cont.

| Disease | Gene | Variant Name |
|---|---|---|
| CFTR-Related Disorders | CFTR | 3791delC, 3791delC |
| CFTR-Related Disorders | CFTR | 3791delC, 3791delC |
| CFTR-Related Disorders | CFTR | 3821delT, 3821delT |
| CFTR-Related Disorders | CFTR | 3821delT, 3821delT |
| CFTR-Related Disorders | CFTR | 3905insT, 3905insT |
| CFTR-Related Disorders | CFTR | 3905insT, 3905insT |
| CFTR-Related Disorders | CFTR | 4016insT, 4016insT |
| CFTR-Related Disorders | CFTR | 4016insT, 4016insT |
| CFTR-Related Disorders | CFTR | 394delTT, 394delTT |
| CFTR-Related Disorders | CFTR | 394delTT, 394delTT |
| CFTR-Related Disorders | CFTR | 405+1G->A |
| CFTR-Related Disorders | CFTR | 405+3A->C |
| CFTR-Related Disorders | CFTR | 444delA |
| CFTR-Related Disorders | CFTR | 444delA |
| CFTR-Related Disorders | CFTR | 3876delA, 3876delA |
| CFTR-Related Disorders | CFTR | 3876delA, 3876delA |
| CFTR-Related Disorders | CFTR | 457TAT->G |
| CFTR-Related Disorders | CFTR | 457TAT->G |
| CFTR-Related Disorders | CFTR | 3199del6, 3199del6 |
| CFTR-Related Disorders | CFTR | 3199del6, 3199del6 |
| CFTR-Related Disorders | CFTR | 406-1G->A |
| CFTR-Related Disorders | CFTR | 663delT, 663delT |
| CFTR-Related Disorders | CFTR | 663delT, 663delT |
| CFTR-Related Disorders | CFTR | 935delA, 935delA |
| CFTR-Related Disorders | CFTR | 935delA, 935delA |
| CFTR-Related Disorders | CFTR | CFTR dele2,3 (21kb) |
| CFTR-Related Disorders | CFTR | CFTR dele2,3 (21kb) |
| CFTR-Related Disorders | CFTR | D1152H |
| CFTR-Related Disorders | CFTR | E60X |
| CFTR-Related Disorders | CFTR | E92X |
| CFTR-Related Disorders | CFTR | F508C, rs1800093 |
| CFTR-Related Disorders | CFTR | G178R |
| CFTR-Related Disorders | CFTR | G330X |
| CFTR-Related Disorders | CFTR | G480C |
| CFTR-Related Disorders | CFTR | G542X |
| CFTR-Related Disorders | CFTR | G551D |
| CFTR-Related Disorders | CFTR | G622D |
| CFTR-Related Disorders | CFTR | G85E |
| CFTR-Related Disorders | CFTR | G91R |
| CFTR-Related Disorders | CFTR | I148T, rs35516286 |
| CFTR-Related Disorders | CFTR | I506V |
| CFTR-Related Disorders | CFTR | IVS8-5T |
| CFTR-Related Disorders | CFTR | IVS8-7T |
| CFTR-Related Disorders | CFTR | IVS8-9T |
| CFTR-Related Disorders | CFTR | K710X |
| CFTR-Related Disorders | CFTR | L206W |
| CFTR-Related Disorders | CFTR | M1101K, rs36210737 |
| CFTR-Related Disorders | CFTR | N1303K |
| CFTR-Related Disorders | CFTR | P574H |

Figure 3 cont.

| Disease | Gene | Variant Name |
|---|---|---|
| CFTR-Related Disorders | CFTR | Q1238X |
| CFTR-Related Disorders | CFTR | Q359K/T360K_wt |
| CFTR-Related Disorders | CFTR | Q493X |
| CFTR-Related Disorders | CFTR | Q552X |
| CFTR-Related Disorders | CFTR | Q890X |
| CFTR-Related Disorders | CFTR | R1066C |
| CFTR-Related Disorders | CFTR | R1070Q |
| CFTR-Related Disorders | CFTR | R1158X |
| CFTR-Related Disorders | CFTR | R1162X |
| CFTR-Related Disorders | CFTR | R117C |
| CFTR-Related Disorders | CFTR | R117H |
| CFTR-Related Disorders | CFTR | R1283M |
| CFTR-Related Disorders | CFTR | R334W |
| CFTR-Related Disorders | CFTR | R347H |
| CFTR-Related Disorders | CFTR | R347P |
| CFTR-Related Disorders | CFTR | R352Q |
| CFTR-Related Disorders | CFTR | R553X |
| CFTR-Related Disorders | CFTR | R560T |
| CFTR-Related Disorders | CFTR | R709X |
| CFTR-Related Disorders | CFTR | R75X |
| CFTR-Related Disorders | CFTR | R764X |
| CFTR-Related Disorders | CFTR | S1196X |
| CFTR-Related Disorders | CFTR | S1235R, rs34911792 |
| CFTR-Related Disorders | CFTR | S1251N |
| CFTR-Related Disorders | CFTR | S1255X |
| CFTR-Related Disorders | CFTR | S364P |
| CFTR-Related Disorders | CFTR | S549I |
| CFTR-Related Disorders | CFTR | S549N |
| CFTR-Related Disorders | CFTR | S549R |
| CFTR-Related Disorders | CFTR | S549R |
| CFTR-Related Disorders | CFTR | T338I |
| CFTR-Related Disorders | CFTR | V520F |
| CFTR-Related Disorders | CFTR | W1089X |
| CFTR-Related Disorders | CFTR | W1204X |
| CFTR-Related Disorders | CFTR | W1204X |
| CFTR-Related Disorders | CFTR | W1282X |
| CFTR-Related Disorders | CFTR | Y1092X |
| CFTR-Related Disorders | CFTR | Y122X |
| Choroideremia | CHM | c.1609+2dupT |
| Choroideremia | CHM | c.1609+2dupT |
| CLN3-Related Neuronal Ceroid-Lipofuscinosis | CLN3 | c.461_677del |
| CLN3-Related Neuronal Ceroid-Lipofuscinosis | CLN3 | c.461_677del |
| CLN3-Related Neuronal Ceroid-Lipofuscinosis | CLN3 | c.791_1056del |
| CLN3-Related Neuronal Ceroid-Lipofuscinosis | CLN3 | c.791_1056del |
| CLN5-Related Neuronal Ceroid-Lipofuscinosis | CLN5 | c.1175_1176delAT |

Figure 3 cont.

| Disease | Gene | Variant Name |
|---|---|---|
| CLN5-Related Neuronal Ceroid-Lipofuscinosis | CLN5 | c.1175_1176delAT |
| CLN5-Related Neuronal Ceroid-Lipofuscinosis | CLN5 | c.225G>A |
| CLN8-Related Neuronal Ceroid-Lipofuscinosis | CLN8 | c.70C>G |
| Cohen Syndrome | VPS13B | c.3348_3349delCT |
| Cohen Syndrome | VPS13B | c.3348_3349delCT |
| Congenital Cataracts, Facial Dysmorphism, and Neuropathy | CTDP1 | IVS6+389C>T |
| Congenital Disorder of Glycosylation Ia | PMM2 | p.F119L |
| Congenital Disorder of Glycosylation Ia | PMM2 | p.R141H |
| Congenital Disorder of Glycosylation Ib | MPI | R295H, rs28928906 |
| Congenital Finnish Nephrosis | NPHS1 | c.121_122del |
| Congenital Finnish Nephrosis | NPHS1 | c.121_122del |
| Congenital Finnish Nephrosis | NPHS1 | c.3325C>T |
| Crohn Disease | NOD2 | 3020 ins C |
| Crohn Disease | NOD2 | 3020 ins C |
| Crohn Disease | NOD2 | G908R, rs2066845 |
| Crohn Disease | NOD2 | R702W, rs2066844 |
| Cystinosis | CTNS | 1035insC |
| Cystinosis | CTNS | 1035insC |
| Cystinosis | CTNS | 537del21 |
| Cystinosis | CTNS | 537del21 |
| Cystinosis | CTNS | 57kb deletion |
| Cystinosis | CTNS | 57kb deletion |
| Cystinosis | CTNS | D205N |
| Cystinosis | CTNS | L158P |
| Cystinosis | CTNS | W138X |
| DFNA 9 (COCH) | COCH | P51S |
| Diabetes and Hearing Loss | mtDNA | 3234A>G |
| Diabetes and Hearing Loss | mtDNA | 3271T>C |
| Diabetes and Hearing Loss | mtDNA | G8363A |
| Diabetes and Hearing Loss | mtDNA | T14709C |
| Early-Onset Primary Dystonia (DYT1) | TOR1A | 904_906delGAG |
| Early-Onset Primary Dystonia (DYT1) | TOR1A | 904_906delGAG |
| Epidermolysis Bullosa Junctional, Herlitz-Pearson Type | LAMB3 | 3024delT |
| Epidermolysis Bullosa Junctional, Herlitz-Pearson Type | LAMB3 | 3024delT |

Figure 3 cont.

| Disease | Gene | Variant Name |
|---|---|---|
| Epidermolysis Bullosa Junctional, Herlitz-Pearson Type | LAMB3 | p.Q243X |
| Epidermolysis Bullosa Junctional, Herlitz-Pearson Type | LAMB3 | R144X |
| Epidermolysis Bullosa Junctional, Herlitz-Pearson Type | LAMB3 | R42X |
| Epidermolysis Bullosa Junctional, Herlitz-Pearson Type | LAMB3 | R635X |
| Epidermolysis Bullosa Junctional, Herlitz-Pearson Type | LAMA3 | R650X |
| Epidermolysis Bullosa Junctional, Herlitz-Pearson Type | LAMC2 | R95X |
| Factor V Leiden Thrombophilia | F5 | H1299R |
| Factor V Leiden Thrombophilia | F5 | R506Q, rs6025 |
| Factor V R2 Mutation Thrombophilia | F5 | rs6027 |
| Factor XI Deficiency | F11 | E117X (576G>T) |
| Factor XI Deficiency | F11 | F283L (1074T>C) |
| Factor XI Deficiency | F11 | IVS14 +1G>A |
| Factor XI Deficiency | F11 | IVS14del14 |
| Factor XI Deficiency | F11 | IVS14del14 |
| Factor XIII Deficiency | F13A1 | V34L, rs5985 |
| Familial Adenomatous Polyposis | APC | I1307K, rs1801155 |
| Familial Dysautonomia | IKBKAP | 2507+6T>C |
| Familial Dysautonomia | IKBKAP | P914L |
| Familial Dysautonomia | IKBKAP | R696P |
| Familial Hypercholesterolemia Type B | APOB | R3500Q, rs5742904 |
| Familial Hypercholesterolemia Type B | APOB | R3500W |
| Familial Hypercholesterolemia Type B | APOB | R3531C, rs12713559 |
| Familial Mediterranean Fever | MEFV | A744S (2230G>T) |
| Familial Mediterranean Fever | MEFV | delI692 (del2076_2078) |
| Familial Mediterranean Fever | MEFV | delI692 (del2076_2078) |
| Familial Mediterranean Fever | MEFV | E148Q (442 G>C), rs3743930 |
| Familial Mediterranean Fever | MEFV | E167D (501 G>C) |

Figure 3 cont.

| Disease | Gene | Variant Name |
|---|---|---|
| Familial Mediterranean Fever | MEFV | F479L (1437 C>G) |
| Familial Mediterranean Fever | MEFV | K695R (2084A>G) |
| Familial Mediterranean Fever | MEFV | M680I (2040G>C) |
| Familial Mediterranean Fever | MEFV | M694I (2082G>A), rs28940578 |
| Familial Mediterranean Fever | MEFV | M694V (2080A>G) |
| Familial Mediterranean Fever | MEFV | P369S (1105 C>T), rs11466023 |
| Familial Mediterranean Fever | MEFV | R408Q (1223G>A), rs11466024 |
| Familial Mediterranean Fever | MEFV | R653H (1958G>A) |
| Familial Mediterranean Fever | MEFV | R761H (2282G>A) |
| Familial Mediterranean Fever | MEFV | T267I (800 C>T) |
| Familial Mediterranean Fever | MEFV | V726A (2177T>C), rs28940579 |
| FANCC-Related Fanconi Anemia | FANCC | 322delG |
| FANCC-Related Fanconi Anemia | FANCC | 322delG |
| FANCC-Related Fanconi Anemia | FANCC | IVS4+4A>T (711 +4A>T) |
| FANCC-Related Fanconi Anemia | FANCC | Q13X (37C>T) |
| FANCC-Related Fanconi Anemia | FANCC | R547X |
| FGFR1-Related Craniosynostosis | FGFR1 | P252R |
| FGFR2-Related Craniosynostosis | FGFR2 | P253R |
| FGFR2-Related Craniosynostosis | FGFR2 | S252W |
| FGFR3-Related Craniosynostosis | FGFR3 | A391E, rs28931615 |
| FGFR3-Related Craniosynostosis | FGFR3 | P250R, rs4647924 |
| Free Sialic Acid Storage Disorders | SLC17A5 | c.1007_1008delTA |
| Free Sialic Acid Storage Disorders | SLC17A5 | c.1007_1008delTA |
| Free Sialic Acid Storage Disorders | SLC17A5 | c.115C>T |
| Frontotemporal Dementia with Parkinsonism-17 | MAPT | IVS10+16 |
| Frontotemporal Dementia with Parkinsonism-17 | MAPT | P301L |
| Frontotemporal Dementia with Parkinsonism-17 | MAPT | P301S |
| Frontotemporal Dementia with Parkinsonism-17 | MAPT | R406W |

Figure 3 cont.

| Disease | Gene | Variant Name |
|---|---|---|
| Fumarase deficiency | FH | c.1431_1433dupAAA |
| Fumarase deficiency | FH | c.1431_1433dupAAA |
| Galactosemia | GALT | 5.0Kb gene deletion |
| Galactosemia | GALT | 5.0Kb gene deletion |
| Galactosemia | GALT | 5'UTR-119del |
| Galactosemia | GALT | 5'UTR-119del |
| Galactosemia | GALT | IVS2-2 A>G |
| Galactosemia | GALT | K285N |
| Galactosemia | GALT | L195P T>C |
| Galactosemia | GALT | L218L |
| Galactosemia | GALT | N314D, rs2070074 |
| Galactosemia | GALT | Phe171Ser |
| Galactosemia | GALT | Q169K |
| Galactosemia | GALT | Q188R |
| Galactosemia | GALT | S135L |
| Galactosemia | GALT | T138M C>T |
| Galactosemia | GALT | X380R |
| Galactosemia | GALT | Y209C A>G |
| Gaucher Disease | GBA | 1035insG |
| Gaucher Disease | GBA | 1035insG |
| Gaucher Disease | GBA | 84insG |
| Gaucher Disease | GBA | 84insG |
| Gaucher Disease | GBA | D409H, rs1064651 |
| Gaucher Disease | GBA | D409V |
| Gaucher Disease | GBA | IVS2(+1)G>A |
| Gaucher Disease | GBA | L444P (1448T>C), rs35095275 |
| Gaucher Disease | GBA | N370S |
| Gaucher Disease | GBA | R463C |
| Gaucher Disease | GBA | R463H |
| Gaucher Disease | GBA | R496H (1604G>A) |
| Gaucher Disease | GBA | V394L |
| GJB2-Related DFNA 3 Nonsyndromic Hearing Loss and Deafness | GJB2 | 167delT |
| GJB2-Related DFNA 3 Nonsyndromic Hearing Loss and Deafness | GJB2 | 167delT |
| GJB2-Related DFNA 3 Nonsyndromic Hearing Loss and Deafness | GJB2 | 235delC |
| GJB2-Related DFNA 3 Nonsyndromic Hearing Loss and Deafness | GJB2 | 235delC |
| GJB2-Related DFNA 3 Nonsyndromic Hearing Loss and Deafness | GJB2 | 35delG |
| GJB2-Related DFNA 3 Nonsyndromic Hearing Loss and Deafness | GJB2 | 35delG |
| GJB2-Related DFNA 3 Nonsyndromic Hearing Loss and Deafness | GJB2 | IVS1+1G>A |

Figure 3 cont.

| Disease | Gene | Variant Name |
|---|---|---|
| GJB2-Related DFNB 1 Nonsyndromic Hearing Loss and Deafness | GJB2 | 101delAG |
| GJB2-Related DFNB 1 Nonsyndromic Hearing Loss and Deafness | GJB2 | 313del14 |
| GJB2-Related DFNB 1 Nonsyndromic Hearing Loss and Deafness | GJB2 | 313del14 |
| GJB2-Related DFNB 1 Nonsyndromic Hearing Loss and Deafness | GJB2 | delE120 |
| GJB2-Related DFNB 1 Nonsyndromic Hearing Loss and Deafness | GJB2 | delE120 |
| GJB2-Related DFNB 1 Nonsyndromic Hearing Loss and Deafness | GJB2 | M34T, rs35887622 |
| GJB2-Related DFNB 1 Nonsyndromic Hearing Loss and Deafness | GJB2 | Q124X |
| GJB2-Related DFNB 1 Nonsyndromic Hearing Loss and Deafness | GJB2 | R184P |
| GJB2-Related DFNB 1 Nonsyndromic Hearing Loss and Deafness | GJB2 | V37I |
| GJB2-Related DFNB 1 Nonsyndromic Hearing Loss and Deafness | GJB2 | W24X |
| GJB2-Related DFNB 1 Nonsyndromic Hearing Loss and Deafness | GJB2 | W77R |
| GJB2-Related DFNB 1 Nonsyndromic Hearing Loss and Deafness | GJB2 | W77X |
| Glucose-6-Phosphate Dehydrogenase Deficiency | G6PD | A335V |
| Glucose-6-Phosphate Dehydrogenase Deficiency | G6PD | R459L |
| Glucose-6-Phosphate Dehydrogenase Deficiency | G6PD | R459P |
| Glucose-6-Phosphate Dehydrogenase Deficiency | G6PD | rs1050828, rs1050828 |
| Glucose-6-Phosphate Dehydrogenase Deficiency | G6PD | rs1050829, rs1050829 |
| Glucose-6-Phosphate Dehydrogenase Deficiency | G6PD | rs5030868, rs5030868 |
| Glutaricacidemia Type 1 | GCDH | A421V |
| Glutaricacidemia Type 1 | GCDH | R402W |
| Glycogen Storage Disease Type 1a | G6PC | 459insTA |
| Glycogen Storage Disease Type 1a | G6PC | 459insTA |

Figure 3 cont.

| Disease | Gene | Variant Name |
|---|---|---|
| Glycogen Storage Disease Type 1a | G6PC | 727G/T |
| Glycogen Storage Disease Type 1a | G6PC | del F327 |
| Glycogen Storage Disease Type 1a | G6PC | del F327 |
| Glycogen Storage Disease Type 1a | G6PC | G188R |
| Glycogen Storage Disease Type 1a | G6PC | G270V |
| Glycogen Storage Disease Type 1a | G6PC | Q242X |
| Glycogen Storage Disease Type 1a | G6PC | Q27fsdelC |
| Glycogen Storage Disease Type 1a | G6PC | Q27fsdelC |
| Glycogen Storage Disease Type 1a | G6PC | Q347X |
| Glycogen Storage Disease Type 1a | G6PC | R83C |
| Glycogen Storage Disease Type 1a | G6PC | R83H |
| Glycogen Storage Disease Type 1b | G6PT1 | 1211delCT |
| Glycogen Storage Disease Type 1b | G6PT1 | A367T |
| Glycogen Storage Disease Type 1b | G6PT1 | G339C |
| Glycogen Storage Disease Type 1b | G6PT1 | G339D |
| Glycogen Storage Disease Type 1b | G6PT1 | W118R |
| Glycogen Storage Disease Type II | GAA | Arg854X |
| Glycogen Storage Disease Type II | GAA | Asp645Glu, rs28940868 |
| Glycogen Storage Disease Type II | GAA | IVS1(-13t>g) |
| Glycogen Storage Disease Type III | AGL | 1484delT |
| Glycogen Storage Disease Type III | AGL | 1484delT |
| Glycogen Storage Disease Type III | AGL | 17delAG |
| Glycogen Storage Disease Type III | AGL | 17delAG |
| Glycogen Storage Disease Type III | AGL | Q6X |
| Glycogen Storage Disease Type V | PYGM | G204S |
| Glycogen Storage Disease Type V | PYGM | K542T |
| Glycogen Storage Disease Type V | PYGM | K542X |
| Glycogen Storage Disease Type V | PYGM | R49X |

Figure 3 cont.

| Disease | Gene | Variant Name |
|---|---|---|
| GNE-Related Myopathies | GNE | M712T, rs28937594 |
| Gracile Syndrome | BCS1L | c.232A>G, rs28937590 |
| Hemoglobin S Beta-Thalassemia | HBB | c.19G>A |
| Hemoglobin S Beta-Thalassemia | HBB | c.20A>T |
| Hemoglobin S Beta-Thalassemia | HBB | c.79G>A |
| Hemoglobin S Beta-Thalassemia | HBB | Hb CS |
| Hemoglobin S Beta-Thalassemia | HBB | Hb D |
| Hemoglobin S Beta-Thalassemia | HBB | Hb O |
| Hereditary Fructose Intolerance | ALDOB | A149P, rs1800546 |
| Hereditary Fructose Intolerance | ALDOB | A174D |
| Hereditary Fructose Intolerance | ALDOB | Delta4E4 |
| Hereditary Fructose Intolerance | ALDOB | Delta4E4 |
| Hereditary Fructose Intolerance | ALDOB | N334K |
| Hereditary Fructose Intolerance | ALDOB | Y203X |
| Hereditary Pancreatitis | PRSS1 | A16V |
| Hereditary Pancreatitis | SPINK1 | M1T |
| Hereditary Pancreatitis | PRSS1 | N29I |
| Hereditary Pancreatitis | SPINK1 | N34S, rs17107315 |
| Hereditary Pancreatitis | PRSS1 | R122C |
| Hereditary Pancreatitis | PRSS1 | R122H |
| Hereditary Thymine-Uraciluria | DPYD | rs3918290 |
| Hexosaminidase A Deficiency | HEXA | 1278insTATC |
| Hexosaminidase A Deficiency | HEXA | 1278insTATC |
| Hexosaminidase A Deficiency | HEXA | G269S (805G>A) |
| Hexosaminidase A Deficiency | HEXA | IVS12 +1G>C |
| Hexosaminidase A Deficiency | HEXA | IVS7 +1G>A |
| Hexosaminidase A Deficiency | HEXA | IVS9 +1G>A |
| Hexosaminidase A Deficiency | HEXA | R178C |
| Hexosaminidase A Deficiency | HEXA | R178H |
| Hexosaminidase A Deficiency | HEXA | R247W (739C>T) |
| Hexosaminidase A Deficiency | HEXA | R249W (745C>T) |

Figure 3 cont.

| Disease | Gene | Variant Name |
|---|---|---|
| HFE-Associated Hereditary Hemochromatosis | HFE | E168Q |
| HFE-Associated Hereditary Hemochromatosis | HFE | E168X |
| HFE-Associated Hereditary Hemochromatosis | HFE | HM971246, H63H |
| HFE-Associated Hereditary Hemochromatosis | HFE | P160delC |
| HFE-Associated Hereditary Hemochromatosis | HFE | P160delC |
| HFE-Associated Hereditary Hemochromatosis | HFE | Q127H, rs28934595 |
| HFE-Associated Hereditary Hemochromatosis | HFE | Q283P |
| HFE-Associated Hereditary Hemochromatosis | HFE | rs1799945, rs1799945 |
| HFE-Associated Hereditary Hemochromatosis | HFE | rs1800562, rs1800562 |
| HFE-Associated Hereditary Hemochromatosis | HFE | rs1800730, rs1800730 |
| HFE-Associated Hereditary Hemochromatosis | HFE | V53M |
| HFE-Associated Hereditary Hemochromatosis | HFE | V59M |
| HFE-Associated Hereditary Hemochromatosis | HFE | W169X |
| Hidrotic Ectodermal Dysplasia 2 | GJB6 | A88V, rs28937872 |
| Hidrotic Ectodermal Dysplasia 2 | GJB6 | G11R |
| Hidrotic Ectodermal Dysplasia 2 | GJB6 | V37E |
| Homocystinuria Caused by Cystathionine Beta-Synthase Deficiency | CBS | G307S 919G->A |
| Homocystinuria Caused by Cystathionine Beta-Synthase Deficiency | CBS | I278T 833T->C, rs5742905 |
| Hyperkalemic Periodic Paralysis Type 1 | SCN4A | I693T |
| Hyperkalemic Periodic Paralysis Type 1 | SCN4A | L689I |
| Hyperkalemic Periodic Paralysis Type 1 | SCN4A | L689V |
| Hyperkalemic Periodic Paralysis Type 1 | SCN4A | M1360V |
| Hyperkalemic Periodic Paralysis Type 1 | SCN4A | M1592V |
| Hyperkalemic Periodic Paralysis Type 1 | SCN4A | p.A1156T |
| Hyperkalemic Periodic Paralysis Type 1 | SCN4A | p.M1370V |
| Hyperkalemic Periodic Paralysis Type 1 | SCN4A | p.R1448C |
| Hyperkalemic Periodic Paralysis Type 1 | SCN4A | p.T1313M |

Figure 3 cont.

| Disease | Gene | Variant Name |
|---|---|---|
| Hyperkalemic Periodic Paralysis Type 1 | SCN4A | R675G |
| Hyperkalemic Periodic Paralysis Type 1 | SCN4A | R675Q |
| Hyperkalemic Periodic Paralysis Type 1 | SCN4A | R675W |
| Hyperkalemic Periodic Paralysis Type 1 | SCN4A | T704M |
| Hyperkalemic Periodic Paralysis Type 1 | SCN4A | V781I |
| Hyperornithinemia-Hyperammonemia-Homocitrullinuria Syndrome | SLC25A15 | F188del |
| Hyperornithinemia-Hyperammonemia-Homocitrullinuria Syndrome | SLC25A15 | F188del |
| Hyperoxaluria, Primary, Type 1 | AGXT | 33insC |
| Hyperoxaluria, Primary, Type 1 | AGXT | 33insC |
| Hyperoxaluria, Primary, Type 1 | AGXT | F152I |
| Hyperoxaluria, Primary, Type 1 | AGXT | G170R |
| Hyperoxaluria, Primary, Type 1 | AGXT | I244T |
| Hyperoxaluria, Primary, Type 2 | GRHPR | 103delG |
| Hyperoxaluria, Primary, Type 2 | GRHPR | 103delG |
| Hypochondroplasia | FGFR3 | Asn328Ile |
| Hypochondroplasia | FGFR3 | I538V |
| Hypochondroplasia | FGFR3 | K650M |
| Hypochondroplasia | FGFR3 | K650N 1950G>T |
| Hypochondroplasia | FGFR3 | K650Q |
| Hypochondroplasia | FGFR3 | N540K 1620C>A |
| Hypochondroplasia | FGFR3 | N540S |
| Hypochondroplasia | FGFR3 | N540T |
| Hypokalemic Periodic Paralysis Type 1 | CACNA1S | R528G |
| Hypokalemic Periodic Paralysis Type 1 | CACNA1S | R528H |
| Hypokalemic Periodic Paralysis Type 1 | CACNA1S | rs28930068, rs28930068 |
| Hypokalemic Periodic Paralysis Type 1 | CACNA1S | rs28930069, rs28930069 |
| Hypokalemic Periodic Paralysis Type 2 | SCN4A | R669H |
| Hypokalemic Periodic Paralysis Type 2 | SCN4A | R672C |
| Hypokalemic Periodic Paralysis Type 2 | SCN4A | R672G |

Figure 3 cont.

| Disease | Gene | Variant Name |
|---|---|---|
| Hypokalemic Periodic Paralysis Type 2 | SCN4A | R672H |
| Hypokalemic Periodic Paralysis Type 2 | SCN4A | R672S |
| Hypophosphatasia | ALPL | Asp361Val |
| Hypophosphatasia | ALPL | c.1559delT |
| Hypophosphatasia | ALPL | c.1559delT |
| Hypophosphatasia | ALPL | E174K |
| Hypophosphatasia | ALPL | G317D |
| Hypophosphatasia | ALPL | Phe310Leu |
| Isovaleric Acidemia | IVD | A282V |
| Isovaleric Acidemia | IVD | rs28940889 |
| Krabbe Disease | GALC | EX11-17DEL |
| Krabbe Disease | GALC | EX11-17DEL |
| Krabbe Disease | GALC | G270D |
| Krabbe Disease | GALC | rs1805078, rs1805078 |
| Krabbe Disease | GALC | rs398607 |
| Leber Hereditary Optic Neuropathy | mtDNA | 14484T>C |
| Leber Hereditary Optic Neuropathy | mtDNA | 15257G>A |
| Leber Hereditary Optic Neuropathy | mtDNA | G14459A |
| Leber Hereditary Optic Neuropathy | mtDNA | G3460A |
| Leber Hereditary Optic Neuropathy | mtDNA | m.11778G>A |
| Leber Hereditary Optic Neuropathy | mtDNA | m.13708G>A |
| Leber Hereditary Optic Neuropathy | mtDNA | m.15812G>A |
| Leber Hereditary Optic Neuropathy | mtDNA | m.3394T>C |
| Leber Hereditary Optic Neuropathy | mtDNA | m.4216T>C |
| Leber Hereditary Optic Neuropathy | mtDNA | m.4917A>G |
| Leigh Syndrome, French-Canadian Type | LRPPRC | A354V |
| LGMD2I | FKRP | L276I, rs28937900 |
| Long Chain 3-Hydroxyacyl-CoA Dehydrogenase Deficiency | HADHA | E474Q c.1528G>C |
| Long Chain 3-Hydroxyacyl-CoA Dehydrogenase Deficiency | HADHA | Q342X 1132C>T |
| Maple Syrup Urine Disease Type 1A | BCKDHA | Y438N |
| Maple Syrup Urine Disease Type 1B | BCKDHB | E372X |
| Maple Syrup Urine Disease Type 1B | BCKDHB | G278S |
| Maple Syrup Urine Disease Type 1B | BCKDHB | R183P |

Figure 3 cont.

| Disease | Gene | Variant Name |
|---|---|---|
| McCune-Albright Syndrome | GNAS | R201C |
| McCune-Albright Syndrome | GNAS | R201G |
| McCune-Albright Syndrome | GNAS | R201H |
| Medium Chain Acyl-Coenzyme A Dehydrogenase Deficiency | ACADM | 244insT |
| Medium Chain Acyl-Coenzyme A Dehydrogenase Deficiency | ACADM | 244insT |
| Medium Chain Acyl-Coenzyme A Dehydrogenase Deficiency | ACADM | 250C>T |
| Medium Chain Acyl-Coenzyme A Dehydrogenase Deficiency | ACADM | 583G>A |
| Medium Chain Acyl-Coenzyme A Dehydrogenase Deficiency | ACADM | 616C>T |
| Medium Chain Acyl-Coenzyme A Dehydrogenase Deficiency | ACADM | 617G>A |
| Medium Chain Acyl-Coenzyme A Dehydrogenase Deficiency | ACADM | 799G>A |
| Medium Chain Acyl-Coenzyme A Dehydrogenase Deficiency | ACADM | K304E |
| Medium Chain Acyl-Coenzyme A Dehydrogenase Deficiency | ACADM | Y42H |
| Megalencephalic Leukoencephalopathy with Subcortical Cysts | MLC1 | 135insC |
| Megalencephalic Leukoencephalopathy with Subcortical Cysts | MLC1 | 135insC |
| MELAS | mtDNA | 3243A>G |
| MELAS | mtDNA | 3250T>C |
| MELAS | mtDNA | 3252A>G |
| MELAS | mtDNA | A12770G |
| MELAS | mtDNA | C3256T |
| MELAS | mtDNA | G13513A |
| MELAS | mtDNA | T3291C |
| MELAS | mtDNA | T8356C |
| MELAS | mtDNA | T9957C |
| MERRF | mtDNA | 8361G>A |
| MERRF | mtDNA | A8296G |
| MERRF | mtDNA | m.8344A>G |
| Metachromatic Leukodystrophy | ARSA | c.459+1G>A |

Figure 3 cont.

| Disease | Gene | Variant Name |
|---|---|---|
| Metachromatic Leukodystrophy | ARSA | p.P426L, rs28940893 |
| Metachromatic Leukodystrophy | ARSA | p.T274M |
| Metachromatic Leukodystrophy | ARSA | P377L |
| Mitochondrial Cardiomyopathy | mtDNA | A3260T |
| Mitochondrial Cardiomyopathy | mtDNA | A4300G |
| Mitochondrial Cardiomyopathy | mtDNA | C3303T |
| Mitochondrial Cardiomyopathy | mtDNA | T9997C |
| Mitochondrial DNA-Associated Leigh Syndrome and NARP | mtDNA | 5537insT |
| Mitochondrial DNA-Associated Leigh Syndrome and NARP | mtDNA | 5537insT |
| Mitochondrial DNA-Associated Leigh Syndrome and NARP | mtDNA | 8993T>C |
| Mitochondrial DNA-Associated Leigh Syndrome and NARP | mtDNA | 8993T>G |
| Mitochondrial DNA-Associated Leigh Syndrome and NARP | mtDNA | C11777A |
| Mitochondrial DNA-Associated Leigh Syndrome and NARP | mtDNA | T10158C |
| Mitochondrial DNA-Associated Leigh Syndrome and NARP | mtDNA | T10191C |
| Mitochondrial DNA-Associated Leigh Syndrome and NARP | mtDNA | T8851C |
| Mitochondrial DNA-Associated Leigh Syndrome and NARP | mtDNA | T9176C |
| Mitochondrial DNA-Associated Leigh Syndrome and NARP | mtDNA | T9176G |
| MTHFR Deficiency | MTHFR | 1298A>C |
| MTHFR Deficiency | MTHFR | rs1801133, rs1801133 |
| MTRNR1-Related Hearing Loss and Deafness | mtDNA | 1095T>C |
| MTRNR1-Related Hearing Loss and Deafness | mtDNA | 1494C>T |
| MTRNR1-Related Hearing Loss and Deafness | mtDNA | 1555A>G |
| MTRNR1-Related Hearing Loss and Deafness | mtDNA | 961T>G |

Figure 3 cont.

| Disease | Gene | Variant Name |
|---|---|---|
| MTRNR1-Related Hearing Loss and Deafness | mtDNA | A7445G |
| MTTS1-Related Hearing Loss and Deafness | mtDNA | 7443A>G |
| MTTS1-Related Hearing Loss and Deafness | mtDNA | 7444G>A |
| MTTS1-Related Hearing Loss and Deafness | mtDNA | 7472insC |
| MTTS1-Related Hearing Loss and Deafness | mtDNA | 7472insC |
| MTTS1-Related Hearing Loss and Deafness | mtDNA | 7510T>C |
| MTTS1-Related Hearing Loss and Deafness | mtDNA | 7511T>C |
| MTTS1-Related Hearing Loss and Deafness | mtDNA | 7512T>C |
| Mucolipidosis IV | MCOLN1 | delEx1 3 Ex7 (511>6944del) |
| Mucolipidosis IV | MCOLN1 | delEx1 3 Ex7 (511>6944del) |
| Mucolipidosis IV | MCOLN1 | IVS-2A>G |
| Mucopolysaccharidosis Type I | IDUA | c.46_57del |
| Mucopolysaccharidosis Type I | IDUA | c.46_57del |
| Mucopolysaccharidosis Type I | IDUA | p.A327P |
| Mucopolysaccharidosis Type I | IDUA | p.P533R |
| Mucopolysaccharidosis Type I | IDUA | Q70X |
| Mucopolysaccharidosis Type I | IDUA | W402X |
| Mucopolysaccharidosis Type IIIA | SGSH | p.R245H |
| Mucopolysaccharidosis Type IIIA | SGSH | p.R74C |
| Mucopolysaccharidosis Type IIIA | SGSH | p.S66W |
| Mucopolysaccharidosis Type VII | GUSB | p.D152N |
| Multiple Endocrine Neoplasia Type 2 | RET | 2047T>A |
| Multiple Endocrine Neoplasia Type 2 | RET | 2047T>A |
| Multiple Endocrine Neoplasia Type 2 | RET | 2047T>C |
| Multiple Endocrine Neoplasia Type 2 | RET | 2047T>G |
| Multiple Endocrine Neoplasia Type 2 | RET | 2048G>A |
| Multiple Endocrine Neoplasia Type 2 | RET | A883F 2647 G>T |
| Multiple Endocrine Neoplasia Type 2 | RET | Glu768Asp G>C |
| Multiple Endocrine Neoplasia Type 2 | RET | M918T |

Figure 3 cont.

| Disease | Gene | Variant Name |
|---|---|---|
| Muscle-Eye-Brain Disease | POMGNT1 | c.1539+1G>A |
| MYH-Associated Polyposis | MUTYH | c.1376C>A |
| MYH-Associated Polyposis | MUTYH | c.494A>G, rs34612342 |
| MYH-Associated Polyposis | GENE_SYMBOL_TBD | rs36053993, rs36053993 |
| Niemann-Pick Disease Due to Sphingomyelinase Deficiency | SMPD1 | c.990delC |
| Niemann-Pick Disease Due to Sphingomyelinase Deficiency | SMPD1 | c.990delC |
| Niemann-Pick Disease Due to Sphingomyelinase Deficiency | SMPD1 | fsP330 |
| Niemann-Pick Disease Due to Sphingomyelinase Deficiency | SMPD1 | fsP330 |
| Niemann-Pick Disease Due to Sphingomyelinase Deficiency | SMPD1 | L302P |
| Niemann-Pick Disease Due to Sphingomyelinase Deficiency | SMPD1 | R496L |
| Niemann-Pick Disease Due to Sphingomyelinase Deficiency | SMPD1 | R608del |
| Niemann-Pick Disease Type C1 | NPC1 | I1061T |
| Nijmegen Breakage Syndrome | NBN | 657del5 |
| Nijmegen Breakage Syndrome | NBN | 657del5 |
| Pallister-Hall Syndrome | GLI3 | 2012delG |
| Pallister-Hall Syndrome | GLI3 | 2012delG |
| Pallister-Hall Syndrome | GLI3 | 2023delG |
| Pallister-Hall Syndrome | GLI3 | 2023delG |
| Pendred Syndrome | SLC26A4 | 1197delT |
| Pendred Syndrome | SLC26A4 | 1197delT |
| Pendred Syndrome | SLC26A4 | E384G |
| Pendred Syndrome | SLC26A4 | IV58+1(G->A) |
| Pendred Syndrome | SLC26A4 | L236P |
| Pendred Syndrome | SLC26A4 | T416P |
| Peroxisomal Bifunctional Enzyme Deficiency | HSD17B4 | c.302+1G>C |
| Peroxisomal Bifunctional Enzyme Deficiency | HSD17B4 | c.303-1G>A |
| Pervasive Developmental Disorders | NLGN4X | D396X |
| Pervasive Developmental Disorders | NLGN4X | D396X |
| Pervasive Developmental Disorders | NLGN4X | NLGN4X:1253delAG |

Figure 3 cont.

| Disease | Gene | Variant Name |
|---|---|---|
| Pervasive Developmental Disorders | NLGN4X | NLGN4X:1253delAG |
| Pervasive Developmental Disorders | NLGN3 | R451C |
| Phenylalanine Hydroxylase Deficiency | PAH | G272X |
| Phenylalanine Hydroxylase Deficiency | PAH | I65T |
| Phenylalanine Hydroxylase Deficiency | PAH | IVS12+1G>T |
| Phenylalanine Hydroxylase Deficiency | PAH | L48S, rs5030841 |
| Phenylalanine Hydroxylase Deficiency | PAH | R158Q, rs5030843 |
| Phenylalanine Hydroxylase Deficiency | PAH | R252W, rs5030847 |
| Phenylalanine Hydroxylase Deficiency | PAH | R261Q, rs5030849 |
| Phenylalanine Hydroxylase Deficiency | PAH | R408Q, rs5030859 |
| Phenylalanine Hydroxylase Deficiency | PAH | R408W, rs5030858 |
| Phenylalanine Hydroxylase Deficiency | PAH | rs5030855 |
| Phenylalanine Hydroxylase Deficiency | PAH | rs5030861 |
| Phenylalanine Hydroxylase Deficiency | PAH | Y414C, rs5030860 |
| Plasminogen Activator Inhibitor I | SERPINE1 | -844 G>A |
| Plasminogen Activator Inhibitor I | SERPINE1 | 4G/5G |
| Polycystic Kidney Disease, Autosomal Recessive | PKHD1 | c.10412T>G |
| Polycystic Kidney Disease, Autosomal Recessive | PKHD1 | c.107C>T |
| Polycystic Kidney Disease, Autosomal Recessive | PKHD1 | c.1486C>T |
| Polycystic Kidney Disease, Autosomal Recessive | PKHD1 | c.5895dupA |
| Polycystic Kidney Disease, Autosomal Recessive | PKHD1 | c.5895dupA |
| Polycystic Kidney Disease, Autosomal Recessive | PKHD1 | c.9689delA |
| Polycystic Kidney Disease, Autosomal Recessive | PKHD1 | c.9689delA |
| PPT1-Related Neuronal Ceroid-Lipofuscinosis | PPT1 | c.364A>T |
| PPT1-Related Neuronal Ceroid-Lipofuscinosis | PPT1 | p.L10X |
| PPT1-Related Neuronal Ceroid-Lipofuscinosis | PPT1 | p.R151X |
| PPT1-Related Neuronal Ceroid-Lipofuscinosis | PPT1 | T75P |
| PROP1-related pituitary hormome deficiency | PROP1 | 301-302delAG |

Figure 3 cont.

| Disease | Gene | Variant Name |
|---|---|---|
| PROP1-related pituitary hormome deficiency | PROP1 | 301-302delAG |
| Prothrombin Thrombophilia | F2 | rs1799963 |
| Prothrombin Thrombophilia | F2 | rs6025, rs6025 |
| Pseudovitamin D Deficiency Rickets | CYP27B1 | 7bp duplication in exon8 |
| Pseudovitamin D Deficiency Rickets | CYP27B1 | 7bp duplication in exon8 |
| Pseudovitamin D Deficiency Rickets | CYP27B1 | 958delG |
| Pseudovitamin D Deficiency Rickets | CYP27B1 | 958delG |
| Rett Syndrome | MECP2 | 806delG |
| Rett Syndrome | MECP2 | 806delG |
| Rett Syndrome | MECP2 | A140V, rs28934908 |
| Rett Syndrome | MECP2 | P152R |
| Rett Syndrome | MECP2 | P225R |
| Rett Syndrome | MECP2 | R106W, rs28934907 |
| Rett Syndrome | MECP2 | R133C |
| Rett Syndrome | MECP2 | R168X |
| Rett Syndrome | MECP2 | R255X |
| Rett Syndrome | MECP2 | R270X |
| Rett Syndrome | MECP2 | R294X |
| Rett Syndrome | MECP2 | R306C, rs28935468 |
| Rett Syndrome | MECP2 | S134C |
| Rett Syndrome | MECP2 | T158M, rs28934906 |
| Rhizomelic Chondrodysplasia Punctata Type 1 | PEX7 | p.A218V |
| Rhizomelic Chondrodysplasia Punctata Type 1 | PEX7 | p.G217R |
| Rhizomelic Chondrodysplasia Punctata Type 1 | PEX7 | p.L292X, rs1805137 |
| Short Chain Acyl-CoA Dehydrogenase Deficiency | ACADS | c.511C>T, rs1800556 |
| Short Chain Acyl-CoA Dehydrogenase Deficiency | ACADS | c.625G>A |
| Short Chain Acyl-CoA Dehydrogenase Deficiency | ACADS | R107C |
| Shwachman-Diamond Syndrome | SBDS | 183_184TA>CT |
| Shwachman-Diamond Syndrome | SBDS | 183_184TA>CT |
| Shwachman-Diamond Syndrome | SBDS | 258+2T>C |
| Sjogren-Larsson Syndrome | ALDH3A2 | c.943C>T |
| Smith-Lemli-Opitz Syndrome | DHCR7 | C380Y |
| Smith-Lemli-Opitz Syndrome | DHCR7 | IVS8-1G>C |

Figure 3 cont.

| Disease | Gene | Variant Name |
|---|---|---|
| Smith-Lemli-Opitz Syndrome | DHCR7 | L109P |
| Smith-Lemli-Opitz Syndrome | DHCR7 | L157P |
| Smith-Lemli-Opitz Syndrome | DHCR7 | R352Q |
| Smith-Lemli-Opitz Syndrome | DHCR7 | R352W |
| Smith-Lemli-Opitz Syndrome | DHCR7 | R404C |
| Smith-Lemli-Opitz Syndrome | DHCR7 | R446Q |
| Smith-Lemli-Opitz Syndrome | DHCR7 | T93M |
| Smith-Lemli-Opitz Syndrome | DHCR7 | V326L |
| Smith-Lemli-Opitz Syndrome | DHCR7 | W151X |
| Smith-Lemli-Opitz Syndrome | DHCR7 | W151X |
| Spastic Paraplegia 13 | HSPD1 | V72I |
| Sulfate Transporter-Related Osteochondrodysplasia | SLC26A2 | 340delV |
| Sulfate Transporter-Related Osteochondrodysplasia | SLC26A2 | 340delV |
| Sulfate Transporter-Related Osteochondrodysplasia | SLC26A2 | c.837C>T |
| Sulfate Transporter-Related Osteochondrodysplasia | SLC26A2 | C653S |
| Sulfate Transporter-Related Osteochondrodysplasia | SLC26A2 | IVS1+2T>C |
| Sulfate Transporter-Related Osteochondrodysplasia | SLC26A2 | R178X |
| TFR2-Related Hereditary Hemochromatosis | TFR2 | AVAQ594-597del |
| TFR2-Related Hereditary Hemochromatosis | TFR2 | AVAQ594-597del |
| TFR2-Related Hereditary Hemochromatosis | TFR2 | E60X |
| TFR2-Related Hereditary Hemochromatosis | TFR2 | E60X |
| TFR2-Related Hereditary Hemochromatosis | TFR2 | M172K |
| TFR2-Related Hereditary Hemochromatosis | TFR2 | Y250X |
| Thanatophoric Dysplasia | FGFR3 | G370C |
| Thanatophoric Dysplasia | FGFR3 | K650E |
| Thanatophoric Dysplasia | FGFR3 | R248C |
| Thanatophoric Dysplasia | FGFR3 | S249C |
| Thanatophoric Dysplasia | FGFR3 | S371C |
| Thanatophoric Dysplasia | FGFR3 | X807C A>T |
| Thanatophoric Dysplasia | FGFR3 | X807G |
| Thanatophoric Dysplasia | FGFR3 | X807L |
| Thanatophoric Dysplasia | FGFR3 | X807R |

Figure 3 cont.

| Disease | Gene | Variant Name |
|---|---|---|
| Thanatophoric Dysplasia | FGFR3 | X807S |
| Thanatophoric Dysplasia | FGFR3 | X807W |
| Thanatophoric Dysplasia | FGFR3 | Y373C |
| TPP1-Related Neuronal Ceroid-Lipofuscinosis | TPP1 | c.509-1G>A |
| TPP1-Related Neuronal Ceroid-Lipofuscinosis | TPP1 | c.509-1G>C |
| TPP1-Related Neuronal Ceroid-Lipofuscinosis | TPP1 | G284V |
| TPP1-Related Neuronal Ceroid-Lipofuscinosis | TPP1 | p.R208X |
| Transthyretin Amyloidosis | TTR | c.148G>A |
| Tyrosine Hydroxylase-Deficient DRD | TH | L205P |
| Tyrosine Hydroxylase-Deficient DRD | TH | R202H |
| Tyrosinemia Type I | FAH | E357X |
| Tyrosinemia Type I | FAH | IVS12+5 G>A |
| Tyrosinemia Type I | FAH | IVS7-6 T>G |
| Tyrosinemia Type I | FAH | IVS8-1G>C |
| Tyrosinemia Type I | FAH | p.W262X |
| Tyrosinemia Type I | FAH | P261L |
| Tyrosinemia Type I | FAH | Q64H |
| Wilson Disease | ATP7B | 1340del4 |
| Wilson Disease | ATP7B | 3402delC |
| Wilson Disease | ATP7B | 3402delC |
| Wilson Disease | ATP7B | H1069Q |
| Wilson Disease | ATP7B | R778G |
| Wilson Disease | ATP7B | W779X |
| Wilson Disease | ATP7B | W779X |
| X-Linked Juvenile Retinoschisis | RS1 | E72K |
| X-Linked Juvenile Retinoschisis | RS1 | G109R |
| X-Linked Juvenile Retinoschisis | RS1 | G74V |
| Zellweger Syndrome Spectrum | PEX1 | c.2097_2098insT |
| Zellweger Syndrome Spectrum | PEX1 | c.2097_2098insT |
| Zellweger Syndrome Spectrum | PEX1 | c.2916delA |
| Zellweger Syndrome Spectrum | PEX1 | c.2916delA |
| Zellweger Syndrome Spectrum | PEX1 | p.G843D |

Figure 4

| SEQ ID NO: 22 | GAGGATTCAGGAGTCAATGACTGAGGATGGGACTCCTTGA |
|---|---|
| SEQ ID NO: 23 | TGAGGGCCTGGACCAAATTCTTCAAGCAAAACAGAAAACA |
| SEQ ID NO: 24 | ACTGGACCGCCCCCTCCACGCCCTCCCACCGCGGGCCCCT |
| SEQ ID NO: 25 | TCTTTTTTCCGAGACAAACTTCATTCTGGAAAGGCTGTCA |
| SEQ ID NO: 26 | TTTTGCTGAGCTTACAGTGGAAATGCTATTAAATTCTTTC |
| SEQ ID NO: 27 | ACTTAGAAAGTTAAAGTAAGAAATTATTAATATCTCCTAT |
| SEQ ID NO: 28 | TCAGAAGGGGCAAAGCTTGCTTCCTCCTGCATCCCTCATG |
| SEQ ID NO: 29 | TTTATTTTGTCTCTGCTGTTCATGGCATAGTTTGGTGGCG |
| SEQ ID NO: 30 | AATGGCCTGCCACCTGAGAATCTATTGTTTATGGCAAGAC |
| SEQ ID NO: 31 | AGAGCAAAGAGGACCTGGGAGGTGCCTGCACCCCATACCA |
| SEQ ID NO: 32 | CAAATAGAAATGCTCTTATAGATGAGTATCAAAAATAAAT |
| SEQ ID NO: 33 | TCCTCCGCTCCTCCTGCGCGGGGTGCTGAAACAGCCCGGG |
| SEQ ID NO: 34 | ACCCGGGCCTGAGCCGTCGCTGGGCCCGTCGCCTTCCCCG |
| SEQ ID NO: 35 | TTCTACCTGTGGACCAGGAATCTAGGACACAGTCCCTGAC |
| SEQ ID NO: 36 | TGCCCTGCTGCAGACCTACACGCCCCCACCATGTGCCCAC |
| SEQ ID NO: 37 | GGGCGTCCTGCTGCTGGGCCTGGTGGGCTACTACATCTTC |
| SEQ ID NO: 38 | GAGCGTGATTAGGTACTGGACACCTGCCAAGTGCTGGGCT |
| SEQ ID NO: 39 | CTGGGATTTGAGGGTTTTCATTACACTTCTGCTAGGATAA |
| SEQ ID NO: 40 | TAAAATTTAAAAAATACAGTTAAAAATCATGGTCATATAA |
| SEQ ID NO: 41 | CCGCTGCACTGACTTCATTTCCTTAGACAAGACACAGTGT |
| SEQ ID NO: 42 | ACTGCAACATTTTCAAAGCAAAAGAATCCCGTTGCTGTCG |
| SEQ ID NO: 43 | CTTAGCTCAGCTCCAGGCTGTGCAGCAGAAGTACAGGGAC |
| SEQ ID NO: 44 | ATTTTAGATTCAAAATTGGTAGCCGATTACATTTTCTCAA |
| SEQ ID NO: 45 | AGGCAAGCTGTCCTCCAGGTCTTTATCAGACAGTGCCCCC |
| SEQ ID NO: 46 | TTTAAGGTTTCTGTGACCTTTGTTAGAAAGTTTTTAAATG |
| SEQ ID NO: 47 | AATAGTAGGCTGTTGGTACATTTCTCAACTTACTTATAAA |
| SEQ ID NO: 48 | AACCAGTTTCTGCCTGTCTGTAACTGCCCTGTCTGCCACA |
| SEQ ID NO: 49 | CCTGAAATCTCTTCTCGAGGCTGAGCTGAGGGCCCTTGGG |
| SEQ ID NO: 50 | CTATTTCTCTCTCTTATTTTCAGAATTAGAAAGCAATTC |
| SEQ ID NO: 51 | CACGGACATACGCATACCGGCCCAGTGACACGTCAGGCAA |
| SEQ ID NO: 52 | ATGCCTTATCAACAGTAAAACAATGAATCACCATAGTACA |
| SEQ ID NO: 53 | TCCTTTGGAACAGTGTGGACCCCAGGTCATGGCTCCCAGA |
| SEQ ID NO: 54 | TGTACAGGATGTTACTGTACTGGATGTTGCAGGCAACTAT |
| SEQ ID NO: 55 | CACTGCTGCATGAGGAGTGGGCCTGGGGCCACTAAACCCG |
| SEQ ID NO: 56 | CCTGCAGTGGGATTTCCTCTGAAGAGAGCACAGTGAGCAG |
| SEQ ID NO: 57 | AACTTATTATTTTATACCTGCTTCATTGTTGAAAAGAAAA |
| SEQ ID NO: 58 | AGCCACTGTGCCCGGCTGCAGATATTCTTTCAGTAAATGA |
| SEQ ID NO: 59 | CATTGCCTGTGAGTGCCCTCAGTTTACATAGTGCTATCTT |
| SEQ ID NO: 60 | TAATTTTATTCGCCATTAGGATGAAATCCATATTCACAAA |
| SEQ ID NO: 61 | TCAAGCCAGCCTGGAAGGGAGATGGAAAAGCTGCGTGCGC |
| SEQ ID NO: 62 | TGCTGTTAAGATGTTACTTTCTTTAAAAAAGATGGGTTAT |
| SEQ ID NO: 63 | AAAAATTATGCCTATTAGAATCAAAATATGATAGCAAAAC |
| SEQ ID NO: 64 | GTTAATATTTTTATGCTAATGCAGACAATATATATTACTG |
| SEQ ID NO: 65 | GCTGTACAGAGCTATATATCATAATTATTTCTATACTATG |
| SEQ ID NO: 66 | CAGGAGGATCAGTCTCTGTAGAGGCAGGGAGGAGCTGGGG |
| SEQ ID NO: 67 | TATTTTCAGGTACTGAATTCTGAAATGATAGCATTTTGTG |
| SEQ ID NO: 68 | TGTTGAGTTTTTCAGTTTCTCTGAAAAGTCATACTCTAGA |
| SEQ ID NO: 69 | TGTAGCCCCTTTGAGCATGAGGTATGCATAGAACATAATG |
| SEQ ID NO: 70 | CTTGCAATCAAGTAAGGTGAAATATTCATATACTGGTTCT |

Figure 4 cont.

| SEQ ID NO: 71 | CGGCGGGCCGCCTAGGGTGATTGGCTGCTGCAGCCCACCC |
|---|---|
| SEQ ID NO: 72 | TTTCGGGAGGAGGGAGAGGGTGGGGTGGCGGGTGCAGACT |
| SEQ ID NO: 73 | CCTCAGCCACAACCATTAGCTGCAACGGTCCAGGCTCGTG |
| SEQ ID NO: 74 | ATCTCTCGCCATTTCTGCTGAGGCCTGTTCTTTTTTCTT |
| SEQ ID NO: 75 | CCCGGGCAGTCCTGGGCTTGAACGTGTGTGTCAGCCGCGC |
| SEQ ID NO: 76 | GGAACAAGGGGTCTTCCGAGCAGCCCCAGCCCTCCCCTC |
| SEQ ID NO: 77 | GCACCTTCCCCGCAGGCGGTGGGTGAGCCCTGGGAGCTGA |
| SEQ ID NO: 78 | AAGGTTTTCAAGAAGTTAAATTGGAATAGAAACATTTTGG |
| SEQ ID NO: 79 | AAATCAATTTCTGTTTCTTAAGTAATTTCTTCATGAGCAT |
| SEQ ID NO: 80 | TAGGCACTTCCACGTGGTGTCAATCCCTGATCACTGGGAG |
| SEQ ID NO: 81 | CAGAAACTTATAAAATATTGATAGGCAGCTTCTTTGGGAG |
| SEQ ID NO: 82 | CCAGCTTGGGACTATGCCCATGAGTGCCCGGCCATGCCCG |
| SEQ ID NO: 83 | GCGCCCCCAGAGTCCCAGGCAAAGCCAGCAAGGGCCAGGC |
| SEQ ID NO: 84 | GTTCTGGAGGAATTCGTCCTCGGGGAGGCAGTGGGCCAGG |
| SEQ ID NO: 85 | TGTCATCCCCAGCCTCATCCTCTCACTGTCTCAGTTTTCC |
| SEQ ID NO: 86 | AGGACTGTCTGTGGCATTCCCCCTGGGATCTGAATGATGG |
| SEQ ID NO: 87 | CCGGAGGAAAAAATCTCTCATCTTTTGAAGCTATTTGAAG |
| SEQ ID NO: 88 | ATATGGTGAGTATTTTGAATATCTCATACAATTATGCCTA |
| SEQ ID NO: 89 | GGGCTGTGGTTGTCACCCGTGACGATCTGCGTGCATGCCA |
| SEQ ID NO: 90 | TACTAGTGTTTTCATTGGTATTAAGCTTGATGTAATATTT |
| SEQ ID NO: 91 | AGCCACCACGCCTGGCCCAGACTCAGAGAATGAATACAAT |
| SEQ ID NO: 92 | GTGGCGAGAAGCATGAGGAATGGAGATGGAGGAGGAGCAG |
| SEQ ID NO: 93 | TCTCAGTTTGGCTGAGAAGCAGGGTGGGGGCCTGAACCCA |
| SEQ ID NO: 94 | CAACATAGCAAGACCCCGTCACTATAAAAATGAAAAAGCC |
| SEQ ID NO: 95 | CCAGTGGGTGGGAGCCCGGGTGGGGAGGGGGCGTGGGCTC |
| SEQ ID NO: 96 | TTATTTTTTATGGATGTAAACAGCCTCTTTGTAGTTTATA |
| SEQ ID NO: 97 | TCCTGAAACAAGCATTAAAGAGGGAATTAACTTAAATAAA |
| SEQ ID NO: 98 | TTATTGTATTGAAACATGATTGTGTATCAAATGTGAGTTT |
| SEQ ID NO: 99 | CTTTTCTTTTATAAAGGAGGACTCTTTTGCCTGATATCTG |
| SEQ ID NO: 100 | CCTGAAGTCTCAGTTTCCATTACATTATACCCTCACTACC |
| SEQ ID NO: 101 | CCCACCCGTGGGTCCCTGGGGGCCTGGGATCCCAGATGGT |
| SEQ ID NO: 102 | ACGGGGATGAGGAGGGCGTGTGGTGCTATGTGGCCGGGAA |
| SEQ ID NO: 103 | CCTCGGATTGAAGAAAGTCTGGTACTCACTGGTGGCGGTA |
| SEQ ID NO: 104 | GTTTAAAAAATTGTCCTTTATTGTCCAAATGTCTGCCTTC |
| SEQ ID NO: 105 | TAATGTGTAATGATAGGTCTTGTCAAATAGTTTAATAAGT |
| SEQ ID NO: 106 | GAGTCCGAGTGCCGCTGACTGTCACTGCCACCATTCATCC |
| SEQ ID NO: 107 | CTGAATGTTGCAAATCTAAATAAACATGTTCCAGAGGAGA |
| SEQ ID NO: 108 | GCCTTTATTCCGTTTCCACTCCTCCTTCCCTAGTTCATCC |
| SEQ ID NO: 109 | TCAGGAAATCCTACAGTCCACACTCCAGTCAGCCCCAGGA |
| SEQ ID NO: 110 | CCTTCTCGGATCTCAAACGAGCAAGGGTTAACACTCATGA |
| SEQ ID NO: 111 | GGGGCGCGGCCCCTCAAGTCCGAGGACCTCCCTTCTGGGG |
| SEQ ID NO: 112 | AGTTCCTCCAGGGCGCCCTGTGGCGGCGCCGCCTGCACCT |
| SEQ ID NO: 113 | ACGACCCTATTACTCTCATAACGATGAGTCTAGCAAGTAC |
| SEQ ID NO: 114 | ACAAAAAAGGTAACTATGTAAAGACATATGTTAATTAGC |
| SEQ ID NO: 115 | CTTCGAGAAATTCTGAAAAACTGCAAAGGTTTGATTGTGT |
| SEQ ID NO: 116 | CTATTTGAAGATTTGTCATCAAATATTGATGCATGATAGG |
| SEQ ID NO: 117 | TTCCAGGCAAAGCAGTAGCCTAAGGGTTTACAGCTGATGA |
| SEQ ID NO: 118 | CCCATCCAAGGAAAATTTAGAAAAGGGAAGGGGATGTGTA |

Figure 4 cont.

| SEQ ID NO: 119 | GAAGTGGGAGGGGTAAAAGGGCTATAAAAAAAAATCTAAA |
| --- | --- |
| SEQ ID NO: 120 | CCAATCATTGCACAAACAGAAACAGCTCTGACAGAGAAGG |
| SEQ ID NO: 121 | AATTTGGAGGACACCAGTGGCATCAGGTCTCCTGTGTTGC |

FIG. 9

FIG. 9A: AIMs that distinguish African and European populations
rs376350, rs675924, rs676290, rs708156, rs717090, rs717091, rs717225, rs718092, rs718387, rs719776, rs720225, rs720888, rs720891, rs720966, rs721684, rs723632, rs723802, rs724729, rs725416, rs725438, rs725472, rs725510, rs725667, rs725908, rs726391, rs726700, rs726777, rs726996, rs727342, rs728606, rs728647, rs736723, rs764051, rs874816, rs951308, rs951412, rs951431, rs951666, rs952109, rs952165, rs952902, rs953035, rs959960, rs1002835, rs1027583, rs1057187, rs1074075, rs1074086, rs1112730, rs1113480, rs1152537, rs1153849, rs1342008, rs1352405, rs1365720, rs1366842, rs1367996, rs1369290, rs1377456, rs1382934, rs1404694, rs1405467, rs1407716, rs1431948, rs1465648, rs1478785, rs1485765, rs1487214, rs1506069, rs1516238, rs1526028, rs1541836, rs1584385, rs1831024, rs1858465, rs1861498, rs1904464, rs1923416, rs1928415, rs1929609, rs1945248, rs1950284, rs1979541, rs2021779, rs2021781, rs2077681, rs2078588, rs2169462, rs2207782, rs2211771, rs2225251, rs2263039, rs2317212, rs2341823

FIG. 9B: AIMs that distinguish African and Asian populations
rs1063, rs326798, rs376350, rs441728, rs717225, rs717531, rs718387, rs718424, rs719213, rs719776, rs720225, rs720888, rs720891, rs720966, rs721684, rs723632, rs723802, rs724729, rs725472, rs725667, rs725908, rs726391, rs726700, rs726777, rs726996, rs728606, rs736723, rs874816, rs879831, rs952109, rs952902, rs959157, rs967445, rs1073768, rs1074075, rs1074086, rs1074182, rs1113480, rs1152537, rs1318822, rs1366842, rs1369290, rs1371048, rs1377456, rs1382934, rs1391681, rs1404694, rs1405467, rs1407716, rs1431948, rs1465648, rs1478785, rs1485765, rs1487214, rs1506069, rs1526028, rs1807912, rs1820556, rs1831024, rs1851204, rs1858465, rs1861498, rs1904464, rs1923416, rs1928415, rs1929609, rs1934009, rs1945248, rs1961640, rs1979541, rs2017684, rs2021779, rs2021781, rs2077681, rs2078588, rs2115467, rs2169462, rs2341823

FIG. 9C: AIMs that distinguish African and American populations
1063, rs326798, rs376350, rs441728, rs483109, rs717090, rs717091, rs717171, rs717225, rs717531, rs718424, rs719213, rs719776, rs720225, rs720888, rs720891, rs720966, rs721684, rs722559, rs722869, rs723632, rs723802, rs723822, rs724246, rs724247, rs724729, rs725416, rs725472, rs725667, rs725908, rs726700, rs726777, rs726996, rs728606, rs764419, rs768324, rs874816, rs879831, rs925140, rs938431, rs951554, rs951784, rs952159, rs953899, rs956065, rs959030, rs959157, rs963170, rs963171, rs967445, rs998410, rs1048610, rs1073768, rs1074075, rs1074086, rs1074182, rs1112806, rs1112828, rs1113480, rs1152537, rs1318822, rs1320892, rs1333208, rs1344870, rs1352405, rs1366842, rs1366847, rs1369290, rs1371048, rs1377456, rs1382934, rs1391681, rs1396799, rs1401385, rs1401608, rs1403454, rs1404694, rs1405467, rs1407716, rs1411106, rs1431948, rs1435090, rs1465648, rs1478785, rs1485765, rs1487214, rs1506069, rs1526028, rs1533224, rs1584385, rs1807912, rs1820556, rs1831024, rs1832443, rs1851204, rs1858465, rs1861498, rs1900099, rs1904464, rs1923416, rs1928415, rs1929609, rs1934009, rs1945248, rs1953054, rs1961273, rs1961320, rs1961640, rs1979541, rs1980888, rs1986644, rs2006996, rs2017684, rs2060319, rs2077681, rs2078588, rs2115467, rs2137636, rs2169462, rs2203099, rs2889670

FIG. 9D: AIMs that distinguish European and Asian populations
rs1063, rs242687, rs326798, rs441728, rs483109, rs708156, rs708726, rs717090, rs717091, rs717373, rs717531, rs718092, rs718686, rs719213, rs720496, rs722559, rs722869, rs723822, rs724246, rs724247, rs724496, rs724806, rs725264, rs725438, rs727342, rs728647, rs754798, rs764051, rs879831, rs925140, rs938431, rs951308, rs951378, rs951412, rs951431, rs951554, rs951666, rs952165, rs953035, rs953899, rs959030, rs959157, rs959960, rs963170, rs963171, rs967445, rs1002835, rs1037796, rs1048610, rs1074182, rs1112730, rs1112806, rs1153849, rs1318822, rs1320892, rs1327805, rs1333208, rs1350462, rs1364184, rs1365720, rs1371048, rs1391681, rs1396799, rs1401385, rs1401608, rs1403454, rs1411106, rs1435090, rs1461227, rs1516238, rs1541836, rs1584385, rs1807912, rs1820556, rs1851204, rs1934009, rs1938684, rs1939546, rs1944872, rs1950284, rs1953054, rs1961273, rs1961640, rs1980888, rs2017684, rs2021215, rs2115467, rs2137636, rs2203099, rs2207782, rs2225251, rs2263039, rs2312211, rs2317212, rs2366882, rs2889670

FIG. 9E: AIMs that distinguish European and American populations
1063, rs242687, rs441728, rs483109, rs675924, rs676290, rs708156, rs708726, rs717171, rs717373, rs717531, rs718092, rs718686, rs719213, rs720050, rs720051, rs720496, rs722559, rs722869, rs723822, rs724246, rs724247, rs724496, rs724806, rs725264, rs727342, rs754798, rs764051, rs764419, rs768324, rs925140, rs938431, rs951378, rs951412, rs951554, rs951666, rs951784, rs952159, rs952165, rs953035, rs953899, rs956065, rs957862, rs958790, rs959030, rs959157, rs959960, rs963170, rs963171, rs998410, rs1002835, rs1027582, rs1027583, rs1037796, rs1048610, rs1112730, rs1112806, rs1112828, rs1153849, rs1318822, rs1320892, rs1327805, rs1333208, rs1344870, rs1350462, rs1364184, rs1365720, rs1366847, rs1371048, rs1395475, rs1396799, rs1401385, rs1401608, rs1403454, rs1411106, rs1435090, rs1461227, rs1533224, rs1541836, rs1820556, rs1822488, rs1832443, rs1900099, rs1934009, rs1938684, rs1939180, rs1939546, rs1944872, rs1950284, rs1953054, rs1961273, rs1961320, rs1980888, rs1986644, rs2006996, rs2021215, rs2060319, rs2086214, rs2115467, rs2137636, rs2203099, rs2207782, rs2211771, rs2225251, rs2312211, rs2317212, rs2366882, rs2889670

FIG. 9F: AIMs that distinguish Asian and American populations
1900099, rs768324, rs1344870, rs717171, rs958790, rs1939180, rs956065, rs1366847, rs1822488, rs1980888, rs951784, rs720051, rs720050, rs2203099, rs1533224, rs1403454, rs720496, rs1037796, rs1832443, rs1961320, rs764419, rs2317212, rs2060319, rs1401385, rs959030, rs1435090, rs1112828, rs1320892, rs1027582, rs0, rs2086214, rs1027583, rs1411106, rs957862, rs242687, rs998410, rs723822, rs725264, rs708726, rs1395475, rs2366882, rs0, rs2006996, rs1327805, rs1939546, rs1986644, rs963170, rs952159, rs1350462, rs952109, rs963171, rs676290, rs959157, rs675924, rs2207782, rs2211771, rs0, rs2021215, rs1342008, rs717373, rs722559, rs725510, rs708156, rs483109, rs953899, rs754798, rs719213, rs1401608, rs2137636, rs718092, rs725908, rs2889670, rs1112730, rs952165, rs1112806, rs951666, rs1953054, rs1333208, rs0, rs1365720, rs2341823, rs1938684, rs1961273, rs717531, rs967445, rs1073768, rs2021779, rs441728, rs726391, rs1944872, rs2021781, rs727342, rs2312211, rs736723, rs1153849, rs951554, rs1057187, rs2225251, rs1934009

FIG. 9G: AIMs that distinguish Northern Europeans from Southern Europeans:
rs1129038, rs3769005, rs2596501, rs1364394, rs969539, rs974020, rs1922286, rs2171209, rs1560569, rs17443616, rs2596834, rs1890131, rs2418844, rs1157492, rs1922086, rs6432110, rs8041327, rs1416467, rs33706, rs379773, rs10496610, rs725974, rs822759, rs1517407, rs2187684, rs7997100, rs959763, rs1003306, rs1854226, rs2367191, rs202546, rs2905347, rs2236876, rs10508372, rs959260, rs920590,

FIG. 9G (Con't)
rs986642, rs2219248, rs923031, rs495347, rs103294, rs2003092, rs1373557, rs16891982, rs1073321, rs2014303, rs1873195, rs1408794, rs9290675, rs7108371, rs1045873, rs523776, rs7163907, rs10853962, rs1777689, rs1032143, rs10512122, rs7908825, rs4859259, rs10516982, rs7965049, rs153595, rs7277342, rs10486207, rs3809125, rs2847502, rs10509384, rs2097884, rs4639533, rs10255965, rs1976033, rs1107820, rs10483853, rs4686497, rs3822616, rs4832640, rs2086085, rs2685159, rs12502036, rs9861816, rs2251432, rs8040452, rs7552548, rs3007711, rs1879558, rs1476162, rs17864053, rs477627, rs2047058, rs1065674, rs9860730, rs1448314, rs554788, rs1582398, rs1660964, rs10509954, rs17457687, rs4307284, rs11586379, rs12124147, rs7548659, rs760607, rs1981135, rs749663, rs1334804, rs10889750, rs1288367, rs213496, rs11207865, rs4915691, rs1566246, rs3101336, rs544858, rs10493649, rs12758138, rs6660484, rs2968485, rs712886, rs12061503, rs12046602, rs731756, rs10776798, rs6587597, rs912572, rs1419074, rs488150, rs1322780, rs859362, rs6680701, rs2146060, rs2784101, rs2494302, rs10494878, rs1930903, rs2275302, rs4916113, rs587913, rs6723966, rs10929646, rs4260216, rs340747, rs1489688, rs4665797, rs1438131, rs13032262, rs10205008, rs605832, rs7594173, rs6544718, rs6713506, rs7577894, rs2075375, rs6720799, rs41420, rs13032535, rs11164050, rs11123861, rs6739285, rs1955394, rs16829231, rs6730157, rs2117742, rs1037266, rs6752189, rs1227131, rs6749847, rs7558428, rs9288172, rs3769823, rs10189499, rs1955117, rs10189760, rs6436553, rs6436883, rs10510268, rs3804989, rs17043611, rs342042, rs2128162, rs3916092, rs11914832, rs744751, rs285327, rs11544593, rs6773085, rs11130841, rs6795735, rs2054956, rs9310279, rs6551458, rs7630043, rs9289584, rs4535234, rs7634702, rs4678297, rs9839394, rs10513729, rs7636818, rs12635682, rs4859259, rs6775595, rs6449375, rs13132286, rs6831024, rs6448770, rs9884706, rs10008492, rs12186184, rs1389037, rs6832891, rs1109501, rs4261956, rs3923243, rs1455313, rs6820697, rs1343921, rs13349989, rs7669241, rs2850971, rs2194860, rs1448817, rs1557815, rs4574434, rs1541745, rs4128688, rs692157, rs1390009, rs10519410, rs1507500, rs10517660, rs1492468, rs1430975, rs11730565, rs1435442, rs4241802, rs10032784, rs2736122, rs7718757, rs1533019, rs29460, rs464923, rs1001935, rs2279095, rs1373967, rs173686, rs6452788, rs174015, rs10478046, rs6863510, rs6866231, rs346650, rs1528961, rs171718, rs4868204, rs2135053, rs7727897, rs248327, rs1933652, rs2326106, rs4960257, rs2876167, rs1992387, rs2237148, rs7763768, rs6918101, rs12660883, rs382259, rs2076173, rs804847, rs12524885, rs4610536, rs638473, rs2451688, rs9389124, rs7753036, rs4896663, rs17551120, rs11756366, rs10428822, rs10950641, rs2041362, rs2189947, rs10267453, rs697518, rs2529015, rs10951140, rs1003549, rs933360, rs17135491, rs4020771, rs7791143, rs4730287, rs7781715, rs12705973, rs12706793, rs1593306, rs11761774, rs4571660, rs7795021, rs7806048, rs1548353, rs4565458, rs12548107, rs13273386, rs1127379, rs10109984, rs7830163, rs6993747, rs7827918, rs2380646, rs4634634, rs11780821, rs11784678, rs1026804, rs1841316, rs4871195, rs4736413, rs396861, rs10758823, rs566820, rs10962589, rs2840790, rs10511715, rs10812520, rs867469, rs2130118, rs10746763, rs10908907, rs884886, rs10739277, rs7860625, rs1009473, rs7090242, rs7921493, rs11255712, rs1324322, rs4948508, rs3858126, rs4746826, rs7072160, rs4691, rs499437, rs1857459, rs7097946, rs11186543, rs701873, rs1023331, rs7071247, rs10509826, rs1325172, rs540609, rs11146457, rs2045272, rs7931276, rs1477569, rs4755844, rs2218868, rs2237997, rs12804561, rs2282504, rs7342241, rs2015747, rs488753, rs7131355, rs4936969, rs740851, rs7976721, rs10770437, rs699039, rs12370505, rs2088170, rs2860493, rs2723891, rs11107018, rs7307510, rs12231308, rs7312155, rs991817, rs11066320, rs1955105, rs2650170, rs1405050, rs3815210, rs11059335, rs2398513, rs377318, rs7323018, rs1979558, rs9539642, rs13379032, rs4885167, rs2175075, rs1678386, rs9556553, rs4982420, rs7152286, rs2038281, rs10498472, rs7492698, rs2180611, rs1531631, rs8003492, rs17126387, rs9671457, rs4906226, rs1947745, rs11634609, rs2611605, rs1153860, rs1906433, rs10519005, rs2292745, rs1320205, rs387727, rs8025028, rs3922394, rs1510058, rs8043261, rs2072986, rs1891325, rs896401, rs949429, rs30237, rs8047148, rs7205880, rs12446160, rs1872678, rs9937047, rs4238802, rs3751834, rs6539986,

FIG. 9G (Con't)
rs2253820, rs7215135, rs7220080, rs685098, rs2165846, rs11870879, rs196948, rs12939848, rs8071270, rs736632, rs400839, rs1786153, rs11564361, rs16948113, rs4941246, rs17079195, rs11151863, rs4799268, rs4536588, rs6510672, rs1552046, rs715159, rs8111998, rs2082455, rs17496703, rs7976, rs7252868, rs8103620, rs4814697, rs6076623, rs6118234, rs1041200, rs8116153, rs1884783, rs6126462, rs6129532, rs6032343, rs477627, rs4811158, rs2041317, rs6092326, rs3916504, rs6071491, rs977712, rs1735899, rs2832643, rs2836824, rs11702531, rs2235338, rs848728, rs11147509, rs4131364

FIG. 9H: AIMs that distinguish Northern Europeans from Ashkenazi Jewish Europeans:
rs3769005, rs7551844, rs2596501, rs3007711, rs1129038, rs6996185, rs847851, rs17443616, rs1922086, rs974020, rs7108371, rs1065674, rs554788, rs1364394, rs1890131, rs1922286, rs10516982, rs477627, rs6448770, rs13084044, rs1355170, rs6432110, rs9860730, rs12713956, rs6028505, rs9576338, rs986642, rs4756052, rs7983897, rs10506555, rs822759, rs6751522, rs1991718, rs10508372, rs10493430, rs33706, rs379773, rs202546, rs920590, rs4307284, rs7163907, rs2251432, rs10762340, rs1660964, rs10853962, rs764255, rs4859259, rs923031, rs959260, rs8029021, rs2596834, rs2418844, rs998401, rs10496610, rs10509384, rs2003092, rs1560569, rs8016025, rs6477998, rs1517407, rs224378, rs17079195, rs10460810, rs6687300, rs2252815, rs1032143, rs1476162, rs17457687, rs4642918, rs4832640, rs7637803, rs7997100, rs6432398, rs6490700, rs4771165, rs359291, rs1373557, rs2171209, rs1073321, rs4787923, rs920559, rs90213, rs10497233, rs3822616, rs7819806, rs12430668, rs12441220, rs10486207, rs2377689, rs4336881, rs1598452, rs605832, rs2219248, rs8078782, rs1045873, rs552976, rs10431948, rs2793471, rs2905347, rs7316723, rs1118962, rs1032355, rs1582398, rs6841252, rs1743789, rs1408794, rs1710807, rs914505, rs2154328, rs1870590, rs12706769, rs1854226, rs2014303, rs881433, rs10868791, rs10504275, rs6502048, rs1904406, rs17026435, rs8041327, rs1400174, rs11744977, rs9290675, rs1462368, rs518457, rs1435260, rs2063092, rs1011340, rs718387, rs9285474, rs2236876, rs2847502, rs1777689, rs706397, rs9993173, rs2363127, rs217627, rs10512122, rs725974, rs7699090, rs7038314, rs7301622, rs10495413, rs1381795, rs2047058, rs969539, rs10494870, rs489381, rs2804756, rs7975512, rs3927745, rs17149147, rs11713873, rs1994952, rs523776, rs10520475, rs349187, rs618897, rs6021183, rs4815707, rs313478, rs3844253, rs10509954, rs12502036, rs1531746, rs7561808, rs163018, rs2176246, rs11248060, rs11245545, rs6864793, rs9861816, rs17310125, rs1157492, rs103294, rs7501724, rs3764796, rs3809125, rs284509, rs11586379, rs153595, rs2419063, rs730566, rs2187684, rs838958, rs10825992, rs4782202, rs12500040, rs7965049, rs10484547, rs7920193, rs4686497, rs2241332, rs7689609, rs12251462, rs10458810, rs2097884, rs7598757, rs2287101

FIG. 9I: AIMs that distinguish Southern Europeans from Ashkenazi Jewish Europeans:
rs7551844, rs6996185, rs1129038, rs6477998, rs1710807, rs1743789, rs6841252, rs6448770, rs11586379, rs1462368, rs8029021, rs13084044, rs847851, rs764255, rs17079195, rs10431948, rs12706769, rs8016025, rs3007711, rs12713956, rs7983897, rs2793471, rs8060233, rs12441220, rs1355170, rs4756052, rs554788, rs881433, rs6687300, rs1065674, rs10493430, rs1011340, rs10825992, rs8078782, rs40459, rs920559, rs605832, rs9285474, rs4815707, rs838958, rs10460810, rs1976033, rs10506555, rs9576338, rs6432398, rs914505, rs969539, rs477627, rs1531746, rs6028505, rs224378, rs6578195, rs6502048, rs4642918, rs6751522, rs1991718, rs4797909, rs11744977, rs1870590, rs2685159, rs2154328, rs7598757, rs9860730, rs163018, rs6678209, rs7108371, rs1994952, rs8040452, rs10516982, rs262216, rs618897, rs284509, rs6490700, rs17026435, rs11713873, rs6907950, rs11259206, rs10762340, rs9993173, rs17149147, rs4639533, rs1381795, rs7316723, rs359291, rs2446653, rs273747, rs2063092, rs10255965, rs4976606, rs7155872, rs730566, rs4307284, rs2377689, rs7689609, rs2411128, rs10517807, rs1435260, rs3927745,

FIG. 9I (Con't)
rs10458810, rs17310125, rs1660964, rs7301622, rs706397, rs1416467, rs998401, rs313478, rs11854557, rs4131048, rs13008, rs2241332, rs4243408, rs951412, rs7920193, rs3844253, rs718387, rs777710, rs4771165, rs132549, rs1389560, rs3856744, rs6460989, rs2252815, rs2251432, rs349187, rs2363127, rs10504275, rs7372209, rs495347, rs4770401, rs1410418, rs1118962, rs7975512, rs7038314, rs1904406, rs489381, rs7277342, rs7699090, rs10497233, rs10494870, rs9323490, rs1157492, rs1032355, rs552976, rs10495413, rs12430668, rs440431, rs6063178, rs12645879, rs1598452, rs2285369, rs7679675, rs7561808, rs7900067, rs1024487, rs7637803, rs217627, rs4787923, rs17457687, rs1400174, rs17439723, rs1435090, rs7819806, rs90213, rs2547116, rs3764796, rs9435, rs986642, rs2589654, rs16922018, rs1352411, rs1984282, rs2287101, rs4859259, rs1107820, rs1476162, rs959763, rs6511703, rs12500040, rs6021183, rs10868791, rs7501724, rs7163907, rs10853962, rs4336881, rs959567, rs6864793, rs10520475, rs11245545, rs17799799, rs518457, rs10509384, rs2366687, rs1003306, rs2367191, rs10504924, rs10507632, rs2728945, rs1905135, rs10516096

FIG. 9J: AIMs that distinguish Irish from English (and distinguish other Northern European populations from one another):
rs354690, rs1200826, rs6133219, rs4937688, rs17595617, rs592229, rs7632151, rs10158939, rs6673923, rs11761305, rs2824976, rs13143572, rs11735755, rs1491610, rs1697143, rs12677633, rs2331295, rs12028395, rs1035218, rs11812285, rs17487804, rs2831507, rs11119274, rs2866904, rs3211663, rs2180046, rs1791648, rs1874777, rs11169282, rs10735745, rs11629910, rs7637171, rs1975944, rs17751406, rs3133719, rs7802273, rs4682664, rs1424341, rs17495345, rs2101869, rs622917, rs11234095, rs11579554, rs2574824, rs985246, rs7172022, rs17043135, rs3934253, rs6796183, rs9400660, rs6542847, rs9537662, rs4391081, rs921656, rs12621435, rs608082, rs969517, rs2279578, rs4741859, rs697387, rs9939450, rs300386, rs201930, rs6569343, rs6978997, rs2742059, rs2616982, rs7834280, rs17057633, rs4521229, rs3132069, rs13322103, rs4568821, rs2241466, rs1546963, rs1039621, rs11152343, rs7615026, rs1124602, rs7998134, rs1168553, rs8027997, rs7585767, rs7015718, rs4854502, rs1916977, rs11759031, rs12282752, rs924247, rs3115769, rs2489772, rs2066284, rs12589358, rs2284759, rs692612, rs1420109, rs17166207, rs6855114, rs2292702, rs150881, rs213759, rs7937428, rs150139, rs2029121, rs3805331, rs9366778, rs2389197, rs4242426, rs2154254, rs1345941, rs2120991, rs384267, rs10982246, rs283310, rs2832146, rs3936367, rs906671, rs11163055, rs725926, rs9353982, rs2251530, rs13032261, rs9981318, rs4561129, rs12193402, rs4854647, rs10045343, rs3937773, rs10016411, rs12618502, rs4857192, rs11706497, rs1361168, rs603089, rs7521746, rs3096700, rs1859218, rs6727787, rs3798315, rs1812458, rs12327639, rs10496354, rs6593652, rs12202888, rs12427378, rs126280, rs1496292, rs13281284, rs10197026, rs3764622, rs632853, rs1334811, rs11258614, rs1432770, rs762324, rs10506479, rs17583414, rs4889126, rs11635677, rs7538393, rs4607068, rs2148379, rs1544908, rs1604528, rs10148024, rs5761163, rs1495085, rs6727258, rs8718, rs1409590, rs13071295, rs12132550, rs4693421, rs1861532, rs10896958, rs6738275, rs9348266, rs1925391, rs42985, rs516925, rs11162802, rs4771561, rs12706465, rs13215804, rs4818059, rs201739, rs13059876, rs17745881, rs3823518, rs4903820, rs2214020, rs6992907, rs9556820, rs10249706, rs3798236, rs7701328, rs12229047, rs10846585, rs936110, rs11851852, rs9300943, rs1926150, rs7872577, rs4868253, rs6586395, rs4832680, rs1979689, rs17325754, rs2803353, rs2109302, rs2840131, rs12645288, rs4241627, rs12065099, rs10511771, rs17264096, rs3026886, rs569908, rs6749268, rs7591709, rs1450878, rs8015618, rs17068823, rs4699356, rs6926578, rs10095717, rs11841049, rs17735123, rs1918098, rs17158154, rs1928027, rs7685881, rs4130719, rs6742202, rs1294875, rs12319392, rs9788522, rs6061663, rs12407446, rs6705555, rs9551221, rs4688639, rs494791, rs11748140, rs10885355, rs4395073, rs6824429, rs11204020, rs2644640, rs6455468, rs10163400, rs2005104, rs907942, rs1007042, rs6452431,

FIG. 9J (Con't)

rs2901100, rs6799064, rs16880382, rs1805313, rs12199314, rs1243974, rs10171287, rs352418, rs10953428, rs4974389, rs7254735, rs7257916, rs639813, rs6431565, rs1435887, rs10761660, rs10118378, rs12533837, rs2503848, rs12363937, rs6752254, rs12906896, rs17537169, rs2268933, rs6939639, rs3775479, rs1691018, rs17463958, rs6741326, rs7019271, rs4509106, rs4743564, rs13395560, rs4751890, rs8058014, rs7946208, rs2023952, rs6066892, rs153645, rs4443343, rs9297395, rs10895115, rs10419661, rs1833208, rs129074, rs1889085, rs12127377, rs32441, rs10886671, rs1363926, rs13221445, rs10501445, rs11811998, rs13225753, rs8034124, rs7906816, rs11189831, rs11147671, rs2809823, rs6538980, rs500906, rs13182055, rs7143468, rs4636972, rs10519510, rs7521399, rs278729, rs1468329, rs10515441, rs566821, rs1882396, rs11906231, rs7909464, rs12030971, rs10047997, rs17866606, rs170644, rs4129526, rs1869092, rs2149973, rs4660438, rs12404676, rs16928653, rs11138141, rs11756439, rs3925053, rs10843894, rs4259484, rs11772445, rs1598859, rs6476962, rs6676680, rs2836604, rs4843426, rs12626954, rs4621050, rs1794275, rs1801212, rs10889272, rs3847580, rs808868, rs10741808, rs2622892, rs17497293, rs7171366, rs7685182, rs12280220, rs4944000, rs6030839, rs1437683, rs11000000, rs1122821, rs6767356, rs10795942, rs10917268, rs605383, rs957881, rs10780596, rs7720751, rs1928091, rs3760440, rs12129709, rs1259866, rs17600119, rs17141252, rs10954006, rs137296, rs9623117, rs10517796, rs1755833, rs17680913, rs4321843, rs10209427, rs7123425, rs17590228, rs16957064, rs1941603, rs4403789, rs827628, rs6782694, rs2335629, rs1405134, rs2651458, rs6478230, rs7152796, rs531539, rs1874494, rs4843507, rs17273267, rs7320534, rs10868262, rs2113574, rs4814983, rs7587228, rs17624713, rs17508376, rs1997458, rs2176313, rs251867, rs1413710, rs7257183, rs1554808, rs1572228, rs7006668, rs338926, rs7135506, rs6427832, rs6766822, rs7591141, rs4781927, rs13106298, rs12874003, rs13071953, rs1910863, rs10433559, rs6092900, rs10196343, rs6448638, rs2110420, rs2871647, rs9873664, rs12634613, rs9465438, rs11767724, rs16999738, rs12488465, rs6992802, rs4902059, rs4308943, rs11183847, rs2887631, rs4278155, rs10486014, rs10795076, rs7204868, rs945704, rs3742673, rs10468473, rs897646, rs11916893, rs4897646, rs1523902, rs972124, rs10510254, rs2718324, rs4740358, rs12440104, rs6582999, rs4257073, rs2127247, rs17006704, rs11165281, rs11642715, rs4968938, rs10235162, rs2218935, rs9353512, rs13096852, rs8037001, rs992499, rs7305812, rs12643434, rs7094594, rs9330294, rs7798936, rs1008645, rs2272786, rs11757369, rs4886026, rs243099, rs1131620, rs10279772, rs7619189, rs10792322, rs11539202, rs2145449, rs11119145, rs12570141, rs3851384, rs527507, rs11590681, rs3804639, rs7584576, rs201328, rs201430, rs10097270, rs133074, rs1964196, rs2135091, rs16885, rs4394088, rs16943989, rs11055697, rs9646474, rs16854813, rs9290227, rs3928425, rs6949364, rs7586333, rs12091966, rs6831436, rs10083961, rs10932040, rs6798997, rs861079, rs12867481, rs6881628, rs753281, rs10496342, rs3117582, rs1463242, rs2408239, rs7744432, rs564968, rs7870926, rs609305, rs4887443, rs1931902, rs11692435, rs2048161, rs4684146, rs4628026, rs1930146, rs11735972, rs1866997, rs3745509, rs12412656, rs295117, rs11686077, rs10282703, rs10869031, rs2047171, rs2616612, rs16874127, rs12249377, rs845787, rs4072374, rs2552353, rs1377554, rs400688, rs1507599, rs4728490, rs10484867, rs845561, rs4334271, rs385773, rs4480424, rs2304572, rs11117791, rs10964808, rs9813516, rs2034781, rs11607746, rs626364, rs6536415, rs6090443, rs2328492, rs1379411, rs2583692, rs9938659, rs9315681, rs11622517, rs13359372, rs10143058, rs7590571, rs12064002, rs10835941, rs17134141, rs1343227, rs10077241, rs10132, rs2761291, rs6432594, rs10499748, rs6746287, rs7709399, rs12669805, rs11793897, rs17762729, rs12596290, rs11153162, rs6940057, rs1316883, rs7186783, rs6982890, rs937816, rs7725438, rs10504180, rs8094458, rs241529, rs980274, rs855395, rs10948327, rs12149783, rs12275853, rs2155854, rs4816612, rs2669331, rs497321, rs669336, rs1333592, rs2270834, rs6076248, rs9692165, rs4776567, rs4652192, rs6942609, rs6565261, rs1339287, rs631661, rs12345503, rs10491367, rs1348338, rs2876507, rs17069574, rs6416581, rs1370031, rs10174187, rs10783028, rs7904364, rs16932027, rs12993717, rs12568609, rs550010, rs4896634, rs6574859, rs1558160,

FIG. 9J (Con't)

rs1772579, rs1878424, rs288057, rs12647859, rs130539, rs7934426, rs7278046, rs1886690, rs1950221, rs17747739, rs13034680, rs3790116, rs6031215, rs10016081, rs966149, rs793096, rs8044334, rs16987794, rs12156286, rs2803183, rs7871735, rs1187763, rs858550, rs2301570, rs1010656, rs1815619, rs2184925, rs10521057, rs11184219, rs2726675, rs10485678, rs7782814, rs489466, rs1093309, rs12439063, rs2396081, rs4887111, rs6979324, rs4233629, rs2189864, rs1267472, rs7006436, rs2839475, rs6874663, rs952579, rs10794696, rs11634215, rs1256992, rs6747820, rs8024685, rs1477798, rs8109759, rs6076954, rs17034929, rs4915886, rs2560301, rs6700849, rs1368406, rs2724031, rs2292719, rs1553664, rs3935801, rs4148298, rs4698844, rs4459724, rs1423089, rs12021671, rs16839940, rs8021670, rs4948235, rs13200910, rs308793, rs10924440, rs7329258, rs4780267, rs282152, rs10824914, rs16907003, rs7153598, rs3010888, rs6957465, rs12441839, rs10192315, rs727637, rs11786174, rs1488214, rs11635749, rs2729910, rs4869578, rs9459128, rs212434, rs1863471, rs12372169, rs472465, rs2908201, rs6010652, rs807704, rs6695712, rs1282557, rs10496954, rs2295682, rs9820762, rs12198061, rs11698898, rs2139747, rs700278, rs2192883, rs6312, rs1486731, rs2684796, rs12795982, rs2839589, rs2184221, rs9640302, rs4746826, rs632547, rs7764278, rs6651164, rs16750, rs13020203, rs9905820, rs1951797, rs10969030, rs10002315, rs4920104, rs7257017, rs9514044, rs2872338, rs3750111, rs1512155, rs4785173, rs2151842, rs2218724, rs1822917, rs1688015, rs11221731, rs887106, rs7809872, rs4532570, rs12554199, rs2773207, rs12314080, rs11881242, rs7225060, rs2518201, rs1010779, rs8048863, rs9299261, rs4586385, rs12642133, rs10777342, rs16901689, rs1859569, rs9300717, rs1154278, rs11174549, rs7140955, rs10108974, rs7852159, rs9419387, rs10831905, rs10498377, rs269850, rs9454096, rs6967514, rs13132569, rs12327342, rs11799558, rs1325156, rs2844651, rs2556097, rs2891409, rs12538916, rs8005808, rs2456220, rs6859290, rs924884, rs12501016, rs11644921, rs907238, rs2331175, rs2800257, rs717966, rs10825066, rs7112734, rs1524600, rs10491030, rs1387329, rs7996510, rs17461905, rs11839068, rs9312336, rs7204900, rs1672376, rs12677340, rs9575619, rs2765584, rs7205649, rs2839349, rs1454149, rs4907404, rs2166488, rs1230313, rs908822, rs2402800, rs913984, rs17651643, rs10979066, rs3024536, rs17173637, rs567384, rs9562077, rs10942957, rs4658702, rs7785682, rs2392147, rs613479, rs12710777, rs2719163, rs12094260, rs483241, rs12083651, rs12279152, rs7971883, rs17527048, rs2231895, rs512458, rs7321658, rs9923061, rs2298608, rs865151, rs11754258, rs270274, rs17567580, rs8021112, rs6506515, rs1553255, rs2492501, rs3781578, rs10780514, rs11695049, rs2022725, rs6959225, rs12796185, rs1369256, rs10063082, rs11966566, rs4427879, rs2395653, rs12018676, rs10154899, rs135551, rs9538094, rs10518452, rs17482565, rs2761384, rs10496557, rs7707491, rs943068, rs4713949, rs4233167, rs767249, rs12191488, rs6855792, rs1541335, rs2868146, rs6564940, rs1497305, rs1465010, rs11603501, rs10230087, rs899069, rs7864459, rs10517677, rs4708459, rs1545255, rs11634465, rs2284944, rs894392, rs10021708, rs7748977, rs9385824, rs7116354, rs11642445, rs3806300, rs4705295, rs2303802, rs791656, rs4387618, rs16972092, rs4891825, rs11712075, rs1978368, rs16858789, rs1446394, rs2060530, rs157237, rs1482363, rs9502971, rs3757791, rs11768706, rs10888101, rs16936082, rs6585474, rs3857176, rs9510565, rs7787246, rs10954638, rs10968042, rs2700230, rs7652486, rs11602256, rs12492695, rs1197701, rs4918844, rs12646895, rs12377016, rs11995144, rs227906, rs4735339, rs7673403, rs7855536, rs760560, rs913259, rs9442235, rs11940490, rs3742076, rs9407554, rs7321548, rs1523250, rs5751691, rs2691244, rs6089457, rs849734, rs897111, rs9613630, rs1432053, rs2616667, rs10159191, rs12619236, rs7660552, rs12731666, rs2841455, rs6454198, rs1466835, rs637001, rs7594872, rs470490, rs1017104, rs10403583, rs7526907, rs10484854, rs1355829, rs12273605, rs691127, rs10930718, rs1543603, rs4936578, rs722113, rs3846456, rs3934711, rs11101312, rs10068902, rs11988550, rs4331742, rs12923978, rs582962, rs12247354, rs10923142, rs9912143, rs2468638, rs11543651, rs16997896, rs2827845, rs10112398, rs1412471, rs1012769, rs153785, rs4368537, rs7820789, rs3813135, rs1554690, rs4890891, rs2114088, rs2327506, rs445275, rs6842443, rs9423942, rs11593576, rs244050, rs1007018, rs2192754,

FIG. 9J (Con't)
rs945249, rs17048973, rs17088268, rs6105221, rs2798950, rs9855729, rs4808416, rs10883479, rs6729229, rs875569, rs2475229, rs2047153, rs10493770, rs10128640, rs7154324, rs17780310, rs1944362, rs3793504, rs12452093, rs4283980, rs2070713, rs11118045, rs12585880, rs7598637, rs10887047, rs915538, rs17293152, rs904269, rs2987380, rs717751, rs6765166, rs10486461, rs7858808, rs6599127, rs11136596, rs16943315, rs7336525, rs9366950, rs6073394, rs1908984, rs2280699, rs2238508, rs7460771, rs7502772, rs7038373, rs1020042, rs11791419, rs11780780, rs11111689, rs743082, rs17242960, rs10500956, rs10431150, rs1689803, rs12743521, rs11778372, rs17271148, rs1360646, rs8066468, rs11831940, rs2966487, rs7018906, rs11180273, rs544603, rs4786780, rs7658820, rs13068538, rs7963499, rs4902562, rs10515998, rs4331170, rs204538, rs666649, rs12691565, rs16876243, rs10504268, rs4397025, rs6793927, rs2735202, rs11172147, rs11632449, rs10733358, rs2048816, rs10942889, rs1475048, rs7698580, rs12504106, rs716953, rs12111723, rs7075768, rs11854173, rs10520656, rs316582, rs13295839, rs824453, rs4596664, rs9289539, rs10275488, rs4981674, rs4955713, rs2387698, rs17277113, rs250413, rs17590785, rs10462465, rs833010, rs7814885, rs10733333, rs6772196, rs1342744, rs10168477, rs10273, rs7221778, rs17187133, rs17827858, rs17279118, rs373531, rs12372697, rs10357, rs2822548, rs1387910, rs4859864, rs17319408, rs1265203, rs12904370, rs10518627, rs10050980, rs3782814, rs17820124, rs2475357, rs1795065, rs4414922, rs7487814, rs13194998, rs7807708, rs17660328, rs4471501, rs8077267, rs4304313, rs2387673, rs3846677, rs17012485, rs4234474, rs11731647, rs6712681, rs2058131, rs2270409, rs6089784, rs17698283, rs6494039, rs2937785, rs260445, rs9641312, rs4911442, rs4688104, rs905570, rs99521, rs12997609, rs504341, rs1748168, rs11196967, rs1791468, rs17455729, rs1393861, rs4623797, rs4819591, rs1009728, rs17019119, rs4943731, rs1036295, rs2793471, rs9283119, rs4248914, rs733044,

FIG. 9K: AIMs that distinguish Spanish from Caucasians:
rs118003, rs166673, rs169088, rs261056, rs280181, rs286804, rs347413, rs374672, rs382515, rs382558, rs455249, rs578363, rs600558, rs640330, rs688858, rs707077, rs717251, rs717471, rs717614, rs718996, rs719628, rs719750, rs720030, rs720229, rs721128, rs721246, rs721288, rs721361, rs721362, rs721363, rs724130, rs724658, rs726512, rs726610, rs727923, rs728506, rs741933, rs754291, rs831451, rs869538, rs894198, rs950132, rs951572, rs951784, rs952020, rs952562, rs953111, rs955770, rs955771, rs956193, rs956377, rs957862, rs958985, rs959763, rs961463, rs965892, rs965917, rs967294, rs967906, rs979050, rs979322, rs988462, rs1016120, rs1023534, rs1032143, rs1033042, rs1035701, rs1073354, rs1074149, rs1074716, rs1074805, rs1075263, rs1075906, rs1108929, rs1113082, rs1113144, rs1114000, rs1116138, rs1116853, rs1158619, rs1202645, rs1210110, rs1331819, rs1343809, rs1359247, rs1363234, rs1363235, rs1366233, rs1368387, rs1368697, rs1373904, rs1375575, rs1375989, rs1376392, rs1377470, rs1378702, rs1380415, rs1382859, rs1384118, rs1388175, rs1390476, rs1391961, rs1393736, rs1395162, rs1395604, rs1399664, rs1400347, rs1402458, rs1404759, rs1405633, rs1410592, rs1411445, rs1412171, rs1414149, rs1417503, rs1418706, rs1419702, rs1420117, rs1449050, rs1451371, rs1454027, rs1478810, rs1479285, rs1485254, rs1498458, rs1501626, rs1537371, rs1537523, rs1546561, rs1548299, rs1549944, rs1572902, rs1579029, rs1585217, rs1585946, rs1587120, rs1599710, rs1603681, rs1605727, rs1820072, rs1824683, rs1830876, rs1854673, rs1900672, rs1917152, rs1917199, rs1927014, rs1929646, rs1931621, rs1951095, rs1951207, rs1951507, rs1951519, rs1961491, rs1986508, rs1990542, rs1992539, rs1999333, rs2008163, rs2008927, rs2010392, rs2011812, rs2014303, rs2014533, rs2015963, rs2017892, rs2017903, rs2028021, rs2040847, rs2040848, rs2057127, rs2067084, rs2078426, rs2134897, rs2139246, rs2194127, rs2196302, rs2210254, rs2216629, rs2226672, rs2351002, rs2355205, rs2358295, rs2366101, rs2366977, rs2369860, rs2373584, rs2374545, rs2389774, rs2409523, rs2418400, rs2419925, rs2865116, rs2868932, rs2886937, rs2887280, rs2899875

FIG. 9L: AIMs that distinguish South, Central and East Asians:
rs32826, rs63319, rs170872, rs187145, rs187861, rs191644, rs205474, rs219562, rs235946, rs266175, rs266177, rs303450, rs305851, rs353599, rs355191, rs366220, rs409914, rs411301, rs428294, rs498046, rs632159, rs664574, rs714857, rs717205, rs717757, rs718137, rs719006, rs719866, rs719910, rs720376, rs720578, rs720844, rs721002, rs721407, rs721684, rs722559, rs722653, rs722711, rs723195, rs723212, rs723686, rs723698, rs723723, rs723794, rs724246, rs724247, rs724258, rs724259, rs725389, rs726108, rs726217, rs726472, rs726493, rs726692, rs727424, rs727708, rs728497, rs728618, rs728647, rs730991, rs791856, rs864736, rs896019, rs910552, rs923976, rs950198, rs950303, rs950400, rs951062, rs951199, rs951998, rs952503, rs952785, rs952976, rs952993, rs953624, rs953680, rs956070, rs956408, rs958478, rs958976, rs963096, rs963170, rs963171, rs966134, rs966285, rs967990, rs978486, rs978488, rs985933, rs985934, rs988913, rs1000313, rs1004246, rs1011873, rs1013063, rs1018616, rs1029554, rs1035076, rs1073109, rs1073119, rs1073985, rs1114000, rs1178328, rs1318710, rs1336672, rs1340846, rs1343981, rs1352514, rs1356763, rs1359932, rs1362987, rs1366267, rs1371063, rs1374499, rs1381331, rs1381972, rs1383965, rs1383970, rs1391221, rs1391961, rs1392096, rs1404501, rs1405567, rs1406012, rs1406218, rs1407043, rs1408830, rs1413724, rs1416615, rs1417503, rs1418102, rs1422004, rs1422323, rs1422895, rs1427356, rs1428702, rs1434193, rs1446966, rs1448229, rs1470248, rs1480951, rs1509421, rs1532517, rs1549690, rs1563353, rs1565138, rs1565534, rs1570699, rs1578243, rs1583355, rs1586149, rs1586597, rs1812624, rs1817186, rs1822811, rs1822812, rs1822813, rs1823100, rs1826873, rs1876545, rs1892114, rs1903189, rs1903746, rs1924257, rs1928045, rs1934008, rs1940006, rs1944086, rs1945146, rs1950284, rs1954119, rs1985835, rs2007397, rs2008011, rs2008686, rs2013708, rs2035799, rs2035801, rs2050137, rs2052291, rs2065443, rs2077811, rs2101551, rs2134897, rs2138212, rs2145231, rs2192874, rs2327790, rs2369898, rs2370672, rs2382193, rs2392002, rs2406519, rs2421172, rs2877455

FIG. 9M: AIMs that distinguish Chinese and Japanese populations:
rs466256, rs1024052, rs6462942, rs6685064, rs244757, rs3924094, rs11087655, rs944664, rs11087655, rs2402820, rs2280100, rs11118295, rs721953, rs2377527, rs296364, rs10894532, rs2842186, rs6462942, rs4820389, rs4632285, rs4838113, rs16966142, rs1500127, rs4925258, rs11118295, rs2280100, rs766144, rs6462942, rs766144, rs2241880, rs1159114, rs4962061, rs5924101, rs7900633, rs11087655, rs715846, rs6817562, rs2185369, rs331332, rs4937787, rs2241880, rs12484697, rs4669614, rs11087655, rs2377527, rs5924101, rs4838113, rs2838665, rs12493799, rs12505641, rs3019711, rs5924101, rs1286041, rs4669614, rs614502, rs2280100, rs4362557, rs5924766, rs6937974, rs782758, rs10488533, rs614502, rs2240800, rs7003901, rs4362557, rs1858234, rs2724863, rs1748944, rs1077834, rs1259807, rs12576800, rs2970869, rs9308712, rs6855567, rs6457300, rs331332, rs2293072, rs4829981, rs1077834, rs4947803, rs7016174, rs7991928, rs2271738, rs9397264, rs4849159, rs1554656, rs1383887, rs12221798, rs1077834, rs2358521, rs1383887, rs12025272, rs2763002, rs9397264, rs4669614, rs7660417, rs2114716, rs4749159, rs1383887, rs542172, rs3805466, rs7016174, rs7991928, rs9397264, rs16993741, rs7016174, rs125980

```
-----[PROBE_WINDOW][RECESS][ROI_TILE][RECESS][PROBE_WINDOW]----
-----[....PROBE...]--------------------------[..PROBE.....]----
```

Figure 19

SYSTEM AND METHODS FOR DETECTING GENETIC VARIATION

BACKGROUND OF THE INVENTION

Next-generation sequencing (NGS) allows small-scale, inexpensive genome sequencing with a turnaround time measured in days. However, as NGS is generally performed and understood, all regions of the genome are sequenced with roughly equal probability, meaning that a large amount of genomic sequence is collected and discarded to collect sequence information from the relatively low percentage of areas where function is understood well enough to interpret potential mutations. Generally, purifying from a full-genome sample only those regions one is interested in is conducted as a separate step from sequencing. It is usually a days-long, low efficiency process in the current state of the art.

Direct Targeted Sequencing (DTS) is a modification to the standard sequencing protocol employed by Illumina, Inc. that allows the sequencing substrate (i.e. the flow cell) to become a genomic sequence capture substrate as well. Without adding another instrument to the normal flow of a typical next generation sequencing protocol, the DTS protocol modifies the sequencing surface to capture gDNA from a specially prepared library. The captured library is then sequenced as a normal gDNA library would be. However, modification of the sequencing substrate and accompanying library preparation according to previous suggestions result in inefficiencies, reduced reliability and reproducibility, and waste valuable sample. Improvements to the DTS process are therefore desirable.

SUMMARY OF THE INVENTION

In one aspect, the invention provides an apparatus and a method of producing an apparatus for sequencing a plurality of target polynucleotides. In one embodiment, the method comprises (a) providing a solid support having a reactive surface; and (b) attaching to the solid support a plurality of oligonucleotides. In some embodiments, the plurality of oligonucleotides comprises (i) a plurality of different first oligonucleotides comprising sequence A and sequence B, wherein sequence A is common among all first oligonucleotides; and further wherein sequence B is different for each different first oligonucleotide, is at the 3' end of each first oligonucleotide, and is complementary to a sequence comprising a causal genetic variant or a sequence within 200 nucleotides of a causal genetic variant; (ii) a plurality of second oligonucleotides comprising sequence A at each 3' end; and (iii) a plurality of third oligonucleotides comprising sequence C at each 3' end, wherein sequence C is the same as a sequence shared by a plurality of different target polynucleotides. In some embodiments, A, B, and C are different sequences and comprise 5 or more nucleotides each.

In some embodiments, sequences A, B, and C have less than 90% sequence identity with one another. In some embodiments, the plurality of oligonucleotides comprise a reactive moiety, such that a reaction between the reactive surface and the reactive moiety attaches the plurality of oligonucleotides to the solid support. In some embodiments, the plurality of first oligonucleotides comprises at least about 100 different first oligonucleotides each comprising a different sequence B. In some embodiments, sequence B of one or more of the plurality of first oligonucleotides comprises a sequence selected from the group consisting of SEQ ID NOs 22-121, shown in FIG. 4. In some embodiments, the solid support is a channel of a flow cell. In some embodiments, the reactive surface comprises functionalized polyacrylamide, which may be produced from a polymerization mixture comprising acrylamide, N-(5-bromoacetamidylpentyl)acrylamide, tetramethylethylenediamine, and potassium persulfate. In some embodiments, the amount of the plurality of second oligonucleotides is at least about 1000-fold or 10000-fold higher than the amount of the plurality of first oligonucleotides; and the amount of the plurality of second oligonucleotides and the amount of the plurality of third oligonucleotides are in a ratio of about 1 to 1. In some embodiments, each of the first oligonucleotides is added to the solid support at a concentration of about 50 pM. In some embodiments, the concentration of the plurality of second oligonucleotides and of the plurality of third oligonucleotides is about 500 nM. In some embodiments, the invention provides a method of sequencing a plurality of target polynucleotides, the method comprising exposing an apparatus produced according to a method of the invention to a sample comprising target polynucleotides and non-target polynucleotides, wherein sequencing data is enriched for target genomic sequences relative to non-target genomic sequences. In some embodiments, the plurality of different first oligonucleotides further comprises additional first oligonucleotides comprising sequence A and sequence B, wherein sequence B is different for each different additional first oligonucleotide, is at the 3' end of each additional first oligonucleotide, and is complementary to a sequence comprising a non-subject sequence or a sequence within 200 nucleotides of a non-subject sequence.

In one aspect, the invention provides a method for sequencing a plurality of target polynucleotides in a sample. In one embodiment, the method comprises: (a) fragmenting target polynucleotides to produce fragmented polynucleotides; (b) joining adapter oligonucleotides to the fragmented polynucleotides, each of the adapter oligonucleotides comprising sequence D, to produce adapted polynucleotides comprising sequence D hybridized to complementary sequence D' at both ends of the adapted polynucleotides, optionally wherein sequence D' is produced by extension of a target polynucleotide 3' end; (c) amplifying the adapted polynucleotides using amplification primers comprising sequence C, sequence D, and a barcode associated with the sample, wherein sequence D is positioned at the 3' end of the amplification primers; (d) hybridizing amplified target polynucleotides to a plurality of different first oligonucleotides that are attached to a solid surface; (e) performing bridge amplification on a solid surface; and (f) sequencing a plurality of polynucleotides from step (e). The solid surface may comprise a plurality of oligonucleotides as described herein, including an apparatus as described herein and optionally produced according to the methods described herein. In some embodiments, the solid surface comprises (i) a plurality of different first oligonucleotides comprising sequence A and sequence B, wherein sequence A is common among all first oligonucleotides; and further wherein sequence B is different for each different first oligonucleotide, is at the 3' end of each first oligonucleotide, and is complementary to a sequence comprising a causal genetic variant or a sequence within 200 nucleotides of a causal genetic variant; (ii) a plurality of second oligonucleotides comprising sequence A at each 3' end; and (iii) a plurality of third oligonucleotides comprising sequence C at each 3' end. In some embodiments, sequences A, B, and C are different sequences and comprise 5 or more nucleotides each.

In some embodiments, the method further comprises a second amplification step before step (d), wherein amplified polynucleotides are amplified using a second amplification primer having a 3' end comprising sequence complementary to at least a portion of one or more sequences added to the target polynucleotides in step (c). In some embodiments, sequences A, B, and C have less than 90% sequence identity with one another. In some embodiments, the plurality of first oligonucleotides comprises at least about 100 different first oligonucleotides each comprising a different sequence B. In some embodiments, sequence B of one or more of the plurality of first oligonucleotides comprises a sequence selected from the group consisting of SEQ ID NOs 22-121, shown in FIG. 4. In some embodiments, each barcode differs from every other barcode in a pool of two or more samples at at least three nucleotide positions. In some embodiments, samples are pooled such that all four nucleotide bases A, G, C, and T are approximately evenly represented at every position along each barcode in the pool. In some embodiments, one or more barcodes are selected from the group consisting of: AGGTCA, CAGCAG, ACTGCT, TAACGG, GGATTA, AACCTG, GCCGTT, CGTTGA, GTAACC, CTTAAC, TGCTAA, GATCCG, CCAGGT, TTCAGC, ATGATC, and TCGGAT. In some embodiments, the barcode is located between sequence C and sequence D. In some embodiments, the method further comprises the step of identifying the sample from which a target polynucleotide is derived based on the barcode sequence. In some embodiments, the fragmented polynucleotides have a median length between about 200 and about 1000 base pairs. In some embodiments, step (f) comprises (i) sequencing by extension of a first sequencing primer that hybridizes to a position located 3' from the barcode; and then (ii) sequencing by extension of a second sequencing primer that hybridizes to a position located 5' from the barcode. In some embodiments, the solid support is a channel of a flow cell. In some embodiments, steps (b) and (c) are performed by an automated system, such as a liquid handler (e.g. a Biomek FXP). In some embodiments, step (d) is performed by an automated system, such as a system comprising a cBot machine. In some embodiments, the automated system that performs step (d) also performs step (e). In some embodiments, sequencing data are generated for at least about 100 different target polynucleotides. In some embodiments, step (d) utilizes at least about 10 μg of DNA in a single flow cell. In some embodiments, the method is performed on a plurality of samples in parallel. In some embodiments, step (c) is performed in quadruplicate for each of a plurality of samples. In some embodiments, the amount of DNA is measured at the completion of one or more of steps (a), (b), and (c). In some embodiments, one or more of steps (a), (b), and (c) has a minimum threshold for the amount of DNA remaining at the end of that step to be used in the next step, such as 1 μg, 0.8 μg, 13 μg, respectively. In some embodiments, sequencing data are generated for at least about $10^8$ target sequences in a single reaction. In some embodiments, sequencing data are generated for less than about $10^7$ target sequences per sample in a single reaction. In some embodiments, presence or absence of one or more causal genetic variants is determined with an accuracy of at least about 90%. In some embodiments, the plurality of different first oligonucleotides further comprises additional first oligonucleotides comprising sequence A and sequence B, wherein sequence B is different for each different additional first oligonucleotide, is at the 3' end of each additional first oligonucleotide, and is complementary to a sequence comprising a non-subject sequence or a sequence within 200 nucleotides of a non-subject sequence.

In one aspect, the invention provides a method of enriching a plurality of different target polynucleotides in a sample. In some embodiments, the method comprises: (a) joining an adapter oligonucleotide to each of the target polynucleotides, wherein the adapter oligonucleotide comprises sequence Y; (b) hybridizing a plurality of different oligonucleotide primers to the adapted target polynucleotides, wherein each oligonucleotide primer comprises sequence Z and sequence W; wherein sequence Z is common among all oligonucleotide primers; and further wherein sequence W is different for each different oligonucleotide primer, is positioned at the 3' end of each oligonucleotide primer, and is complementary to a sequence comprising a causal genetic variant or a sequence within 200 nucleotides of a causal genetic variant; (c) in an extension reaction, extending the oligonucleotide primers along the adapted target polynucleotides to produce extended primers comprising sequence Z and sequence Y', wherein sequence Y' is complementary to sequence Y; and (d) exponentially amplifying the purified extension products using a pair of amplification primers comprising (i) a first amplification primer comprising sequence V and sequence Z, wherein sequence Z is positioned at the 3' end of the first amplification primer; and (ii) a second amplification primer comprising sequence X and sequence Y, wherein sequence Y is positioned at the 3' end of the second amplification primer. In some embodiments, sequences W, Y, and Z are different sequences and comprise 5 or more nucleotides each. Each oligonucleotide primer may or may not comprise a first binding partner. In some embodiments, the method further comprises, before step (d), exposing the extended primers to a solid surface comprising a second binding partner that binds to the first binding partner, thereby purifying the extended primers away from one or more components of the extension reaction. In some embodiments, the method does not comprise a purification step.

In some embodiments, the plurality of oligonucleotide primers comprises at least about 100 different oligonucleotide primers each comprising a different sequence W. In some embodiments, sequence W of one or more of the plurality of oligonucleotide primers comprises a sequence selected from the group consisting of SEQ ID NOs 22-121, shown in FIG. 4. In some embodiments, the target polynucleotides comprise fragmented polynucleotides. In some embodiments, the fragmented polynucleotides have a median length between about 200 and about 1000 base pairs. In some embodiments, the fragmented polynucleotides are treated to produce blunt ends or to have a defined overhang prior to step (a), such as an overhang consisting of an adenine. In some embodiments, the first binding partner and the second binding partner are members of a binding pair, such as streptavidin and biotin. In some embodiments, the solid surface is a bead, such as a bead that is responsive to a magnetic field. In some embodiments, the purifying step comprises application of a magnetic field to purify the beads. In some embodiments, the extended primers are purified away from the target polynucleotides. In some embodiments, the method further comprises sequencing the products of step (d). In some embodiments, sequencing comprises amplifying the products of step (d) by bridge amplification with bound oligonucleotides attached to a solid support to produce double-stranded bridge polynucleotides; cleaving one strand of a bridge polynucleotide at a cleavage site in a bound oligonucleotide; denaturing the cleaved bridge polynucleotide to produce a free single-stranded polynucleotide comprising a target sequence attached to the solid support; and sequencing the target sequence by extending a sequencing primer hybridized to at least a portion of one or more sequences added during one or more of steps (a), (c), or (d). In some embodiments, sequencing comprises amplifying the products of step (d) by extension of a bound primer on a solid support to produce bound templates, hybridizing a sequencing primer to a bound template, extending the sequencing primer, and identifying nucleotides added by extension of the sequencing primer. In some embodiments, the plurality of different oligonucleotide primers further comprises additional oligonucleotide primers comprising sequence Z and sequence W, wherein sequence W is different for each different additional oligonucleotide primer, is at the 3' end of each additional oligonucleotide primer, and is complementary to a sequence comprising a non-subject sequence or a sequence within 200 nucleotides of a non-subject sequence.

In one aspect, the invention provides a method of enriching a plurality of different target polynucleotides in a sample. In some embodiments, the method comprises: (a) hybridizing a plurality of different oligonucleotide primers to the target polynucleotides, wherein each oligonucleotide primer comprises sequence Z and sequence W; wherein sequence Z is common among all oligonucleotide primers; and further wherein sequence W is different for each different oligonucleotide primer, is positioned at the 3' end of each oligonucleotide primer, and is complementary to a sequence comprising a causal genetic variant or a sequence within 200 nucleotides of a causal genetic variant; (b) in an extension reaction, extending the oligonucleotide primers along the target polynucleotides to produce extended primers; (c) joining an adapter oligonucleotide to each extended primer, wherein the adapter oligonucleotide comprises sequence Y', and further wherein sequence Y' is the complement of a sequence Y; and (d) exponentially amplifying the purified extension products using a pair of amplification primers comprising (i) a first amplification primer comprising sequence V and sequence Z, wherein sequence Z is positioned at the 3' end of the first amplification primer; and (ii) a second amplification primer comprising sequence X and sequence Y, wherein sequence Y is positioned at the 3' end of the second amplification primer. In some embodiments, sequences W, Y, and Z are different sequences and comprise 5 or more nucleotides each. Each oligonucleotide primer may or may not comprise a first binding partner. In some embodiments, the method further comprises, before step (d), exposing the extended primers to a solid surface comprising a second binding partner that binds to the first binding partner, thereby purifying the extended primers away from one or more components of the extension reaction. In some embodiments, the method does not comprise a purification step.

In some embodiments, the plurality of oligonucleotide primers comprises at least about 100 different oligonucleotide primers each comprising a different sequence W. In some embodiments, sequence W of one or more of the plurality of oligonucleotide primers comprises a sequence selected from the group consisting of SEQ ID NOs 22-121, shown in FIG. 4. In some embodiments, the target polynucleotides comprise fragmented polynucleotides. In some embodiments, the fragmented polynucleotides have a median length between about 200 and about 1000 base pairs. In some embodiments, step (b) further comprises treating the extended primers and the target polynucleotides to which they are hybridized to produce blunt ends or to have a defined overhang prior to step (c), such as an overhang consisting of an adenine. In some embodiments, the first binding partner and the second binding partner are members of a binding pair, such as streptavidin and biotin. In some embodiments, the solid surface is a bead, such as a bead that is responsive to a magnetic field. In some embodiments, the purifying step comprises application of a magnetic field to purify the beads. In some embodiments, the extended primers are purified away from the target polynucleotides. In some embodiments, the method further comprises sequencing the products of step (d). In some embodiments, sequencing comprises amplifying the products of step (d) by bridge amplification with bound oligonucleotides attached to a solid support to produce double-stranded bridge polynucleotides, cleaving one strand of a bridge polynucleotide at a cleavage site in a bound oligonucleotide, denaturing the cleaved bridge polynucleotide to produce a free single-stranded polynucleotide comprising a target sequence attached to the solid support, and sequencing the target sequence by extending a sequencing primer hybridized to at least a portion of one or more sequences added during one or more of steps (b), (c), or (d). In some embodiments, sequencing comprises amplifying the products of step (d) by extension of a bound primer on a solid support to produce bound templates, hybridizing a sequencing primer to a bound template, extending the sequencing primer, and identifying nucleotides added by extension of the sequencing primer. In some embodiments, the plurality of different oligonucleotide primers further comprises additional oligonucleotide primers comprising sequence Z and sequence W, wherein sequence W is different for each different additional oligonucleotide primer, is at the 3' end of each additional oligonucleotide primer, and is complementary to a sequence comprising a non-subject sequence or a sequence within 200 nucleotides of a non-subject sequence.

In one aspect, the invention provides a method of detecting genetic variation in a subject's genome. In some embodiments, the method comprises: (a) providing a plurality of clusters of polynucleotides, wherein (i) each cluster comprises multiple copies of a nucleic acid duplex attached to a support; (ii) each duplex in a cluster comprises a first molecule comprising sequences A-B-G'-D'-C' from 5' to 3' and a second molecule comprising sequences C-D-G-B'-A' from 5' to 3'; (iii) sequence A' is complementary to sequence A, sequence B' is complementary to sequence B, sequence C' is complementary to sequence C, sequence D' is complementary to sequence D, and sequence G' is complementary to sequence G; (iv) sequence G is a portion of a target polynucleotide sequence from a subject and is different for each of a plurality of clusters; and (v) sequence B' is located 5' with respect to sequence G in the corresponding target polynucleotide sequence; (b) sequencing sequence G' by extension of a first primer comprising sequence D to produce an R1 sequence for each cluster; (c) sequencing sequence B' by extension of a second primer comprising sequence A to produce R2 sequence for each cluster; (d) performing a first alignment using a first algorithm to align all R1 sequences to a first reference sequence; (e) performing a second alignment using a second algorithm to locally align R1 sequences identified in said first alignment as likely to contain an insertion or deletion with respect to the first reference sequence, to produce a single consensus alignment for each insertion or deletion; (f) performing an R2 alignment by aligning all R2 sequences to a second reference sequence; and (g) transmitting a report identifying sequence variation identified by steps (d) to (f) to a receiver.

In some embodiments, the first reference sequence comprises a reference genome. In some embodiments, the second reference sequence consists of every sequence B for every different target polynucleotide. In some embodiments, R2 sequences are aligned independently of R1 sequences. In some embodiments, the method further comprises discarding an R1 sequence that aligns to a first position in the first reference sequence that is more than 10,000 base pairs away from a second position in the first reference sequence to which the R2 sequence for the same cluster aligns. In some embodiments, the method further comprises deleting a portion of an R1 sequence for a cluster when the portion of R1 sequence to be deleted is identical to at least a portion of sequence B' for that cluster and sequence G is shorter than the R1 sequence for that cluster. In some embodiments, the method further comprises deleting a portion of an R1 sequence for a cluster when the portion of R1 sequence to be deleted is identical to at least a portion of any sequence B', the portion includes either the 5' or 3' nucleotide of R1, and either (i) no R2 sequence was produced for the cluster or (ii) R2 sequence produced is not identical to any sequence B. In some embodiments, performing the first alignment with a system using the first algorithm takes less time and/or uses less system memory to align all R1 reads than would be taken and/or used if the system used the second algorithm to perform the first alignment. In some embodiments, the first algorithm is based on the Burrows-Wheeler transform. In some embodiments, the second algorithm is based on the Smith-Waterman algorithm or a hash function. In some embodiments, R1 and R2 sequences are generated for at least 100 different target polynucleotides. In some embodiments, sequences A, B, C, and D are at least 5 nucleotides in length. In some embodiments, sequence G of every cluster is 1 to 1000 nucleotides in length. In some embodiments, each probe sequence B of a plurality of clusters is complementary to a sequence comprising a causal genetic variant or a sequence within 200 nucleotides of a causal genetic variant. In some embodiments, sequence B of one or more of the clusters comprises a sequence selected from the group consisting of SEQ ID NOs: 22-121. In some embodiments, an R1 sequence is produced for at least about $10^8$ clusters in a single reaction. In some embodiments, presence, absence, or allele ratio of one or more causal genetic variants is determined with an accuracy of at least about 90%. In some embodiments, the consensus sequence identifies an insertion, a deletion, or an insertion and a deletion in a target polynucleotide with an accuracy of at least about 90%. In some embodiments each probe sequence B of a plurality of clusters is complementary to a sequence comprising a non-subject sequence or a sequence within 200 nucleotides of a non-subject sequence. In some embodiments, the presence or absence of one or more non-subject sequences is determined with an accuracy of at least about 90%. In some embodiments, the method further comprises calculating a plurality of probabilities based on the R1 sequences for the subject and including the probabilities in the report, wherein each probability is a probability of the subject or a subject's offspring having or developing a disease or trait.

In some embodiments, each first molecule comprises a barcode sequence. In some embodiments, each barcode differs from every other barcode in a plurality of different barcodes analyzed in parallel. In some embodiments, the barcode sequence is associated with a single sample in a pool of samples sequenced in a single reaction. In some embodiments, each of a plurality of barcode sequences is uniquely associated with a single sample in a pool of samples sequenced in a single reaction. In some embodiments, the barcode sequence is located 5' from sequence D'. In some embodiments, the method further comprises hybridizing a third primer to sequence C' and sequencing the barcode sequence by extension of the third primer to produce a barcode sequence for each cluster. In some embodiments, the method further comprises grouping sequences from the clusters based on the barcode sequences. In some embodiments, the method further comprises discarding all but one of a plurality of R1 sequences having the same sequence and alignment within a barcode sequence grouping.

In one aspect, the invention provides a method of detecting genetic variation in a subject's genome. In some embodiments, the method comprises: (a) providing sequencing data for a plurality of clusters of polynucleotides, wherein (i) each cluster comprised multiple copies of a nucleic acid duplex attached to a support; (ii) each duplex in a cluster comprised a first molecule comprising sequences A-B-G'-D'-C' from 5' to 3' and a second molecule comprising sequences C-D-G-B'-A' from 5' to 3'; (iii) sequence A' is complementary to sequence A, sequence B' is complementary to sequence B, sequence C' is complementary to sequence C, sequence D' is complementary to sequence D, and sequence G' is complementary to sequence G; (iv) sequence G is a portion of a target polynucleotide sequence from a subject and is different for each of a plurality of clusters; (v) sequence B' is located 5' with respect to sequence G in the corresponding target polynucleotide sequence; (viii) the sequencing data comprises R1 sequences generated by extension of a first primer comprising sequence D; and (vi) the sequencing data comprises R2 sequences generated by extension of a second primer comprising sequence A; (b) performing a first alignment using a first algorithm to align all R1 sequences to a first reference sequence; (c) performing a second alignment using a second algorithm to locally align R1 sequences identified in said first alignment as likely to contain an insertion or deletion with respect to the first reference sequence, to produce a single consensus alignment for each insertion or deletion; (d) performing an R2 alignment by aligning all R2 sequences to a second reference sequence; and (e) transmitting a report identifying sequence variation identified by steps (b) to (d) to a receiver.

In some embodiments, the first reference sequence comprises a reference genome. In some embodiments, the second reference sequence consists of every sequence B for every different target polynucleotide. In some embodiments, R2 sequences are aligned independently of R1 sequences. In some embodiments, the method further comprises discarding an R1 sequence that aligns to a first position in the first reference sequence that is more than 10,000 base pairs away from a second position in the first reference sequence to which the R2 sequence for the same cluster aligns. In some embodiments, the method further comprises deleting a portion of an R1 sequence for a cluster when the portion of R1 sequence to be deleted is identical to at least a portion of sequence B' for that cluster and sequence G is shorter than the R1 sequence for that cluster. In some embodiments, the method further comprises deleting a portion of an R1 sequence for a cluster when the portion of R1 sequence to be deleted is identical to at least a portion of any sequence B', the portion includes either the 5' or 3' nucleotide of R1, and either (i) no R2 sequence was produced for the cluster or (ii) R2 sequence produced is not identical to any sequence B. In some embodiments, performing the first alignment with a system using the first algorithm takes less time and/or uses less system memory to align all R1 reads than would be taken and/or used if the system used the second algorithm to perform the first alignment. In some embodiments, the first algorithm is based on the Burrows-Wheeler transform. In some embodiments, the second algorithm is based on the Smith-Waterman algorithm or a hash function. In some embodiments, the sequencing data comprises R1 and R2 sequences for at least 100 different target polynucleotides. In some embodiments, sequences A, B, C, and D are at least 5 nucleotides in length. In some embodiments, sequence G of every cluster is 1 to 1000 nucleotides in length. In some embodiments, each probe sequence B of a plurality of clusters is complementary to a sequence comprising a causal genetic variant or a sequence within 200 nucleotides of a causal genetic variant. In some embodiments, sequence B of one or more of the clusters comprises a sequence selected from the group consisting of SEQ ID NOs: 22-121. In some embodiments, sequencing data comprises at least about $10^8$ R1 sequences from a single reaction. In some embodiments, presence, absence, or allele ratio of one or more causal genetic variants is determined with an accuracy of at least about 90%. In some embodiments, the consensus sequence identifies an insertion, a deletion, or an insertion and a deletion in a target polynucleotide with an accuracy of at least about 90%. In some embodiments each probe sequence B of a plurality of clusters is complementary to a sequence comprising a non-subject sequence or a sequence within 200 nucleotides of a non-subject sequence. In some embodiments, the presence or absence of one or more non-subject sequences is determined with an accuracy of at least about 90%. In some embodiments, the method further comprises calculating a plurality of probabilities based on the R1 sequences for the subject and including the probabilities in the report, wherein each probability is a probability of the subject or a subject's offspring having or developing a disease or trait.

In some embodiments, each first molecule comprises a barcode sequence. In some embodiments, each barcode differs from every other barcode in a plurality of different barcodes analyzed in parallel. In some embodiments, the barcode sequence is associated with a single sample in a pool of samples sequenced in a single reaction and represented in the sequencing data. In some embodiments, each of a plurality of barcode sequences is uniquely associated with a single sample in a pool of samples sequenced in a single reaction. In some embodiments, the barcode sequence is located 5' from sequence D'. In some embodiments, the sequencing data further comprises a barcode sequence for each cluster generated by extension of a third primer comprising sequence C. In some embodiments, the method further comprises grouping sequences from the clusters based on the barcode sequences. In some embodiments, the method further comprises discarding all but one of a plurality of R1 sequences having the same sequence and alignment within a barcode sequence grouping.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 3 provides a table of example causal genetic variants.

FIG. 4 provides a table of example sequences that are complementary to example specific target sequences.

FIG. 9 provides a number of AIMs that distinguish different populations. The entries refer to items in the dbSNP database, a database of genetic variants maintained by the US government: www.ncbi.nlm.nih.gov/projects/SNP/. Curated records in dbSNP contain information that describes the sequence and location of genetic variants, and where available the frequency of alleles of those variants in different populations. rs numbers (for example, rs332, rs25, etc.) are the ID numbers used to index the portion of the dbSNP database.

FIG. 19 illustrates the positional relationship of sequence regions considered in a step of a sample probe design process.

DETAILED DESCRIPTION OF THE INVENTION

Figure 1:
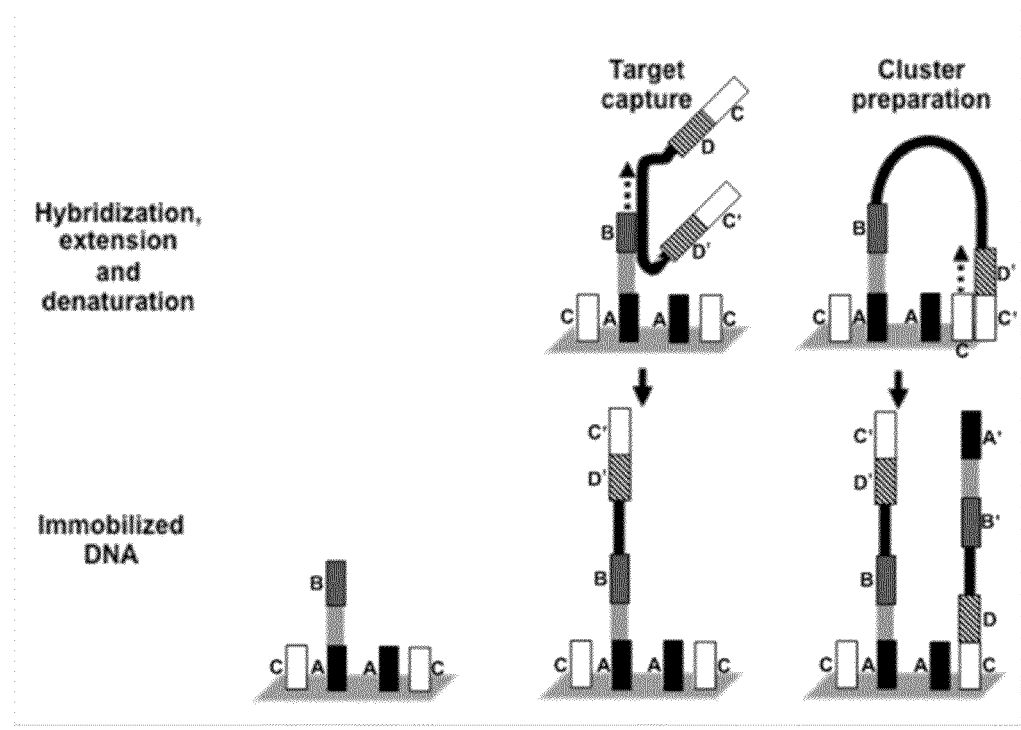
FIG. 1 illustrates a portion of an example solid support comprising attached oligonucleotides, and the first steps in an example bridge amplification process to amplify a target polynucleotide.

The terms "polynucleotide", "nucleotide", "nucleotide sequence", "nucleic acid" and "oligonucleotide" are used interchangeably. They refer to a polymeric form of nucleotides of any length, either deoxyribonucleotides or ribonucleotides, or analogs thereof. Polynucleotides may have any three dimensional structure, and may perform any function, known or unknown. The following are non limiting examples of polynucleotides: coding or non-coding regions of a gene or gene fragment, intergenic DNA, loci (locus) defined from linkage analysis, exons, introns, messenger RNA (mRNA), transfer RNA, ribosomal RNA, short interfering RNA (siRNA), short-hairpin RNA (shRNA), microRNA (miRNA), small nucleolar RNA, ribozymes, cDNA, recombinant polynucleotides, branched polynucleotides, plasmids, vectors, isolated DNA of any sequence, isolated RNA of any sequence, nucleic acid probes, adapters, and primers. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non nucleotide components. A polynucleotide may be further modified after polymerization, such as by conjugation with a labeling component, tag, reactive moiety, or binding partner. Polynucleotide sequences, when provided, are listed in the 5' to 3' direction, unless stated otherwise.

As used herein, the term "target polynucleotide" refers to a nucleic acid molecule or polynucleotide in a population of nucleic acid molecules having a target sequence to which one or more oligonucleotides of the invention are designed to hybridize. In some embodiments, a target sequence uniquely identifies a sequence derived from a sample, such as a particular genomic, mitochondrial, bacterial, viral, or RNA (e.g.

mRNA, miRNA, primary miRNA, or pre-miRNA) sequence. In some embodiments, a target sequence is a common sequence shared by multiple different target polynucleotides, such as a common adapter sequence joined to different target polynucleotides. "Target polynucleotide" may be used to refer to a double-stranded nucleic acid molecule comprising a target sequence on one or both strands, or a single-stranded nucleic acid molecule comprising a target sequence, and may be derived from any source of or process for isolating or generating nucleic acid molecules. A target polynucleotide may comprise one or more (e.g. 1, 2, 3, 4, 5, 6, 7, 8, 9, 10, or more) target sequences, which may be the same or different. In general, different target polynucleotides comprise different sequences, such as one or more different nucleotides or one or more different target sequences.

"Hybridization" and "annealing" refer to a reaction in which one or more polynucleotides react to form a complex that is stabilized via hydrogen bonding between the bases of the nucleotide residues. The hydrogen bonding may occur by Watson Crick base pairing, Hoogstein binding, or in any other sequence specific manner. The complex may comprise two strands forming a duplex structure, three or more strands forming a multi stranded complex, a single self hybridizing strand, or any combination of these. A hybridization reaction may constitute a step in a more extensive process, such as the initiation of a PCR, or the enzymatic cleavage of a polynucleotide by a ribozyme. A first sequence that can be stabilized via hydrogen bonding with the bases of the nucleotide residues of a second sequence is said to be "hybridizable" to the second sequence. In such a case, the second sequence can also be said to be hybridizable to the first sequence.

In general, a "complement" of a given sequence is a sequence that is fully complementary to and hybridizable to the given sequence. In general, a first sequence that is hybridizable to a second sequence or set of second sequences is specifically or selectively hybridizable to the second sequence or set of second sequences, such that hybridization to the second sequence or set of second sequences is preferred (e.g. thermodynamically more stable under a given set of conditions, such as stringent conditions commonly used in the art) to hybridization with non-target sequences during a hybridization reaction. Typically, hybridizable sequences share a degree of sequence complementarity over all or a portion of their respective lengths, such as between 25%-100% complementarity, including at least about 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, and 100% sequence complementarity.

The term "hybridized" as applied to a polynucleotide refers to a polynucleotide in a complex that is stabilized via hydrogen bonding between the bases of the nucleotide residues. The hydrogen bonding may occur by Watson Crick base pairing, Hoogstein binding, or in any other sequence specific manner. The complex may comprise two strands forming a duplex structure, three or more strands forming a multi-stranded complex, a single self hybridizing strand, or any combination of these. The hybridization reaction may constitute a step in a more extensive process, such as the initiation of a PCR reaction, ligation reaction, sequencing reaction, or cleavage reaction.

The practice of the present invention employs, unless otherwise indicated, conventional techniques of immunology, biochemistry, chemistry, molecular biology, microbiology, cell biology, genomics and recombinant DNA, which are within the skill of the art. See e.g. Sambrook, Fritsch and Maniatis, MOLECULAR CLONING: A LABORATORY MANUAL, 2nd edition (1989); CURRENT PROTOCOLS IN MOLECULAR BIOLOGY (F. M. Ausubel, et al. eds., (1987)); the series METHODS IN ENZYMOLOGY (Academic Press, Inc.): PCR 2: A PRACTICAL APPROACH (M. J. MacPherson, B. D. Hames and G. R. Taylor eds. (1995)), Harlow and Lane, eds. (1988) ANTIBODIES, A LABORATORY MANUAL, and ANIMAL CELL CULTURE (R. I. Freshney, ed. (1987)).

In one aspect, the invention provides a method of producing an apparatus for sequencing a plurality of target polynucleotides. In one embodiment, the method comprises (a) providing a solid support having a reactive surface; and (b) attaching to the solid support a plurality of oligonucleotides. In some embodiments, the plurality of oligonucleotides comprises (i) a plurality of different first oligonucleotides comprising sequence A and sequence B, wherein sequence A is common among all first oligonucleotides; and further wherein sequence B is different for each different first oligonucleotide, is at the 3' end of each first oligonucleotide, and is complementary to a sequence comprising a causal genetic variant or a sequence within 200 nucleotides of a causal genetic variant; (ii) a plurality of second oligonucleotides comprising sequence A at each 3' end; and (iii) a plurality of third oligonucleotides comprising sequence C at each 3' end, wherein sequence C is the same as a sequence shared by a plurality of different target polynucleotides. In some embodiments, one or more of sequences A, B, and C are different sequences. In some embodiments, one or more of sequences A, B, and C are about, less than about, or more than about 5%, 10%, 15%, 20%, 25%, 30%, 40%, 50%, 60%, 70%, 80%, 90%, or more different from one or more of the other of sequences A, B, and C (e.g. have less than about 10%, 20%, 30%, 40%, 50%, 60%, 70%, 80%, 90%, or more sequence identity). In some embodiments, one or more of sequences A, B, and C comprise about, less than about, or more than about 1, 2, 3, 4, 5, 6, 7, 8, 9, 10, 15, 20, or more nucleotides each.

A variety of suitable solid support materials are known in the art. Non-limiting examples of solid support materials include silica-based substrates, such as glass, fused silica and other silica-containing materials; silicone hydrides or plastic materials, such as polyethylene, polystyrene, poly (vinyl chloride), polypropylene, nylons, polyesters, polycarbonates, poly (methyl methacrylate), and cyclic olefin polymer substrates; and other solid support materials, such as gold, titanium dioxide, or silicon supports. The solid support materials may be provided in any suitable form, including but not limited to beads, nanoparticles, nanocrystals, fibers, microfibers, nanofibers, nanowires, nanotubes, mats, planar sheets, planar wafers or slides, multiwell plates, optical slides, flow cells, and channels. A solid support may further include one or more additional structures, such as channels, microfluidic channels, capillaries, and wells. In some embodiments, the solid support is a channel of a flow cell.

When referring to immobilization or attachment of molecules (e.g. nucleic acids) to a solid support, the terms "immobilized" and "attached" are used interchangeably herein and both terms, are intended to encompass direct or indirect, covalent or non-covalent attachment, unless indicated otherwise. In some embodiments of the invention, covalent attachment may be preferred, but generally all that is required is that the molecules (e.g. nucleic acids) remain immobilized or attached to the support under the conditions in which it is intended to use the support, for example in nucleic acid amplification and/or sequencing applications.

In some embodiments, a solid support material comprises a material that is reactive, such that under specified conditions, a molecule (such as an oligonucleotide or modified oligonucleotide) can be attached directly to the surface of the solid support. In some embodiments, a solid support material comprises an inert substrate or matrix (e.g. glass slides, polymer beads, or other solid support material) that has been "functionalized", for example by application of a layer or coating of an intermediate material comprising reactive groups which permit attachment (e.g. covalent attachment) to biomolecules, such as polynucleotides. Examples of such supports include, but are not limited to, polyacrylamide hydrogels supported on an inert substrate such as glass. In such embodiments, the biomolecules (e.g. oligonucleotide) may be directly covalently attached to the intermediate material (e.g. the hydrogel) but the intermediate material may itself be non-covalently attached to the substrate or matrix (e.g. the glass substrate).

A non-limiting example of a reactive surface includes the use of biotinylated albumins (BSA) to form a stable attachment of biotin groups by physisorption of the protein onto surfaces. Covalent modification can be performed using silanes, which have been used to attach molecules to a solid support, usually a glass slide. By way of example, a mixture of tetraethoxysilane and triethoxy-bromoacetamidopropyl-silane (e.g. in a ratio of 1:100) can be used to prepare functionalized glass slides which permit attachment of nucleic acids including a thiophosphate or phosphorothioate functionality. Biotin molecules can be attached to surfaces using appropriately reactive species such as biotin-PEG-succinimidyl ester which reacts with an amino surface.

In some embodiments, oligonucleotides to be attached to the solid support comprise a reactive moiety. In general, a reactive moiety includes any moiety that facilitates attachment to the solid support by reacting with the reactive surface. In some embodiments, functionalized polyacrylamide hydrogels are used to attach a plurality of oligonucleotides comprising a reactive moiety, wherein the reactive moiety is a sulfur-containing nucleophilic group. Examples of appropriate sulfur nucleophile-containing polynucleotides are disclosed in Zhao et al (Nucleic Acids Research, 2001, 29(4), 955-959) and Pirrung et al (Langmuir, 2000, 16, 2185-2191) and include, for example, simple thiols, thiophosphates, and thiophosphoramidates. Preferred hydrogels are those formed from a mixture of (i) a first co-monomer which is acrylamide, methacrylamide, hydroxyethyl methacrylate, or N-vinyl pyrrolidinone; and (ii) a second co-monomer which is a functionalized acrylamide or acrylate, such as N-(5-bromoacetamidylpentyl)acrylamide, tetramethylethylenediamine In some embodiments, a reactive surface comprising a functionalized polyacrylamide is produced from a polymerization mixture comprising acrylamide, N-(5-bromoacetamidylpentyl)acrylamide, tetramethylethylenediamine, and potassium persulfate. Further non-limiting examples of support materials and reactive surfaces are provided by US20120053074 and WO2005065814, which are hereby incorporated by reference in their entireties.

Oligonucleotides to which the solid support is exposed for attachment may be of any suitable length, and may comprise one or more sequence elements. Examples of sequence elements include, but are not limited to, one or more amplification primer annealing sequences or complements thereof, one or more sequencing primer annealing sequences or complements thereof, one or more common sequences shared among multiple different oligonucleotides or subsets of different oligonucleotides, one or more restriction enzyme recognition sites, one or more target recognition sequences complementary to one or more target polynucleotide sequences, one or more random or near-random sequences (e.g. one or more nucleotides selected at random from a set of two or more different nucleotides at one or more positions, with each of the different nucleotides selected at one or more positions represented in a pool of oligonucleotides comprising the random sequence), one or more spacers, and combinations thereof. Two or more sequence elements can be non-adjacent to one another (e.g. separated by one or more nucleotides), adjacent to one another, partially overlapping, or completely overlapping. For example, an amplification primer annealing sequence can also serve as a sequencing primer annealing sequence. Sequence elements can be located at or near the 3' end, at or near the 5' end, or in the interior of the oligonucleotide. In general, as used herein, a sequence element located "at the 3' end" includes the 3'-most nucleotide of the oligonucleotide, and a sequence element located "at the 5' end" includes the 5'-most nucleotide of the oligonucleotide. In some embodiments, a sequence element is about, less than about, or more than about 1, 2, 3, 4, 5, 6, 7, 8, 9, 10, 11, 12, 13, 14, 15, 16, 17, 18, 19, 20, 25, 30, 35, 40, 50, or more nucleotides in length. In some embodiments, an oligonucleotide is about, less than about, or more than about 5, 10, 15, 20, 25, 30, 35, 40, 45, 50, 60, 70, 80, 90, 100, or more nucleotides in length.

A spacer may consist of a repeated single nucleotide (e.g. 1, 2, 3, 4, 5, 6, 7, 8, 9, 10, or more of the same nucleotide in a row), or a sequence of 2, 3, 4, 5, 6, 7, 8, 9, 10, or more nucleotides repeated 1, 2, 3, 4, 5, 6, 7, 8, 9, 10, or more times. A spacer may comprise or consist of a specific sequence, such as a sequence that does not hybridize to any target sequence in a sample. A spacer may comprise or consist of a sequence of randomly selected nucleotides.

In some embodiments, a plurality of different first oligonucleotides are attached to the solid support, each comprising a sequence A that is common among all first oligonucleotides and a sequence B that is different for each different first oligonucleotide. In some embodiments, sequence B of each first oligonucleotide is complementary to a different target sequence. In some embodiments, the plurality of first oligonucleotides comprises about, less than about, or more than about 5, 10, 25, 50, 75, 100, 125, 150, 175, 200, 300, 400, 500, 750, 1000, 2500, 5000, 7500, 10000, 20000, 50000, or more different first oligonucleotides, each comprising a different sequence B. In some embodiments, sequence B of one or more of the plurality of first oligonucleotides comprises a sequence selected from the group consisting of SEQ ID NOs 22-121, shown in FIG. 4 (e.g. 1, 5, 10, 25, 50, 75, or 100 different oligonucleotides each with a different sequence from FIG. 4). In some embodiments, sequence B or the target sequence to which it specifically hybridizes comprises a causal genetic variant. In some embodiments, sequence B or the target sequence to which it specifically hybridizes is within about, less than about, or more than about 1, 2, 3, 4, 5, 6, 7, 8, 9, 10, 15, 20, 25, 30, 35, 40, 45, 50, 60, 70, 80, 90, 100, 200, 500 or more nucleotides of a causal genetic variant. Causal genetic variants are typically located downstream of a first oligonucleotide, such that at least a portion of the causal genetic variant serves as template for extension of a first oligonucleotide. In general, causal genetic variants are genetic variants for which there is statistical, biological, and/or functional evidence of association with a disease or trait. A single causal genetic variant can be associated with more than one disease or trait. In some embodiments, a causal genetic variant can be associated with a Mendelian trait, a non-Mendelian trait, or both. Causal genetic variants can manifest as variations in a polynucleotide, such 1, 2, 3, 4, 5, 6, 7, 8, 9, 10, 20, 50, or more sequence differences (such as between a polynucleotide comprising the causal genetic variant and a polynucleotide lacking the causal genetic variant at the same relative genomic position). Non-limiting examples of types of causal genetic variants include single nucleotide polymorphisms (SNP), deletion/insertion polymorphisms (DIP), copy number variants (CNV), short tandem repeats (STR), restriction fragment length polymorphisms (RFLP), simple sequence repeats (SSR), variable number of tandem repeats (VNTR), randomly amplified polymorphic DNA (RAPD), amplified fragment length polymorphisms (AFLP), inter-retrotransposon amplified polymorphisms (IRAP), long and short interspersed elements (LINE/SINE), long tandem repeats (LTR), mobile elements, retrotransposon microsatellite amplified polymorphisms, retrotransposon-based insertion polymorphisms, sequence specific amplified polymorphism, and heritable epigenetic modification (for example, DNA methylation). A causal genetic variant may also be a set of closely related causal genetic variants. Some causal genetic variants may exert influence as sequence variations in RNA polynucleotides. At this level, some causal genetic variants are also indicated by the presence or absence of a species of RNA polynucleotides. Also, some causal genetic variants result in sequence variations in protein polypeptides. A number of causal genetic variants are known in the art. An example of a causal genetic variant that is a SNP is the Hb S variant of hemoglobin that causes sickle cell anemia. An example of a causal genetic variant that is a DIP is the delta508 mutation of the CFTR gene which causes cystic fibrosis. An example of a causal genetic variant that is a CNV is trisomy 21, which causes Down's syndrome. An example of a causal genetic variant that is an STR is tandem repeat that causes Huntington's disease. FIG. 3 provides a table of non-limiting examples of causal genetic variants, and associated diseases. Non-limiting examples of causal genetic variants are also described in US20100022406, which is hereby incorporated by reference in its entirety.

Causal genetic variants can be originally discovered by statistical and molecular genetic analyses of the genotypes and phenotypes of individuals, families, and populations. The causal genetic variants for Mendelian traits are typically identified in a two-stage process. In the first stage, families in which multiple individuals who possess the trait are examined for genotype and phenotype. Genotype and phenotype data from these families is used to establish the statistical association between the presence of the Mendelian trait and the presence of a number of genetic markers. This association establishes a candidate region in which the causal genetic variant is likely to map. In a second stage, the causal genetic variant itself is identified. The second step typically entails sequencing the candidate region. More sophisticated, one-stage processes are possible with more advanced technologies which permit the direct identification of a causal genetic variant or the identification of smaller candidate regions. After one causal genetic variant for a trait is discovered, additional variants for the same trait can be discovered by simple methods. For example, the gene associated with the trait can be sequenced in individuals who possess the trait or their relatives. The invention of new methods for discovering causal genetic variants is an active area of research. The application of existing methods and the incorporation of new methods is expected to continue to result in the discovery of additional causal genetic variants which can be used or tested for by the devices, systems, and methods herein. Many causal genetic variants are cataloged in databases including the Online Mendelian Inheritance in Man (OMIM) and the Human Gene Mutation Database (HGMD). Causal genetic variants are also reported in the scholarly literature, at conferences, and in personal communications between scholars.

A causal genetic variant may exist at any frequency within a specified populations. In some embodiments, at least one of the causal genetic variants causes a trait having an incidence of no more than 1% a reference population. In another embodiment at least one of the causal genetic variants causes a trait having an incidence of no more than 1/10,000 in a reference population. In some embodiments, a causal genetic variant is associated with a disease or trait. In some embodiments, a causal genetic variant is a genetic variant the presence of which increases the risk of having or developing a disease or trait by about, less than about, or more than about 1%, 5%, 10%, 15%, 20%, 25%, 30%, 40%, 50%, 60%, 70%, 80%, 90%, 100%, 200%, 300%, 400%, 500%, or more. In some embodiments, a causal genetic variant is a genetic variant the presence of which increases the risk of having or developing a disease or trait by about, less than about, or more than about 1-fold, 2-fold, 3-fold, 4-fold, 5-fold, 6-fold, 7-fold, 8-fold, 9-fold, 10-fold, 25-fold, 50-fold, 100-fold, 500-fold, 1000-fold, 10000-fold, or more. In some embodiments, a causal genetic variant is a genetic variant the presence of which increases the risk of having or developing a disease or trait by any statistically significant amount, such as an increase having a p-value of about or less than about $0.1, 0.05, 10^{-3}, 10^{-4}, 10^{-5}, 10^{-6}, 10^{-7}, 10^{-8}, 10^{-9}, 10^{-10}, 10^{-11}, 10^{-12}, 10^{-13}, 10^{-14}, 10^{-15}$, or smaller.

In some embodiments, a causal genetic variant has a different degree of association with a disease or trait between two or more different populations of individuals, such as between two or more human populations. In some embodiments, a causal genetic variant has a statistically significant association with a disease or trait only within one or more populations, such as one or more human populations. A human population can be a group of people sharing a common genetic inheritance, such as an ethnic group (for example, Caucasian). A human population can be a haplotype population or group of haplotype populations (for example, haplotype H1, M52). A human population can be a national group (for example, Americans, English, Irish). A human population can be a demographic population such as those delineated by age, sex, and socioeconomic factors. Human populations can be historical populations. A population can consist of individuals distributed over a large geographic area such that individuals at extremes of the distribution may never meet one another. The individuals of a population can be geographically dispersed into discontinuous areas. Populations can be informative about biogeographical ancestry. Populations can also be defined by ancestry. Genetic studies can define populations. In some embodiments, a population may be based on ancestry and genetics, with major human populations corresponding to continental scale groupings, which include Western Eurasian, sub-Saharan African, East Asian, and Native American. Most humans can be assigned to at least one of these populations on the basis of ancestry. A number of smaller populations are also distinguished as continental groups, including Indigenous Australian, Oceanian, and Bushmen.

Very often, populations can be further decomposed into sub-populations. The relationship between populations and subpopulations can be hierarchical. For example, the Oceanian population can be further sub-divided into sub-populations including Polynesians, Melanesians and Micronesians. The Western Eurasian population can be further sub-divided into sub-populations including European, Western/Central Asian, South Asian, and North African. The European population can be further sub-divided into sub-populations including North-Western European, Southern European, and Ashkenazi Jewish populations. The North-Western European population can be further sub-divided into national populations including English, Irish, German, Finnish, and the like.

The East Asian population can be further sub-divided into Chinese, Japanese, and Korean subpopulations. The South Asian population can be further sub-divided into Indian and Pakistani populations. The Indian population can be further sub-divided into Dravidian people, Brahui people, Kannadigas, Malayalis, Tamils, Telugus, Tuluvas, and Gonds. A subpopulation may serve as a population for the purpose of identifying a causal genetic variant.

In some embodiments, a causal genetic variant is associated with a disease, such as a rare genetic disease. Examples of diseases with which a causal genetic variant may be associated include, but are not limited to: 21-Hydroxylase Deficiency, ABCC8-Related Hyperinsulinism, ARSACS, Achondroplasia, Achromatopsia, Adenosine Monophosphate Deaminase 1, Agenesis of Corpus Callosum with Neuronopathy, Alkaptonuria, Alpha-1-Antitrypsin Deficiency, Alpha-Mannosidosis, Alpha-Sarcoglycanopathy, Alpha-Thalassemia, Alzheimers, Angiotensin II Receptor, Type I, Apolipoprotein E Genotyping, Argininosuccinicaciduria, Aspartylglycosaminuria, Ataxia with Vitamin E Deficiency, Ataxia-Telangiectasia, Autoimmune Polyendocrinopathy Syndrome Type 1, BRCA1 Hereditary Breast/Ovarian Cancer, BRCA2 Hereditary Breast/Ovarian Cancer, one or more other types of cancer, Bardet-Biedl Syndrome, Best Vitelliform Macular Dystrophy, Beta-Sarcoglycanopathy, Beta-Thalassemia, Biotinidase Deficiency, Blau Syndrome, Bloom Syndrome, CFTR-Related Disorders, CLN3-Related Neuronal Ceroid-Lipofuscinosis, CLN5-Related Neuronal Ceroid-Lipofuscinosis, CLN8-Related Neuronal Ceroid-Lipofuscinosis, Canavan Disease, Carnitine Palmitoyltransferase IA Deficiency, Carnitine Palmitoyltransferase II Deficiency, Cartilage-Hair Hypoplasia, Cerebral Cavernous Malformation, Choroideremia, Cohen Syndrome, Congenital Cataracts, Facial Dysmorphism, and Neuropathy, Congenital Disorder of Glycosylationla, Congenital Disorder of Glycosylation Ib, Congenital Finnish Nephrosis, Crohn Disease, Cystinosis, DFNA 9 (COCH), Diabetes and Hearing Loss, Early-Onset Primary Dystonia (DYTI), Epidermolysis Bullosa Junctional, Herlitz-Pearson Type, FANCC-Related Fanconi Anemia, FGFR1-Related Craniosynostosis, FGFR2-Related Craniosynostosis, FGFR3-Related Craniosynostosis, Factor V Leiden Thrombophilia, Factor V R2 Mutation Thrombophilia, Factor XI Deficiency, Factor XIII Deficiency, Familial Adenomatous Polyposis, Familial Dysautonomia, Familial Hypercholesterolemia Type B, Familial Mediterranean Fever, Free Sialic Acid Storage Disorders, Frontotemporal Dementia with Parkinsonism-17, Fumarase deficiency, GJB2-Related DFNA 3 Nonsyndromic Hearing Loss and Deafness, GJB2-Related DFNB 1 Nonsyndromic Hearing Loss and Deafness, GNE-Related Myopathies, Galactosemia, Gaucher Disease, Glucose-6-Phosphate Dehydrogenase Deficiency, Glutaricacidemia Type 1, Glycogen Storage Disease Type 1a, Glycogen Storage Disease Type 1b, Glycogen Storage Disease Type II, Glycogen Storage Disease Type III, Glycogen Storage Disease Type V, Gracile Syndrome, HFE-Associated Hereditary Hemochromatosis, Halder AIMs, Hemoglobin S Beta-Thalassemia, Hereditary Fructose Intolerance, Hereditary Pancreatitis, Hereditary Thymine-Uraciluria, Hexosaminidase A Deficiency, Hidrotic Ectodermal Dysplasia 2, Homocystinuria Caused by Cystathionine Beta-Synthase Deficiency, Hyperkalemic Periodic Paralysis Type 1, Hyperornithinemia-Hyperammonemia-Homocitrullinuria Syndrome, Hyperoxaluria, Primary, Type 1, Hyperoxaluria, Primary, Type 2, Hypochondroplasia, Hypokalemic Periodic Paralysis Type 1, Hypokalemic Periodic Paralysis Type 2, Hypophosphatasia, Infantile Myopathy and Lactic Acidosis (Fatal and Non-Fatal Forms), Isovaleric Acidemias, Krabbe Disease, LGMD2I, Leber Hereditary Optic Neuropathy, Leigh Syndrome, French-Canadian Type, Long Chain 3-Hydroxyacyl-CoA Dehydrogenase Deficiency, MELAS, MERRF, MTHFR Deficiency, MTHFR Thermolabile Variant, MTRNR1-Related Hearing Loss and Deafness, MTTS1-Related Hearing Loss and Deafness, MYH-Associated Polyposis, Maple Syrup Urine Disease Type 1A, Maple Syrup Urine Disease Type 1B, McCune-Albright Syndrome, Medium Chain Acyl-Coenzyme A Dehydrogenase Deficiency, Megalencephalic Leukoencephalopathy with Subcortical Cysts, Metachromatic Leukodystrophy, Mitochondrial Cardiomyopathy, Mitochondrial DNA-Associated Leigh Syndrome and NARP, Mucolipidosis IV, Mucopolysaccharidosis Type I, Mucopolysaccharidosis Type IIIA, Mucopolysaccharidosis Type VII, Multiple Endocrine Neoplasia Type 2, Muscle-Eye-Brain Disease, Nemaline Myopathy, Neurological phenotype, Niemann-Pick Disease Due to Sphingomyelinase Deficiency, Niemann-Pick Disease Type C1, Nijmegen Breakage Syndrome, PPT1-Related Neuronal Ceroid-Lipofuscinosis, PROP1-related pituitary hormome deficiency, Pallister-Hall Syndrome, Paramyotonia Congenita, Pendred Syndrome, Peroxisomal Bifunctional Enzyme Deficiency, Pervasive Developmental Disorders, Phenylalanine Hydroxylase Deficiency, Plasminogen Activator Inhibitor I, Polycystic Kidney Disease, Autosomal Recessive, Prothrombin G20210A Thrombophilia, Pseudovitamin D Deficiency Rickets, Pycnodysostosis, Retinitis Pigmentosa, Autosomal Recessive, Bothnia Type, Rett Syndrome, Rhizomelic Chondrodysplasia Punctata Type 1, Short Chain Acyl-CoA Dehydrogenase Deficiency, Shwachman-Diamond Syndrome, Sjogren-Larsson Syndrome, Smith-Lemli-Opitz Syndrome, Spastic Paraplegia 13, Sulfate Transporter-Related Osteochondrodysplasia, TFR2-Related Hereditary Hemochromatosis, TPP1-Related Neuronal Ceroid-Lipofuscinosis, Thanatophoric Dysplasia, Transthyretin Amyloidosis, Trifunctional Protein Deficiency, Tyrosine Hydroxylase-Deficient DRD, Tyrosinemia Type I, Wilson Disease, X-Linked Juvenile Retinoschisis, and Zellweger Syndrome Spectrum.

In some embodiments, sequence B of one or more of the plurality of first oligonucleotides or the target sequence to which it specifically hybridizes comprises a non-subject sequence. In some embodiments, sequence B or the target sequence to which it specifically hybridizes is within about, less than about, or more than about 1, 2, 3, 4, 5, 6, 7, 8, 9, 10, 15, 20, 25, 30, 35, 40, 45, 50, 60, 70, 80, 90, 100, 200, 500 or more nucleotides of a non-subject sequence. In general, a non-subject sequence corresponds to a polynucleotide derived from an organism other than the individual being tested, such as DNA or RNA from bacteria, archaea, viruses, protists, fungi, or other organism. A non-subject sequence may be indicative of the identity of an organism or class of organisms, and may further be indicative of a disease state, such as infection. An example of non-subject sequences useful in identifying an organism include, without limitation, rRNA sequences, such as 16s rRNA sequences (see e.g. WO2010151842). In some embodiments, non-subject sequences are analyzed instead of, or separately from causal genetic variants. In some embodiments, causal genetic variants and non-subject sequences are analyzed in parallel, such as in the same sample (e.g. using a mixture of first oligonucleotides, some with a sequence B that specifically hybridizes to a sequence comprising or near a causal genetic variant, and some with a sequence B that specifically hybridizes to a sequence comprising or near a non-subject sequence) and/or in the same report.

In some embodiments, sequence B of one or more of the plurality of first oligonucleotides or the target sequence to which it specifically hybridizes comprises an ancestry informative marker (AIM). In some embodiments, sequence B or the target sequence to which it specifically hybridizes is within about, less than about, or more than about 1, 2, 3, 4, 5, 6, 7, 8, 9, 10, 15, 20, 25, 30, 35, 40, 45, 50, 60, 70, 80, 90, 100, 200, 500 or more nucleotides of an AIM. In general, an AIM is a genetic variant that differs in frequency between two or more populations of individuals, such as two or more human populations, and may be used to infer the ancestry of a subject, either alone or in combination with one or more other AIMs. An AIM may be used to classify a person as belonging to or not belonging to one or more populations, such as a population that is at increased risk for one of the causal genetic variants. For example, an AIM can be diagnostic for a population in which a trait is at increased prevalence. In certain instances the AIM may distinguish between populations with finer granularity, for example, between sub-continental groups or related ethnic groups. In some embodiments, AIMs are analyzed instead of, or separately from causal genetic variants and/or non-subject sequences. In some embodiments, AIMs, causal genetic variants, and/or non-subject sequences are analyzed in parallel, such as in the same sample (e.g. using a mixture of first oligonucleotides, some with a sequence B that specifically hybridizes to a sequence comprising or near a causal genetic variant, and some with a sequence B that specifically hybridizes to a sequence comprising or near an AIM) and/or in the same report. Non-limiting examples of types of AIMs include single nucleotide polymorphisms (SNP), deletion/insertion polymorphisms (DIP), copy number variants (CNV), short tandem repeats (STR), restriction fragment length polymorphisms (RFLP), simple sequence repeats (SSR), variable number of tandem repeats (VNTR), randomly amplified polymorphic DNA (RAPD), amplified fragment length polymorphisms (AFLP), inter-retrotransposon amplified polymorphisms (IRAP), long and short interspersed elements (LINE/SINE), long tandem repeats (LTR), mobile elements, retrotransposon microsatellite amplified polymorphisms, retrotransposon-based insertion polymorphisms, sequence specific amplified polymorphism, and heritable epigenetic modification (for example, DNA methylation). AIMs can also be sequence variations in RNA polynucleotides. Some AIMs can also be indicated by the presence or the concentration of a species of RNA polynucleotides. Some AIMs can also be sequence variations in protein polypeptides. Some AIMs can also be indicated by the presence or absence of a species of protein polypeptides. A number of ancestry informative markers are identified in FIG. 9. Other AIMs are described in US 2007/0037182. An AIM may or may not also be a causal genetic variant. For example, the Duffy Null (FY*0) genetic variant causes an absence of a blood antigen. This variant is at nearly 100% frequency in sub-Saharan African populations and at nearly 0% frequency in populations outside of sub-Saharan Africa. Many causal genetic variants associated with pigmentation are also AIMs. AIMs that are not causal genetic variants can be indirectly associated with traits caused by other AIMs.

AIMs can be discovered by determining the frequency of genetic variants in a plurality of populations. This may be achieved by determining the frequency of already known variants in individuals from various populations. It may also be achieved intrinsically during the process of variant discovery. Both tasks were undertaken by the International HapMap project, which catalogued SNP polymorphisms. Ancestry informative markers can be ranked by a variety of measurements which judge their predictive power. One measurement is Wright's F-statistic, called Fst or FST. This variable is known by other names, including Fixation index. Another metric for ranking AIMs is informativeness. Another method of ranking AIMs is the PCA-correlated SNPs method of Paschou et al. (Paschou et al. PCA-correlated SNPs for structure identification in worldwide human populations. PLoS Genet (2007) vol. 3 (9) pp. 1672-86).

To achieve a pre-selected degree of confidence (e.g. at least about 80%, 85%, 90%, 95%, 97.5%, 99%, or more) in ancestry inference on the basis of ancestry informative markers, and to achieve ancestry inference for a plurality of populations, it may be necessary to examine more than one ancestry informative marker. A sufficiently large panel of randomly selected genetic variants can be used to infer ancestry (e.g. about or more than about 5, 10, 15, 25, 50, 100, 250, 500, 1000, 2500, 5000, or more AIMs). A targeted set of especially appropriate AIMs can be constructed. Many researchers have published lists of suggested ancestry informative markers (for example: Seldin et al. Application of ancestry informative markers to association studies in European Americans. PLoS Genet (2008) vol. 4 (1) pp. e5; Halder et al. A panel of ancestry informative markers for estimating individual bio-geographical ancestry and admixture from four continents: utility and applications. Hum Mutat (2008) vol. 29 (5) pp. 648-58; Tian et al. Analysis and application of European genetic substructure using 300 K SNP information. PLoS Genet (2008) vol. 4 (1) pp. e4; Price et al. Discerning the ancestry of European Americans in genetic association studies. PLoS Genet (2008) vol. 4 (1) pp. e236; Paschou et al. PCA-correlated SNPs for structure identification in worldwide human populations. PLoS Genet (2007) vol. 3 (9) pp. 1672-86; and Bauchet et al. Measuring European population stratification with microarray genotype data. Am J Hum Genet (2007) vol. 80 (5) pp. 948-56). These and similar lists can be used to build a panel of AIMs for which a device or method herein can be configured to test for.

In some embodiments, a plurality of second nucleotides and a plurality of third nucleotides are attached to the solid support in addition to the plurality of first nucleotides. In some embodiments, the second nucleotides all comprise sequence A at the 3' end, where sequence A in the plurality of second oligonucleotides is the same as sequence A in all of the first oligonucleotides. In some embodiments, the third oligonucleotides comprise sequence C at the 3' end, where sequence C is complementary to a sequence shared by a plurality of different target polynucleotides. In some embodiments, extension of a first oligonucleotide along a target polynucleotide serving as a template generates an extension product comprising sequence C', which is complementary and specifically hybridizable to sequence C. In some embodiments, the amount of the plurality of second oligonucleotides exposed to the solid support is about, less than about, or more than about 10-fold, 50-fold, 100-fold, 1000-fold, 5000-fold, 7500-fold, 10000-fold, 12500-fold, 15000-fold, 20000-fold, 50000-fold, 100000-fold, or more higher than the amount of the plurality of first oligonucleotides exposed to the solid support, such as in a reaction for attached the plurality of oligonucleotides to the solid support. In some embodiments, the ratio (or the inverse ratio) of the amount of the plurality of second oligonucleotides to the amount of third oligonucleotides exposed to the solid support is about, less than about, or more than about 1:1, 2:1, 3:1, 4:1, 5:1, 6:1, 7:1, 8:1, 9:1, 10:1, or more. In some embodiments, the plurality of first oligonucleotides is added to the solid support at a concentration of about, less than about, or more than about 0.5 pM, 1 pM, 5 pM, 10 pM, 25 pM, 50 pM, 75 pM, 100 pM, 200 pM, 500 pM, 1 nM, 10 nM, 100 nM, 500 nM, or higher. In some embodiments, the concentration of the plurality of second oligonucleotides and/or the third oligonucleotides is about, less than about, or more than about 0.5 nM, 1 nM, 5 nM, 10 nM, 25 nM, 50 nM, 75 nM, 100 nM, 200 nM, 500 nM, 1 μM, 5 μM, 10 μM, 25 μM, 50 μM, 100 μM, 500 μM, or higher.

In some embodiments, one or more the plurality of oligonucleotides comprise one or more blocking groups. In general, a blocking group is any modification that prevents extension of a 3' end of an oligonucleotide, such as by a polymerase, a ligase, and/or other enzymes. A blocking group may be added before or after an oligonucleotide is attached to the solid support. In some embodiments, a blocking group is added during an amplification or sequencing process. Examples of blocking groups include, but are not limited to, alkyl groups, non-nucleotide linkers, phosphorothioate, alkane-diol residues, peptide nucleic acid, and nucleotide derivatives lacking a 3'-OH, including, for example, cordycepin.

In some embodiments, one or more of the oligonucleotides attached to the substrate comprise a cleavage site, such that cleavage at that site releases all or a portion of the cleaved polynucleotide from attachment to the solid support. In some embodiments, cleavage produces a 3' end that may be extended along a polynucleotide template. In some embodiments, only a portion of the plurality of first, second, and/or third oligonucleotides comprise a cleavage site (e.g. about, less than about, or more than about 10%, 20%, 30%, 40%, 50%, 60%, 70%, 80%, 90%, or more). The cleavage site may be cleavable by any suitable means, including but not limited to chemical, enzymatic, and photochemical cleavage. The cleavage groups may be positioned between the first nucleotide and the solid support, or at or after any number of nucleotides in the oligonucleotide, such as about, less than about, or more than about 1, 2, 3, 4, 5, 6, 7, 8, 9, 10, 11, 12, 13, 14, 15, 20, or more nucleotides from the point of attachment to the solid support.

Processes for chemical, enzymatic, and photochemical cleavage, and cleavage sites cleaved by such processes are known in the art. Examples of cleavage means include, but are not limited to, restriction enzyme digestion, in which case the cleavage site is an appropriate restriction site for the enzyme which directs cleavage of one or both strands of a duplex template; RNase digestion or chemical cleavage of a bond between a deoxyribonucleotide and a ribonucleotide, in which case the cleavage site may include one or more ribonucleotides; chemical reduction of a disulphide linkage with a reducing agent (e.g. TCEP), in which case the cleavage site should include an appropriate disulphide linkage; chemical cleavage of a diol linkage with periodate, in which case the cleavage site should include a diol linkage; generation of an abasic site and subsequent hydrolysis. Cleavage may be followed by blocking to produce a 3' end that cannot be extended, such as by a polymerase, a ligase, and/or other enzymes. An example of a blocking agents include, but are not limited to amines (e.g. ethanolamine), which may be added before, during, or after the addition of a cleaving agent. Additional non-limiting examples of cleavage processes and cleavage sites are described in US20120053074, which is incorporated by reference in its entirety.

In some embodiments, a plurality of target polynucleotides are amplified according to a method that comprises exposing a sample comprising a plurality of target polynucleotides to an apparatus of the invention. In some embodiments, the amplification process comprises bridge amplification. General methods for conducting standard bridge amplification are known in the art. By way of example, WO/1998/044151 and WO/2000/018957 both describe methods of nucleic acid amplification which allow amplification products to be immobilized on a solid support in order to form arrays comprised of clusters or "colonies" formed from a plurality of identical immobilized polynucleotide strands and a plurality of identical immobilized complementary strands. In some embodiments, a plurality of polynucleotides are sequenced according to a method that comprises exposing a sample comprising a plurality of target polynucleotides to an apparatus of the invention. General methods for conducting sequencing using a plurality of oligonucleotides attached to a solid support are known in the art, such as methods disclosed in US20120053074 and US20110223601, which are hereby incorporated by reference in their entirety. Non-limiting, exemplary methods for amplifying and/or sequencing target polynucleotides in accordance with the methods and apparatuses of the invention are provided herein. In general, amplification of specific target polynucleotides permits the generation of sequencing data that is enriched for target polynucleotides, such as target genomic sequences, relative to non-target polynucleotides. In some embodiments, the enrichment of sequencing data for target polynucleotides (especially sequencing data for causal genetic variants) relative to non-target polynucleotides is about or at least about 10-fold, 100-fold, 500-fold, 1000-fold, 5000-fold, 10000-fold, 50000-fold, 100000-fold, 1000000-fold, or more.

Non-limiting examples of substrates comprising oligonucleotides, methods for their production, and systems and methods for their operation are provided in WO/2008/002502, which in hereby incorporated by reference in its entirety.

In one aspect, the invention provides a method for sequencing a plurality of target polynucleotides in a sample. In one embodiment, the method comprises: (a) fragmenting target polynucleotides to produce fragmented polynucleotides; (b) joining adapter oligonucleotides to the fragmented polynucleotides, each of the adapter oligonucleotides comprising sequence D, to produce adapted polynucleotides comprising sequence D hybridized to complementary sequence D' at both ends of the adapted polynucleotides, optionally wherein sequence D' is produced by extension of a target polynucleotide 3' end; (c) amplifying the adapted polynucleotides using amplification primers comprising sequence C, sequence D, and a barcode associated with the sample, wherein sequence D is positioned at the 3' end of the amplification primers; (d) hybridizing amplified target polynucleotides to a plurality of different first oligonucleotides that are attached to a solid surface; (e) performing bridge amplification on a solid surface; and (f) sequencing a plurality of polynucleotides from step (e). The solid surface may comprise a plurality of oligonucleotides as described herein, including an apparatus as described herein and optionally produced according to the methods described herein. In some embodiments, the solid surface comprises (i) a plurality of different first oligonucleotides comprising sequence A and sequence B, wherein sequence A is common among all first oligonucleotides; and further wherein sequence B is different for each different first oligonucleotide, is at the 3' end of each first oligonucleotide, and is complementary to a sequence comprising a causal genetic variant or a sequence within 200 nucleotides of a causal genetic variant; (ii) a plurality of second oligonucleotides comprising sequence A at each 3' end; and (iii) a plurality of third oligonucleotides comprising sequence C at each 3' end. In some embodiments, one or more of sequences A, B, C, and D are different sequences. In some embodiments, one or more of sequences A, B, C, and D are about, less than about, or more than about 5%, 10%, 15%, 20%, 25%, 30%, 40%, 50%, 60%, 70%, 80%, 90%, or more different from one or more of the other of sequences A, B, C, and D (e.g. have less than about 10%, 20%, 30%, 40%, 50%, 60%, 70%, 80%, 90%, or more sequence identity). In some embodiments, one or more of sequences A, B, C, and D comprise about, less than about, or more than about 1, 2, 3, 4, 5, 6, 7, 8, 9, 10, 15, 20, or more nucleotides each.

Samples from which the target polynucleotides are derived can comprise multiple samples from the same individual, samples from different individuals, or combinations thereof. In some embodiments, a sample comprises a plurality of polynucleotides from a single individual. In some embodiments, a sample comprises a plurality of polynucleotides from two or more individuals. An individual is any organism or portion thereof from which target polynucleotides can be derived, non-limiting examples of which include plants, animals, fungi, protists, monerans, viruses, mitochondria, and chloroplasts. Sample polynucleotides can be isolated from a subject, such as a cell sample, tissue sample, fluid sample, or organ sample derived therefrom (or cell cultures derived from any of these), including, for example, cultured cell lines, biopsy, blood sample, cheek swab, or fluid sample containing a cell (e.g. saliva). The subject may be an animal, including but not limited to, a cow, a pig, a mouse, a rat, a chicken, a cat, a dog, etc., and is usually a mammal, such as a human. Samples can also be artificially derived, such as by chemical synthesis. In some embodiments, samples comprise DNA. In some embodiments, samples comprise genomic DNA. In some embodiments, samples comprise mitochondrial DNA, chloroplast DNA, plasmid DNA, bacterial artificial chromosomes, yeast artificial chromosomes, oligonucleotide tags, polynucleotides from an organism (e.g. bacteria, virus, or fungus) other than the subject from whom the sample is taken, or combinations thereof. In some embodiments, the samples comprise DNA generated by amplification, such as by primer extension reactions using any suitable combination of primers and a DNA polymerase, including but not limited to polymerase chain reaction (PCR), reverse transcription, and combinations thereof. Where the template for the primer extension reaction is RNA, the product of reverse transcription is referred to as complementary DNA (cDNA). Primers useful in primer extension reactions can comprise sequences specific to one or more targets, random sequences, partially random sequences, and combinations thereof. Reaction conditions suitable for primer extension reactions are known in the art. In general, sample polynucleotides comprise any polynucleotide present in a sample, which may or may not include target polynucleotides. In some embodiments, a sample from a single individual is divided into multiple separate samples (e.g. 2, 3, 4, 5, 6, 7, 8, 9, 10, or more separate samples) that are subjected to the methods of the invention independently, such as analysis in duplicate, triplicate, quadruplicate, or more.

Methods for the extraction and purification of nucleic acids are well known in the art. For example, nucleic acids can be purified by organic extraction with phenol, phenol/chloroform/isoamyl alcohol, or similar formulations, including TRIzol and TriReagent. Other non-limiting examples of extraction techniques include: (1) organic extraction followed by ethanol precipitation, e.g., using a phenol/chloroform organic reagent (Ausubel et al., 1993), with or without the use of an automated nucleic acid extractor, e.g., the Model 341 DNA Extractor available from Applied Biosystems (Foster City, Calif.); (2) stationary phase adsorption methods (U.S. Pat. No. 5,234,809; Walsh et al., 1991); and (3) salt-induced nucleic acid precipitation methods (Miller et al., (1988), such precipitation methods being typically referred to as "salting-out" methods. Another example of nucleic acid isolation and/or purification includes the use of magnetic particles to which nucleic acids can specifically or non-specifically bind, followed by isolation of the beads using a magnet, and washing and eluting the nucleic acids from the beads (see e.g. U.S. Pat. No. 5,705,628). In some embodiments, the above isolation methods may be preceded by an enzyme digestion step to help eliminate unwanted protein from the sample, e.g., digestion with proteinase K, or other like proteases. See, e.g., U.S. Pat. No. 7,001,724. If desired, RNase inhibitors may be added to the lysis buffer. For certain cell or sample types, it may be desirable to add a protein denaturation/digestion step to the protocol. Purification methods may be directed to isolate DNA, RNA, or both. When both DNA and RNA are isolated together during or subsequent to an extraction procedure, further steps may be employed to purify one or both separately from the other. Sub-fractions of extracted nucleic acids can also be generated, for example, purification by size, sequence, or other physical or chemical characteristic. In addition to an initial nucleic acid isolation step, purification of nucleic acids can be performed after any step in the methods of the invention, such as to remove excess or unwanted reagents, reactants, or products. Methods for determining the amount and/or purity of nucleic acids in a sample are known in the art, and include absorbance (e.g. absorbance of light at 260 nm, 280 nm, and a ratio of these) and detection of a label (e.g. fluorescent dyes and intercalating agents, such as SYBR green, SYBR blue, DAPI, propidium iodine, Hoechst stain, SYBR gold, ethidium bromide).

In some embodiments, target polynucleotides are fragmented into a population of fragmented polynucleotides of one or more specific size range(s). In some embodiments, the amount of sample polynucleotides subjected to fragmentation is about, less than about, or more than about 50 ng, 100 ng, 200 ng, 300 ng, 400 ng, 500 ng, 600 ng, 700 ng, 800 ng, 900 ng, 1000 ng, 1500 ng, 2000 ng, 2500 ng, 5000 ng, 10 µg, or more. In some embodiments, fragments are generated from about, less than about, or more than about 1, 10, 100, 1000, 10000, 100000, 300000, 500000, or more genome-equivalents of starting DNA. Fragmentation may be accomplished by methods known in the art, including chemical, enzymatic, and mechanical fragmentation. In some embodiments, the fragments have an average or median length from about 10 to about 10,000 nucleotides. In some embodiments, the fragments have an average or median length from about 50 to about 2,000 nucleotides. In some embodiments, the fragments have an average or median length of about, less than about, more than about, or between about 100-2500, 200-1000, 10-800, 10-500, 50-500, 50-250, or 50-150 nucleotides. In some embodiments, the fragments have an average or median length of about, less than about, or more than about 200, 300, 500, 600, 800, 1000, 1500 or more nucleotides. In some embodiments, the fragmentation is accomplished mechanically comprising subjecting sample polynucleotides to acoustic sonication. In some embodiments, the fragmentation comprises treating the sample polynucleotides with one or more enzymes under conditions suitable for the one or more enzymes to generate double-stranded nucleic acid breaks. Examples of enzymes useful in the generation of polynucleotide fragments include sequence specific and non-sequence specific nucleases. Non-limiting examples of nucleases include DNase I, Fragmentase, restriction endonucleases, variants thereof, and combinations thereof. For example, digestion with DNase I can induce random double-stranded breaks in DNA in the absence of $Mg^{++}$ and in the presence of $Mn^{++}$. In some embodiments, fragmentation comprises treating the sample polynucleotides with one or more restriction endonucleases. Fragmentation can produce fragments having 5' overhangs, 3' overhangs, blunt ends, or a combination thereof. In some embodiments, such as when fragmentation comprises the use of one or more restriction endonucleases, cleavage of sample polynucleotides leaves overhangs having a predictable sequence. In some embodiments, the method includes the step of size selecting the fragments via standard methods such as column purification or isolation from an agarose gel. In some embodiments, the method comprises determining the average and/or median fragment length after fragmentation. In some embodiments, samples having an average and/or median fragment length above a desired threshold are again subjected to fragmentation. In some embodiments, samples having an average and/or median fragment length below a desired threshold are discarded.

In some embodiments, the 5' and/or 3' end nucleotide sequences of fragmented polynucleotides are not modified prior to ligation with one or more adapter oligonucleotides (also referred to as "adapters"). For example, fragmentation by a restriction endonuclease can be used to leave a predictable overhang, followed by ligation with one or more adapter oligonucleotides comprising an overhang complementary to the predictable overhang on a polynucleotide fragment. In another example, cleavage by an enzyme that leaves a predictable blunt end can be followed by ligation of blunt-ended polynucleotide fragments to adapter oligonucleotides comprising a blunt end. In some embodiments, the fragmented polynucleotides are blunt-end polished (or "end repaired") to produce polynucleotide fragments having blunt ends, prior to being joined to adapters. The blunt-end polishing step may be accomplished by incubation with a suitable enzyme, such as a DNA polymerase that has both 3' to 5' exonuclease activity and 5' to 3' polymerase activity, for example T4 polymerase. In some embodiments, end repair is followed by or concludes with addition of 1, 2, 3, 4, 5, 6, 7, 8, 9, 10, 11, 12, 13, 14, 15, 16, 17, 18, 19, 20 or more nucleotides, such as one or more adenine ("A tailing"), one or more thymine, one or more guanine, or one or more cytosine, to produce an overhang. Polynucleotide fragments having an overhang can be joined to one or more adapter oligonucleotides having a complementary overhang, such as in a ligation reaction. For example, a single adenine can be added to the 3' ends of end repaired polynucleotide fragments using a template independent polymerase, followed by ligation to one or more adapters each having an overhanging thymine at a 3' end. In some embodiments, adapter oligonucleotides can be joined to blunt end double-stranded DNA fragment molecules which have been modified by extension of the 3' end with one or more nucleotides followed by 5' phosphorylation. In some cases, extension of the 3' end may be performed with a polymerase such as for example Klenow polymerase or any other suitable polymerases known in the art, or by use of a terminal deoxynucleotide transferase, in the presence of one or more dNTPs in a suitable buffer containing magnesium. In some embodiments, target polynucleotides having blunt ends are joined to one or more adapters comprising a blunt end. Phosphorylation of 5' ends of fragmented polynucleotides may be performed for example with T4 polynucleotide kinase in a suitable buffer containing ATP and magnesium. The fragmented polynucleotides may optionally be treated to dephosphorylate 5' ends or 3' ends, for example, by using enzymes known in the art, such as phosphatases.

In some embodiments, fragmentation is followed by ligation of adapter oligonucleotides to the fragmented polynucleotides. An adapter oligonucleotide includes any oligonucleotide having a sequence, at least a portion of which is known, that can be joined to a target polynucleotide. Adapter oligonucleotides can comprise DNA, RNA, nucleotide analogues, non-canonical nucleotides, labeled nucleotides, modified nucleotides, or combinations thereof. Adapter oligonucleotides can be single-stranded, double-stranded, or partial duplex. In general, a partial-duplex adapter comprises one or more single-stranded regions and one or more double-stranded regions. Double-stranded adapters can comprise two separate oligonucleotides hybridized to one another (also referred to as an "oligonucleotide duplex"), and hybridization may leave one or more blunt ends, one or more 3' overhangs, one or more 5' overhangs, one or more bulges resulting from mismatched and/or unpaired nucleotides, or any combination of these. In some embodiments, a single-stranded adapter comprises two or more sequences that are able to hybridize with one another. When two such hybridizable sequences are contained in a single-stranded adapter, hybridization yields a hairpin structure (hairpin adapter). When two hybridized regions of an adapter are separated from one another by a non-hybridized region, a "bubble" structure results. Adapters comprising a bubble structure can consist of a single adapter oligonucleotide comprising internal hybridizations, or may comprise two or more adapter oligonucleotides hybridized to one another. Internal sequence hybridization, such as between two hybridizable sequences in an adapter, can produce a double-stranded structure in a single-stranded adapter oligonucleotide. Adapters of different kinds can be used in combination, such as a hairpin adapter and a double-stranded adapter, or adapters of different sequences. Different adapters can be joined to target polynucleotides in sequential reactions or simultaneously. In some embodiments, identical adapters are added to both ends of a target polynucleotide. For example, first and second adapters can be added to the same reaction. Adapters can be manipulated prior to combining with target polynucleotides. For example, terminal phosphates can be added or removed.

In some embodiments, an adapter is a mismatched adapter formed by annealing two partially complementary polynucleotide strands so as to provide, when the two strands are annealed, at least one double-stranded region and at least one unmatched region. The "double-stranded region" of the adapter is a short double-stranded region, typically comprising 5 or more consecutive base pairs, formed by annealing of the two partially complementary polynucleotide strands. This term simply refers to a double-stranded region of nucleic acid in which the two strands are annealed and does not imply any particular structural conformation. In some embodiments, the double-stranded region is about, less than about, or more than about 5, 10, 15, 20, 25, 30, or more nucleotides in length. Generally it is advantageous for the double-stranded region of a mismatched adapter to be as short as possible without loss of function. By "function" in this context is meant that the double-stranded region form a stable duplex under standard reaction conditions for an enzyme-catalyzed nucleic acid ligation reaction, which conditions are known to those skilled in the art (e.g. incubation at a temperature in the range of from 4° C. to 25° C. in a ligation buffer appropriate for the enzyme), such that the two strands forming the adapter remain partially annealed during ligation of the adapter to a target molecule. It is not absolutely necessary for the double-stranded region to be stable under the conditions typically used in the annealing steps of primer extension or PCR reactions. Typically, the double-stranded region is adjacent to the "ligatable" end of the adapter, i.e. the end that is joined to a target polynucleotide in a ligation reaction. The ligatable end of the adapter may be blunt or, in other embodiments, short 5' or 3' overhangs of one or more nucleotides may be present to facilitate/promote ligation. The 5' terminal nucleotide at the ligatable end of the adapter is typically phosphorylated to enable phosphodiester linkage to a 3' hydroxyl group on a sample polynucleotide. The term "unmatched region" refers to a region of the adapter wherein the sequences of the two polynucleotide strands forming the adapter exhibit a degree of non-complementarity such that the two strands are not capable of annealing to each other under standard annealing conditions for a primer extension or PCR reaction. The two strands in the unmatched region may exhibit some degree of annealing under standard reaction conditions for an enzyme-catalyzed ligation reaction, provided that the two strands revert to single stranded form under annealing conditions.

Adapter oligonucleotides can contain one or more of a variety of sequence elements, including but not limited to, one or more amplification primer annealing sequences or complements thereof, one or more sequencing primer annealing sequences or complements thereof, one or more barcode sequences, one or more common sequences shared among multiple different adapters or subsets of different adapters, one or more restriction enzyme recognition sites, one or more overhangs complementary to one or more target polynucleotide overhangs, one or more probe binding sites (e.g. for attachment to a sequencing platform, such as a flow cell for massive parallel sequencing, such as an apparatus as described herein, or flow cells as developed by Illumina, Inc.), one or more random or near-random sequences (e.g. one or more nucleotides selected at random from a set of two or more different nucleotides at one or more positions, with each of the different nucleotides selected at one or more positions represented in a pool of adapters comprising the random sequence), and combinations thereof. Two or more sequence elements can be non-adjacent to one another (e.g. separated by one or more nucleotides), adjacent to one another, partially overlapping, or completely overlapping. For example, an amplification primer annealing sequence can also serve as a sequencing primer annealing sequence. Sequence elements can be located at or near the 3' end, at or near the 5' end, or in the interior of the adapter oligonucleotide. When an adapter oligonucleotide is capable of forming secondary structure, such as a hairpin, sequence elements can be located partially or completely outside the secondary structure, partially or completely inside the secondary structure, or in between sequences participating in the secondary structure. A sequence element may be of any suitable length, such as about, less than about, or more than about 3, 4, 5, 6, 7, 8, 9, 10, 15, 20, 25, 30, 35, 40, 45, 50 or more nucleotides in length. Adapter oligonucleotides can have any suitable length, at least sufficient to accommodate the one or more sequence elements of which they are comprised. In some embodiments, adapters are about, less than about, or more than about 10, 15, 20, 25, 30, 35, 40, 45, 50, 55, 60, 65, 70, 75, 80, 90, 100, 200, or more nucleotides in length In some embodiments, the adapter oligonucleotides joined to fragmented polynucleotides from one sample comprise one or more sequences common to all adapter oligonucleotides and a barcode that is unique to the adapters joined to polynucleotides of that particular sample, such that the barcode sequence can be used to distinguish polynucleotides originating from one sample or adapter joining reaction from polynucleotides originating from another sample or adapter joining reaction. In some embodiments, an adapter oligonucleotide comprises a 5' overhang, a 3' overhang, or both that is complementary to one or more target polynucleotide overhangs. Complementary overhangs can be one or more nucleotides in length, including but not limited to 1, 2, 3, 4, 5, 6, 7, 8, 9, 10, 11, 12, 13, 14, 15, or more nucleotides in length. Complementary overhangs may comprise a fixed sequence. Complementary overhangs of an adapter oligonucleotide may comprise a random sequence of one or more nucleotides, such that one or more nucleotides are selected at random from a set of two or more different nucleotides at one or more positions, with each of the different nucleotides selected at one or more positions represented in a pool of adapters with complementary overhangs comprising the random sequence. In some embodiments, an adapter overhang is complementary to a target polynucleotide overhang produced by restriction endonuclease digestion. In some embodiments, an adapter overhang consists of an adenine or a thymine.

In some embodiments, adapter oligonucleotides comprise one strand comprising the sequence element sequence D. In some embodiments, adapter oligonucleotides comprise sequence D hybridized to complementary sequence D', where sequence D' is on the same or different strand as sequence D. In some embodiments, the 3' end of a target polynucleotide is extended along an adapter oligonucleotide to generate complementary sequence D'. In a preferred embodiment, fragmented polynucleotides and adapter oligonucleotides are combined and treated (e.g. by ligation and optionally by fragment extension) to produce double-stranded, adapted polynucleotides comprising fragmented polynucleotide sequence joined to adapter oligonucleotide sequences at both ends, where both ends of the adapted polynucleotides comprise sequence D hybridized to sequence D'. In some embodiments, the amount of fragmented polynucleotides subjected to adapter joining is about, less than about, or more than about 50 ng, 100 ng, 200 ng, 300 ng, 400 ng, 500 ng, 600 ng, 700 ng, 800 ng, 900 ng, 1000 ng, 1500 ng, 2000 ng, 2500 ng, 5000 ng, 10 μg, or more (e.g. a threshold amount). In some embodiments, the amount of fragmented polynucleotides is determined before proceeding with adapter joining, where adapter joining is not performed if the amount is below a threshold amount.

The terms "joining" and "ligation" as used herein, with respect to two polynucleotides, such as an adapter oligonucleotide and a sample polynucleotide, refers to the covalent attachment of two separate polynucleotides to produce a single larger polynucleotide with a contiguous backbone. Methods for joining two polynucleotides are known in the art, and include without limitation, enzymatic and non-enzymatic (e.g. chemical) methods. Examples of ligation reactions that are non-enzymatic include the non-enzymatic ligation techniques described in U.S. Pat. Nos. 5,780,613 and 5,476,930, which are herein incorporated by reference. In some embodiments, an adapter oligonucleotide is joined to a fragmented polynucleotide by a ligase, for example a DNA ligase or RNA ligase. Multiple ligases, each having characterized reaction conditions, are known in the art, and include, without limitation $NAD^+$-dependent ligases including tRNA ligase, Taq DNA ligase, *Thermus filiformis* DNA ligase, *Escherichia coli* DNA ligase, Tth DNA ligase, *Thermus scotoductus* DNA ligase (I and II), thermostable ligase, Ampligase thermostable DNA ligase, VanC-type ligase, 9° N DNA Ligase, Tsp DNA ligase, and novel ligases discovered by bioprospecting; ATP-dependent ligases including T4 RNA ligase, T4 DNA ligase, T3 DNA ligase, T7 DNA ligase, Pfu DNA ligase, DNA ligase 1, DNA ligase III, DNA ligase IV, and novel ligases discovered by bioprospecting; and wild-type, mutant isoforms, and genetically engineered variants thereof. Ligation can be between polynucleotides having hybridizable sequences, such as complementary overhangs. Ligation can also be between two blunt ends. Generally, a 5' phosphate is utilized in a ligation reaction. The 5' phosphate can be provided by the fragmented polynucleotide, the adapter oligonucleotide, or both. 5' phosphates can be added to or removed from polynucleotides to be joined, as needed. Methods for the addition or removal of 5' phosphates are known in the art, and include without limitation enzymatic and chemical processes. Enzymes useful in the addition and/or removal of 5' phosphates include kinases, phosphatases, and polymerases. In some embodiments, both of the two ends joined in a ligation reaction (e.g. an adapter end and a fragmented polynucleotide end) provide a 5' phosphate, such that two covalent linkages are made in joining the two ends, at one or both ends of a fragmented polynucleotide. In some embodiments, 3' phosphates are removed prior to ligation. In some embodiments, an adapter oligonucleotide is added to both ends of a fragmented polynucleotide, wherein one or both strands at each end are joined to one or more adapter oligonucleotides. In some embodiments, separate ligation reactions are carried out for different samples using a different adapter oligonucleotide comprising at least one different barcode sequence for each sample, such that no barcode sequence is joined to the target polynucleotides of more than one sample to be analyzed in parallel.

Non-limiting examples of adapter oligonucleotides include the double-stranded adapter formed by hybridizing CACTCAGCAGCACGACGATCACAGATGT-GTATAAGAGACAGT (SEQ ID NO: 17) to GTGAGTCGTCGTGCTGCTAGTGTCTACA-CATATTCTCTGTC (SEQ ID NO: 18). Additional non-limiting examples of adapter oligonucleotides are described in US20110319290 and US20070128624, which are incorporated herein by reference.

In some embodiments, adapted polynucleotides are subjected to an amplification reaction that amplifies target polynucleotides in the sample. In some embodiments, amplification uses primers comprising sequence C, sequence D, and a barcode associated with the sample, wherein sequence D is positioned at the 3' end of the amplification primers. Amplification primers may be of any suitable length, such as about, less than about, or more than about 5, 10, 15, 20, 25, 30, 35, 40, 45, 50, 55, 60, 65, 70, 75, 80, 90, 100, or more nucleotides, any portion or all of which may be complementary to the corresponding target sequence to which the primer hybridizes (e.g. about, less than about, or more than about 5, 10, 15, 20, 25, 30, 35, 40, 45, 50, or more nucleotides). "Amplification" refers to any process by which the copy number of a target sequence is increased. Methods for primer-directed amplification of target polynucleotides are known in the art, and include without limitation, methods based on the polymerase chain reaction (PCR). Conditions favorable to the amplification of target sequences by PCR are known in the art, can be optimized at a variety of steps in the process, and depend on characteristics of elements in the reaction, such as target type, target concentration, sequence length to be amplified, sequence of the target and/or one or more primers, primer length, primer concentration, polymerase used, reaction volume, ratio of one or more elements to one or more other elements, and others, some or all of which can be altered. In general, PCR involves the steps of denaturation of the target to be amplified (if double stranded), hybridization of one or more primers to the target, and extension of the primers by a DNA polymerase, with the steps repeated (or "cycled") in order to amplify the target sequence. Steps in this process can be optimized for various outcomes, such as to enhance yield, decrease the formation of spurious products, and/or increase or decrease specificity of primer annealing. Methods of optimization are well known in the art and include adjustments to the type or amount of elements in the amplification reaction and/or to the conditions of a given step in the process, such as temperature at a particular step, duration of a particular step, and/or number of cycles. In some embodiments, an amplification reaction comprises at least 5, 10, 15, 20, 25, 30, 35, 50, or more cycles. In some embodiments, an amplification reaction comprises no more than 5, 10, 15, 20, 25, 35, 50, or more cycles. Cycles can contain any number of steps, such as 1, 2, 3, 4, 5, 6, 7, 8, 9, 10 or more steps. Steps can comprise any temperature or gradient of temperatures, suitable for achieving the purpose of the given step, including but not limited to, strand denaturation, primer annealing, and primer extension. Steps can be of any duration, including but not limited to about, less than about, or more than about 1, 5, 10, 15, 20, 25, 30, 35, 40, 45, 50, 55, 60, 70, 80, 90, 100, 120, 180, 240, 300, 360, 420, 480, 540, 600, or more seconds, including indefinitely until manually interrupted. Cycles of any number comprising different steps can be combined in any order.

In some embodiments, amplification comprises hybridization between sequence D at the 3' end of an amplification primer and sequence D' of an adapted polynucleotide, extension of the amplification primer along the adapted polynucleotide to produce a primer extension product comprising sequence D derived from the amplification primer and sequence D' produced during primer extension. In some embodiments, the amplification process is repeated one or more times by denaturing the primer extension product from a template polynucleotide, and repeating the process using the primer extension product as template for further primer extension reactions. In some embodiments, the first cycle of primer extension is repeated using the same primer as the primer used in the first primer extension reaction, such as for about, less than about, or more than about 5, 10, 15, 20, 25, 30, 35, 50, or more cycles. In some embodiments, one or more primer extensions by the amplification primer is followed by one or more amplification cycles using a second amplification primer having a 3' end comprising a sequence complementary to a sequence added to the adapted polynucleotides by amplification with the first amplification primer (e.g. complementary to the complement of sequence C, or a portion thereof). In some embodiments, the second amplification primer comprises sequence C, or a portion thereof, at the 3' end. A non-limiting example of a second amplification primer includes CGAGATCTACACGCCTCCCTCGCGCCAT-CAG (SEQ ID NO: 19). In some embodiments, amplification by the second amplification primer comprises about, less than about, or more than about 5, 10, 15, 20, 25, 30, 35, 50, or more cycles. In some embodiments, the amount of adapted polynucleotides subjected to amplification is about, less than about, or more than about 50 ng, 100 ng, 200 ng, 300 ng, 400 ng, 500 ng, 600 ng, 700 ng, 800 ng, 900 ng, 1000 ng, 1500 ng, 2000 ng, 2500 ng, 5000 ng, 10 µg, or more (e.g. a threshold amount). In some embodiments, the amount of adapted polynucleotides is determined before proceeding with amplification, where amplification is not performed if the amount is below a threshold amount.

In some embodiments, the amplification primer comprises a barcode. As used herein, the term "barcode" refers to a known nucleic acid sequence that allows some feature of a polynucleotide with which the barcode is associated to be identified. In some embodiments, the feature of the polynucleotide to be identified is the sample from which the polynucleotide is derived. In some embodiments, barcodes are about or at least about 3, 4, 5, 6, 7, 8, 9, 10, 11, 12, 13, 14, 15, or more nucleotides in length. In some embodiments, barcodes are shorter than 10, 9, 8, 7, 6, 5, or 4 nucleotides in length. In some embodiments, barcodes associated with some polynucleotides are of different lengths than barcodes associated with other polynucleotides. In general, barcodes are of sufficient length and comprise sequences that are sufficiently different to allow the identification of samples based on barcodes with which they are associated. In some embodiments, a barcode, and the sample source with which it is associated, can be identified accurately after the mutation, insertion, or deletion of one or more nucleotides in the barcode sequence, such as the mutation, insertion, or deletion of 1, 2, 3, 4, 5, 6, 7, 8, 9, 10, or more nucleotides. In some embodiments, each barcode in a plurality of barcodes differ from every other barcode in the plurality at at least three nucleotide positions, such as at least 3, 4, 5, 6, 7, 8, 9, 10, or more nucleotide positions. A plurality of barcodes may be represented in a pool of samples, each sample comprising polynucleotides comprising one or more barcodes that differ from the barcodes contained in the polynucleotides derived from the other samples in the pool. Samples of polynucleotides comprising one or more barcodes can be pooled based on the barcode sequences to which they are joined, such that all four of the nucleotide bases A, G, C, and T are approximately evenly represented at one or more positions along each barcode in the pool (such as at 1, 2, 3, 4, 5, 6, 7, 8, or more positions, or all positions of the barcode). In some embodiments, the methods of the invention further comprise identifying the sample from which a target polynucleotide is derived based on a barcode sequence to which the target polynucleotide is joined. In general, a barcode comprises a nucleic acid sequence that when joined to a target polynucleotide serves as an identifier of the sample from which the target polynucleotide was derived.

In some embodiments, separate amplification reactions are carried out for separate samples using amplification primers comprising at least one different barcode sequence for each sample, such that no barcode sequence is joined to the target polynucleotides of more than one sample in a pool of two or more samples. In some embodiments, amplified polynucleotides derived from different samples and comprising different barcodes are pooled before proceeding with subsequent manipulation of the polynucleotides (such as before amplification and/or sequencing on a solid support). Pools can comprise any fraction of the total constituent amplification reactions, including whole reaction volumes. Samples can be pooled evenly or unevenly. In some embodiments, target polynucleotides are pooled based on the barcodes to which they are joined. Pools may comprise polynucleotides derived from about, less than about, or more than about 2, 3, 4, 5, 6, 7, 8, 9, 10, 11, 12, 13, 14, 15, 16, 20, 25, 30, 40, 50, 75, 100, or more different samples. Samples can be pooled in multiples of four in order to represent all four of the nucleotide bases A, G, C, and T at one or more positions along the barcode evenly, for example 4, 8, 12, 16, 20, 24, 28, 32, 36, 40, 44, 48, 52, 56, 60, 64, 96, 128, 192, 256, 384, and so on. Non-limiting examples of barcodes include AGGTCA, CAGCAG, ACTGCT, TAACGG, GGATTA, AACCTG, GCCGTT, CGTTGA, GTAACC, CTTAAC, TGCTAA, GATCCG, CCAGGT, TTCAGC, ATGATC, and TCGGAT. In some embodiments, the barcode is positioned between sequence D and sequence C of an amplification primer, or after sequence C and sequence D in a 5' to 3' direction ("downstream"). In some embodiments, the amplification primer comprises or consists of the sequence CGAGATCTACACGCCTCCCTCGCGCCATCAG CACTCAGCAGCACGACGATCAC (SEQ ID NO: 21), where each "X" represents zero, one, or more nucleotides of a barcode sequence.

Non-limiting examples of amplification primers are provided in Table 1:

TABLE 1

| | |
|---|---|
| SEQ ID NO: 1 | CGAGATCTACACGCCTCCCTCGCGCCATCAGAGGTCACACTCAGCAGCACGACGATCAC |
| SEQ ID NO: 2 | CGAGATCTACACGCCTCCCTCGCGCCATCAGCAGCAGCACTCAGCAGCACGACGATCAC |
| SEQ ID NO: 3 | CGAGATCTACACGCCTCCCTCGCGCCATCAGACTGCTCACTCAGCAGCACGACGATCAC |
| SEQ ID NO: 4 | CGAGATCTACACGCCTCCCTCGCGCCATCAGTAACGGCACTCAGCAGCACGACGATCAC |
| SEQ ID NO: 5 | CGAGATCTACACGCCTCCCTCGCGCCATCAGGGATTACACTCAGCAGCACGACGATCAC |
| SEQ ID NO: 6 | CGAGATCTACACGCCTCCCTCGCGCCATCAGAACCTGCACTCAGCAGCACGACGATCAC |
| SEQ ID NO: 7 | CGAGATCTACACGCCTCCCTCGCGCCATCAGGCCGTTCACTCAGCAGCACGACGATCAC |
| SEQ ID NO: 8 | CGAGATCTACACGCCTCCCTCGCGCCATCAGCGTTGACACTCAGCAGCACGACGATCAC |
| SEQ ID NO: 9 | CGAGATCTACACGCCTCCCTCGCGCCATCAGGTAACCCACTCAGCAGCACGACGATCAC |
| SEQ ID NO: 10 | CGAGATCTACACGCCTCCCTCGCGCCATCAGCTTAACCACTCAGCAGCACGACGATCAC |
| SEQ ID NO: 11 | CGAGATCTACACGCCTCCCTCGCGCCATCAGTGCTAACACTCAGCAGCACGACGATCAC |
| SEQ ID NO: 12 | CGAGATCTACACGCCTCCCTCGCGCCATCAGGATCCGCACTCAGCAGCACGACGATCAC |
| SEQ ID NO: 13 | CGAGATCTACACGCCTCCCTCGCGCCATCAGCCAGGTCACTCAGCAGCACGACGATCAC |

TABLE 1-continued

SEQ ID NO: 14   CGAGATCTACACGCCTCCCTCGCGCCATCAGTTCAGCCACTCAGCAGCACGACGATCAC

SEQ ID NO: 15   CGAGATCTACACGCCTCCCTCGCGCCATCAGATGATCCACTCAGCAGCACGACGATCAC

SEQ ID NO: 16   CGAGATCTACACGCCTCCCTCGCGCCATCAGTCGGATCACTCAGCAGCACGACGATCAC

In some embodiments, target polynucleotides are hybridized to a plurality of oligonucleotides that are attached to a solid support, such as any apparatus described herein. Hybridization may be before or after one or more sample processing steps, such as adapter joining and amplification. In preferred embodiments, target polynucleotides are hybridized to oligonucleotides on a solid support after both adapter joining and one or more amplification reactions. Oligonucleotides on the solid support may hybridize to random polynucleotide sequences, specific sequences common to multiple different target polynucleotides (e.g. one or more sequences derived from an adapter oligonucleotide, such as sequences D, D', or a portion thereof; one or more sequences derived from an amplification primer, such as sequences C, C', or a portion thereof; or combinations of these), sequences specific to different target polynucleotides (such as represented by sequence B as described herein), or combinations of these. In some embodiments, the solid support comprises a plurality of different first oligonucleotides comprising sequence A and sequence B, wherein sequence A is common among all first oligonucleotides; and further wherein sequence B is different for each different first oligonucleotide, is at the 3' end of each first oligonucleotide. In some embodiments, the plurality of first oligonucleotides comprises about, less than about, or more than about 5, 10, 25, 50, 75, 100, 125, 150, 175, 200, 300, 400, 500, 750, 1000, 2500, 5000, 7500, 10000, 20000, 50000, or more different oligonucleotides, each comprising a different sequence B. In some embodiments, sequence B of one or more of the plurality of first oligonucleotides comprises a sequence selected from the group consisting of SEQ ID NOs 22-121, shown in FIG. 4 (e.g. 1, 5, 10, 25, 50, 75, or 100 different oligonucleotides each with a different sequence from FIG. 4). In some embodiments, sequence B or the target sequence to which it specifically hybridizes comprises a causal genetic variant, as described herein. In some embodiments, sequence B or the target sequence to which it specifically hybridizes is within about, less than about, or more than about 1, 2, 3, 4, 5, 6, 6, 7, 8, 9, 10, 15, 20, 25, 30, 35, 40, 45, 50, 60, 70, 80, 90, 100, 200, 500 or more nucleotides of a causal genetic variant, as described herein. Causal genetic variants are typically located downstream of a first oligonucleotide, such that at least a portion of the causal genetic variant serves as template for extension of a first oligonucleotide. The solid support may further comprise a plurality of second oligonucleotides comprising sequence A at the 3' end of each second oligonucleotide, and a plurality of third oligonucleotides comprising sequence C at the 3' end of each third oligonucleotide, as described herein.

In some embodiments, sequence B of one or more of the plurality of first oligonucleotides or the target sequence to which it specifically hybridizes comprises a non-subject sequence. In some embodiments, sequence B or the target sequence to which it specifically hybridizes is within about, less than about, or more than about 1, 2, 3, 4, 5, 6, 7, 8, 9, 10, 15, 20, 25, 30, 35, 40, 45, 50, 60, 70, 80, 90, 100, 200, 500 or more nucleotides of a non-subject sequence. In general, a non-subject sequence corresponds to a polynucleotide derived from an organism other than the individual being tested or from whom a sample is taken, such as DNA or RNA from bacteria, archaea, viruses, protists, fungi, or other organism. Non-subject sequence can also include nucleic acids from a fetus, such as cell-free nucleic acid (also referred to as extracellular nucleic acid) from a fetus. A non-subject sequence may be indicative of the identity of an organism or class of organisms, and may further be indicative of a disease state, such as infection. An example of non-subject sequences useful in identifying an organism include, without limitation, rRNA sequences, such as 16s rRNA sequences (see e.g. WO2010151842). In some embodiments, non-subject sequences are analyzed instead of, or separately from causal genetic variants. In some embodiments, causal genetic variants and non-subject sequences are analyzed in parallel, such as in the same sample (e.g. using a mixture of first oligonucleotides, some with a sequence B that specifically hybridizes to a sequence comprising or near a causal genetic variant, and some with a sequence B that specifically hybridizes to a sequence comprising or near a non-subject sequence) and/or in the same report.

In some embodiments, sequence B of one or more of the plurality of first oligonucleotides or the target sequence to which it specifically hybridizes comprises an ancestry informative marker (AIM). In some embodiments, sequence B or the target sequence to which it specifically hybridizes is within about, less than about, or more than about 1, 2, 3, 4, 5, 6, 7, 8, 9, 10, 15, 20, 25, 30, 35, 40, 45, 50, 60, 70, 80, 90, 100, 200, 500 or more nucleotides of an AIM. An AIM may be used to classify a person as belonging to or not belonging to one or more populations, such as a population that is at increased risk for one of the causal genetic variants. For example, an AIM can be diagnostic for a population in which a trait is at increased prevalence. In certain instances the AIM may distinguish between populations with finer granularity, for example, between sub-continental groups or related ethnic groups. In some embodiments, AIMs are analyzed instead of, or separately from causal genetic variants and/or non-subject sequences. In some embodiments, AIMs, causal genetic variants, and/or non-subject sequences are analyzed in parallel, such as in the same sample (e.g. using a mixture of first oligonucleotides, some with a sequence B that specifically hybridizes to a sequence comprising or near a causal genetic variant, and some with a sequence B that specifically hybridizes to a sequence comprising or near an AIM) and/or in the same report.

In some embodiments, the method further comprises performing bridge amplification on the solid support. In general, bridge amplification uses repeated steps of annealing of primers to templates, primer extension, and separation of extended primers from templates. These steps can generally be performed using reagents and conditions known to those skilled in PCR (or reverse transcriptase plus PCR) techniques. Thus a nucleic acid polymerase can be used together with a supply of nucleoside triphosphate molecules (or other molecules that function as precursors of nucleotides present in DNA/RNA, such as modified nucleoside triphosphates) to extend primers in the presence of a suitable template. Excess deoxyribonucleoside triphosphates are desirably provided. Preferred deoxyribonucleoside triphosphates are abbreviated; dTTP (deoxythymidine nucleoside triphosphate), dATP (deoxyadenosine nucleoside triphosphate), dCTP (deoxycytosine nucleoside triphosphate) and dGTP (deoxyguanosine nucleoside triphosphate). Preferred ribonucleoside triphosphates are UTP, ATP, CTP and GTP. However, alternatives are possible. These may be naturally or non-naturally occurring. A buffer of the type generally used in PCR reactions may also be provided. A nucleic acid polymerase used to incorporate nucleotides during primer extension is preferably stable under the reaction conditions utilized in order that it can be used several times. Thus, where heating is used to separate a newly synthesized nucleic acid strand from its template, the nucleic acid polymerase is preferably heat stable at the temperature used. Such heat stable polymerases are known to those skilled in the art. They are obtainable from thermophilic micro-organisms, and include the DNA dependent DNA polymerase known as Taq polymerase and also thermostable derivatives thereof.

Typically, annealing of a primer to its template takes place at a temperature of 25 to 90° C. A temperature in this range will also typically be used during primer extension, and may be the same as or different from the temperature used during annealing and/or denaturation. Once sufficient time has elapsed to allow annealing and also to allow a desired degree of primer extension to occur, the temperature can be increased, if desired, to allow strand separation. At this stage the temperature will typically be increased to a temperature of 60 to 100° C. High temperatures can also be used to reduce non-specific priming problems prior to annealing, and/or to control the timing of amplification initiation, e.g. in order to synchronize amplification initiation for a number of samples. Alternatively, the strands may be separated by treatment with a solution of low salt and high pH (>12) or by using a chaotropic salt (e.g. guanidinium hydrochloride) or by an organic solvent (e.g. formamide).

Following strand separation (e.g. by heating), a washing step may be performed. The washing step may be omitted between initial rounds of annealing, primer extension and strand separation, such as if it is desired to maintain the same templates in the vicinity of immobilized primers. This allows templates to be used several times to initiate colony formation. The size of colonies produced by amplification on the solid support can be controlled, e.g. by controlling the number of cycles of annealing, primer extension and strand separation that occur. Other factors which affect the size of colonies can also be controlled. These include the number and arrangement on a surface of immobilized primers, the conformation of a support onto which the primers are immobilized, the length and stiffness of template and/or primer molecules, temperature, and the ionic strength and viscosity of a fluid in which the above-mentioned cycles can be performed.

A non-limiting example of an amplification process in accordance with the methods of the invention is illustrated in FIG. 1, and described below. First, a first oligonucleotide attached to the solid support and comprising sequence B at its 3' end hybridizes to a complementary target sequence B', such as a sequence unique to a specific target polynucleotide in a plurality of different target polynucleotides (e.g. a particular genomic DNA sequence). In this way, sequence B serves as a probe. The target polynucleotide in FIG. 1 comprises sequences derived from adapter oligonucleotides (e.g. sequences D and D') and from amplification primers (e.g. C and C'). Extension of the first oligonucleotide produces a first extension product attached to the solid support, the first extension product comprising, from 5' to 3', sequences A, B, C', and D', where sequence C' is complementary to sequence C and sequence D' is complementary to sequence D. The first extension product is then separated from the target polynucleotide template (e.g. by heat or chemical denaturation). Sequence C' of the first extension product then hybridizes to one of a plurality of third oligonucleotides attached to the solid support, the third oligonucleotide comprising sequence C at its 3' end. Extension of the third oligonucleotide produces a second extension product attached to the solid support, the second extension product comprising, from 5' to 3', sequences C, D, B' and A', where sequence B' is complementary to sequence B and sequence A' is complementary to sequence A. The two extension products form a double-stranded polynucleotide "bridge," with one strand at both ends attached to the solid support. The first and second extension products are then denatured, and subsequence hybridizations between the extension products and other oligonucleotides followed by extension replicate the first and second extension products. For example, each first extension product may hybridize to a further third oligonucleotide to produce additional copies of the second extension product. In addition, a second extension product may hybridize to one of a plurality of second oligonucleotides attached to the solid support, the second oligonucleotide comprising sequence A at its 3' end. Extension of the second oligonucleotide produces an extension product comprising the sequence of a first extension product. Successive rounds of extension along extension products radiates outward from an initial first extension product to produce a cluster or "colony" of first extension products and their complementary second extension products derived from a single target polynucleotide. This process may be modified to accommodate oligonucleotides comprising different sequences or sequence arrangements, different target polynucleotides or combinations of target polynucleotides, types of solid supports, and other considerations depending on a particular bridge amplification reaction. In general, this process provides for amplification on a solid support of specific target polynucleotides from sample polynucleotides comprising target polynucleotides and non-target polynucleotides. Generally, target polynucleotides are selectively amplified while non-target polynucleotides in the sample are not amplified, or are amplified to a much lower degree, such as about or less than about 10-fold, 100-fold, 500-fold, 1000-fold, 2500-fold, 5000-fold, 10000-fold, 25000-fold, 50000-fold, 100000-fold, 1000000-fold, or more lower than one or more target polynucleotides.

In some embodiments, the amount of amplified polynucleotides from a previous amplification step that is subjected to bridge amplification is about, less than about, or more than about 50 ng, 100 ng, 500 ng, 1 µg, 2 µg, 3 µg, 4 µg, 5 µg, 6 µg, 7 µg, 8 µg, 9 µg, 10 µg, 12 µg, 13 µg, 14 µg, 15 µg, 20 µg, 25 µg, 26 µg, 27 µg, 28 µg, 29 µg, 30 µg, 40 µg, 50 µg, or more (e.g. a threshold amount). In some embodiments, the amount of amplified polynucleotides from a previous amplification step is determined before proceeding with bridge amplification, where bridge amplification is not performed if the amount is below a threshold amount.

In some embodiments, bridge amplification is followed by sequencing a plurality of oligonucleotides attached to the solid support. General methods for sequencing polynucleotides attached to a solid support, including reagents and reaction conditions, are known in the art. In some embodiments, sequencing comprises or consists of single-end sequencing. In some embodiments, sequencing comprises or consists of paired-end sequencing. Sequencing can be carried out using any suitable sequencing technique, wherein nucleotides are added successively to a free 3' hydroxyl group, resulting in synthesis of a polynucleotide chain in the 5' to 3' direction. The identity of the nucleotide added is preferably determined after each nucleotide addition. Sequencing techniques using sequencing by ligation, wherein not every contiguous base is sequenced, and techniques such as massively parallel signature sequencing (MPSS) where bases are removed from, rather than added to the strands on the surface are also within the scope of the invention, as are techniques using detection of pyrophosphate release (pyrosequencing). Such pyrosequencing based techniques are particularly applicable to sequencing arrays of beads where the beads have been amplified in an emulsion such that a single template from the library molecule is amplified on each bead.

One particular sequencing method which can be used in the methods of the invention relies on the use of modified nucleotides that can act as reversible chain terminators. Such reversible chain terminators comprise removable 3' blocking groups, for example as described in WO04018497 and U.S. Pat. No. 7,057,026. Once such a modified nucleotide has been incorporated into the growing polynucleotide chain complementary to the region of the template being sequenced there is no free 3'-OH group available to direct further sequence extension and therefore the polymerase cannot add further nucleotides. Once the identity of the base incorporated into the growing chain has been determined, the 3' block may be removed to allow addition of the next successive nucleotide. By ordering the products derived using these modified nucleotides it is possible to deduce the DNA sequence of the DNA template. Such reactions can be done in a single experiment if each of the modified nucleotides has attached thereto a different label, known to correspond to the particular base, to facilitate discrimination between the bases added at each incorporation step. Non-limiting examples of suitable labels are described in WO/2007/135368, the contents of which are incorporated herein by reference in their entirety. Alternatively, a separate reaction may be carried out containing each of the modified nucleotides added individually.

The modified nucleotides may carry a label to facilitate their detection. In a particular embodiment, the label is a fluorescent label. Each nucleotide type may carry a different fluorescent label. However, the detectable label need not be a fluorescent label. Any label can be used which allows the detection of the incorporation of the nucleotide into the DNA sequence. One method for detecting fluorescently labeled nucleotides comprises using laser light of a wavelength specific for the labeled nucleotides, or the use of other suitable sources of illumination. Fluorescence from the label on an incorporated nucleotide may be detected by a CCD camera or other suitable detection means. Suitable detection means are described in WO/2007/123744, the contents of which are incorporated herein by reference in their entirety.

In some embodiments, a first sequencing reaction proceeds from a 3' end created by cleavage at a cleavage site contained in an oligonucleotide attached to the solid support, which oligonucleotide was extended during bridge amplification. In some embodiments, the cleaved strand is separated from its complementary strand before sequencing by extension of the attached oligonucleotide. In some embodiments, the attached oligonucleotide having the newly freed 3' end created by cleavage is extended using a polymerase having strand displacement activity, such that the cleaved strand is displaced as the new strand is extended. In some embodiments extension of the attached oligonucleotide proceeds along the full length of the template extension product from the amplification reaction, which in some embodiments includes extension beyond a last identified nucleotide. In some embodiments, the template extension product is then cleaved at a cleavage site contained in an oligonucleotide attached to the solid support, and the oligonucleotide extended during the sequencing reaction is linearized, for produce a freed first sequencing extension product. The 5' end of the first sequencing product may then serve as a template for a second sequencing reaction, which can proceed by extension of a sequencing primer (such as a sequencing primer described herein) or by extension from the 3' end created by cleavage at the cleavage site. In some embodiments, the average or median number of nucleotides identified along a template polynucleotide being sequenced is about, less than about, or more than about 10, 15, 20, 25, 30, 35, 40, 45, 50, 60, 70, 80, 90, 100, 150, 200, 300, 400, 500, or more.

In some embodiments, sequencing comprises treating bridge amplification products to remove substantially all or remove or displace at least a portion of one of the immobilized strands in the "bridge" structure in order to generate a template that is at least partially single-stranded. The portion of the template which is single-stranded will thus be available for hybridization with a sequencing primer. The process of removing all or a portion of one immobilized strand in a bridged double-stranded nucleic acid structure may be referred to herein as "linearization," and is described in further detail in WO07010251, the contents of which are incorporated herein by reference in their entirety.

Bridged template structures may be linearized by cleavage of one or both strands with a restriction endonuclease or by cleavage of one strand with a nicking endonuclease. Other methods of cleavage can be used as an alternative to restriction enzymes or nicking enzymes, including but not limited to chemical cleavage (e.g. cleavage of a diol linkage with periodate), cleavage of abasic sites by cleavage with endonuclease (for example "USER," as supplied by NEB, part number M5505S), by exposure to heat or alkali, cleavage of ribonucleotides incorporated into amplification products otherwise comprised of deoxyribonucleotides, photochemical cleavage or cleavage of a peptide linker. In some embodiments, a linearization step may be avoided, such as when the solid-phase amplification reaction is performed with only one amplification oligonucleotide covalently immobilized and another amplification oligonucleotide free in solution. Following the cleavage step, regardless of the method used for cleavage, the product of the cleavage reaction may be subjected to denaturing conditions in order to remove the portion(s) of the cleaved strand(s) that are not attached to the solid support. Suitable denaturing conditions, for example sodium hydroxide solution, formamide solution, or heat, are known in the art, such as described in standard molecular biology protocols (Sambrook et al., 2001, Molecular Cloning, A Laboratory Manual, 3rd Ed, Cold Spring Harbor Laboratory Press, Cold Spring Harbor Laboratory Press, NY; Current Protocols, eds Ausubel et al.). Denaturation results in the production of a sequencing template which is partially or substantially single-stranded. A sequencing reaction may then be initiated by hybridization of a sequencing primer to the single-stranded portion of the template. Thus, the invention encompasses methods wherein the nucleic acid sequencing reaction comprises hybridizing a sequencing primer to a single-stranded region of a linearized amplification product, sequentially incorporating one or more nucleotides into a polynucleotide strand complementary to the region of amplified template strand to be sequenced, identifying the base present in one or more of the incorporated nucleotide(s) and thereby determining the sequence of a region of the template strand.

In some embodiments, the sequencing primer comprises a sequence complementary to one or more sequences derived from an adapter oligonucleotide, an amplification primer, an oligonucleotide attached to the solid support, or a combination of these. In some embodiments, the sequencing primer comprises sequence D, or a portion thereof. In some embodiments, a sequencing primer comprises sequence C, or a portion thereof. A sequencing primer can be of any suitable length, such as about, less than about, or more than about 5, 10, 15, 20, 25, 30, 35, 40, 45, 50, 55, 60, 65, 70, 75, 80, 90, 100, or more nucleotides, any portion or all of which may be complementary to the corresponding target sequence to which the primer hybridizes (e.g. about, less than about, or more than about 5, 10, 15, 20, 25, 30, 35, 40, 45, 50, or more nucleotides). In some embodiments, a sequencing primer comprises the sequence CACTCAGCAGCACGACGATCA-CAGATGTGTATAAGAGACAG (SEQ ID NO: 20).

In general, extension of a sequencing primer produces a sequencing extension product. The number of nucleotides added to the sequencing extension product that are identified in the sequencing process may depend on a number of factors, including template sequence, reaction conditions, reagents used, and other factors. In some embodiments, the average or median number of nucleotides identified along a growing sequencing primer is about, less than about, or more than about 10, 15, 20, 25, 30, 35, 40, 45, 50, 60, 70, 80, 90, 100, 150, 200, 300, 400, 500, or more. In some embodiments, a sequencing primer is extended along the full length of the template primer extension product from the amplification reaction, which in some embodiments includes extension beyond a last identified nucleotide.

In some embodiments, the sequencing extension product is subjected to denaturing conditions in order to remove the sequencing extension product from the attached template strand to which it is hybridized, in order to make the template partially or completely single-stranded and available for hybridization with a second sequencing primer. The second sequencing primer may be the same as or different from the first sequencing primer. In some embodiments, the second sequencing primer hybridizes to a sequence located closer to the 5' end of the target nucleic acid than the sequence to which the first sequencing primer hybridizes. In some embodiments, the second sequencing primer hybridizes to a sequence located closer to the 3' end of the target nucleic acid than the sequence to which the first sequencing primer hybridizes. In some embodiments, only one of the first and second sequencing primers is extended along a barcode sequence, thereby identifying the nucleotides in the barcode sequence. In some embodiments, one sequencing primer (e.g. the first sequencing primer) hybridizes to a sequence located 5' from the barcode (such that extension of this sequencing primer does not generate sequence complementary to the barcode), and another sequencing primer (e.g. the second sequencing primer) hybridizes to a sequence located 3' from the barcode (such that extension of this sequencing primer generates sequence complementary to the barcode). In some embodiments, the second sequencing primer comprises SEQ ID NO: 19.

The invention is not intended to be limited to use of the sequencing methods outlined above, as essentially any sequencing methodology which relies on successive incorporation of nucleotides into a polynucleotide chain can be used. Suitable techniques include, for example, those described in U.S. Pat. No. 6,306,597, US20090233802, US20120053074, and US20110223601, which are incorporated by reference in their entireties. In the cases where strand resynthesis is employed, both strands must be immobilized to the surface in a way that allows subsequent release of a portion of the immobilized strand. This can be achieved through a number of mechanisms as described in WO07010251, the contents of which are incorporated herein by reference in their entirety. For example, one primer can contain a uracil nucleotide, which means that the strand can be cleaved at the uracil base using the enzyme uracil DNA glycosylase (UDG) which removes the nucleotide base, and endonuclease VIII that excises the abasic nucleotide. This enzyme combination is available as USER™ from New England Biolabs (NEB part number M5505). The second primer may comprise an 8-oxoguanine nucleotide, which is then cleavable by the enzyme FPG (NEB part number M0240). This design of primers provides complete control of which primer is cleaved at which point in the process, and also where in the cluster the cleavage occurs. The primers may also be chemically modified, for example with a disulfide or diol modification that allows chemical cleavage at specific locations.

In some embodiments, sequencing data are generated for about, less than about, or more than about 5, 10, 25, 50, 100, 150, 200, 250, 300, 400, 500, 750, 1000, 2500, 5000, 7500, 10000, 20000, 50000, or more different target polynucleotides from a sample in a single reaction container (e.g. a channel in a flow cell). In some embodiments, sequencing data are generated for a plurality of samples in parallel, such as about, less than about, or more than about 2, 3, 4, 5, 6, 7, 8, 9, 10, 11, 12, 13, 14, 15, 16, 17, 18, 19, 20, 24, 48, 96, 192, 384, 768, 1000, or more samples. In some embodiments, sequencing data are generated for a plurality of samples in a single reaction container (e.g. a channel in a flow cell), such as about, less than about, or more than about 2, 3, 4, 5, 6, 7, 8, 9, 10, 11, 12, 13, 14, 15, 16, 17, 18, 19, 20, 24, 48, 96, 192, 384, 768, 1000, or more samples, and sequencing data are subsequently grouped according to the sample from which the sequenced polynucleotides originated. In a single reaction, sequencing data may be generated for about or at least about $10^6$, $10^7$, $10^8$, $2\times10^8$, $3\times10^8$, $4\times10^8$, $5\times10^8$, $10^9$, $10^{10}$, or more target polynucleotides or clusters from a bridge amplification reaction, which may comprise sequencing data for about, less than about, or more than about $10^4$, $10^5$, $10^6$, $2\times10^6$, $3\times10^6$, $4\times10^6$, $5\times10^6$, $10^7$, $10^8$, or more target polynucleotides or clusters for each sample in the reaction. In some embodiments, the presence, absence, or genotype of about, less than about, or more than about 5, 10, 25, 50, 75, 100, 125, 150, 175, 200, 300, 400, 500, 750, 1000, 2500, 5000, 7500, 10000, 20000, 50000, or more causal genetic variants is determined for a sample based on the sequencing data. The presence, absence, or genotype of one or more causal genetic variants may be determined with an accuracy of about or more than about 80%, 85%, 90%, 95%, 97.5%, 99%, 99.5%, 99.9% or higher.

In some embodiments, one or more, or all, of the steps in a method of the invention are automated, such as by use of one or more automated devices. In general, automated devices are devices that are able to operate without human direction—an automated system can perform a function during a period of time after a human has finished taking any action to promote the function, e.g. by entering instructions into a computer, after which the automated device performs one or more steps without further human operation. Software and programs, including code that implements embodiments of the present invention, may be stored on some type of data storage media, such as a CD-ROM, DVD-ROM, tape, flash drive, or diskette, or other appropriate computer readable medium. Various embodiments of the present invention can also be implemented exclusively in hardware, or in a combination of software and hardware. For example, in one embodiment, rather than a conventional personal computer, a Programmable Logic Controller (PLC) is used. As known to those skilled in the art, PLCs are frequently used in a variety of process control applications where the expense of a general purpose computer is unnecessary. PLCs may be configured in a known manner to execute one or a variety of control programs, and are capable of receiving inputs from a user or another device and/or providing outputs to a user or another device, in a manner similar to that of a personal computer. Accordingly, although embodiments of the present invention are described in terms of a general purpose computer, it should be appreciated that the use of a general purpose computer is exemplary only, as other configurations may be used.

In some embodiments, automation may comprise the use of one or more liquid handlers and associated software. Several commercially available liquid handling systems can be utilized to run the automation of these processes (see for example liquid handlers from Perkin-Elmer, Beckman Coulter, Caliper Life Sciences, Tecan, Eppendorf, Apricot Design, Velocity 11 as examples). In some embodiments, automated steps include one or more of fragmentation, end-repair, A-tailing (addition of adenine overhang), adapter joining, PCR amplification, sample quantification (e.g. amount and/or purity of DNA), and sequencing. In some embodiments, hybridization of amplified polynucleotides to oligonucleotides attached to a solid surface, extension along the amplified polynucleotides as templates, and/or bridge amplification is automated (e.g. by use of an Illumina cBot). Non-limiting examples of devices for conducting bridge amplification are described in WO2008002502. In some embodiments, sequencing is automated. A variety of automated sequencing machines are commercially available, and include sequencers manufactured by Life Technologies (SOLiD platform, and pH-based detection), Roche (454 platform), Illumina (e.g. flow cell based systems, such as Genome Analyzer, HiSeq, or MiSeq systems). Transfer between 2, 3, 4, 5, or more automated devices (e.g. between one or more of a liquid handler, bridge a amplification device, and a sequencing device) may be manual or automated. In some embodiments, one or more steps in a method of the invention (e.g. all steps or all automated steps) are completed in about or less than about 72, 48, 24, 20, 18, 16, 14, 12, 10, 9, 8, 7, 6, 5, 4, 3, 2, 1, or fewer hours. In some embodiments, the time from sample receipt, DNA extraction, fragmentation, adapter joining, amplification, or bridge amplification to production of sequencing data is about or less than about 72, 48, 24, 20, 18, 16, 14, 12, 10, 9, 8, 7, 6, 5, 4, 3, 2, 1, or fewer hours.

In one aspect, the invention provides a method of enriching a plurality of different target polynucleotides in a sample. In some embodiments, the method comprises: (a) joining an adapter oligonucleotide to each of the target polynucleotides, wherein the adapter oligonucleotide comprises sequence Y; (b) hybridizing a plurality of different oligonucleotide primers to the adapted target polynucleotides, wherein each oligonucleotide primer comprises sequence Z and sequence W; wherein sequence Z is common among all oligonucleotide primers; and further wherein sequence W is different for each different oligonucleotide primer, is positioned at the 3' end of each oligonucleotide primer, and is complementary to a sequence comprising a causal genetic variant or a sequence within 200 nucleotides of a causal genetic variant; (c) in an extension reaction, extending the oligonucleotide primers along the adapted target polynucleotides to produce extended primers comprising sequence Z and sequence Y', wherein sequence Y' is complementary to sequence Y; and (d) exponentially amplifying the purified extension products using a pair of amplification primers comprising (i) a first amplification primer comprising sequence V and sequence Z, wherein sequence Z is positioned at the 3' end of the first amplification primer; and (ii) a second amplification primer comprising sequence X and sequence Y, wherein sequence Y and is positioned at the 3' end of the second amplification primer. In some embodiments, each oligonucleotide primer comprises a first binding partner. In some embodiments, the method further comprises, before step (d), exposing the extended primers to a solid surface comprising a second binding partner that binds to the first binding partner, thereby purifying the extended primers away from one or more components of the extension reaction. In some embodiments, one or more of sequences V, W, X, Y, and Z are different sequences. In some embodiments, sequence V and sequence X are the same. In some embodiments, sequence V and/or sequence X are not included in their respective primers. In some embodiments, one or more of sequences V, W, X, Y, and Z are about, less than about, or more than about 5%, 10%, 15%, 20%, 25%, 30%, 40%, 50%, 60%, 70%, 80%, 90%, or more different from one or more of the other of sequences V, W, X, Y, and Z (e.g. have less than about 10%, 20%, 30%, 40%, 50%, 60%, 70%, 80%, 90%, or more sequence identity). In some embodiments, one or more of sequences V, W, X, Y, and Z comprise about, less than about, or more than about 1, 2, 3, 4, 5, 6, 7, 8, 9, 10, 15, 20, or more nucleotides each. In some embodiments, sequence V or sequence Z is equivalent to sequence A, sequence W is equivalent to sequence B, sequence X is equivalent to sequence C, and/or sequence Y is equivalent to sequence D, as described with respect to other aspects of the invention.

In one aspect, the invention provides a method of enriching a plurality of different target polynucleotides in a sample. In some embodiments, the method comprises: (a) hybridizing a plurality of different oligonucleotide primers to the target polynucleotides, wherein each oligonucleotide primer comprises sequence Z and sequence W; wherein sequence Z is common among all oligonucleotide primers; and further wherein sequence W is different for each different oligonucleotide primer, is positioned at the 3' end of each oligonucleotide primer, and is complementary to a sequence comprising a causal genetic variant or a sequence within 200 nucleotides of a causal genetic variant; (b) in an extension reaction, extending the oligonucleotide primers along the target polynucleotides to produce extended primers; (c) joining an adapter oligonucleotide to each extended primer, wherein the adapter oligonucleotide comprises sequence Y', and further wherein sequence Y' is the complement of a sequence Y; and (d) exponentially amplifying the purified extension products using a pair of amplification primers comprising (i) a first amplification primer comprising sequence V and sequence Z, wherein sequence Z is positioned at the 3' end of the first amplification primer; and (ii) a second amplification primer comprising sequence X and sequence Y, wherein sequence Y and is positioned at the 3' end of the second amplification primer. In some embodiments, each oligonucleotide primer comprises a first binding partner. In some embodiments, the method further comprises, before step (c), exposing the extended primers to a solid surface comprising a second binding partner that binds to the first binding partner, thereby purifying the extended primers away from one or more components of the extension reaction. In some embodiments, one or more of sequences V, W, X, Y, and Z are different sequences. In some embodiments, sequence V and sequence X are the same. In some embodiments, sequence V and/or sequence X are not included in their respective primers. In some embodiments, one or more of sequences V, W, X, Y, and Z are about, less than about, or more than about 5%, 10%, 15%, 20%, 25%, 30%, 40%, 50%, 60%, 70%, 80%, 90%, or more different from one or more of the other of sequences V, W, X, Y, and Z (e.g. have less than about 10%, 20%, 30%, 40%, 50%, 60%, 70%, 80%, 90%, or more sequence identity). In some embodiments, one or more of sequences V, W, X, Y, and Z comprise about, less than about, or more than about 1, 2, 3, 4, 5, 6, 7, 8, 9, 10, 15, 20, or more nucleotides each. In some embodiments, sequence V or sequence Z is equivalent to sequence A, sequence W is equivalent to sequence B, sequence X is equivalent to sequence C, and/or sequence Y is equivalent to sequence D, as described with respect to other aspects of the invention.

Samples from which the target polynucleotides are derived can comprise multiple samples from the same individual, samples from different individuals, or combinations thereof. In some embodiments, a sample comprises a plurality of polynucleotides from a single individual. In some embodiments, a sample comprises a plurality of polynucleotides from two or more individuals. Examples of sources of sample polynucleotides and methods for their purification are described herein, such as with regard to other aspects of the invention.

In some embodiments, target polynucleotides are fragmented into a population of fragmented polynucleotides of one or more specific size range(s). In some embodiments, the amount of sample polynucleotides subjected to fragmentation is about, less than about, or more than about 50 ng, 100 ng, 200 ng, 300 ng, 400 ng, 500 ng, 600 ng, 700 ng, 800 ng, 900 ng, 1000 ng, 1500 ng, 2000 ng, 2500 ng, 5000 ng, 10 µg, or more. In some embodiments, fragments are generated from about, less than about, or more than about 1, 10, 100, 1000, 10000, 100000, 300000, 500000, or more genome-equivalents of starting DNA. Fragmentation may be accomplished by methods known in the art, including chemical, enzymatic, and mechanical fragmentation. In some embodiments, the fragments have an average or median length from about 10 to about 10,000 nucleotides. In some embodiments, the fragments have an average or median length from about 50 to about 2,000 nucleotides. In some embodiments, the fragments have an average or median length of about, less than about, more than about, or between about 100-2500, 200-1000, 10-800, 10-500, 50-500, 50-250, or 50-150 nucleotides. In some embodiments, the fragments have an average or median length of about, less than about, or more than about 200, 300, 500, 600, 800, 1000, 1500, or more nucleotides. Example methods of fragmentation and optional end repair (including optional A-tailing) are described herein, such as with regard to other aspects of the invention. End repair may be performed at any step before joining of adapter oligonucleotides, such as before or after extension of oligonucleotide primers.

Figure 5:
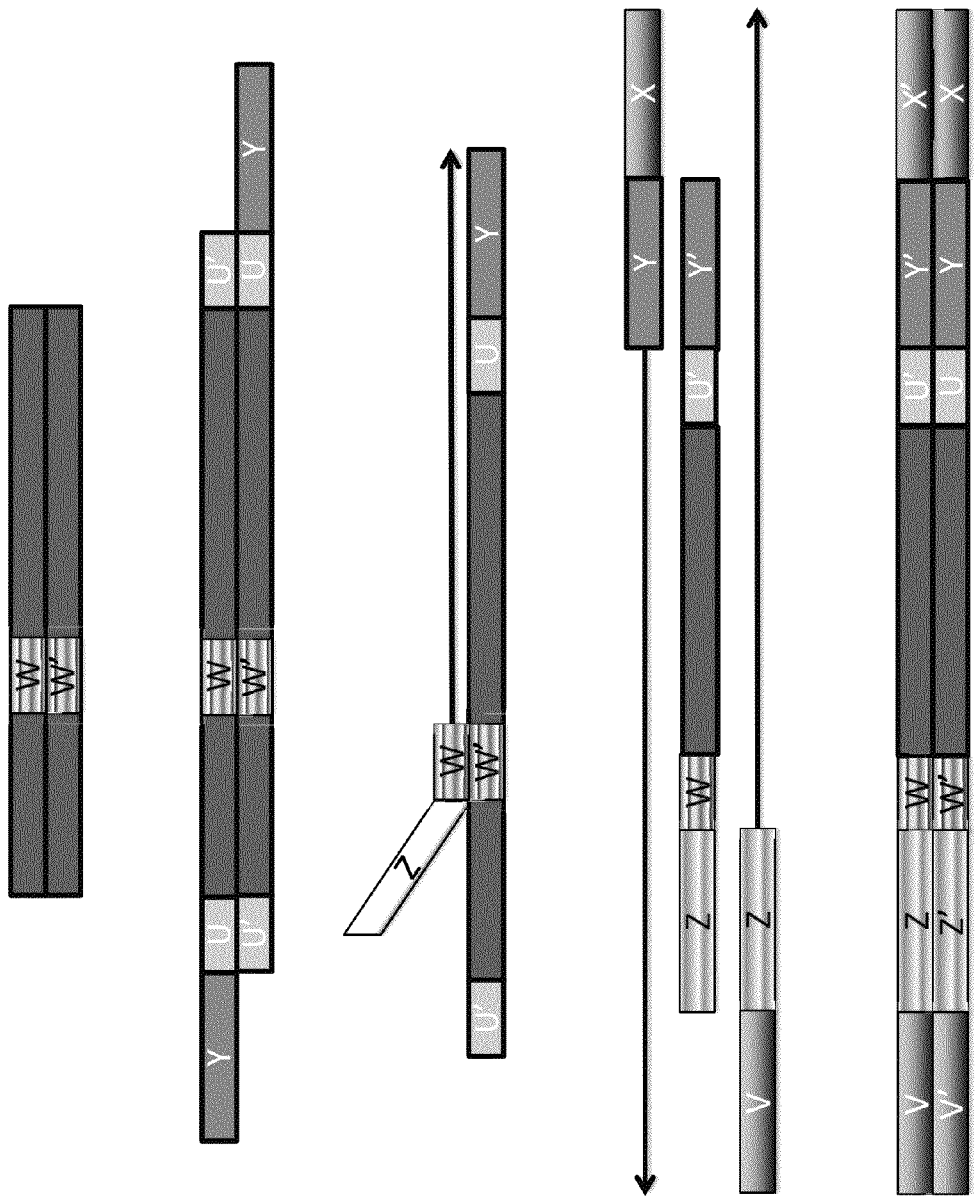
FIG. 5 illustrates an example amplification process in accordance with an embodiment of the invention.
Figure 7:
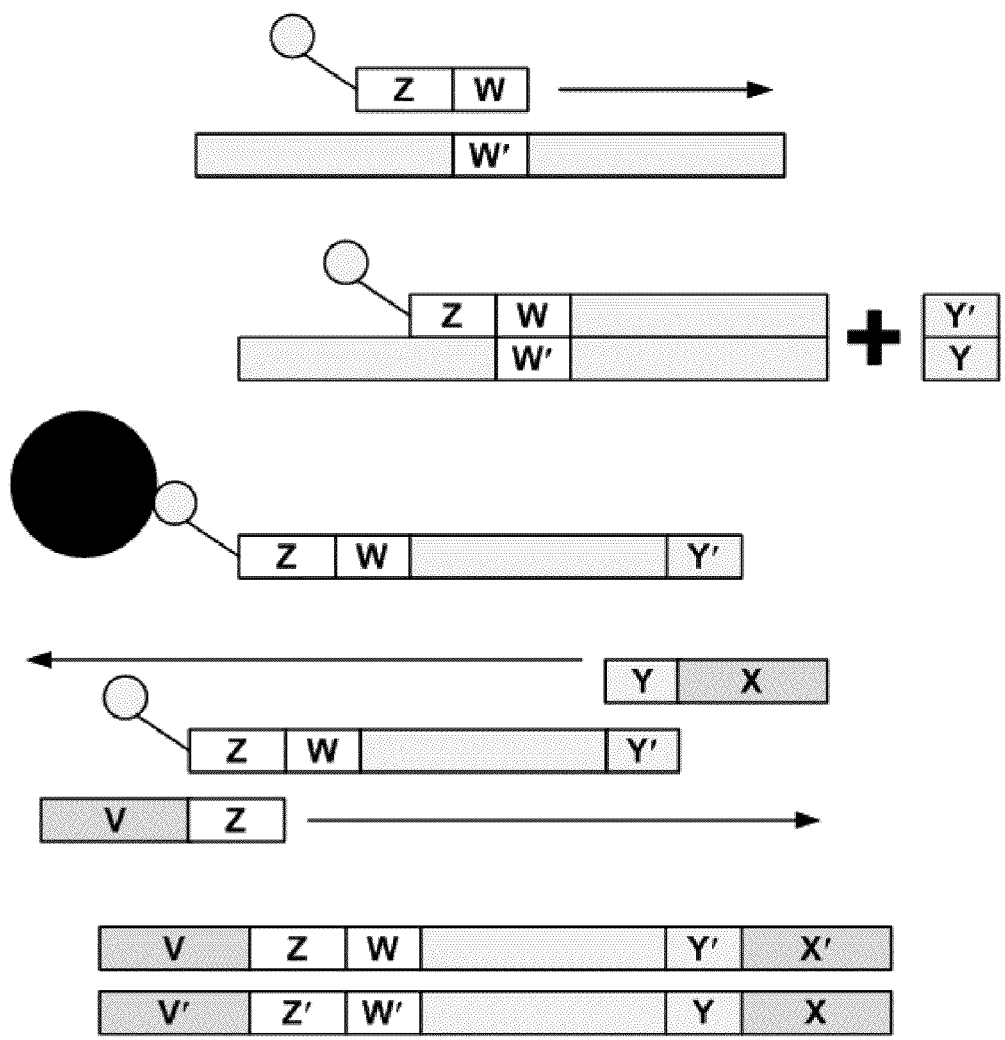
FIG. 7 illustrates an example amplification process in accordance with an embodiment of the invention.

In some embodiments, fragmentation or oligonucleotide primer extension is followed by ligation of adapter oligonucleotides to the fragmented or extended polynucleotides (see e.g. FIGS. 5 and 7). Examples of adapter oligonucleotides, and methods for their manipulation and joining to target polynucleotides are described herein, such as with regard to other aspects of the invention. In some embodiments, adapter oligonucleotides comprise one strand comprising the sequence element sequence Y. In some embodiments, adapter oligonucleotides comprise one strand comprising the sequence element sequence Y', which is the complement of sequence Y. In some embodiments, adapter oligonucleotides comprise sequence Y hybridized to complementary sequence Y', where sequence Y' is on the same or different strand as sequence Y. In some embodiments, the 3' end of a target polynucleotide or extended primer is extended along an adapter oligonucleotide to generate sequence Y or sequence Y'. In some embodiments, fragmented polynucleotides and adapter oligonucleotides are combined and treated (e.g. by ligation and optionally by fragment extension) to produce double-stranded, adapted polynucleotides comprising fragmented polynucleotide sequence joined to adapter oligonucleotide sequences at both ends, where both ends of the adapted polynucleotides comprise sequence Y hybridized to sequence Y'. In some embodiments, extended primers that are hybridized to target polynucleotides are combined and treated (e.g. by ligation and optionally by 3'-end extension) to produce double-stranded, adapted polynucleotides comprising sequence Y hybridized to sequence Y' at one end. In some embodiments, the amount of fragmented polynucleotides subjected to further manipulation (e.g. adapter joining or oligonucleotide primer extension) is about, less than about, or more than about 50 ng, 100 ng, 200 ng, 300 ng, 400 ng, 500 ng, 600 ng, 700 ng, 800 ng, 900 ng, 1000 ng, 1500 ng, 2000 ng, 2500 ng, 5000 ng, 10 µg, or more (e.g. a threshold amount). In some embodiments, the amount of fragmented polynucleotides is determined before proceeding with further manipulation, where further manipulation is not performed if the amount is below a threshold amount.

In some embodiments, primer extension products comprising sequences complementary to target polynucleotide sequences are produced in an extension reaction. In general, an extension reaction comprises extension of an oligonucleotide primer hybridized to a target polynucleotide. Oligonucleotide primers may be of any suitable length, such as about, less than about, or more than about 5, 10, 15, 20, 25, 30, 35, 40, 45, 50, 55, 60, 65, 70, 75, 80, 90, 100, or more nucleotides, any portion or all of which may be complementary to the corresponding target sequence to which the primer hybridizes (e.g. about, less than about, or more than about 5, 10, 15, 20, 25, 30, 35, 40, 45, 50, or more nucleotides). Primer extension may comprise one or more cycles of a PCR reaction, such as denaturation, primer annealing, and primer extension, which may be repeated any number of times with or without a reverse primer. For example, in the absence of a reverse primer, multiple cycles may be used to linearly amplify one or more target polynucleotides by repeated extension of primers along the corresponding targets, without using extended primers as templates for further amplification. Examples of oligonucleotides useful as primers and methods for their use in primer extension reactions (e.g. amplification) are provided herein, such as with regard to other aspects of the invention. An illustration of a non-limiting example of an amplification method is provided in FIG. 2.

In some embodiments, an oligonucleotide primer comprises sequence Z, which is common to each of a plurality of different oligonucleotide primers in a reaction, and sequence W, which is different for each different oligonucleotide primer and is positioned at the 3' end of each oligonucleotide primer. In some embodiments, the plurality of oligonucleotide primers comprises about, less than about, or more than about 5, 10, 25, 50, 75, 100, 125, 150, 175, 200, 300, 400, 500, 750, 1000, 2500, 5000, 7500, 10000, 20000, 50000, or more different oligonucleotides, each comprising a different sequence W. In some embodiments, sequence W of one or more of the plurality of oligonucleotide primers comprises a sequence selected from the group consisting of SEQ ID NOs 22-121, shown in FIG. 4 (e.g. 1, 5, 10, 25, 50, 75, or 100 different oligonucleotides each with a different sequence from FIG. 4). In some embodiments, sequence W or the target sequence to which it specifically hybridizes comprises a causal genetic variant, as described herein. In some embodiments, sequence W or the target sequence to which it specifically hybridizes is within about, less than about, or more than about 1, 2, 3, 4, 5, 6, 6, 7, 8, 9, 10, 15, 20, 25, 30, 35, 40, 45, 50, 60, 70, 80, 90, 100, 200, 500 or more nucleotides of a causal genetic variant, as described herein. Causal genetic variants are typically located downstream of an oligonucleotide primer, such that at least a portion of the causal genetic variant serves as template for extension of an oligonucleotide primer. Typically, extension of an oligonucleotide primer along a target polynucleotide comprising sequence Y derived from an adapter oligonucleotide produces a primer extension product comprising primer-derived sequences a the 5' end and sequences complementary to adapter-derived sequences near the 3' end (e.g. sequence Y', the complement of Y).

In some embodiments, sequence W of one or more of the plurality of oligonucleotide primers or the target sequence to which it specifically hybridizes comprises a non-subject sequence. In some embodiments, sequence W or the target sequence to which it specifically hybridizes is within about, less than about, or more than about 1, 2, 3, 4, 5, 6, 7, 8, 9, 10, 15, 20, 25, 30, 35, 40, 45, 50, 60, 70, 80, 90, 100, 200, 500 or more nucleotides of a non-subject sequence. In general, a non-subject sequence corresponds to a polynucleotide derived from an organism other than the individual being tested, such as DNA or RNA from bacteria, archaea, viruses, protists, fungi, or other organism. A non-subject sequence may be indicative of the identity of an organism or class of organisms, and may further be indicative of a disease state, such as infection. An example of non-subject sequences useful in identifying an organism include, without limitation, rRNA sequences, such as 16s rRNA sequences (see e.g. WO2010151842). In some embodiments, non-subject sequences are analyzed instead of, or separately from causal genetic variants. In some embodiments, causal genetic variants and non-subject sequences are analyzed in parallel, such as in the same sample (e.g. using a mixture of oligonucleotide primers, some with a sequence W that specifically hybridizes to a sequence comprising or near a causal genetic variant, and some with a sequence W that specifically hybridizes to a sequence comprising or near a non-subject sequence) and/or in the same report.

In some embodiments, sequence W of one or more of the plurality of oligonucleotide primers or the target sequence to which it specifically hybridizes comprises an ancestry informative marker (AIM). In some embodiments, sequence W or the target sequence to which it specifically hybridizes is within about, less than about, or more than about 1, 2, 3, 4, 5, 6, 7, 8, 9, 10, 15, 20, 25, 30, 35, 40, 45, 50, 60, 70, 80, 90, 100, 200, 500 or more nucleotides of an AIM. An AIM may be used to classify a person as belonging to or not belonging to one or more populations, such as a population that is at increased risk for one of the causal genetic variants. For example, an AIM can be diagnostic for a population in which a trait is at increased prevalence. In certain instances the AIM may distinguish between populations with finer granularity, for example, between sub-continental groups or related ethnic groups. In some embodiments, AIMs are analyzed instead of, or separately from causal genetic variants and/or non-subject sequences. In some embodiments, AIMs, causal genetic variants, and/or non-subject sequences are analyzed in parallel, such as in the same sample (e.g. using a mixture of first oligonucleotides, some with a sequence B that specifically hybridizes to a sequence comprising or near a causal genetic variant, and some with a sequence B that specifically hybridizes to a sequence comprising or near an AIM) and/or in the same report.

In some embodiments, the oligonucleotide primers comprise a first binding partner, such as a member of a binding pair. In general, "binding partner" refers to one of a first and a second moiety, wherein the first and the second moiety have a specific binding affinity for each other. Suitable binding pairs for use in the invention include, but are not limited to, antigens/antibodies (for example, digoxigenin/anti-digoxigenin, dinitrophenyl (DNP)/anti-DNP, dansyl-X-anti-dansyl, Fluorescein/anti-fluorescein, lucifer yellow/anti-lucifer yellow, and rhodamine anti-rhodamine); biotin/avidin (or biotin/streptavidin); calmodulin binding protein (CBP)/calmodulin; hormone/hormone receptor; lectin/carbohydrate; peptide/cell membrane receptor; protein A/antibody; hapten/antihapten; enzyme/cofactor; and enzyme/substrate. Other suitable binding pairs include polypeptides such as the FLAG-peptide (Hopp et al., BioTechnology, 6:1204-1210 (1988)); the KT3 epitope peptide (Martin et al., Science, 255:192-194 (1992)); tubulin epitope peptide (Skinner et al., J. Biol. Chem., 266: 15163-15166 (1991)); and the T7 gene 10 protein peptide tag (Lutz-Freyermuth et al., Proc. Natl. Acad. Sci. USA, 87:6393-6397 (1990)) and the antibodies each thereto. Further non-limiting examples of binding partners include agonists and antagonists for cell membrane receptors, toxins and venoms, viral epitopes, hormones such as steroids, hormone receptors, peptides, enzymes and other catalytic polypeptides, enzyme substrates, cofactors, drugs including small organic molecule drugs, opiates, opiate receptors, lectins, sugars, saccharides including polysaccharides, proteins, and antibodies including monoclonal antibodies and synthetic antibody fragments, cells, cell membranes and moieties therein including cell membrane receptors, and organelles. In some embodiments, the first binding partner is a reactive moiety, and the second binding partner is a reactive surface that reacts with the reactive moiety, such as described herein with respect to other aspects of the invention. In some embodiments, the oligonucleotide primers are attached to the solid surface prior to initiating the extension reaction. Methods for the addition of binding partners to oligonucleotides are known in the art, and include addition during (such as by using a modified nucleotide comprising the binding partner) or after synthesis.

In some embodiments, extension of the oligonucleotide primers is followed by purification of extended primers on a solid surface. In some embodiments, adapter joining is followed by purification of extended primers on a solid surface. Typically, the solid surface comprises a second binding partner, which is the second member of a binding pair and binds to the first binding partner. In some embodiments, a solid surface may have a wide variety of forms, including membranes, slides, plates, micromachined chips, microparticles, beads, and the like. Solid surfaces may comprise a wide variety of materials including, but not limited to, glass, plastic, silicon, alkanethiolate derivatized gold, cellulose, low cross linked and high cross linked polystyrene, silica gel, polyamide, and the like, and can have various shapes and features (e.g., wells, indentations, channels, etc.). The surface can be hydrophilic or capable of being rendered hydrophilic and may comprise inorganic powders such as silica, magnesium sulfate, and alumina; natural polymeric materials, particularly cellulosic materials and materials derived from cellulose, such as fiber containing papers, e.g., filter paper, chromatographic paper, etc.; synthetic or modified naturally occurring polymers, such as nitrocellulose, cellulose acetate, poly (vinyl chloride), polyacrylamide, cross linked dextran, agarose, polyacrylate, polyethylene, polypropylene, poly(4-methylbutene), polystyrene, polymethacrylate, poly(ethylene terephthalate), nylon, poly(vinyl butyrate), etc.; either used by themselves or in conjunction with other materials; glass available as Bioglass, ceramics, metals, and the like. Natural or synthetic assemblies such as liposomes, phospholipid vesicles, and cells can also be employed. The surface can have any one of a number of shapes, such as strip, rod, particle, including bead, and the like.

In some embodiments, the solid surface comprises a bead or plurality of beads. The beads may be of any convenient size and fabricated from any number of known materials. Example of such materials include: inorganics, natural polymers, and synthetic polymers. Specific examples of these materials include: cellulose, cellulose derivatives, acrylic resins, glass, silica gels, polystyrene, gelatin, polyvinyl pyrrolidone, co-polymers of vinyl and acrylamide, polystyrene cross-linked with divinylbenzene or the like (as described, e.g, in Merrifield, Biochemistry 1964, 3, 1385-1390), polyacrylamides, latex gels, polystyrene, dextran, rubber, silicon, plastics, nitrocellulose, natural sponges, silica gels, control pore glass, metals, cross-linked dextrans (e.g., Sephadex) agarose gel (Sepharose), and other solid phase supports known to those of skill in the art. The beads are generally about 2 to about 100 μm in diameter, or about 5 to about 80 pm in diameter, in some cases, about 10 to about 40 μm in diameter. In some embodiments the beads can be magnetic, paramagnetic, or otherwise responsive to a magnetic field. Having beads responsive to a magnetic field can be useful for isolation and purification of the beads having polynucleotides attached thereto, such as by the application of a magnetic field and isolation of the beads (e.g. by removal of the beads from solution, or removal of solution from the beads). Non-limiting examples of beads responsive to a magnetic field include Dynabeads, manufactured by Life Technologies (Carlsbad, Calif.). Other methods to separate beads can also be used. For example, the capture beads may be labeled with a fluorescent moiety which would make the nucleic acid-bead complex fluorescent. The target capture bead complex may be separated, for example, by flow cytometry or fluorescence cell sorter. Beads may also be separated by centrifugation. Isolation of polynucleotides by attachment to beads may further comprise the step of washing the beads, such as in a suitable wash buffer. Generally, purification of primer extension products comprises purification away from one or more components of the primer extension reaction, such that the one or more components from which the extension products are purified are reduced in amount, such as by 10-fold, 5-fold, 100-fold, 500-fold, 1000-fold, 10000-fold, 100000-fold, or more, or below detectable levels. In some embodiments, purification includes a denaturation step such that primer extension products are purified away from the target polynucleotide templates to which they were hybridized.

Extended primers may be subjected to amplification, such as linear or exponential amplification. Methods for amplification are known in art, examples of which are described herein, such as with respect to other aspects of the invention. Exponential amplification includes PCR amplification, and any other amplification methods where primer extension products serve as templates for further rounds of primer extension. Amplification typically utilizes one or more amplification primers, examples of which are described herein, such as with regard to other aspects of the invention. Amplification primers may be of any suitable length, such as about, less than about, or more than about 5, 10, 15, 20, 25, 30, 35, 40, 45, 50, 55, 60, 65, 70, 75, 80, 90, 100, or more nucleotides, any portion or all of which may be complementary to the corresponding target sequence to which the primer hybridizes (e.g. about, less than about, or more than about 5, 10, 15, 20, 25, 30, 35, 40, 45, 50, or more nucleotides). In general, PCR involves the steps of denaturation of the target to be amplified (if double stranded), hybridization of one or more primers to the target, and extension of the primers by a DNA polymerase, with the steps repeated (or "cycled") in order to amplify the target sequence. Steps in this process can be optimized for various outcomes, such as to enhance yield, decrease the formation of spurious products, and/or increase or decrease specificity of primer annealing. Methods of optimization are well known in the art and include adjustments to the type or amount of elements in the amplification reaction and/or to the conditions of a given step in the process, such as temperature at a particular step, duration of a particular step, and/or number of cycles. In some embodiments, an amplification reaction comprises at least 5, 10, 15, 20, 25, 30, 35, 50, or more cycles. In some embodiments, an amplification reaction comprises no more than 5, 10, 15, 20, 25, 35, 50, or more cycles. Cycles can contain any number of steps, such as 1, 2, 3, 4, 5, 6, 7, 8, 9, 10 or more steps. Steps can comprise any temperature or gradient of temperatures, suitable for achieving the purpose of the given step, including but not limited to, strand denaturation, primer annealing, and primer extension. Steps can be of any duration, including but not limited to about, less than about, or more than about 1, 5, 10, 15, 20, 25, 30, 35, 40, 45, 50, 55, 60, 70, 80, 90, 100, 120, 180, 240, 300, 360, 420, 480, 540, 600, or more seconds, including indefinitely until manually interrupted. Cycles of any number comprising different steps can be combined in any order.

In some embodiments, amplification comprises generating primer extension products using a pair of amplification primers. Amplification primers may comprise sequences complementary to complete or one or more portions of sequences derived from adapter oligonucleotide sequences, sequences derived from oligonucleotide primer sequences, sequences that are not complementary to template polynucleotides (e.g. 5' non-complementary sequences), one or more other sequence elements (e.g. sequence elements as described herein), or combinations of these. In some embodiments, a second amplification primer comprises sequence X and sequence Y, where sequence Y is positioned at the 3' end of the second amplification primer.

Figure 2:
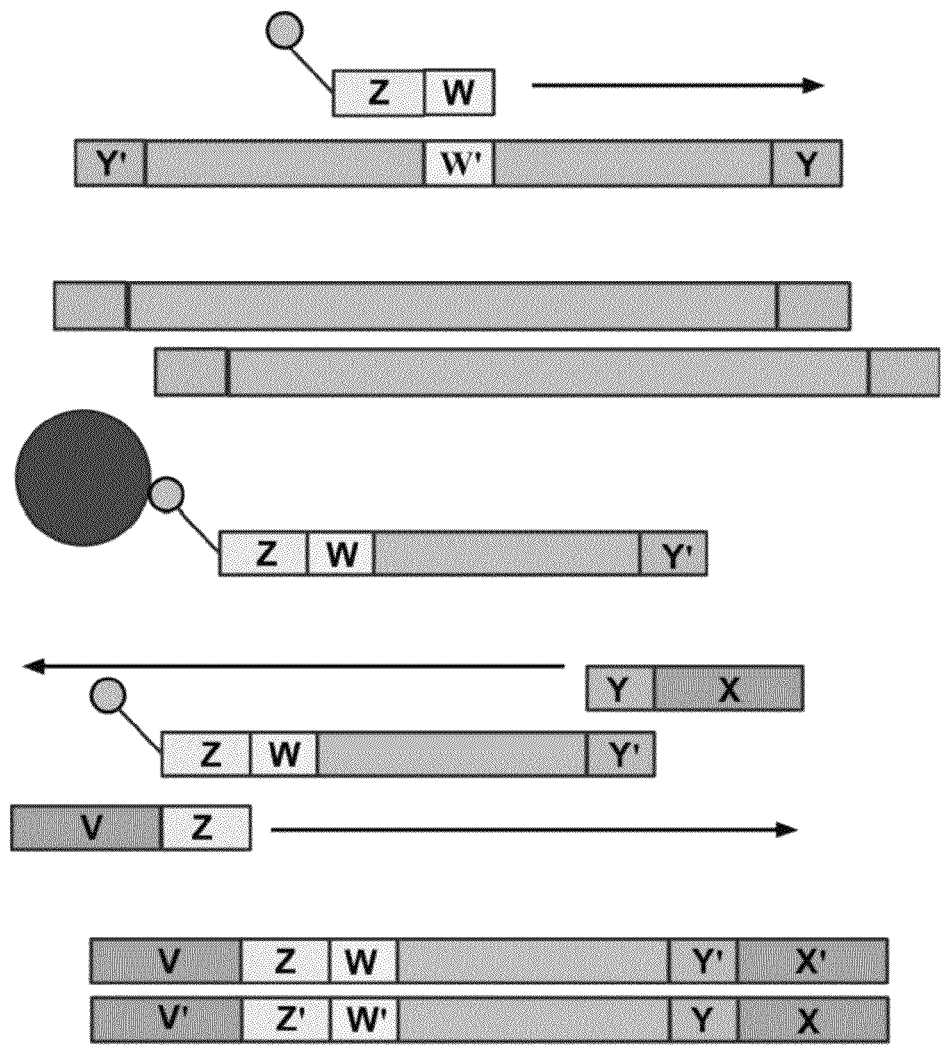
FIG. 2 illustrates an example capture and amplification process in accordance with an embodiment of the invention.

FIG. 2 illustrates a non-limiting example of an amplification process. In a first step of an example exponential amplification reaction, sequence Y of the second amplification primer hybridizes to the complementary sequence Y' of an extended primer from a previous oligonucleotide primer extension reaction. Extension of the second amplification primer (e.g. by a polymerase) produces a second-amplification-primer extension product comprising sequences X, Y, W', and Z' in a 5' to 3' direction, where sequence W' is the complement of sequence W, and sequence Z' is the complement of sequence Z. The primer extension product is then denatured, freeing the template target polynucleotide to serve as template for hybridization with and extension of a further second amplification primer, and the extension product for hybridization with and extension of a first amplification primer. In some embodiments, the first amplification primer comprises sequence V and sequence Z, where sequence Z is positioned at the 3' end of the first amplification primer. In this example amplification reaction, sequence Z hybridizes to sequence Z' of a second amplification primer extension product. Extension of the first amplification primer (e.g. by a polymerase) produces a first-amplification-primer extension product comprising sequences V, Z, W, Y', and X' in a 5' to 3' direction, where sequence X' is complementary to sequence X, which itself can serve as a template for extension of a second amplification primer. Repeated cycles of denaturation, hybridization, and extension thus produce duplexes of primer extension products comprising one strand comprising sequences V, Z, W, Y', and X' (from 5' to 3') hybridized to a second strand comprising sequences X, Y, W', Z', and V' (from 5' to 3'). In accordance with this example amplification reaction, target polynucleotide sequence will generally be positioned between sequences Z and Y' on one strand, and between sequences Z' and Y on the other strand.

In some embodiments the oligonucleotide primer and/or one or more amplification primers comprise a barcode. Examples of barcodes are described herein, such as with regard to other aspects of the invention. In some embodiments, separate amplification reactions are carried out for separate samples using amplification primers comprising at least one different barcode sequence for each sample, such that no barcode sequence is joined to the target polynucleotides of more than one sample to be analyzed in parallel. In some embodiments, amplified polynucleotides derived from different samples and comprising different barcodes are pooled before proceeding with subsequent manipulation of the polynucleotides (such as before sequencing). Pools may comprise polynucleotides derived from about, less than about, or more than about 2, 3, 4, 5, 6, 7, 8, 9, 10, 11, 12, 13, 14, 15, 20, 25, 30, 40, 50, 75, 100, or more different samples. Pools may subsequently be subjected to sequencing, and the source samples of sequenced target polynucleotides may be identified based on their associated barcodes.

In some embodiments, exponentially amplified target polynucleotides are sequenced. Sequencing may be performed according to any method of sequencing known in the art, including sequencing processes described herein, such as with reference to other aspects of the invention. Sequence analysis using template dependent synthesis can include a number of different processes. For example, in the ubiquitously practiced four-color Sanger sequencing methods, a population of template molecules is used to create a population of complementary fragment sequences. Primer extension is carried out in the presence of the four naturally occurring nucleotides, and with a sub-population of dye labeled terminator nucleotides, e.g., dideoxyribonucleotides, where each type of terminator (ddATP, ddGTP, ddTTP, ddCTP) includes a different detectable label. As a result, a nested set of fragments is created where the fragments terminate at each nucleotide in the sequence beyond the primer, and are labeled in a manner that permits identification of the terminating nucleotide. The nested fragment population is then subjected to size based separation, e.g., using capillary electrophoresis, and the labels associated with each different sized fragment is identified to identify the terminating nucleotide. As a result, the sequence of labels moving past a detector in the separation system provides a direct readout of the sequence information of the synthesized fragments, and by complementarity, the underlying template (See, e.g., U.S. Pat. No. 5,171,534).

Other examples of template dependent sequencing methods include sequence by synthesis processes, where individual nucleotides are identified iteratively, as they are added to the growing primer extension product.

Pyrosequencing is an example of a sequence by synthesis process that identifies the incorporation of a nucleotide by assaying the resulting synthesis mixture for the presence of by-products of the sequencing reaction, namely pyrophosphate. In particular, a primer/template/polymerase complex is contacted with a single type of nucleotide. If that nucleotide is incorporated, the polymerization reaction cleaves the nucleoside triphosphate between the $\alpha$ and $\beta$ phosphates of the triphosphate chain, releasing pyrophosphate. The presence of released pyrophosphate is then identified using a chemiluminescent enzyme reporter system that converts the pyrophosphate, with AMP, into ATP, then measures ATP using a luciferase enzyme to produce measurable light signals. Where light is detected, the base is incorporated, where no light is detected, the base is not incorporated. Following appropriate washing steps, the various bases are cyclically contacted with the complex to sequentially identify subsequent bases in the template sequence. See, e.g., U.S. Pat. No. 6,210,891.

In related processes, the primer/template/polymerase complex is immobilized upon a substrate and the complex is contacted with labeled nucleotides. The immobilization of the complex may be through the primer sequence, the template sequence and/or the polymerase enzyme, and may be covalent or noncovalent. For example, immobilization of the complex can be via a linkage between the polymerase or the primer and the substrate surface. In alternate configurations, the nucleotides are provided with and without removable terminator groups. Upon incorporation, the label is coupled with the complex and is thus detectable. In the case of terminator bearing nucleotides, all four different nucleotides, bearing individually identifiable labels, are contacted with the complex. Incorporation of the labeled nucleotide arrests extension, by virtue of the presence of the terminator, and adds the label to the complex, allowing identification of the incorporated nucleotide. The label and terminator are then removed from the incorporated nucleotide, and following appropriate washing steps, the process is repeated. In the case of non-terminated nucleotides, a single type of labeled nucleotide is added to the complex to determine whether it will be incorporated, as with pyrosequencing. Following removal of the label group on the nucleotide and appropriate washing steps, the various different nucleotides are cycled through the reaction mixture in the same process. See, e.g., U.S. Pat. No. 6,833,246, incorporated herein by reference in its entirety for all purposes. For example, the Illumina Genome Analyzer System is based on technology described in WO 98/44151, hereby incorporated by reference, wherein DNA molecules are bound to a sequencing platform (flow cell) via an anchor probe binding site (otherwise referred to as a flow cell binding site) and amplified in situ on a glass slide. A solid surface on which DNA molecules are amplified typically comprise a plurality of first and second bound oligonucleotides, the first complementary to a sequence near or at one end of a target polynucleotide and the second complementary to a sequence near or at the other end of a target polynucleotide. This arrangement permits bridge amplification, such as described herein. The DNA molecules are then annealed to a sequencing primer and sequenced in parallel base-by-base using a reversible terminator approach. Hybridization of a sequencing primer may be preceded by cleavage of one strand of a double-stranded bridge polynucleotide at a cleavage site in one of the bound oligonucleotides anchoring the bridge, thus leaving one single strand not bound to the solid substrate that may be removed by denaturing, and the other strand bound and available for hybridization to a sequencing primer. Typically, the Illumina Genome Analyzer System utilizes flow-cells with 8 channels, generating sequencing reads of 18 to 36 bases in length, generating >1.3 Gbp of high quality data per run (see www.illumina.com).

In yet a further sequence by synthesis process, the incorporation of differently labeled nucleotides is observed in real time as template dependent synthesis is carried out. In particular, an individual immobilized primer/template/polymerase complex is observed as fluorescently labeled nucleotides are incorporated, permitting real time identification of each added base as it is added. In this process, label groups are attached to a portion of the nucleotide that is cleaved during incorporation. For example, by attaching the label group to a portion of the phosphate chain removed during incorporation, i.e., a β,γ, or other terminal phosphate group on a nucleoside polyphosphate, the label is not incorporated into the nascent strand, and instead, natural DNA is produced. Observation of individual molecules typically involves the optical confinement of the complex within a very small illumination volume. By optically confining the complex, one creates a monitored region in which randomly diffusing nucleotides are present for a very short period of time, while incorporated nucleotides are retained within the observation volume for longer as they are being incorporated. This results in a characteristic signal associated with the incorporation event, which is also characterized by a signal profile that is characteristic of the base being added. In related aspects, interacting label components, such as fluorescent resonant energy transfer (FRET) dye pairs, are provided upon the polymerase or other portion of the complex and the incorporating nucleotide, such that the incorporation event puts the labeling components in interactive proximity, and a characteristic signal results, that is again, also characteristic of the base being incorporated (See, e.g., U.S. Pat. Nos. 6,056,661, 6,917,726, 7,033,764, 7,052,847, 7,056,676, 7,170,050, 7,361,466, and 7,416,844; and US 20070134128).

In some embodiments, the nucleic acids in the sample can be sequenced by ligation. This method uses a DNA ligase enzyme to identify the target sequence, for example, as used in the polony method and in the SOLiD technology (Applied Biosystems, now Invitrogen). In general, a pool of all possible oligonucleotides of a fixed length is provided, labeled according to the sequenced position. Oligonucleotides are annealed and ligated; the preferential ligation by DNA ligase for matching sequences results in a signal corresponding to the complementary sequence at that position.

In some embodiments, sequencing data are generated for a plurality of samples in parallel, such as about, less than about, or more than about 2, 3, 4, 5, 6, 7, 8, 9, 10, 11, 12, 13, 14, 15, 16, 17, 18, 19, 20, 24, 48, 96, 192, 384, 768, 1000, or more samples. In some embodiments, sequencing data are generated for a plurality of samples in a single reaction container (e.g. a channel in a flow cell), such as about, less than about, or more than about 2, 3, 4, 5, 6, 7, 8, 9, 10, 11, 12, 13, 14, 15, 16, 17, 18, 19, 20, 24, 48, 96, 192, 384, 768, 1000, or more samples, and sequencing data are subsequently grouped according to the sample from which the sequenced polynucleotides originated (e.g. based on a barcode sequence).

In some embodiments, sequencing data are generated for about, less than about, or more than about 5, 10, 25, 50, 100, 150, 200, 250, 300, 400, 500, 750, 1000, 2500, 5000, 7500, 10000, 20000, 50000, or more different target polynucleotides from a sample in a single reaction container (e.g. a channel in a flow cell). In some embodiments, sequencing data are generated for a plurality of samples in parallel, such as about, less than about, or more than about 2, 3, 4, 5, 6, 7, 8, 9, 10, 11, 12, 13, 14, 15, 16, 17, 18, 19, 20, 24, 48, 96, 192, 384, 768, 1000, or more samples. In some embodiments, sequencing data are generated for a plurality of samples in a single reaction container (e.g. a channel in a flow cell), such as about, less than about, or more than about 2, 3, 4, 5, 6, 7, 8, 9, 10, 11, 12, 13, 14, 15, 16, 17, 18, 19, 20, 24, 48, 96, 192, 384, 768, 1000, or more samples, and sequencing data are subsequently grouped according to the sample from which the sequenced polynucleotides originated. In a single reaction, sequencing data may be generated for about or at least about $10^6$, $10^7$, $10^8$, $2\times10^8$, $3\times10^8$, $4\times10^8$, $5\times10^8$, $10^9$, $10^{10}$, or more target polynucleotides or clusters from a bridge amplification reaction, which may comprise sequencing data for about, less than about, or more than about $10^4$, $10^5$, $10^6$, $2\times10^6$, $3\times10^6$, $4\times10^6$, $5\times10^6$, $10^7$, $10^8$ target polynucleotides or clusters for each sample in the reaction. In some embodiments, the presence or absence of about, less than about, or more than about 5, 10, 25, 50, 75, 100, 125, 150, 175, 200, 300, 400, 500, 750, 1000, 2500, 5000, 7500, 10000, 20000, 50000, or more causal genetic variants is determined for a sample based on the sequencing data. The presence or absence of one or more causal genetic variants may be determined with an accuracy of about or more than about 80%, 85%, 90%, 95%, 97.5%, 99%, 99.5%, 99.9% or higher.

In some embodiments, one or more, or all, of the steps in a method of the invention are automated, such as by use of one or more automated devices. In general, automated devices are devices that are able to operate without human direction—an automated system can perform a function during a period of time after a human has finished taking any action to promote the function, e.g. by entering instructions into a computer, after which the automated device performs one or more steps without further human operation. Software and programs, including code that implements embodiments of the present invention, may be stored on some type of data storage media, such as a CD-ROM, DVD-ROM, tape, flash drive, or diskette, or other appropriate computer readable medium. Various embodiments of the present invention can also be implemented exclusively in hardware, or in a combination of software and hardware. For example, in one embodiment, rather than a conventional personal computer, a Programmable Logic Controller (PLC) is used. As known to those skilled in the art, PLCs are frequently used in a variety of process control applications where the expense of a general purpose computer is unnecessary. PLCs may be configured in a known manner to execute one or a variety of control programs, and are capable of receiving inputs from a user or another device and/or providing outputs to a user or another device, in a manner similar to that of a personal computer. Accordingly, although embodiments of the present invention are described in terms of a general purpose computer, it should be appreciated that the use of a general purpose computer is exemplary only, as other configurations may be used.

In some embodiments, automation may comprise the use of one or more liquid handlers and associated software. Several commercially available liquid handling systems can be utilized to run the automation of these processes (see for example liquid handlers from Perkin-Elmer, Beckman Coulter, Caliper Life Sciences, Tecan, Eppendorf, Apricot Design, Velocity 11 as examples). In some embodiments, automated steps include one or more of fragmentation, end-repair, A-tailing (addition of adenine overhang), adapter joining, PCR amplification, sample quantification (e.g. amount and/or purity of DNA), and sequencing. In some embodiments, bridge amplification is automated (e.g. by use of an Illumina cBot). In some embodiments, sequencing is automated. A variety of automated sequencing machines are commercially available, and include sequencers manufactured by Life Technologies (SOLiD platform, and pH-based detection), Roche (454 platform), Illumina (e.g. flow cell based systems, such as Genome Analyzer devices). Transfer between 2, 3, 4, 5, or more automated devices (e.g. between one or more of a liquid handler, bridge a amplification device, and a sequencing device) may be manual or automated. In some embodiments, one or more steps in a method of the invention (e.g. all steps or all automated steps) are completed in about or less than about 72, 48, 24, 20, 18, 16, 14, 12, 10, 9, 8, 7, 6, 5, 4, 3, 2, 1, or fewer hours. In some embodiments, the time from sample receipt, DNA extraction, fragmentation, adapter joining, amplification, or bridge amplification to production of sequencing data is about or less than about 72, 48, 24, 20, 18, 16, 14, 12, 10, 9, 8, 7, 6, 5, 4, 3, 2, 1, or fewer hours.

In one aspect, the invention provides a method of detecting genetic variation in a subject's genome. In some embodiments, the method comprises generating and analyzing sequencing data. In one embodiment, the method comprises: (a) providing a plurality of clusters of polynucleotides, wherein (i) each cluster comprises multiple copies of a nucleic acid duplex attached to a support; (ii) each duplex in a cluster comprises a first molecule comprising sequences A-B-G'-D'-C' from 5' to 3' and a second molecule comprising sequences C-D-G-B'-A' from 5' to 3'; (iii) sequence A' is complementary to sequence A, sequence B' is complementary to sequence B, sequence C' is complementary to sequence C, sequence D' is complementary to sequence D, and sequence G' is complementary to sequence G; (iv) sequence G is a portion of a target polynucleotide sequence from a subject and is different for each of a plurality of clusters; and (v) sequence B' is located 5' with respect to sequence G in the corresponding target polynucleotide sequence; (b) sequencing sequence G' by extension of a first primer comprising sequence D to produce an R1 sequence for each cluster; (c) sequencing sequence B' by extension of a second primer comprising sequence A to produce R2 sequence for each cluster; (d) performing a first alignment using a first algorithm to align all R1 sequences to one or more first reference sequences; (e) performing a second alignment using a second algorithm to locally align R1 sequences identified in said first alignment as likely to contain an insertion or deletion with respect to said one or more first reference sequences, to produce a single consensus alignment for each insertion or deletion; (f) performing an R2 alignment by aligning all R2 sequences to one or more second reference sequences; and (g) transmitting a report identifying sequence variation identified by steps (d) to (f) to a receiver. In some embodiments, sequence A, B, C, and D correspond to sequence A, B, C, and D, respectively, as described with regard to other aspects of the invention.

In some embodiments, the method comprises: (a) providing sequencing data for a plurality of clusters of polynucleotides, wherein (i) each cluster comprised multiple copies of a nucleic acid duplex attached to a support; (ii) each duplex in a cluster comprised a first molecule comprising sequences A-B-G'-D'-C' from 5' to 3' and a second molecule comprising sequences C-D-G-B'-A' from 5' to 3'; (iii) sequence A' is complementary to sequence A, sequence B' is complementary to sequence B, sequence C' is complementary to sequence C, sequence D' is complementary to sequence D, and sequence G' is complementary to sequence G; (iv) sequence G is a portion of a target polynucleotide sequence from a subject and is different for each of a plurality of clusters; (v) sequence B' is located 5' with respect to sequence G in the corresponding target polynucleotide sequence; (viii) the sequencing data comprises R1 sequences generated by extension of a first primer comprising sequence D; and (vi) the sequencing data comprises R2 sequences generated by extension of a second primer comprising sequence A; (b) performing a first alignment using a first algorithm to align all R1 sequences to one or more first reference sequences; (c) performing a second alignment using a second algorithm to locally align R1 sequences identified in said first alignment as likely to contain an insertion or deletion with respect to said one or more first reference sequences, to produce a single consensus alignment for each insertion or deletion; (d) performing an R2 alignment by aligning all R2 sequences to one or more second reference sequences; and (e) transmitting a report identifying sequence variation identified by steps (b) to (d) to a receiver. In some embodiments, sequence A, B, C, and D correspond to sequence A, B, C, and D, respectively, as described with regard to other aspects of the invention.

In general, a cluster of polynucleotides comprises multiple copies of a nucleic acid duplex that co-localize to a position on a support. A variety of suitable solid supports and support materials are known in the art, non-limiting examples of which are provided herein, such as with regard to other aspects of the invention. Clusters of polynucleotides may be produced by bridge amplification. Suitable methods and apparatuses for performing bridge amplification are provided herein, such as with regard to other aspects of the invention. In some embodiments, a solid support comprises a plurality of clusters, with each cluster in the plurality formed by amplification of a different target polynucleotide sequence. The portion of a target polynucleotide sequence to be amplified, such as a sequence G, may be bound to a support in a process comprising extension of a first oligonucleotide immobilized on the support. In some embodiments, the solid support comprises a plurality of different first oligonucleotides comprising sequence A and sequence B, wherein sequence A is common among all first oligonucleotides; and further wherein sequence B is different for each different first oligonucleotide, and is at the 3' end of each first oligonucleotide. In some embodiments, the plurality of first oligonucleotides comprises about, less than about, or more than about 5, 10, 25, 50, 75, 100, 125, 150, 175, 200, 300, 400, 500, 750, 1000, 2500, 5000, 7500, 10000, 20000, 50000, or more different oligonucleotides, each comprising a different sequence B. In some embodiments, sequence B of one or more of the plurality of first oligonucleotides comprises a sequence selected from the group consisting of SEQ ID NOs 22-121, shown in FIG. 4 (e.g. 1, 5, 10, 25, 50, 75, or 100 different oligonucleotides each with a different sequence from FIG. 4). In some embodiments, sequence B or the target sequence to which it specifically hybridizes comprises a causal genetic variant, as described herein. In some embodiments, sequence B or the target sequence to which it specifically hybridizes is within about, less than about, or more than about 1, 2, 3, 4, 5, 6, 6, 7, 8, 9, 10, 15, 20, 25, 30, 35, 40, 45, 50, 60, 70, 80, 90, 100, 200, 500 or more nucleotides of a causal genetic variant, as described herein. Causal genetic variants are typically located downstream of a first oligonucleotide, such that at least a portion of the causal genetic variant serves as template for extension of a first oligonucleotide. The solid support may further comprise a plurality of second oligonucleotides comprising sequence A at the 3' end of each second oligonucleotide, and a plurality of third oligonucleotides comprising sequence C at the 3' end of each third oligonucleotide, as described herein. An example of bridge amplification of a portion of a target polynucleotide sequence using bound first, second, and third oligonucleotides to produce clusters of duplexes is illustrated in FIG. 1, with sequence G' represented by the black line between sequences B and D', and sequence G represented by the black line between sequence B' and D.

In some embodiments, sequence B of one or more of the plurality of first oligonucleotides or the target sequence to which it specifically hybridizes comprises a non-subject sequence. In some embodiments, sequence B or the target sequence to which it specifically hybridizes is within about, less than about, or more than about 1, 2, 3, 4, 5, 6, 7, 8, 9, 10, 15, 20, 25, 30, 35, 40, 45, 50, 60, 70, 80, 90, 100, 200, 500 or more nucleotides of a non-subject sequence. In general, a non-subject sequence corresponds to a polynucleotide derived from an organism other than the individual being tested or from whom a sample is taken, such as DNA or RNA from bacteria, archaea, viruses, protists, fungi, or other organism. Non-subject sequence can also include nucleic acids from a fetus, such as cell-free nucleic acid (also referred to as extracellular nucleic acid) from a fetus. A non-subject sequence may be indicative of the identity of an organism or class of organisms, and may further be indicative of a disease state, such as infection. An example of non-subject sequences useful in identifying an organism include, without limitation, rRNA sequences, such as 16s rRNA sequences (see e.g. WO2010151842). In some embodiments, non-subject sequences are analyzed instead of, or separately from causal genetic variants. In some embodiments, causal genetic variants and non-subject sequences are analyzed in parallel, such as in the same sample (e.g. using a mixture of first oligonucleotides, some with a sequence B that specifically hybridizes to a sequence comprising or near a causal genetic variant, and some with a sequence B that specifically hybridizes to a sequence comprising or near a non-subject sequence) and/or in the same report.

In some embodiments, sequence B of one or more of the plurality of first oligonucleotides or the target sequence to which it specifically hybridizes comprises an ancestry informative marker (AIM). In some embodiments, sequence B or the target sequence to which it specifically hybridizes is within about, less than about, or more than about 1, 2, 3, 4, 5, 6, 7, 8, 9, 10, 15, 20, 25, 30, 35, 40, 45, 50, 60, 70, 80, 90, 100, 200, 500 or more nucleotides of an AIM. An AIM may be used to classify a person as belonging to or not belonging to one or more populations, such as a population that is at increased risk for one of the causal genetic variants. For example, an AIM can be diagnostic for a population in which a trait is at increased prevalence. In certain instances the AIM may distinguish between populations with finer granularity, for example, between sub-continental groups or related ethnic groups. In some embodiments, AIMs are analyzed instead of, or separately from causal genetic variants and/or non-subject sequences. In some embodiments, AIMs, causal genetic variants, and/or non-subject sequences are analyzed in parallel, such as in the same sample (e.g. using a mixture of first oligonucleotides, some with a sequence B that specifically hybridizes to a sequence comprising or near a causal genetic variant, and some with a sequence B that specifically hybridizes to a sequence comprising or near an AIM) and/or in the same report.

In some embodiments, one or more sequences of a plurality of clusters are sequenced. Example methods of sequencing are described herein, such as with regard to other aspects of the invention. Sequencing data may be produced by extension of one or more sequencing primers for each cluster. A sequencing primer can be of any suitable length, such as about, less than about, or more than about 5, 10, 15, 20, 25, 30, 35, 40, 45, 50, 55, 60, 65, 70, 75, 80, 90, 100, or more nucleotides, any portion or all of which may be complementary to the corresponding target sequence to which the primer hybridizes (e.g. about, less than about, or more than about 5, 10, 15, 20, 25, 30, 35, 40, 45, 50, or more nucleotides). A sequencing primer, primer D, may comprise or consist of sequence D, such that it specifically hybridizes to complementary sequence D'. In some embodiments, the first nucleotide downstream of sequence D' is the first nucleotide of sequence G', such that the first nucleotide added in extension of primer D corresponds to sequence G. A sequencing primer, primer C, may comprise or consist of sequence C, such that it specifically hybridizes to complementary sequence C'. In some embodiments, the first nucleotide downstream of sequence C' is the first nucleotide of a barcode sequence, such that the first nucleotide added in extension of primer C corresponds to a barcode sequence. A sequencing primer, primer A, may comprise or consist of sequence A, such that it specifically hybridizes to complementary sequence A'. In some embodiments, the first nucleotide downstream of sequence A' is the first nucleotide of sequence B', such that the first nucleotide added in extension of primer A corresponds to sequence B. In some embodiments, a sequencing primer comprises the sequence CACTCAGCAGCACGACGATCACAGATGT-GTATAAGAGACAG (SEQ ID NO: 20).

Two or more different sequencing primers may be used in successive sequencing reactions to produce multiple sequencing reads for each cluster. For example, successive sequencing reactions may be performed for each of primers A, C, and D, in any order (e.g. primer D, then primer C, then primer A). A sequencing reaction may be preceded by one or more of: strand cleavage, strand denaturation, or a wash step to remove one or more components of a previous reaction (e.g. a sequencing primer). A sequencing reaction may comprise multiple cycles of individual nucleotide primer extension, with each addition followed by an identification step to determine the identity of the added base. The number of cycles of individual nucleotide extension may be about or more than about 1, 2, 3, 4, 5, 6, 7, 8, 9, 10, 11, 12, 13, 14, 15, 16, 17, 18, 19, 20, 30, 40, 50, 60, 70, 80, 90, 100, 150, 200, 250, 500, or more, such as for each of a plurality of sequencing primers used in successive sequencing reactions, or collectively for all sequencing primers used in successive sequencing reactions. In some embodiments, the number of cycles of individual nucleotide extension is selected based on the length of the sequence to be identified, such as a barcode or probe sequence, and may be less than about 30, 25, 20, 15, 10, 9, 8, 7, 6, 5, or fewer cycles. The number of cycles for each of a plurality of sequencing primers used in successive sequencing reactions may be different. For example, 59 cycles of extension of primer D may be followed by 6 cycles of extension of primer C, which may then be followed by 15 cycles of extension of primer A, for 80 total cycles of extension.

Extension of a first sequencing primer, second sequencing primer, and a third primer that is an indexing primer may produce an R1, an R2, and a barcode sequence, respectively, for each cluster. In general, multiple sequences are identified as originating from a single cluster based on physical co-localization of successive extension reactions, such as a position on an array of clusters. In some embodiments, sequencing data (e.g. R1 and/or R2 sequences) are generated for about, less than about, or more than about 5, 10, 25, 50, 100, 150, 200, 250, 300, 400, 500, 750, 1000, 2500, 5000, 7500, 10000, 20000, 50000, or more different target polynucleotides from a sample in a single reaction container (e.g. a channel in a flow cell), such as by extension of one or more sequencing primers. In some embodiments, sequencing data are generated for a plurality of samples in parallel, such as about, less than about, or more than about 2, 3, 4, 5, 6, 7, 8, 9, 10, 11, 12, 13, 14, 15, 16, 17, 18, 19, 20, 24, 48, 96, 192, 384, 768, 1000, or more samples. In some embodiments, sequencing data are generated for a plurality of samples in a single reaction container (e.g. a channel in a flow cell), such as about, less than about, or more than about 2, 3, 4, 5, 6, 7, 8, 9, 10, 11, 12, 13, 14, 15, 16, 17, 18, 19, 20, 24, 48, 96, 192, 384, 768, 1000, or more samples, and sequencing data are subsequently grouped according to the sample from which the sequenced polynucleotides originated (e.g. based on a barcode sequence). Grouping of sequencing data based on barcode sequences may be performed before or after performing one or more alignments, such as described herein, and optionally before removing one or more sequences from analysis. In general, once sequencing reads are grouped based on a barcode, each group of reads is further processed independently of other groups. In some embodiments, each barcode differs from every other barcode in a plurality of different barcodes analyzed in parallel. Typically, a barcode sequence is associated with a single sample in a pool of samples sequenced in a single reaction. In some embodiments, each of a plurality of barcode sequences is uniquely associated with a single sample in a pool of samples sequenced simultaneously. In some embodiments, a barcode sequence is located 5' from sequence D'.

In a single reaction, sequencing data (e.g. R1 and/or R2 sequence) may be generated for about or at least about $10^6$, $10^7$, $10^8$, $2 \times 10^8$, $3 \times 10^8$, $4 \times 10^8$, $5 \times 10^8$, $10^9$, $10^{10}$, or more target polynucleotides or clusters from a bridge amplification reaction, which may comprise sequencing data for about, less than about, or more than about $10^4$, $10^5$, $10^6$, $2 \times 10^6$, $3 \times 10^6$, $4 \times 10^6$, $5 \times 10^6$, $10^7$, $10^8$ target polynucleotides or clusters for each sample in the reaction. A sequencing system may output sequencing data in any of a variety of output data file types or formats, including, but not limited to, *.fasta, *.csfasta, *seq.txt, *qseq.txt, *.fastq, *.sff, *prb.txt, *.sms, *srs and/or *.qv. In some embodiments, the presence or absence of about, less than about, or more than about 5, 10, 25, 50, 75, 100, 125, 150, 175, 200, 300, 400, 500, 750, 1000, 2500, 5000, 7500, 10000, 20000, 50000, or more causal genetic variants is determined for a sample based on the sequencing data. The presence, absence, or allele ratio of one or more causal genetic variants may be determined with an accuracy of about or more than about 80%, 85%, 90%, 95%, 97.5%, 99%, 99.5%, 99.9% or higher. In some embodiments, the presence, absence, or quantity of one or more non-subject sequence and/or one or more AIM is determined with an accuracy of about or more than about 80%, 85%, 90%, 95%, 97.5%, 99%, 99.5%, 99.9% or higher.

In some embodiments, sequences identified in one or more sequencing reactions for a plurality of clusters are aligned to a reference sequence. In general, alignment involves placing one sequence along another sequence, iteratively introducing gaps along each sequence, scoring how well the two sequences match, and preferably repeating for various positions along the reference. The best-scoring match is deemed to be the alignment and represents an inference about the degree of relationship between the sequences. In some embodiments, a reference sequence to which sequencing reads are compared is a reference genome, such as the genome of a member of the same species as the subject. A reference genome may be complete or incomplete. In some embodiments, a reference genome consists only of regions containing target polynucleotides. In some embodiments, a reference sequence comprises or consists of a human genome. In some embodiments, a reference sequence comprises or consists of sequences of polynucleotides of one or more organisms other than the individual being tested or from whom a sample is taken, such as sequences from one or more bacteria, archaea, viruses, protists, fungi, or other organism. In some embodiments, a reference sequence comprises or consists of a plurality of known sequences, such as all probe sequences used to amplify target polynucleotide sequences (e.g. every sequence B and/or sequence B' for every different target polynucleotide). Sequencing data generated from the extension of one primer (e.g. R1 sequences from primer D) may be aligned to the same or different reference sequence as sequencing data generated from the extension of another primer (e.g. R2 sequences from primer A). Sequencing data generated from the extension of one primer may be aligned to a reference sequence two or more times, with each alignment using a different alignment algorithm. R1 sequences may be aligned independently of R2 sequences. A first alignment of R1 and R2 sequences may use the same alignment algorithm.

In an alignment, a base in the sequencing read alongside a non-matching base in the reference indicates that a substitution mutation has occurred at that point. Similarly, where one sequence includes a gap alongside a base in the other sequence, an insertion or deletion mutation (an "indel") is inferred to have occurred. When it is desired to specify that one sequence is being aligned to one other, the alignment is sometimes called a pairwise alignment. Multiple sequence alignment generally refers to the alignment of two or more sequences, including, for example, by a series of pairwise alignments. In some embodiments, scoring an alignment involves setting values for the probabilities of substitutions and indels. When individual bases are aligned, a match or mismatch contributes to the alignment score by a substitution probability, which could be, for example, 1 for a match and 0.33 for a mismatch. An indel deducts from an alignment score by a gap penalty, which could be, for example, −1. Gap penalties and substitution probabilities can be based on empirical knowledge or a priori assumptions about how sequences mutate. Their values affect the resulting alignment. Examples of algorithms for performing alignments include, without limitation, the Smith-Waterman (SW) algorithm, the Needleman-Wunsch (NW) algorithm, algorithms based on the Burrows-Wheeler Transform (BWT), and hash function aligners such as Novoalign (Novocraft Technologies; available at www.novocraft.com), ELAND (Illumina, San Diego, Calif.), SOAP (available at soap.genomics.org.cn), and Maq (available at maq.sourceforge.net).

In some embodiments, an alignment according to the invention is performed using a computer program. One exemplary alignment program, which implements a BWT approach, is Burrows-Wheeler Aligner (BWA) available from the SourceForge web site maintained by Geeknet (Fairfax, Va.). BWT typically occupies 2 bits of memory per nucleotide, making it possible to index nucleotide sequences as long as 4G base pairs with a typical desktop or laptop computer. The pre-processing includes the construction of BWT (i.e., indexing the reference) and the supporting auxiliary data structures. BWA includes two different algorithms, both based on BWT. Alignment by BWA can proceed using the algorithm bwa-short, designed for short queries up to about 200 bp with low error rate (<3%) (Li H. and Durbin R. Bioinformatics, 25:1754-60 (2009)). The second algorithm, BWA-SW, is designed for long reads with more errors (Li H. and Durbin R. (2010). Fast and accurate long-read alignment with Burrows-Wheeler Transform. Bioinformatics, Epub.). One skilled in the art will recognize that bwa-sw is sometimes referred to as "bwa-long", "bwa long algorithm", or similar.

An alignment program that implements a version of the Smith-Waterman algorithm is MUMmer, available from the SourceForge web site maintained by Geeknet (Fairfax, Va.). MUMmer is a system for rapidly aligning entire genomes, whether in complete or draft form (Kurtz, S., et al., Genome Biology, 5:R12 (2004); Delcher, A. L., et al., Nucl. Acids Res., 27:11 (1999)). For example, MUMmer 3.0 can find all 20-basepair or longer exact matches between a pair of 5-megabase genomes in 13.7 seconds, using 78 MB of memory, on a 2.4 GHz Linux desktop computer. MUMmer can also align incomplete genomes; it can easily handle the 100s or 1000s of contigs from a shotgun sequencing project, and will align them to another set of contigs or a genome using the NUCmer program included with the system.

Other non-limiting examples of alignment programs include: BLAT from Kent Informatics (Santa Cruz, Calif.) (Kent, W. J., Genome Research 4: 656-664 (2002)); SOAP2, from Beijing Genomics Institute (Beijing, Conn.) or BGI Americas Corporation (Cambridge, Mass.); Bowtie (Langmead, et al., Genome Biology, 10:R25 (2009)); Efficient Large-Scale Alignment of Nucleotide Databases (ELAND) or the ELANDv2 component of the Consensus Assessment of Sequence and Variation (CASAVA) software (Illumina, San Diego, Calif.); RTG Investigator from Real Time Genomics, Inc. (San Francisco, Calif.); Novoalign from Novocraft (Selangor, Malaysia); Exonerate, European Bioinformatics Institute (Hinxton, UK) (Slater, G., and Birney, E., BMC Bioinformatics 6:31(2005)), Clustal Omega, from University College Dublin (Dublin, Ireland) (Sievers F., et al., Mol Syst Biol 7, article 539 (2011)); ClustalW or ClustalX from University College Dublin (Dublin, Ireland) (Larkin M. A., et al., Bioinformatics, 23, 2947-2948 (2007)); and FASTA, European Bioinformatics Institute (Hinxton, UK) (Pearson W. R., et al., PNAS 85(8):2444-8 (1988); Lipman, D. J., Science 227(4693):1435-41 (1985)).

In some embodiments, any or all of the steps of the invention are automated. For example, a Perl script or shell script can be written to invoke any of the various programs discussed above (see, e.g., Tisdall, Mastering Perl for Bioinformatics, O'Reilly & Associates, Inc., Sebastopol, Calif. 2003; Michael, R., Mastering Unix Shell Scripting, Wiley Publishing, Inc., Indianapolis, Ind. 2003). Alternatively, methods of the invention may be embodied wholly or partially in one or more dedicated programs, for example, each optionally written in a compiled language such as C++ then compiled and distributed as a binary. Methods of the invention may be implemented wholly or in part as modules within, or by invoking functionality within, existing sequence analysis platforms. In certain embodiments, methods of the invention include a number of steps that are all invoked automatically responsive to a single starting queue (e.g., one or a combination of triggering events sourced from human activity, another computer program, or a machine). Thus, the invention provides methods in which any or the steps or any combination of the steps can occur automatically responsive to a queue. The output can be provided in the format of a computer file. In certain embodiments, the output is a FASTA file, VCF file, text file, or an XML file containing sequence data such as a sequence of the nucleic acid aligned to a sequence of the reference genome. In other embodiments, the output contains coordinates or a string describing one or more mutations in the subject nucleic acid relative to the reference genome. Alignment strings known in the art include Simple UnGapped Alignment Report (SUGAR), Verbose Useful Labeled Gapped Alignment Report (VULGAR), and Compact Idiosyncratic Gapped Alignment Report (CIGAR) (Ning, Z., et al., Genome Research 11(10):1725-9 (2001)). In some embodiments, the output is a sequence alignment—such as, for example, a sequence alignment map (SAM) or binary alignment map (BAM) file—comprising a CIGAR string (the SAM format is described, e.g., in Li, et al., The Sequence Alignment/Map format and SAMtools, Bioinformatics, 2009, 25(16):2078-9). In some embodiments, CIGAR displays or includes gapped alignments one-per-line. CIGAR is a compressed pairwise alignment format reported as a CIGAR string.

In some embodiments, R1 sequence from a cluster comprises sequence G from a plurality of different target polynucleotides and R2 sequence from a cluster comprises sequence B, where sequence B is a probe sequence used to generate a cluster of amplified duplexes. When each sequence B is selected to target a specific target polynucleotide, its sequence and location within the reference sequences (e.g. reference genome) is generally known, and R1 sequences from the same cluster may be expected to fall within an anticipated nucleotide distance. An anticipated nucleotide distance may be based on an average or median fragment length for samples comprising fragmented sample polynucleotides, or an upper threshold distance representing an unlikely fragment length based on such median or average fragment length. Thus, in some embodiments, an R1 sequence that aligns to a position further away than the threshold distance from the R2 sequence from the same cluster may be erroneous and is discarded. In some embodiments, the upper threshold distance along a reference sequence between aligned R1 and R2 sequences from the same cluster, above which sequence reads for a cluster are discarded, is about, or more than about 1000, 2500, 5000, 7500, 10000, 12500, 15000, 20000 or more base pairs. In some embodiments, alignments of R1 sequences to non-unique regions of a reference sequence (e.g. a reference genome) are discarded and the sequences re-aligned to a smaller subset of unique sequences within the reference sequence.

Typically, a base quality score is determined for each nucleotide in a sequencing result, and relates to the probability that a particular base call is wrong. An example of a base quality score is a Phred quality score Q, where $Q=-10 \log_{10} P$, and where P represents the probability that the corresponding base call is incorrect. In some embodiments, base quality scores are used to evaluate alignments of sequencing reads to a reference sequence, such as by determining a mapping quality score for each of a plurality of alignments. Methods for calculating mapping quality scores are known in the art. For example, alignments having a quality score below a threshold value may be discarded, re-aligned, or replaced with an alternative alignment having a higher score. In some embodiments, an alignment with a mapping quality score below a threshold value and having more than one optimal alignment is re-aligned to a subset of sequences within the reference sequence, such as only regions of a reference genome containing target polynucleotides. In some embodiments, a threshold mapping quality score is about, or less than about 100, 75, 50, 25, 20, 10, 5, 4, 3, 2, 1, or 0.

In some embodiments, sequencing reads likely to be duplicative are removed following an initial alignment. When sequencing reads are mapped, duplicative reads may be marked as duplicates by the alignment algorithm. For example, a mark duplicates subroutine within the alignment algorithm examines all of the records in a file of aligned sequences (e.g. a *.BAM file) and decides which reads are duplicates of other reads. Generally speaking, there are two types of duplicates: optical duplicates, which are typically caused by defects in the primary analysis software, and PCR duplicates, which are caused by duplicative PCR reactions. However from a computational point of view, optical duplicates and PCR duplicates are indistinguishable. One way to determine if two sequence reads are duplicates or not is to compare the base sequences—two duplicate reads should have duplicate base sequences. However, due to sequencing errors, it may be the case that two duplicate reads are sequenced such that a sequencing error for one read will cause its base sequence to differ significantly from the other read. Therefore, rather than compare base sequences to determine if two reads are duplicates, their alignments can be compared instead. If two reads are duplicates, then the entire set of alignments for both reads will generally be the same. In some embodiments, duplicates are marked for removal and/or discarded using one or more algorithms distinct from the alignment algorithm. In general, when barcode sequences are used, sequencing reads are only deleted when occurring within the same barcode sequence grouping.

In some embodiments, a second alignment using a second algorithm is performed after a first alignment using a first algorithm. The second alignment may be with respect to the same reference sequence as the first alignment, a different reference sequence from that used in the first alignment, or without use of a reference sequence (such as when all sequencing reads overlapping a particular region are aligned with one another). For example, sequences identified in a first alignment as likely to contain an insertion and/or deletion (indel) with respect to the first reference sequence may be locally aligned to produce a single consensus sequence for an insertion and/or deletion contained in a target polynucleotide. A first alignment may align individual sequences to a reference sequence independently. In some cases, a sequencing read with a true indel may be aligned with multiple mismatches rather than an indel when an alignment model with multiple mismatches scores higher than the indel-containing alignment. Typically, multiple sequences are aligned as overlapping a single nucleotide position (such as in a tiled fashion). Overlapping regions containing more than a predicted amount of sequence variation (for example, more than two alleles for a unique locus in a genome of a human subject) may indicate the likely presence of an indel. The location of some indels for a particular reference sequence may be known, such that sequences overlapping the location of a known indel identifies the sequence as likely to contain an indel. The likelihood of containing an indel may be expressed numerically, based on one or more such factors, such as a likelihood of at least about 60%, 70%, 80%, 90%, 95%, 99%, or more. In some embodiments, all sequences overlapping a region of interest, such as a causal genetic variant, and optionally also containing or likely to contain an indel are locally aligned using a second algorithm in order to produce a single consensus sequence for the region of interest. A region of interest may be of any suitable size, such as about, less than about, or more than about 5, 10, 15, 20, 25, 50, 100, 250, 500, or more nucleotides in length. A second alignment may be a local multiple-sequence alignment of all sequencing reads overlapping one or more nucleotide positions. In some embodiments, the second alignment identifies a single consensus sequence by optimizing the alignment of all sequencing reads at a position. In some embodiments, the consensus sequence produced by the second alignment contains at least 1, 2, 3, 4, 5, 6, 7, 8, 9, 10, 15, 20, or 25 fewer nucleotide mismatches with respect to the reference sequence than one or more of the sequences realigned to produce the consensus sequence. In some embodiments, the algorithm used to perform the second alignment is capable of identifying an insertion and/or a deletion of about, or more than about 1, 2, 3, 4, 5, 6, 7, 8, 9, 10, 15, 20, 25, or more nucleotides relative to the reference sequence with an accuracy of about or more than about 80%, 85%, 90%, 95%, 97%, 99%, or higher.

Typically, the second algorithm is different from the first algorithm, and the second algorithm may require more resources of the system (e.g. a computer system) running the algorithm to perform the same number of alignments. For example, performing the first alignment with a system using the first algorithm may take less time to align all R1 reads than would be taken if the system used the second algorithm to perform the first alignment of all R1 reads. In some embodiments, performing the first alignment with the first algorithm takes about or less than about 90%, 80%, 70%, 60%, 50%, 40%, 30%, 25%, 20%, 15%, 10%, 5%, or less of the time that would be taken by the same system to perform the first alignment using the second algorithm. As a further example, performing the first alignment with a system using the first algorithm may use less system memory to align all R1 reads than would be used if the system used the second algorithm to perform the first alignment of all R1 reads. In some embodiments, performing the first alignment with the first algorithm uses about or less than about 90%, 80%, 70%, 60%, 50%, 40%, 30%, 25%, 20%, 15%, 10%, 5%, or less memory than would be used by the same system to perform the first alignment using the second algorithm. The first algorithm may perform the first alignment using heuristics. In some embodiments, the first algorithm is based on the Burrows-Wheeler transform, such as the Burrows-Wheeler Aligner. In some embodiments, the second algorithm is based on the Smith-Waterman algorithm.

In some embodiments, an amplified sequence derived from one or more target polynucleotides from a sample (e.g. sequence G from at least 75%, 80%, 85%, 90%, 95%, or 100% of all clusters) is from 1 nucleotide in length to about, less than about, or more than about 10, 25, 50, 100, 250, 500, 1000, 2000, 5000, or more nucleotides in length. In general, if an amplified sequence derived from a target polynucleotide for a cluster (e.g. sequence G) is shorter than the number of cycles of nucleotide extension performed in sequencing the amplified sequence (also referred to as the "read length"), then sequence data returned for that sequencing read will likely contain sequence of a first oligonucleotide used to initially capture the amplified sequence (e.g. sequence B or B'). When sequence B or B' exists in the reference sequence (e.g. reference genome), the sequence may correctly align, but any true mutation in the target polynucleotide may be masked or inferred with lower confidence. To avoid negative effects of first oligonucleotide sequence contained in an R1 sequence, base calls likely to correspond to sequence B or B' for a cluster may be deleted. Sequence B or B' for a cluster may be identified in a separate sequencing reaction, such as producing R2 sequence. R1 sequence may then be compared to R2 sequence for the same cluster to determine whether or not one or more nucleotides of R1 correspond to sequence B or B'. If no R2 sequence (or no R2 sequence comprising any sequence B) is obtained for a cluster, deleting first oligonucleotide sequence may comprise deleting a portion of an R1 sequence for a cluster when the portion of R1 sequence to be deleted is identical to at least a portion of any sequence B' (such as any B' found in any cluster, or corresponding to any sequence B used to amplify a target polynucleotide), the portion includes either the 5' or 3' nucleotide of R1, and either (i) no R2 sequence was produced for the cluster or (ii) R2 sequence produced is not identical to any sequence B. In general, nucleotide sequence comprising sequence B or B' found in the interior of an R1 sequence (that is, not including the 5' or 3' end of the sequencing read) indicates that the amplified sequence was captured using a more distant sequence B.

In some embodiments, genetic variation detected by a method of the invention is used to calculate a plurality of probabilities. Each probability may be a probability of a subject or a subject's present or future offspring having or developing a disease or trait. In some embodiments, each probability is based on the R1 sequences for the subject, and one or more such probabilities may be included in a report of analysis results. In general, calculation of a probability that the tested subject has or will develop a disease or trait is based on a level of risk associated with one or more tested causal genetic variants, non-subject sequences, and/or AIMs. For example, if two causal genetic variants contribute to the risk of developing a disease in an additive fashion, then the presence of both causal genetic variants in a subject would indicate that the risk of that disease in the subject is increased by the value resulting from adding the risks associated with each. In general, calculation of a probability that an offspring of the subject will have a disease or trait is based on a level of risk associated with one or more tested causal genetic variants and/or AIMs, and the probability that an offspring will inherit the causal genetic variants and/or AIMs. Risk calculations may be based on risk correlations maintained in one or more databases, which databases may be updated based on external reports and/or records of genotyping results and associated phenotypes of tested subjects. In some embodiments, the calculations are performed by a computer in accordance with instructions contained in a computer readable medium. In some embodiments, the statistical confidence of a probability that the subject or subject's offspring will have or develop a disease or trait is at least about 70%, 80%, 85%, 90%, 95%, 97.5%, 99%, or higher. Confidence may be based on a number of factors, such as confidence in sequencing accuracy, number of associated genetic variants tested, and confidence in the risk associate with each genetic variant. Example methods for calculating probabilities are described in US20100022406.

Figure 8:
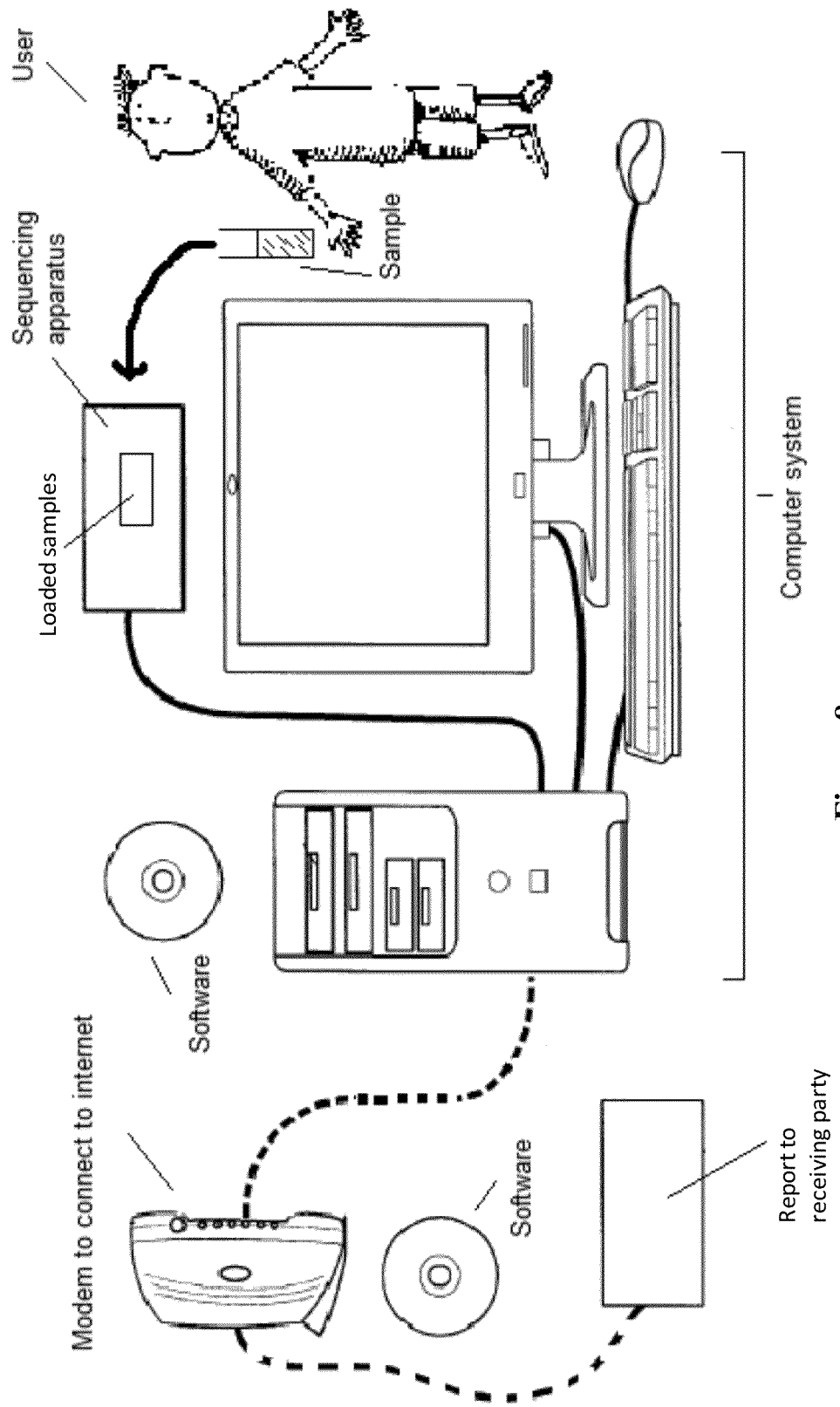
FIG. 8 illustrates a non-limiting example of a computer system useful in the methods of the invention.

In some embodiments of any aspect of the invention, a computer system is used to execute one or more steps of the described methods. FIG. 8 illustrates a non-limiting example of a computer system useful in the methods of the invention. In some embodiments, the computer system is integrated into and is part of an analysis system, like a liquid handler, bridge amplification system (e.g. an Illumina cBot), and/or a sequencing system (e.g. an Illumina Genome Analyzer, HiSeq, or MiSeq system). In some embodiments, the computer system is connected to or ported to an analysis system. In some embodiments, the computer system is connected to an analysis system by a network connection. A computer system (or digital device) may be used to receive and store results, analyze the results, and/or produce a report of the results and analysis. The computer system may be understood as a logical apparatus that can read instructions from media (e.g. software) and/or network port (e.g. from the internet), which can optionally be connected to a server having fixed media. A computer system may comprise one or more of a CPU, disk drives, input devices such as keyboard and/or mouse, and a display (e.g. a monitor). Data communication, such as transmission of instructions or reports, can be achieved through a communication medium to a server at a local or a remote location. The communication medium can include any means of transmitting and/or receiving data. For example, the communication medium can be a network connection, a wireless connection, or an internet connection. Such a connection can provide for communication over the World Wide Web. It is envisioned that data relating to the present invention can be transmitted over such networks or connections (or any other suitable means for transmitting information, including but not limited to mailing a physical report, such as a print-out) for reception and/or for review by a receiver. The receiver can be but is not limited to an individual, a health care provider, a health care manager, or electronic system (e.g. one or more computers, and/or one or more servers). In some embodiments, a computer-readable medium includes a medium suitable for transmission of a result of an analysis of a biological sample. The medium can include a result regarding analysis of an individual's genetic profile, wherein such a result is derived using the methods described herein. The data and or results may be displayed at any time on a display, such as a monitor, and may also be stored or printed in the form of a genetic report.

Causal genetic variants associated with phenotypes may be obtained from scientific literature and sent to a computer system for comparison with sequence results for a sample from a subject. Genotypes of causal genetic variants and results from biological samples may be sent to, stored, and analyzed by a computer system (or other digital device), which produces a report of the results and analyses of genomic data. The results and analyses may be accessed online by a receiver, such as a health care provider, via an online portal or website. The results and analyses may be viewed online, saved on a receiver's computer, printed, or be mailed to a receiver. The results may be used for personalized health management, such as at the direction of a physician or other health professional. For example, the subject may be referred to or contacted by a genetic counselor to receive genetic counseling.

The database may have one or more of a variety of optional components that, for example, provide more information about the sequencing results produced by methods of the invention. In some embodiments there is provided a computer readable medium encoded with computer executable software that includes instructions for a computer to execute functions associated with the identified causal genetic variants. Such computer system may include any combination of such codes or computer executable software, depending upon the types of evaluations desired to be completed. The computer system may also have code for linking each of the sequences (e.g. genotypes for causal genetic variants) to at least one phenotype, such as a condition, for example, a medical condition, including but not limited to a risk for having or developing the phenotype. Each medical condition in turn can be linked to at least one recommendation by a medical specialist and code for generating a report comprising the recommendation. The system can also have code for generating a report. Different types of reports can be generated, for example, reports based on the level of detail a receiver may want or have paid for. For example, a receiver may have ordered analysis for a single phenotype, such as a condition, and thus a report may comprise the results for that single phenotype, such as a condition. Another receiver may have requested a genetic profile for a panel or an organ system, or another individual may have requested a comprehensive genetic profile that includes analysis of all clinically relevant causal genetic variants. Reports may comprise one or more of: subject information (e.g. name, date of birth, ethnicity, sample type, date of sample collection, and/or date of sample receipt); description of analysis method(s); results for all causal genetic variants tested; results for all disease or traits tested; results for diseases or traits having a positive score (e.g. a risk above a threshold level, such as about or more than about 1/50000, 1/25000, 1/10000, 1/5000, 1/2500, 1/1000, 1/500, 1/100, 1/50, 1/10, or higher); results for causal genetic variants associated with a disease or trait having a positive score; results for two or more individuals (such as individuals that are parents or planning to have children); risk of having or developing a disease or trait; risk of a present or future child having or developing a disease or trait; risk of a fetus having or developing a disease or trait; methods of risk calculation; and recommendations for further action.

The report generated can be reviewed and further analyzed by a genetic counselor and/or other medical professional, such as a managing doctor or licensed physician, or other third party. The genetic counselor or medical professional or both, or other third party, can meet with the individual to discuss the results, analysis, and the genetic report. Discussions can include information about: the causal genetic variant(s), such as the causal genetic variant(s) that is or are tested (presence, absence, and/or genotype), how the causal genetic variant(s) can be inherited or transmitted (for example using the pedigree generated from a questionnaire), the prevalence of the causal genetic variant(s); prevalence or incidence of associated phenotypes; and information about associated phenotypes (for example, specific conditions or traits, such as medically or clinically relevant conditions), such as how the phenotype may affect the individual, and preventative measures that may be taken. The genetic counselor or medical professional may incorporate other information, such as other genetic information or information from questionnaires in their analysis and discussion with the individual. Information about the phenotype, such as condition or trait, can include recommendations, such as follow-up suggestions such as further genetic counseling, predictive medicine recommendations, or preventive medicine recommendations for the individual's personal physician or other healthcare provider. Screening information, such as methods of breast cancer screening, may be discussed for example if an individual was found to be at a higher risk of breast cancer. Other topics that may be discussed include lifestyle modifications and medications. For example, lifestyle modifications may be suggested such as dietary changes and specific diet plans may be recommended or an exercise regimen may be suggested and specific exercise facilities or trainers may be referred to the individual. Common misconceptions may also be included, allowing the individual to be aware of preventive measures or other interventions that may be thought of as being helpful or useful but that have been shown in published literature to either not be beneficial or to actually be harmful. Alternative therapies may also be included, such as alternative medicines, such as dietary supplements, or alternative therapies, such as acupuncture or yoga. Family planning options may also be included, as well as monitoring options, such as such as screening exams or laboratory tests that may detect or help monitor for the presence of a phenotype, or the progression of a phenotype. Medications that may prevent, limit the onset, or delay the progression of a phenotype, such as a disease to which the individual is predisposed, or a medication with high efficacy and low side effects may be suggested for an individual, or medications or classes of medications that an individual should avoid due to possibility of adverse reaction(s). For example, the medical professional may make an assessment of the individual's likely drug response including metabolism, efficacy and/or safety. The medical professional can also discuss therapeutic treatments, such as prophylactic treatments and monitoring (such as doctor visits and exams, radiologic exams, self exams, or laboratory tests) for potential need of treatment or effects of treatment based on information from the individual's genetic profile either alone or in combination with information about the individual's environmental factors (such as lifestyle, habits, diagnosed medical conditions, current medications, and others). Additional resources may also be listed, such as including information for the individual or the individual's physician or other healthcare professional to acquire additional information about the phenotype, the causal genetic variant(s), or both, such as links to websites that contain information on the phenotype, such as an internal website from the company that produces the genetic report or external websites, such as national organizations for the phenotype. Additional resources may also include reference to telephone numbers, books, or people that the individual may seek out to acquire more information about the phenotype, the causal genetic variant(s) or both.

In one aspect, the invention provides a method comprising offering a first and optionally a second service, wherein: a) the first service comprises predicting the probability that an offspring of the couple will have each of a plurality of traits caused by causal genetic variants, wherein the prediction is based on the respective genotypes of the two individuals in the couple; and b) the second service comprises predicting the probable phenotype of an offspring of the couple for a plurality of traits, wherein the probability is determined based on the respective phenotypes and/or the family history of the individuals in the couple. In one embodiment at least one prediction is further based on the respective genetically inferred ancestries of the individuals. In another embodiment the first service is offered as a service for a fee and the second service is offered as a free service.

In one aspect this invention provides a system comprising: a) computer readable medium configured to store family history information from each member of a couple; b) computer readable medium configured to store data comprising genetic information about each member of the couple; c) computer readable medium comprising computer code that, when executed: i) predicts each individual's carrier status with respect to traits caused by alleles identified in the genetic information; or ii) predicts probable traits of offspring of the couple determinable by the family histories and/or the genetic information; and d) a display that displays: i) carrier status of at least one member of the couple or ii) probable traits of the offspring. In some embodiments the system further comprises e) a webpage configured to accept an offer to purchase a DNA test kit. In some embodiments the display is electronic, for example, a webpage. In some embodiments the system further comprises e) a display that displays referrals to a genetic counselor and/or other medical professional (for example, medical geneticists or obstetrician/gynecologist) based on the genetic information.

The internet and the world wide web offer access to and distribution of information. In some embodiments, a website can be particularly suited to efficiently providing various functionality for allowing customers to purchase genetic testing and receive the results of genetic testing. The system typically will include a server on which the website resides. Users use an interface connected to the server, such as a computer monitor or a telephone screen, to interact with the website by clicking or rolling over links that pop up information or direct the user to another webpage. Websites typically are interactive, allowing the user to input information or a query and obtain a response on the interface.

In some embodiments of a system and business method, a website can allow a customer to purchase, manage, and view the results of genetic testing as well as to learn more generally about the probability that potential offspring will develop a disease or trait. For example, a customer can be a couple of prospective parents who seek to learn whether their offspring will be at risk for developing Mendelian disease. A customer can be presented with the offer to purchase genetic testing to determine one or more of: (i) the carrier status of the customer; (ii) the likelihood that the customer will develop one or more diseases or traits; and (iii) the probability that an offspring of the customer will develop one or more diseases or traits, based on causal genetic variants identified in the customer's DNA.

If the customer chooses to purchase genetic testing, then the customer may pay a fee, for example through an online credit card transaction, in exchange for genetic testing, direct phone consultation with a genetic counselor on the company's staff and/or referrals to genetic counselors and/or other relevant medical professionals. The genetic testing and referrals can be paid for by a fee at the point of purchase or can be included in an initial user registration fee. In some embodiments, the services are free and revenue is generated by the company by advertising other products in conjunction with a particular product. For example, after a customer places an order online, the order is sent to a server for processing. Once payment has been verified, the order processing server can send an electronic notification to a shipping vendor to mail a DNA collection kit to the customer. In an embodiment, the DNA collection kit is separate from the genetic testing service, or the user or customer already has or obtains the DNA collection kit from another source. Notifications can also periodically be sent electronically to the customer comprising order confirmation and updates on order and shipping status. In some embodiments of a business method of the invention, a customer can deposit a sample into the collection kit. Any sample that would be obvious to one skilled in the art can be deposited into or onto a collection kit. A sample can be any material containing nucleic acid to be analyzed that would be obvious to one skilled in the art, such as bodily fluid like saliva or blood. The collection kit can then be returned to the company for sending to a genotyping lab or can be returned directly to a genotyping lab for processing. A genotyping lab, either internal within the company, contracted to work with the company, or external from the company, can isolate the customer's DNA from the provided sample. After the DNA has been isolated from the sample, a genotyping device (such as an apparatus described herein) can be used to test the DNA for the presence of one or more of (i) ancestry informative markers, (ii) causal genetic variants, and (iii) non-subject sequences (one or more of which are also referred to herein as, Raw Genotypic Information). In some embodiments, the DNA does not have to be isolated from the sample to test the DNA for the presence of Raw Genotypic Information.

Raw Genotypic Information can be sent electronically to a server for storage and processing. Computer code on the server can execute on the Raw Genotypic Information to infer the ancestry of the customer and/or to confirm the presence of causal genetic variants and/or non-subject sequences, if any. The processed genotypic information can then be electronically sent to a server, where computer code on the server can execute on the processed genotypic information to predict the probability that an offspring of the customer will have each of a plurality of traits caused by causal genetic variants found to be present in the customer's processed genotypic information. Results can then be electronically transmitted to a server for storage.

In an example, a notification can be sent to the customer to alert the customer to the availability of the results. The notification can be electronic, non-limiting examples of which include a text message, an email, or other data packet; or the notification can be non-electronic, non-limiting examples of which include a phone call from a genetic counselor or printed communication such as a report sent through the mail. The results provided to a customer can inform the customer of the carrier status of the customer for one or more diseases or traits and/or the chances that the customer or customer's future offspring will develop one or more diseases or traits. After the customer has received results and referrals, the customer's order can be considered fulfilled, and results and referrals can remain accessible to the customer through an online website account. The customer can then choose to further pursue a referral offline if the customer so desires but outside of the purview of the website.

In one aspect, the invention provides compositions that can be used in the above described methods. Compositions of the invention can comprise any one or more of the elements described herein. For example, compositions may include one or more of the following: one or more solid supports comprising oligonucleotides attached thereto, one or more oligonucleotides for attachment to a solid support, one or more adapter oligonucleotides, one or more amplification primers, one or more oligonucleotide primers comprising a first binding partner, one or more solid surfaces (e.g. beads) comprising a second binding partner, one or more sequencing primers, reagents for utilizing any of these, reaction mixtures comprising any of these, and instructions for using any of these.

In one aspect, the invention provides kits containing any one or more of the elements disclosed in the above methods and compositions. In some embodiments, a kit comprises a composition of the invention, in one or more containers. For example, kits may include one or more of the following: one or more solid supports comprising oligonucleotides attached thereto, one or more oligonucleotides for attachment to a solid support, one or more adapter oligonucleotides, one or more amplification primers, one or more oligonucleotide primers comprising a first binding partner, one or more solid surfaces (e.g. beads) comprising a second binding partner, one or more sequencing primers, reagents for utilizing any of these, and instructions for using any of these. In some embodiments, the kit further comprises one or more of: (a) a DNA ligase, (b) a DNA-dependent DNA polymerase, (c) an RNA-dependent DNA polymerase, (d) random primers, (e) primers comprising at least 4 thymidines at the 3' end, (f) a DNA endonuclease, (g) a DNA-dependent DNA polymerase having 3' to 5' exonuclease activity, (h) a plurality of primers, each primer having one of a plurality of selected sequences, (i) a DNA kinase, (j) a DNA exonuclease, (k) magnetic beads, and (1) one or more buffers suitable for one or more of the elements contained in the kit. The adapters, primers, other oligonucleotides, and reagents can be, without limitation, any of those described herein. Elements of the kit can further be provided, without limitation, in any amount and/or combination (such as in the same kit or same container). The kits may further comprise additional agents for use according to the methods of the invention. The kit elements can be provided in any suitable container, including but not limited to test tubes, vials, flasks, bottles, ampules, syringes, or the like. The agents can be provided in a form that may be directly used in the methods of the invention, or in a form that requires preparation prior to use, such as in the reconstitution of lyophilized agents. Agents may be provided in aliquots for single-use or as stocks from which multiple uses, such as in a number of reaction, may be obtained.

EXAMPLES

The following examples are given for the purpose of illustrating various embodiments of the invention and are not meant to limit the present invention in any fashion. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1

Sample Preparation and Sequencing Process

Genomic DNA (gDNA) is extracted in 96-well format, leaving wells A1, G12, and H12 empty (which will later contain a no-template control, the universal negative standard containing Coriell sample NA12878 genomic DNA lacking every causal genetic variant tested, and a sample comprising one of a plurality of known causal genetic variants, respectively). 50 µL from each well are transferred into a corresponding well of an absorbance plate. Absorbance at 260 nm is measured using a Tecan M200 plate reader to calculate DNA quantity. 50 µL of gDNA are transferred from the absorbance plate into an Eppendorf twin.tec plate. Control samples are added to their respective position on the twin.tec plate. The gDNA and controls are fragmented in a SonicMan (Matrical, Spokane Wash.) sonicator, according to the following protocol at 10° C.: Pre-chill 180 s, cycles 100, sonication 3.0 s, power 35%, lid chill 1.0 s, plate chill 0, post chill 0. A 2 µL sample is analyzed for fragmentation size distribution using a Fragment Analyzer (Advanced Analytical Technologies, Ames Iowa). Samples having a median fragment size of at least 200 base pairs and no more than 1000 bp are subjected to further processing. Samples with a median fragment size below 200 bp are discarded and reprocessed from extracted gDNA. Samples with a median fragment size above 1000 bp are either subjected to further sonication to reach the desired size range, or are discarded and reprocessed from extracted gDNA.

Sonicated gDNA is transferred into a round-bottomed sample plate for use in conjunction with the Beckman Biomek FXP. The Biomek automates the processes of end-repair, addition of adenine overhangs, and adapter ligation. The Biomek system comprises an Agencourt SPRIPlate Super Magnet Plate, a Biomek FXP Dual-Arm System with Multichannel Pipettor and Span-8 Pipettor (with pump control module, computer and monitor, peltier controller, two waste containers, and two water containers), and BioMek FXP Control Software. This process utilizes the SPRIworks HT Fragmentation Library Kit, which contains end-repair buffer and enzyme, a-tailing buffer and enzyme, ligation buffer and enzyme, and Agencourt AMPure XP beads. After each reaction, processed gDNA is cleaned using magnetic bead separation. Adapter ligation is followed by quantifying DNA in the processed sample using absorbance at 260 nm, as measured by the Tecan M200. Samples with less than 900 ng are not processed further, but are instead reprocessed from the original extracted sample. After the absorbance reading, the sample plate is returned to the Biomek FXP for PCR amplification. The first step is division of each sample into four separate samples on a 384-well plate, such that amplification for each sample source is performed in quadruplicate. Amplification primers comprise a barcode sequence to allow identification of the sample source of a sequence. PCR includes the use of an ABI GeneAmp PCR system 9700 with dual 384-well blocks, 1.5 mL tube racks, 24-channel 200 µL multichannel pipettor, and 96-well aluminum plate holder. Samples are automatically thermally cycled according to following protocol: 95 C for 5 minutes; 27 cycles of 98 C for 20 seconds, 65 C for 15 seconds, 72 C for 1 minute. When amplification is complete, the four sub-samples from each sample source are recombined into a single well of a 96-well plate.

Amplified polynucleotides are purified by magnetic bead separation. 1.8 sample volumes of magnetic beads are added to each sample, which are allowed to sit at room temperature for about 5 minutes. The plate is placed on a magnetic separator for about 2 minutes, until the slurry is completely clear and all beads have been collected on the side of each well. Buffer solution is then aspirated, and 200 µL of 70% ethanol are added. The ethanol is allowed to sit at room temperature for about 30 seconds before being aspirated. The plate is then removed from the magnet and DNA is eluted in about 40 µL of elution buffer (EB; 10 mM Tris-HCl, pH 8.5). The plate is returned to the magnet and allowed to sit at room temperature for about 2 minutes, until the beads have collected on the sides of the well. The 40 µL sample from each well is then transferred to a corresponding well of a new absorbance quantitation plate. DNA quantity in each well is checked by measuring absorbance at 260 nm as above. Samples having a concentration of at least 500 ng/µL are further processed for sequencing. Wells with lower concentrations are failed, and the corresponding samples are re-amplified.

Amplified samples are pooled across rows of the 96-well plate, to produce pools of 12 samples, where amplified polynucleotides of each sample comprise a barcode unique to that sample among the 12 samples in the pool. The volume of each sample added to the pool is calculated such that the total amount of DNA in the sample submitted for sequencing is approximately 11.25 µg. Each pool is concentrated by cleanup on magnetic beads, as above, with elution in 38.5 µL EB. 1 µL of each pool is used to quantify total DNA on a NanoDrop machine (Thermo Scientific, Wilmington Del.). Samples below 10 µg are failed, and pooling and cleanup are repeated. Samples having at least 10 µg are further processed for sequencing.

Before polynucleotides in each pool are attached, bridge amplified, and sequenced, a cBot reagent plate is prepared. Reagent plates are prepared ten at a time, using commercially supplied Phusion High-Fidelity PCR Master Mix with HF Buffer (New England Biolabs), Detergent-free Phusion HF Buffer Pack (New England Biolabs), 0.1N NaOH, HT1 buffer (5×SSC+0.05% Tween 20), and HT2 buffer (0.3×SSC+ 0.05% Tween 20). Five Nova Biostorage 8-tube strips are placed into positions 1, 2, 3, 7, and 10 of ten separate Nova Biostorage RoBo Racks. 1.25 mL of Phusion master mix are added to a 15 mL tube, followed by addition of 1.25 mL of RNase- and DNase-free water, and vortexing for 10 seconds to generate 1× Phusion master mix. 440 µL of 5× Phusion HF buffer are added to another 15 mL tube labeled "HF," followed by addition of 1760 µL of RNase- and DNase-free water, and mixed to generate 1× HF buffer. Reagents are dispensed into rows of the reagent plates as follows: Row 1-720 µL HT1 buffer; Row 2-230 µL Phusion master mix; Row 3-200 µL 1× HF buffer; Row 7-300 µL HT2 buffer; and Row 10-215 µL 0.1N NaOH. Each tube strip is then covered with Nova Biostage tube caps, and all plates are frozen until needed.

Each sample pool is then prepared for sequencing by attachment to a flow cell. The system for attachment and bridge amplification comprises a cBot system, a NanoDrop Absorbance Spectrometer, Applied Biosystems Veriti 96-well Thermal Cycler (0.2 mL), Veriti Thermocycler Program, and cBot attachment and bridge amplification programs. Samples are heated to 95° C. for 5 minutes. 12.5 µL of 4× Hybridization buffer (10×SSC+0.2% Tween-20) is added to each sample, which are placed on ice until loaded on the Illumina cBot machine. A sipper comb, flowcell, reagent plate, and sample tubes are then loaded on the cBot. For each sample pool, polynucleotides are attached to a channel of the flow cell by extension of oligonucleotides attached to the surface of the channel ("target capture" step of FIG. 1). The attached oligonucleotides comprise a collection of different oligonucleotides that specifically hybridize to members of a collection of about 5000 different interrogation positions located upstream of selected causal genetic variants. Clusters of bridge amplified sequences are then generated on the cBot using standard procedures.

Clusters are sequenced using a Genome Analyzer IIx (GAIIx; Illumina, San Diego Calif.). The sequencing system comprises a Genome Analyzer IIx, a Paired-End Module, Sequencing Control Software, GAIIx programs (sequencing, pre-wash, prime, post-wash), 500 mL capacity plastic beakers, a large square ice bucket, and a scale with 0.1 g tolerance. Sequencing is performed in two rounds. In a first round, sequencing data is generated from a first primer that hybridizes downstream of (3' along the extended strand) the barcode and adjacent to the target genomic DNA sequences, thereby generating sequencing data for the target gDNA regions comprising causal genetics variants. In the second round, sequencing data is generated from a second primer that hybridizes upstream of (5' along the extended strand) the barcode sequence, such that barcode sequence data is produced for each cluster. The order of these sequencing reactions could be reversed. Barcodes for each cluster are then matched to their corresponding gDNA sequence, such that the sample source for each gDNA sequence can be identified. The raw data from the GAIIx is combined into individual reads, each with quality scores, using standard Illumina software. Reads are aligned to a reference genome using a Burrows-Wheeler Aligner, and variants are found from this alignment using the genome analysis toolkit GATK. The output file from the GATK listing all found discrepancies between the sequencing reads and the reference assembly is then used to generate a genotype report, which is sent securely to the ordering physician for a consultation with the patient that provided the sample.

Example 2

Amplification and Sequencing Process

Figure 6:
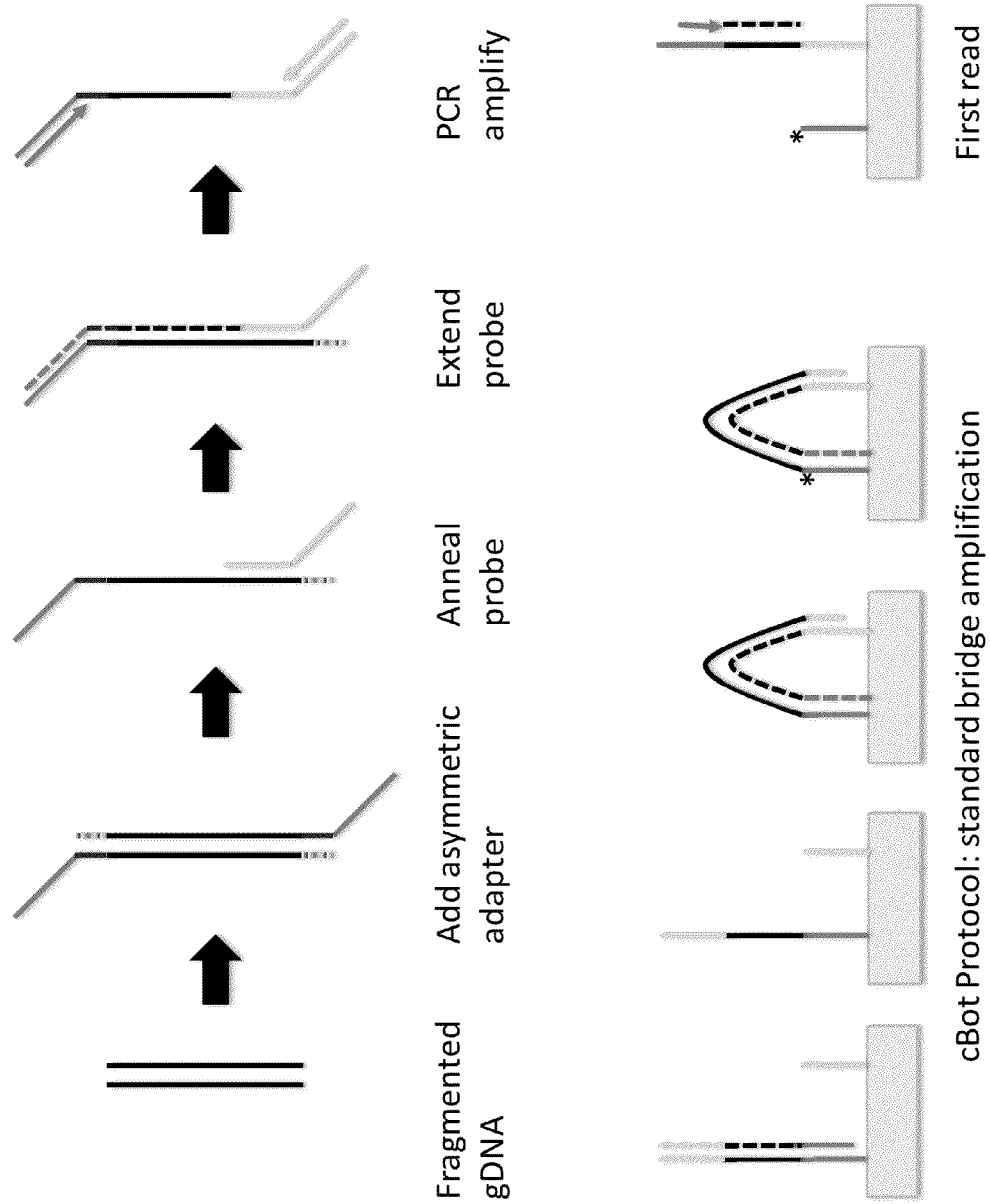
FIG. 6 illustrates an example process of target amplification, bridge amplification, and sequencing.

Example processes for the amplification of a plurality of different target polynucleotides are illustrated in FIGS. 2 and 5, which differ primarily in the inclusion of a solid-phase purification step in FIG. 2. FIG. 7 also illustrates an example amplification process, and differs from the process illustrated in FIG. 2 primarily in that oligonucleotide primer extension is performed before adapter joining, instead of after adapter joining Amplification may or may not include a solid-phase purification step. FIG. 6 illustrates an amplification process as in FIG. 5, and also example bridge amplification and sequencing processes. The amplification process illustrated in FIG. 6 may be used in conjunction with any bridge amplification method and associated sequencing method.

First, a partially single-stranded adapter is ligated to fragmented polynucleotides. The partially single-stranded adapter has a double-stranded region at one end (sequence U hybridized to complementary sequence U') and the single-stranded sequence Y that does not hybridize to the target polynucleotide under the hybridization and extension conditions used. Ligation adds sequence Y to both 5' ends of the target polynucleotides. Next, a plurality of different oligonucleotide primers, each having a different target-specific sequence W at the 3' end, are hybridized to their respective target polynucleotides, and extended, producing an extended oligonucleotide with sequence Y' (complement of Y) at the 3' end. Extension may be performed before adapter ligation, such as illustrated in FIG. 7. The oligonucleotide primers may lack a first binding partner, as in FIG. 5, or may comprise a first binding partner, as the in the small overhanging circle in FIGS. 2 and 7. If the extended oligonucleotides do comprise a binding partner, they may be purified by selectively binding to a solid surface comprising a second binding partner that binds to the first binding partner, as in the bead (larger circle) in FIG. 2. Bound and extended oligonucleotides may be purified, such as by holding in place on a magnetically responsive bead in the presence of a magnetic field while reaction solution is removed, beads washed, and new reaction solution added (e.g. components of a further amplification reaction). Extended oligonucleotides, purified or not, are then amplified with a pair of amplification primers. One amplification primer comprises sequence X and sequence Y, with sequence Y at the 3' end for hybridization to sequence Y'. The X-Y primer is extended along the extended oligonucleotides to produce a plurality of extended X-Y oligonucleotides comprising sequences X, Y, W', and Z' (5' to 3'; where W' is the complement of W, and Z' is the complement of Z). Another amplification primer comprises sequences V and Z, with Z at the 3' end for hybridization to sequence Z' of an extended X-Y primer. The V-Z primer is extended along the extended X-Y primer to produce a plurality of sequences comprising V, Z, Y', and X' (5' to 3'; where X' is the complement of X), which may then serve as a template for extension of a further X-Y primer, which may then serve as a template for extension of a further V-Z primer, and so on for each successive primer extension reaction in the amplification process. The predominant amplified sequences comprise a plurality of different target polynucleotides, each contained in a polynucleotide comprising one strand comprising sequences V, Z, W, Y', and X' (from 5' to 3'), and another strand comprising sequences X, Y, W', Z', and V' (from 5' to 3'), with target polynucleotide sequence located between Z/Y' and between Z'/Y. These amplified polynucleotides may then be subjected to sequencing.

Sequencing may follow the process illustrated in the lower half of FIG. 6. A first bound oligonucleotide is hybridized to a sequence near or at the 3' end of an amplified polynucleotide, typically by complementarity to a sequence added during the exponential amplification step (thereby specifically amplifying, and ultimately sequencing, exponentially amplified products). Extension of each first bound oligonucleotide provides nucleation points for bridge amplification to produce clusters of double-stranded bridge polynucleotides with the same sequence. Extension products of first bound oligonucleotides are denatured to remove the hybridized templates. An extended first bound oligonucleotide then hybridize to a second bound oligonucleotide, typically by complementarity to a sequence at or near the 3' end and derived from sequence added during the exponential amplification step. Extended second bound oligonucleotides may then serve as templates for extension of further first oligonucleotides, which may then serve as templates for extension of further second oligonucleotides, and so on. Here, some or all first oligonucleotides comprise a cleavage site, which is cleaved after completing the bridge amplification process. Bound polynucleotides are then subjected to denaturing conditions, such as heating (e.g. about 95° C.) or chemically denatured, to remove one strand of a plurality of bound bridge polynucleotides. The remaining, bound strands are then free for hybridization with a sequencing primer, illustrated above "first read" in FIG. 6. Sequencing data is then generated by sequential steps of nucleotide extension and detection, extending the sequencing primer. The extended first sequencing primer may then be denatured and removed from the template, in order to repeat the sequencing process from a second sequencing primer that is different from the first. Where one sequencing primer is used only to generate enough sequencing data to identify a barcode sequence, that sequencing reaction may be significantly shorter than the other sequencing reaction (e.g. less than about 3, 4, 5, 6, 7, 8, 9, 10, 11, 12, 13, 14, 15, or more cycles of nucleotide addition). While FIG. 6 only illustrates bridge amplification and sequencing of a single target polynucleotide, bridge amplification and sequencing typically involves a plurality of different target polynucleotides amplified in a previous amplification step, all of which are bridge amplified and sequenced in parallel.

Example 3

Identification of Non-Subject Sequences

Polynucleotides (e.g. DNA and/or RNA) are extracted from a sample from a subject suspected to contain viral and/or bacterial polynucleotides using standard methods known in the art. Sample polynucleotides are fragmented, end-repaired, and A-tailed, such as in Example 1. Adapter oligonucleotides comprising sequence D are then joined to the sample polynucleotides, which are then amplified using amplification primers comprising sequence C, sequence D, and a barcode. Amplified target polynucleotides are hybridized to a plurality of different first oligonucleotides that are attached to a solid surface. Each first oligonucleotide comprises sequence A and sequence B, where sequence B is different for each different first oligonucleotide, is at the 3' end of each first oligonucleotide, and is complementary to a sequence comprising a non-subject sequence or a sequence within 200 nucleotides of a non-subject sequence. Specifically, the first oligonucleotides are selected to amplify sequences having high depth outside the subject's genome, such as viral or bacterial sequences unique to a particular class, order, family, genus, species or other taxonomic group of virus or bacteria. Sequences amplified may include 16s rRNA sequences. Polynucleotides from a healthy control are processed simultaneously. Target polynucleotides are then bridge amplified and sequenced, according to methods of the invention. Sequencing data produced for the non-subject sequences may be used to identify an infectious agent. Sequencing data produced for the non-subject sequences may be used to detect relative levels of different taxonomic groups of bacteria (e.g. ratios of one or more taxonomic groups to one or more other taxonomic groups), or shifts in these. The identities or relative levels of bacteria or infectious agent are then used as the basis for making a medical recommendation or taking medical action.

Example 4

Alignment of Nucleic Acid Sequences for Detecting Genetic Variation

This example sequence manipulation and alignment procedure ("pipeline") begins with raw data from Genome Analyzer IIx (GAIIx) or HiSeq sequencers (Illumina; San Diego, Calif.) to infer genotypes and compute metrics from patient samples. Sequencing data is generated from runs of barcoded samples in a 12× multiplexed configuration per Flowcell lane according to a method of the invention. The sequencer raw data includes basecalls (BCL files) and various quality-control and calibration metrics. The raw basecalls and metrics are first compiled into QSEQ files and then filtered, merged, and demultiplexed (based on barcode sequences) into sample-specific FASTQ files. FASTQ reads are aligned to the HG19 genome to create an initial BAM file. This BAM file undergoes several transformations to filter, clip, and refine alignments, and to recalibrate quality metrics. The final BAM file is used to infer genotypes for known variants and to discover novel ones, producing a callset. The callset (VCF files) is then filtered using various call metrics to create a final set of high-confidence (such as about or more than about 80%, 85%, 90%, 95%, 99%, or higher confidence) variant calls per sample. Finally, various metrics are computed per sample, lane, and batch and the calls and metrics are loaded into a laboratory information management system (HMS) for visualization, review, and final report generation. The pipeline can be run (in whole or in part) locally and/or using cloud computing, such as on the Amazon cloud. Users may interact with the pipeline using any suitable communication mechanism. For example, interaction may be via Django management commands (Django Software Foundation, Lawrence, Kans.), a shell script for executing each step of the pipeline, or an application programming interface written in a suitable programming language (e.g. PHP, Ruby on Rails, Django, or an interface like Amazon EC2). Overviews of the operation of this example pipeline are illustrated in FIGS. 10 and 11.

Sequencing occurs on a flowcell with 8 lanes. Each lane has 12 (or more with HiSeq) samples, each with a unique 6-7 nucleotide barcode sequence. Each lane is subdivided into some number of tiles (120 for GAIIx, 48 for HiSeq). The sequencer outputs 3 reads per flowcell cluster. Read1 (R1) is the sequence of one edge of a gDNA fragment (59 bp), generated by extension of a first primer. Read2 is the barcode sequence (6 bp) generated by extension of a third primer. Read3 (R2) is part of the probe sequence (15 bp), generated by extension of a second primer.

The raw sequencing data processed in the first step of the pipeline (creating FASTQ files) is typically large (such as about or more than about 100 GB, 150 GB, 200 GB, 250 GB, 300 GB, 400 GB, 500 GB, 1000 GB, or more). Accordingly, it can be advantageous to utilize cloud computing for some or all of the analysis steps. In this example, the first step is run locally, and the resulting FASTQ files are uploaded to Amazon S3 (an online storage web service provided by Amazon; Seattle, Wash.) and processed using Amazon EC2 instances (a cloud computing web service provided by Amazon; Seattle, Wash.). Amazon's Simple Queue Service (SQS) is used to assign tasks. The final calls and metrics are then downloaded and loaded into a local database. The EC2 instances pull tasks and FAQSTQ files from SQS and S3, respectively, process them, and upload the results to S3. Instances may be initiated and/or terminated manually, or may be partially or fully automated.

Figure 10:
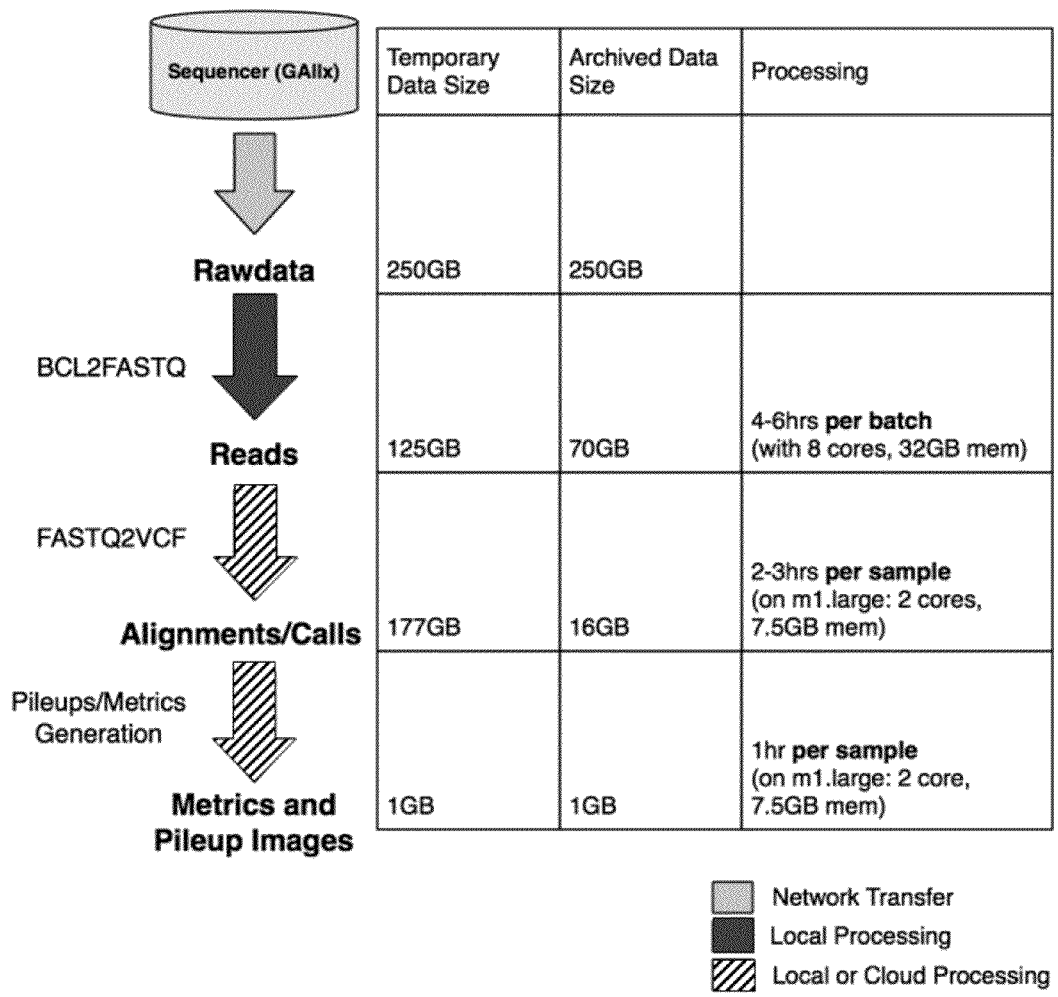
FIG. 10 illustrates an example data-handling process for aligning sequencing data.
Figure 11:
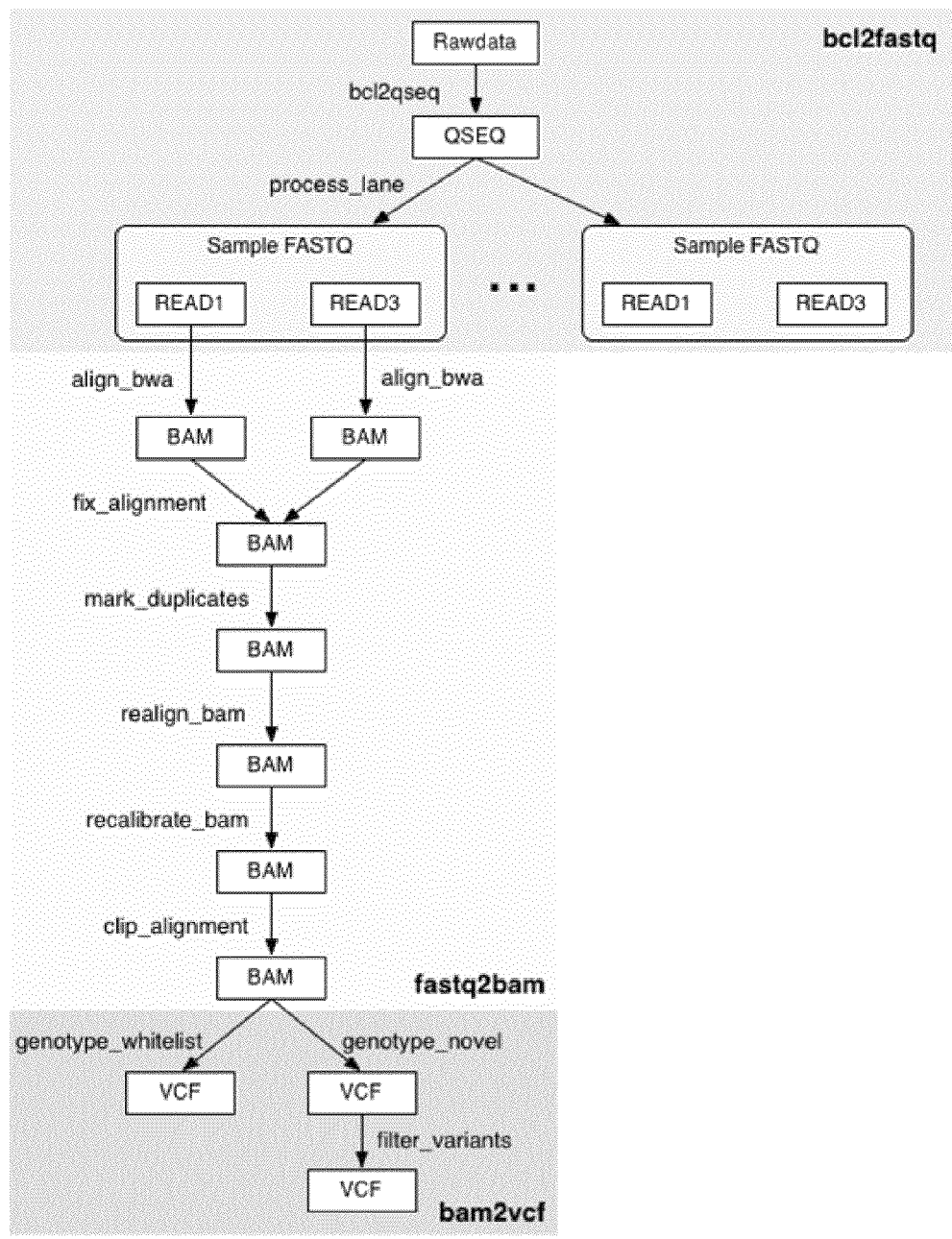
FIG. 11 illustrates an example process for generating an alignment using sequencing data.

FIG. 10 shows an example of temporary and archival storage space utilized and processing runtime for the pipeline on Illumina GAIIx sequencing data. The BCL2FASTQ step is run on the entire batch and subsequent steps are run per sample. To reduce processing time, BCL2QSEQ is run locally and then the remaining steps are run on 96 Amazon EC2 instances, one per sample. Running the pipeline using the cloud takes 7 to 10 hours depending on the batch yield. Use of cloud computing for one or more of the data processing steps may reduce the total time needed to generate final alignments for a sample by more than about 10%, 25%, 50%, 75%, 90%, or more.

FIG. 11 shows an example sequencing data manipulation process. The BCL2FASTQ process converts raw basecalls into filtered, merged, and demultiplexed reads, and comprises bcl2qseq and process_lane steps. The input for bcl2qseq is the rawdata directory for a sequencing batch, which are converted to QSEQ files (one per tile and read number) using an Illumina tool—this is run locally on the entire batch. The QSEQ files are processed in process_lane to filter out poor reads (using the Illumina "chastity filter"), merge reads from different tiles, and demultiplex read1 and read3 into sample-specific FASTQ files using the barcodes in read2. Each lane may be run in parallel.

Figure 12B:
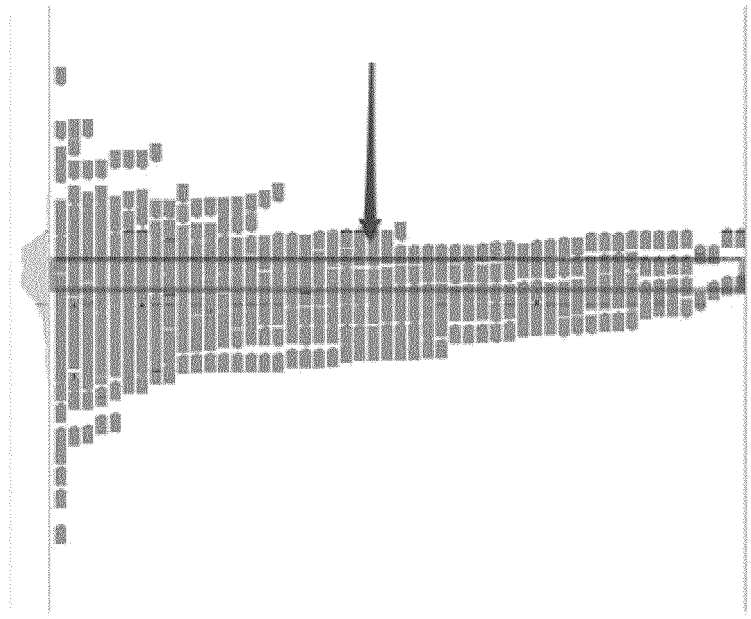
FIGS. 12A and 12B illustrate an alignment before and after a fix_align step in an example alignment process.
Figure 12A:
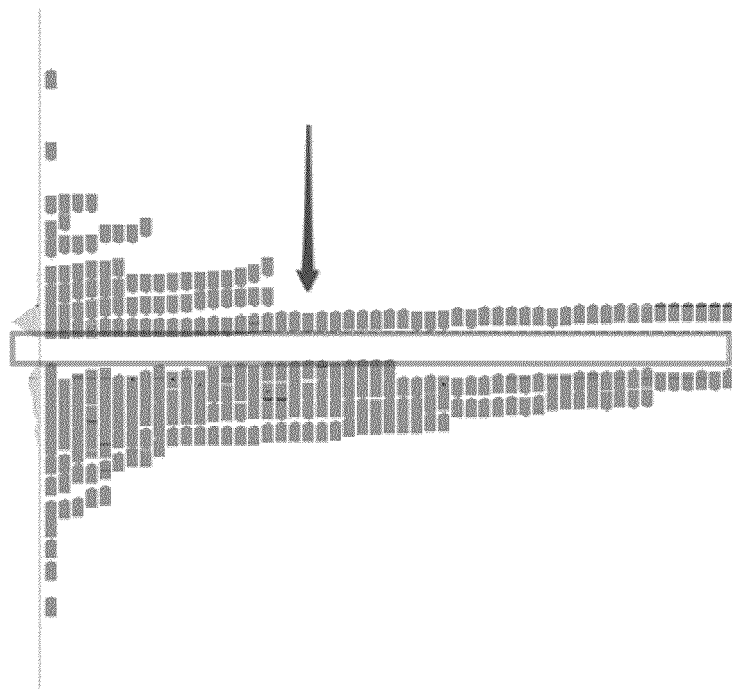

The FASTQ2BAM process aligns reads to the genome and further processes the alignment. Format changing, sorting, and indexing are performed as needed. All steps are run on files for individual samples, and all samples represented in a batch may be run in parallel on different machines. The steps in FASTQ2BAM include align_bwa, fix_align, mark_duplicates, realign_bam, recalibrate_bam, and clip_alignment. In the align_bwa step, reads in a FASTQ file are aligned to the reference genome using the BWA aligner. This step is called twice, once to align read1 to a reference genome and once to align read3 to a collection of the probe sequences used to amplify target polynucleotides. The output sequence alignment/map (SAM) file is converted to a binary alignment/map (BAM) file and then sorted and indexed. In order to improve detection of indels, the default BWA parameters are modified as follows: decrease seed length to 16; increase number of allowed gaps in alignment to 3; decrease the gap open and extension penalties to 6 and 2, respectively; increase the number of allowed gap extensions to 20 (for larger variants, custom contigs may be added to the genome to infer their presence). The fix_alignment step then modifies some of the alignments to improve their accuracy and remove alignments likely to be erroneous. Because read3 includes probe-derived sequence at variable distances from read1 in this scenario, it does not fit some of the statistical assumptions made by aligners (such as expected distance between reads), and customary paired-end mapping would be less efficient. To improve alignment accuracy, read1 and read3 are aligned independently (which is generally faster than paired-end mapping), and then the fix_alignment step processes the results to: discard any reads where read1 and read3 are on different strands or positioned more than 10000 base pairs away from each other (read1 not filtered if read3 does not map); and remap reads with multiple best-scoring positions to a subset of the genome consisting only of regions of interest (ROI; e.g. regions containing a causal genetic variant, non-subject sequence, or AIM; typically near a probe sequence). FIGS. 12A and 12B illustrate an example alignment of reads in a CFTR exon with a non-unique region before and after fix_align, respectively, which closes an artificial gap in the illustrated sequence pileup.

The mark_duplicates step identifies and tags PCR and optical duplicates using a tool from the Picard toolset (java-based command-line utilities for processing sequencing data in BAM format; available from the SourceForge web site maintained by Geeknet (Fairfax, Va.)). Without discarding duplicates, non-uniform PCR efficiency between the reference and alternate allele could lead to allelic bias, where the counts of reference and alternate alleles for a variant may be biased by PCR. Without additional information, it is assumed that two reads from a sample that map to the same position are duplicates and thus, all except one are marked as duplicates and excluded from subsequent analysis. Depth of coverage may be increased by using primers with different barcodes in the same sample, such that an additional read having the same sequence as another would not be discarded if the associated barcodes from the respective clusters were different.

Figure 13A:
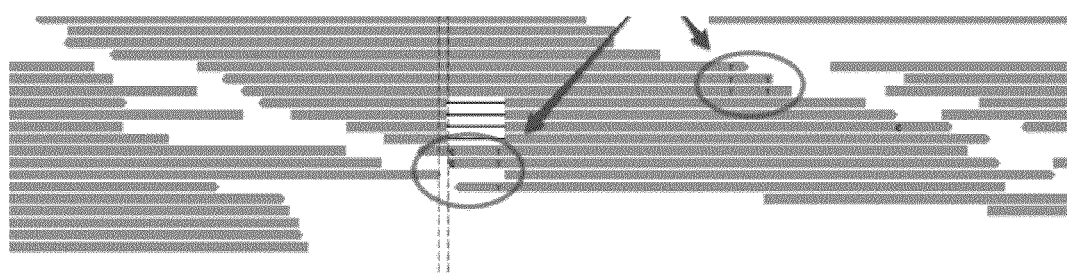
FIGS. 13A and 13B illustrate an alignment before and after an example local alignment step.
Figure 13B:
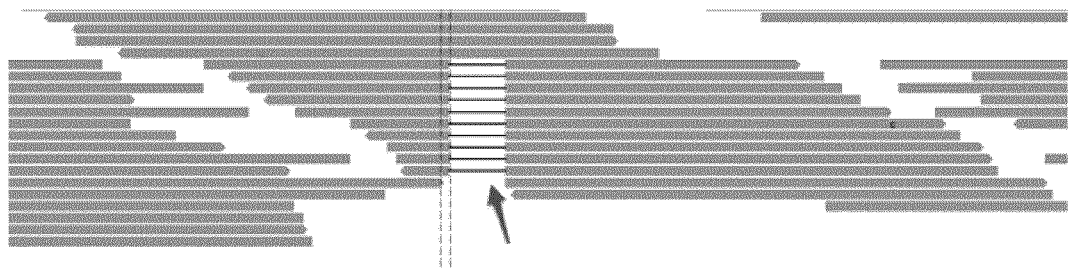

The realign_bam step performs multiple sequence Smith-Waterman alignment around indels, and typically has the effects of better identifying true indels, and reducing or eliminating the number of false-positive SNPs. The initial aligner (BWA or any similar tool) aligns each read independently and heuristically. A read with a true INDEL may align as a read with a cluster of SNPs because that alignment model scores better than one with the INDEL given the set of parameters and heuristics used. In multiple sequence alignment of the same reads, the aligner tries to optimize the score of an alignment model of all reads (to the reference and to each other); thus, unless the same cluster of SNPs can align all reads, the true alignment will typically score higher. The realignment step performs a multiple-sequence exact realignment around any INDELs found in the ROI. FIGS. 13A and 13B show the same reads before and after local realignment. A realignment may be performed around any indel in an ROI. Alternatively or additionally, a realignment may be performed around known indels, such as around indels in one or more reference sets of indels (such as sets reported in Mills et al., Genome Res. (2011) June; 21(6): 830-839; Durbin et al., Nature (2010) October 28; 467(7319): 1061-1073; and Bhangale et al., Nature Genetics (2006) 38, 1457-1462).

The recalibrate_bam step recalibrates base qualities using empirical batch data. Illumina software estimates a quality value for each base using various quality control metrics using a simple model of the sequencing chemistry—it does not take specific error modes into account. In this step, a GATK tool that uses high-scoring alignments is used to determine empirical base quality, analyze the covariation in empirical quality between many features of a sequenced base (reported quality, surrounding bases, read position, etc), and recalibrate all qualities using the covariation model. This step provides more accurate base qualities which leads to more accurate calling statistics.

The clip_alignment step removes bases from aligned reads that include probe sequence from the corresponding cluster. For amplified sequences from a subject that are shorter than the read-length, read1 will typically contain sequences from the corresponding probe. When probe sequences are derived from the reference genome, these reads will align to the genome but will mask out any true SNPs, thus introducing an allelic bias towards the reference sequence. This step identifies when a read overlaps its own probe and selectively removes the overlapping bases from the read. For all reads where both read1 and read3 map and where read1 overlaps the probe, the overlapping bases of read1 are removed from the alignment ("clipped"). If read3 of a read doesn't map, then read1 is clipped if it overlaps any probe, but only if the overlap occurs at either end of the read (probe sequence that does not include a terminal base indicates the read was not generated from that probe). In either case, clipping is performed by modifying the CIGAR alignment string to include the "S" operation for the clipped bases, updating the start position and setting the base qualities of the clipped bases to 0. Thus, the sequence still exists, but the alignment is modified to exclude the clipped bases.

The BAM2VCF process uses the final alignments (BAM files from the FASTQ2BAM process) to determine genotypes using a Bayesian method to compute probability of variants given sequencing data and prior knowledge. All steps are run on files for individual samples and can be run in parallel and on different machines. The strategy for variant identification ("calling") is to create an initial set of identified variants (a "callset") using very lenient thresholds to maximize sensitivity and then to filter it based on call metrics and other criteria. The steps in the BAM2VCF process include genome_whitelist, genotype_novel, and hard_filter_vcf steps. The genome_whitelist step infers genotypes for an input BAM file based on a comparison to a given a reference list of known variant positions and alleles at those positions. In this step, a computer algorithm programmed to identify variants (a "caller") is configured to output all variants and to skip any confidence-based filtering. The output of this step is a variant call format (VCF) file, which is further processed in additional steps.

The genotype_novel step identifies variant sites within the ROI that differ from the reference genome, and infers the genotypes at those sites. In this step, the caller is configured to output only genotypes not included in the reference list of known variants used in the previous step, and to skip any confidence-based filtering. Calls from the genotype_novel step may contain many false positives. The hard_filter_vcf step filters genotype determinations using several call metrics. These metrics fall into two broad categories: (1) those that quantify the confidence of the base calls, mapping, variant, or genotype determination and (2) those that quantify the likelihood of common sources of errors such as strand bias, position bias, or presence of sequence features such as homopolymer runs that are known to cause Illumina chemistry errors. Modified thresholds may be based on recommendations by the Genome Analysis Tool Kit (GATK). Alternatively or additionally, a machine learning approach may be used to identify thresholds for a desired sensitivity and specificity.

To aid the evaluation of the processes in this example, a record for each sample is made of the number of: reads with corresponding barcode, reads mapped to the genome, reads after fix_align step, reads after excluding PCR/optical duplicates, reads where read1 and read3 map more than 10000 bp apart, reads in non-unique regions that the fix_align step attempts to remap, reads successfully remapped, reads that are clipped and have a corresponding read3, reads that are clipped and do not have a corresponding read3, reads in X and Y chromosomes (which may be used to infer sex), and SNP calls that match the SNP identity in the reference genome. Thresholds as to any one or combination of these metrics may be set, such that results for any sample falling below the threshold are discarded. Any one or combination of these metrics may also be aggregated for an entire sequencing lane, in addition to the total number of reads per lane and the number of reads passing an initial filter. Thresholds as to any one or combination of sequencing lane metrics may also be set for the exclusion of data resulting from lanes failing to pass the threshold(s). Concordance and discordance between any two callsets may be analyzed for validation studies or for setting thresholds for future sample analyses.

For any genomic variants identified, a pileup image may be generated, which illustrates an alignment of all reads underlying any variant call. A pileup image may be produced using a genomics data visualizer, such as the Integrative Genomics Viewer (IGV; provided by the Broad Institute, Cambridge, Mass.). To do this, an IGV script is generated that (1) loads the genome and BAM files and (2) iterates through each variant position and outputs a snapshot PNG of the pileups. IGV is run under a virtual framebuffer (e.g. xvfb) and the resulting PNG files are cropped (using command line Imagick tool) to remove IGV chrome.

Example 5

Selecting Probe Sequences

An algorithm is used in a process of selecting optimal probe sequences for initial capture of target sequence for amplification and sequencing (a process also referred to as "probe design"). The probe sequences may then be used in the production of a collection of oligonucleotide primers or first oligonucleotides bound to a solid support. The probe design process may be repeated, such as to incorporate additions to the list of variants and corresponding target sequences to be sequenced. Accordingly, the algorithm allows the addition of previously designed regions of interest (ROIs) and probes so that regions that are already covered by a previously designed ROI are not redesigned.

The initial unit of probe design is the Region of Interest (ROI), which can be a list of the exons of a gene, a single genomic base, regions or points that are non-coding, or combinations of these that can possibly overlap. The first step in the process is to load and then reconcile all of the different regions for which probes are to be designed. The "design engine" class keeps track of all ROIs to be considered and, later, all of the probes that have been designed for each ROI. Small ROIs, such as variants initially entered as point mutations, are padded to a length of 100 bp before being processed further. Then, all overlapping ROIs are combined into single ROIs so that duplicate probes are not designed.

Two ROIs are merged if and only if they reduce the number of ROI Tiles covering the combined ROIs. The number of tiles covering the two separate areas is calculated along with the number of tiles to cover a hypothetically joined ROI. The case that requires the fewest tiles is used for subsequent steps of probe design. An algorithm is used to determine the number of tiles covering a given genomic region.

Once ROIs have been padded and merged, all ROIs are at least 100 bp long and none overlap. The resulting ROIs are long (e.g. longer than a specified tile length) or short (e.g. less than or equal to a specified tile length). Long ROIs are subdivided into ROI tiles, which are unit lengths of sequence for which a probe will be designed. Short ROIs, being less than or equal to the tile length, are not subdivided. Each potential ROI tile is evaluated on how well the probes designed from it perform. The maximum number of tiles is also calculated as the upper bound on this calculation. All tile numbers between the minimum and the maximum number of tiles possible are considered in order from least number of tiles to greatest. These numbers of tiles are equal to the ceiling of the number of bases in the ROI to be split divided by the min or max length of the ROI, depending on what number is being calculated. These numbers are ROI_TILE (250 bases) and MAX_ROI_TILE, where MAX_ROI_TILE=(TILE_SIZE)–(READ_LENGTH)–(RECESS). TILE_SIZE is between 300-440 bases long. READ_LENGTH is 40-60 bases long. RECESS is set at 10 bases in length. Once a number of tiles whose probe design yields all valid probes is found, the iteration ends. This in effect minimizes the number of tiles required to cover a region while at the same time ensuring the best probes are chosen according to the criteria below.

The probe design algorithm works on a given ROI tile in isolation from other ROI tiles, so the ROI tile can be considered the fundamental unit of this probe design process. Each ROI tile will have a forward and reverse tile designed for it, so that all bases may be evidenced from either strand upon sequencing. The probe design algorithm works by considering the forward and reverse primers for every READ_LENGTH tile in a "probe design window" that is calculated for each ROI tile. Each probe in this window is then scored based on criteria described below to create a set of scores from most important to least important where, for all scores, a lower score is better. Therefore, the best probe is merely the one that appears first in a multiple-field ascending sort of the probe score sets. Each ROI tile partition causes the probe design algorithm to be run for each of the possible ROI tiles. The iteration starts with the condition of the fewest ROI tiles and, if such a partition doesn't yield valid probes (conditions of which are described below), the number of ROI tiles is increased and the partition is re-done.

The probe window is defined as follows: (1) the length of the probe window is defined as (TILE_SIZE)−(length of the current ROI tile)−(RECESS); (2) the start coordinate is then defined as RECESS by away from the end of the ROI itself, and the stop coordinate is calculated by adding the length of the probe window above to the RECESS coordinate; and (3) all 40 mers in this range are then considered as probes for evaluation. FIG. 19 provides an illustration of the positional relationship of sequence regions considered in this step.

Criteria used to evaluate each probe, in the order considered, include uniqueness of the "near 24-mer," overlap with any common SNPs in the near 24 mer, mappability of the entire 40 mer, NtBspQI overlap, repeat masking, overlap with any common SNPs in entire 40 mer, near 24 mer overlap with disease variant, 40 mer overlap with disease variant, GC %, and Distance to ROI. While an ideal probe is unique across the genome, sometimes finding such a location near an arbitrary site is not possible. To compensate, the "near 24-mer" (defined as the 3'-most 24 bases of the oligonucleotide comprising the probe sequence or its complement) is selected to be as unique as possible. Because the extension of the captured genomic species occurs from 5' to 3', the quality of the base-pair binding site nearest the double-stranded to single-stranded junction has a large effect on the efficiency of the capture—a stronger bond making it more likely that the captured sequence will be extended. To measure binding quality, the University of California Santa Cruz 24 mer mappability track (available through the UCSC genome browser) is used, which gives, for each base in the genome, the mapping score of the 24 mer beginning at that base. The score is given as 1/N, where N is the number of matches to that 24 mer in the genome. Only two results out of this test are considered: whether the score equals 1 (i.e. is unique) or is less than one (i.e. has multiple binding sites). The first case is preferred.

Overlap with common SNPs in the near 24-mer is not desired. Any mismatch in the capture probe binding site reduces binding efficiency. Because nearby SNPs are often in linkage disequilibrium, this difference in binding efficiency would introduce a great deal of allelic bias. It is therefore desirable for any allele found to have the greatest chance possible of having the same probe binding site as other alleles in that gene. The UCSC Common SNP Track is used to make this calculation. There are two categories: those with no overlaps and those with one or more overlaps. The former is greatly preferred.

The mappability of the entire 40 mer determines the same score with the same categories as the 24 mer mappability, but using the UCSC 40 mer Mappability track instead of the 24 mer track. This new track has a similar definition, only 40 mer mappability is considered instead of 24 mer mappability.

The enzyme NtBspQI may be useful in oligonucleotide synthesis or manipulation. Accordingly, the number of bases of overlap between the probe and the recognition site of the enzyme is scored.

In evaluating repeat masking, the UCSC repeat mask track (annotated repeats) is used to calculate the weighted average of the values for the bases that makeup the each 40 mer. The repeat mask track assigns values 0 or 1 to each base depending on whether it is masked or not. Thus, the higher the score, the more it is masked. Designing probes for masked bases is not desired, so a lower, ideally 0, score is better. These scores are divided into quartiles: so, up to 25% masked comprises a class (scored as 0), up to 50% another, as does 75% and 100%.

Just as overlap of a probe' near-24 mer with any common SNP is evaluated, so too is overlap of the entire 40 mer probe sequence with any common SNP evaluated and scored.

Whether or not the near-24 mer overlaps a disease variant is also evaluated. This test is similar to the common SNP overlap test, except the near-24 mer is evaluate for overlap with any causal genetic variants to be sequenced. A score of 0 is given for no overlap, and a score of 1 is given for the presence of overlap. A similar analysis is then performed for the entire 40-mer.

The GC % of a probe sequence received one of two scores—0 for a GC % between 20-80%, and 1 for outside this range. Finally, distance to the ROI is evaluated. All other things being equal, the probe closest to the ROI is preferred. The score for ROI distance is equal to the number of base pairs between the end of the probe and the start of the ROI it targets.

A valid probe is a probe that meets all of the following criteria and for which no further iteration of probe design for the ROI is required: (1) mappability of the near 24 mer≥1/3.5; (2) Mappability of the entire 40 mer≥1/3.5; (3) repeat fraction≥0.25; (4) no overlaps with common SNPs in the near 24-mer; no NtBspQI recognition site in the probe sequence.

Example 6

Sample Collection and Analysis

Figure 14:
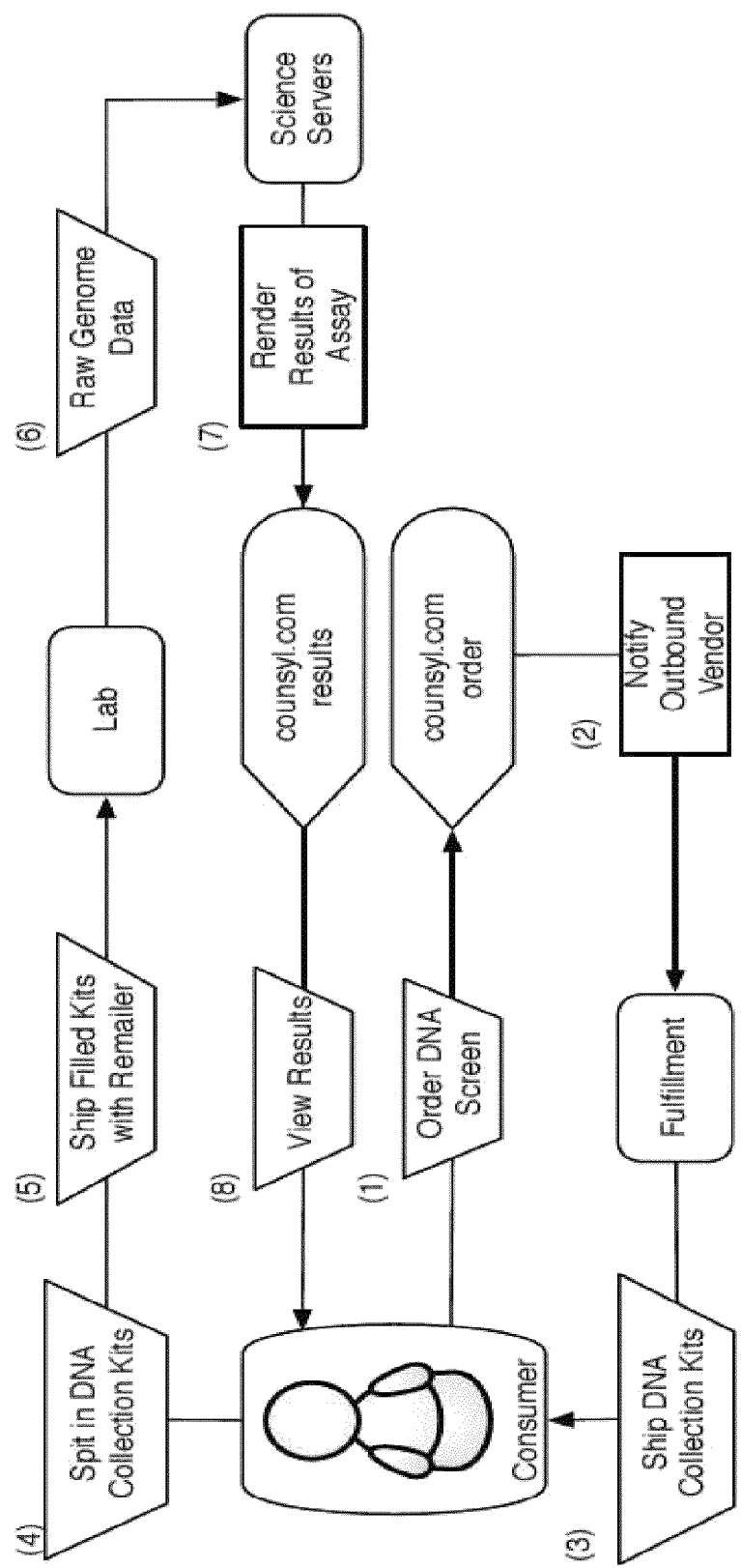
FIGS. 14-17 demonstrate exemplary processes of delivering a probability that a user is a carrier of rare genetic disease.
Figure 15:
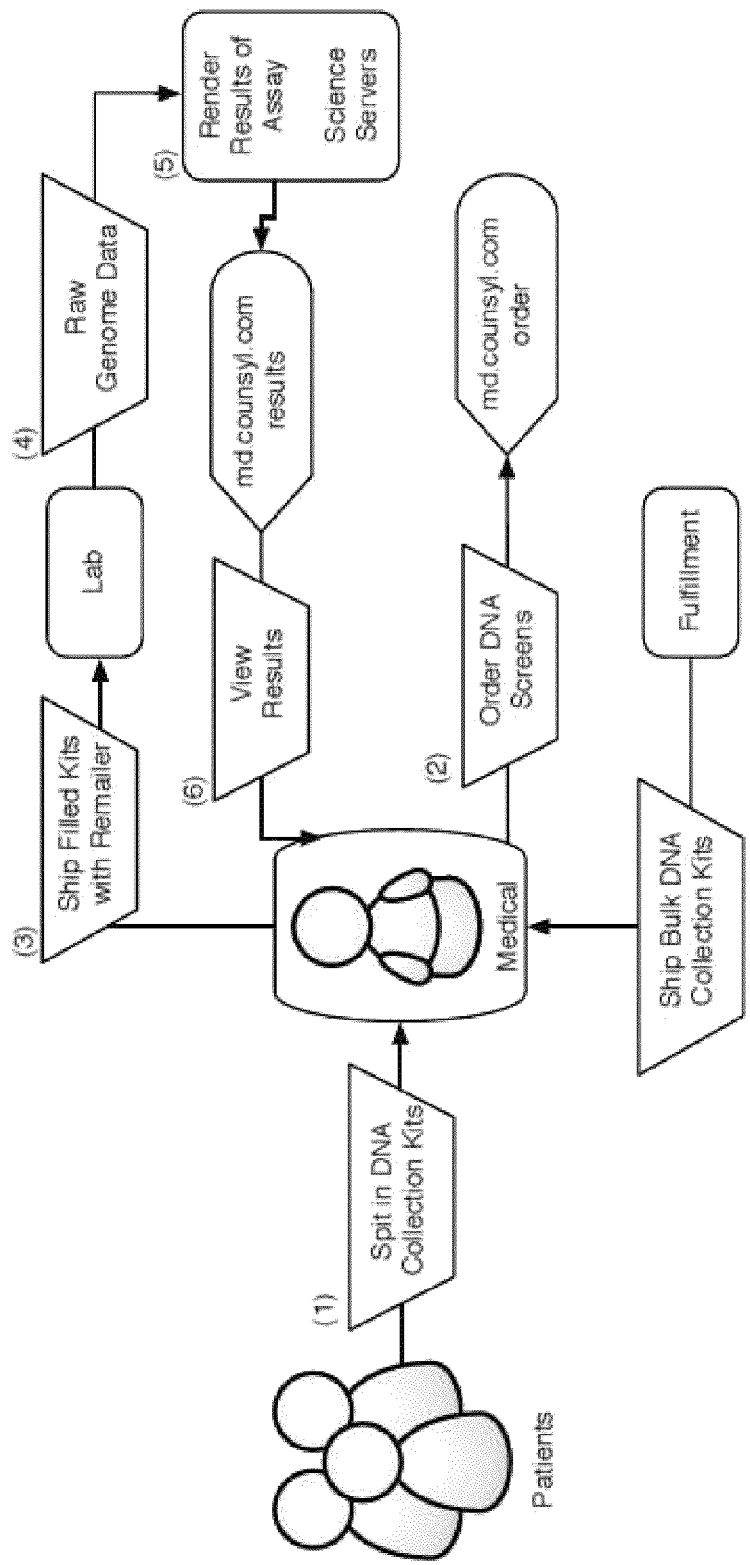

Exemplary processes of delivering a probability that a user is a carrier of rare genetic disease are demonstrated in FIGS. 14-17. FIGS. 14-15 illustrate pipelines for order fulfillment for web and medical customers respectively. An order can be placed by a physician or a consumer. An order can be placed for a single test or for a couple or family. The order can be accepted through a web site. The ordering system can accept contact information, demographic details and billing information. Contact information can include, without limitation, name, address, telephone number, and email addresses. Demographic information can include, without limitation, sex, date of birth, and self-reported ethnicity. An order confirmation notification can be sent using the provided contact information. Acceptable orders are added to a database, and the states of these orders can be subsequently maintained by a state machine.

A sample collection kit is then sent to the user. A sample is collected that is any human tissue or fluid. The sample can also be isolated DNA from a human. Examples of samples useful for this example include, but are not limited to: saliva, blood, urine, buccal cells, amniotic fluid, cell scrapings, and cell culture. The sample is then genotyped using a device described herein. Phenotype solicitation, for example, retrieving self-identification of phenotypic traits of a user, can be performed in parallel with sample processing.

Sample collection can be performed at home, in a physician's office, or at a specialized collection site. Sample collection and return can be tracked by advancing the state of the order-tracking state machine. Samples received by the accessioning facility can be registered in the database system by advancing their state in the state machine. After acceptance at the accessioning facility, samples can be delivered to the genotyping facility. The genotyping facility can return raw genome data to a secure data storage server by secure file transfer protocols. File upload can trigger an advance of the state machine. This advance can trigger a server configured to perform genotype calling to retrieve the raw genome data from the data storage server as well as any phenotype data associated with the order. The genotyping algorithm can produce a fully probabilistic genotype call.

Figure 16:
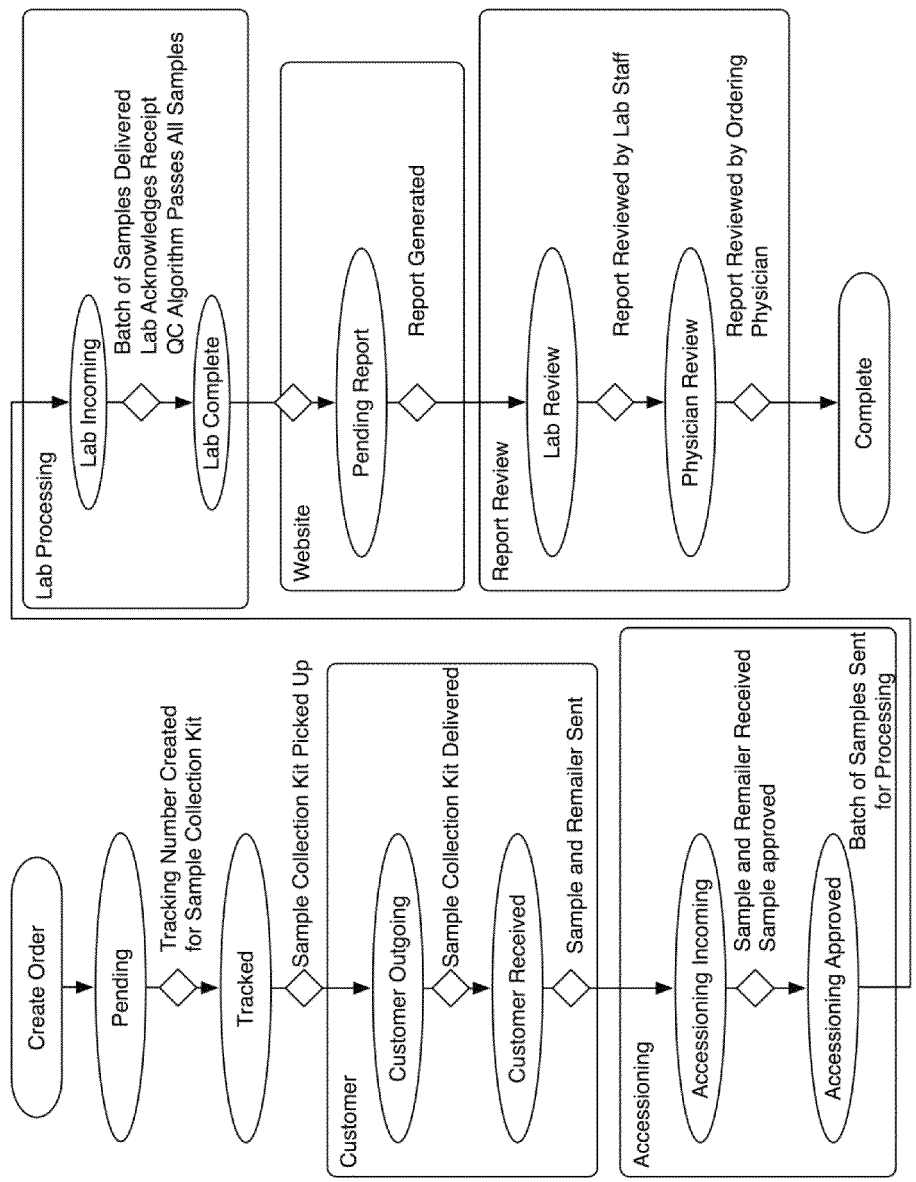
Figure 17:
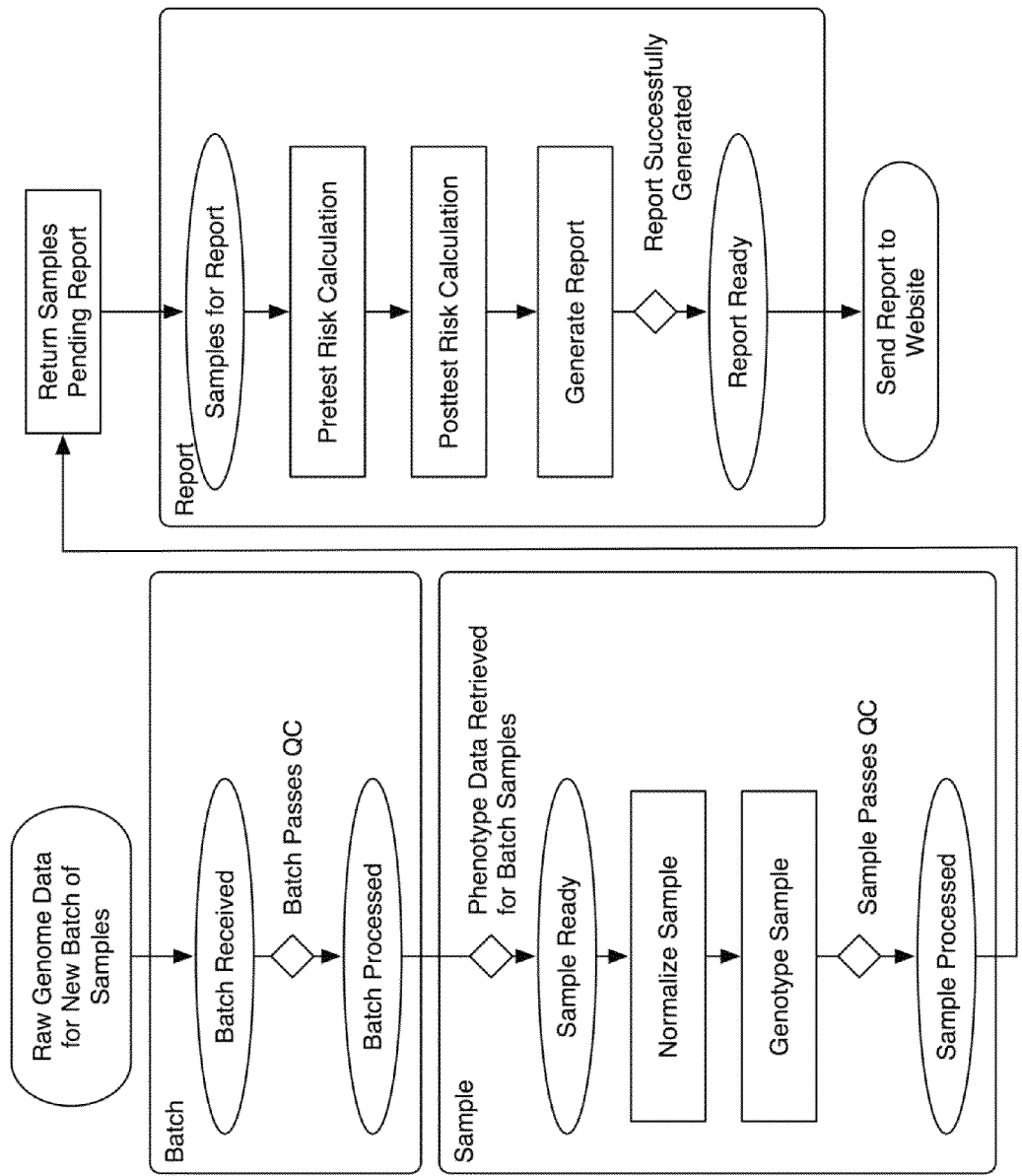

FIGS. 16-17 illustrate a high level sample processing pipeline and detailed computational pipeline respectively.

Batches of samples are received and measured for quality control purposes (Batch passes QC). Information such as family history, gender, or self-reported ancestry is used to serve as an independent check on calling for each sample (Phenotype data retrieved for batch samples). In parallel with this process, a report with child predictions is constantly updated. First pre-test risk calculations are delivered, based on phenotype (such as family history and other answers to an online questionnaire). Once a genotype sample is received and processed, post-test calculations are given. The report is then generated and sent to the final stages of the pipeline, for laboratory staff and physician approval as shown in FIG. 16.

Quality control metrics can be generated from the calling process. An example quality control metric is the percentage of probabilistic genotype calls in which at least one genotype has a posterior probability greater than a threshold value. A batch of samples is processed together. When processed as a batch, the individual probabilistic genotype calls can be used to generate batch-level quality control statistics. Probabilistic genotype calls can be stored in a database. Successful genotype calling can trigger an advance of the order state. For a couple or family order, the state machine can hold for completion of the entire order, else single orders can be passed to the next state. If phenotype data is required for risk calculation, then the state machine can delay processing until all phenotype data is collected. The state machine can also trigger a notification to the patient that phenotype data is required. If all genotype and phenotype data are ready, then the state machine can advance, trigger the risk calculation server to perform risk calculation. The results of risk calculation can be serialized and transferred to a results reporting system. This is a machine-readable format of the results. The state machine can advance the order when the transfer is completed. The results reporting server can combine the probabilistic risk calculation with appropriate text and formatting to generate a human-readable report. This human readable report can be further formatted for display on a website. This human readable report can be formatted for other media such as PDF files for printing. The final results reports can be automatically released using an auto-verification system. A human can review the reports for release. The reviewers may be a clinical laboratory scientist and a physician. The results are accessed via a web portal which links to a view of the results and a summary of the quality control metrics. Acceptance of the report by the clinical laboratory scientist releases the results to the physician. The physician can review the results in a similar portal and approve the final release of the results.

Figure 18:
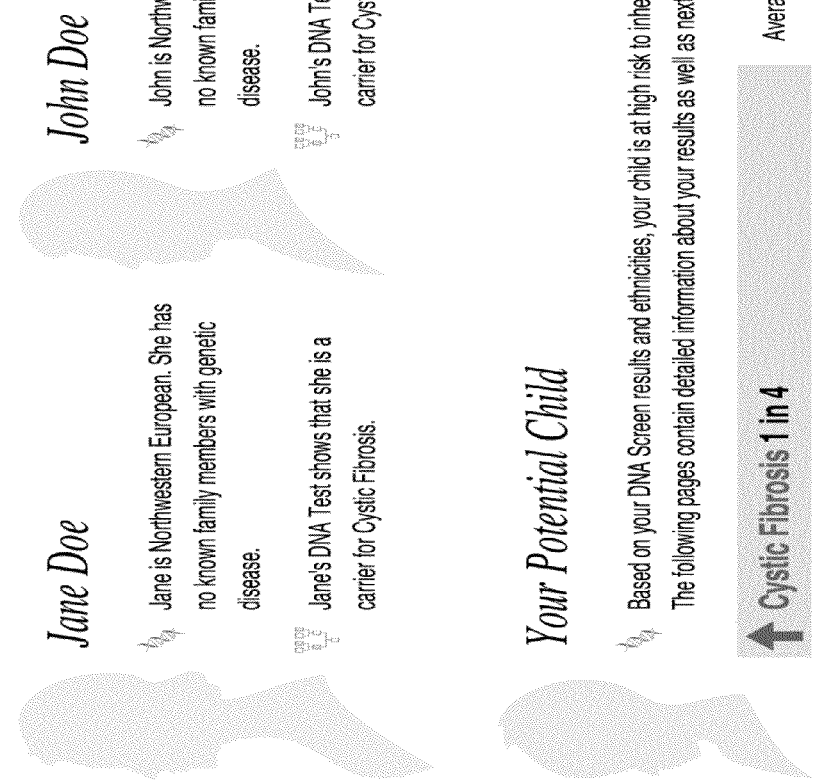
FIG. 18 illustrates exemplary the input and output steps for report generation for two hypothetical parents: Mama Hen (Jane Doe) and Papa Hen (John Doe).

FIG. 18 illustrates exemplary input and output steps for report generation for two hypothetical parents: Mama Hen and Papa Hen. A child prediction is produced that incorporates mother and father genotypes, mother and father phenotypes, and relative genotypes and phenotypes. Any or all of these variables can be missing values, with defaults initialized from demographically similar individuals (and if this is not known, from the world population). The resulting child prediction may include not only disease or trait risk, but also other variables such as height and weight. Different variables in the child prediction will use different weights of genotype and phenotype.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of detecting genetic variation in a subject's genome comprising:
   (a) providing a plurality of clusters of polynucleotides, wherein (i) each cluster comprises multiple copies of a nucleic acid duplex attached to a support; (ii) each duplex in a cluster comprises a first molecule comprising sequences A-B-G'-D'-C' from 5' to 3' and a second molecule comprising sequences C-D-G-B'-A' from 5' to 3'; (iii) sequence A' is complementary to sequence A, sequence B' is complementary to sequence B, sequence C' is complementary to sequence C, sequence D' is complementary to sequence D, and sequence G' is complementary to sequence G; (iv) sequence G is a portion of a target polynucleotide sequence from a subject and is different for each of a plurality of clusters; (v) sequence B' is located 5' with respect to sequence G in the corresponding target polynucleotide sequence; and (vi) each first molecule comprises a barcode sequence;
(b) sequencing sequence G' by extension of a first primer comprising sequence D to produce an R1 sequence for each cluster;
(c) sequencing sequence B' by extension of a second primer comprising sequence A to produce R2 sequence for each cluster;
(d) performing a first alignment using a first algorithm to align all R1 sequences to a first reference sequence;
(e) performing a second alignment using a second algorithm to locally align R1 sequences identified in said first alignment as likely to contain an insertion or deletion with respect to the first reference sequence, to produce a single consensus alignment for each insertion or deletion;
(f) performing an R2 alignment by aligning all R2 sequences to a second reference sequence;
(g) transmitting a report identifying sequence variation identified by steps (d) to (f) to a receiver; and
(h) hybridizing a third primer to sequence C' and sequencing the barcode sequence by extension of the third primer to produce a barcode sequence for each cluster.

2. The method of claim 1, wherein the first reference sequence comprises a reference genome.

3. The method of claim 1, wherein the second reference sequence consists of every sequence B for every different target polynucleotide.

4. The method of claim 1, wherein R2 sequences are aligned independently of R1 sequences.

5. The method of claim 1, further comprising discarding an R1 sequence that aligns to a first position in the first reference sequence that is more than 10,000 base pairs away from a second position in the first reference sequence to which the R2 sequence for the same cluster aligns.

6. The method of claim 1, further comprising deleting a portion of an R1 sequence for a cluster when the portion of R1 sequence to be deleted is identical to at least a portion of sequence B' for that cluster and sequence G is shorter than the R1 sequence for that cluster.

7. The method of claim 1, further comprising deleting a portion of an R1 sequence for a cluster when the portion of R1 sequence to be deleted is identical to at least a portion of any sequence B', the portion includes either the 5' or 3' nucleotide of R1, and either (i) no R2 sequence was produced for the cluster or (ii) R2 sequence produced is not identical to any sequence B.

8. The method of claim 1, wherein performing the first alignment with a system using the first algorithm takes less time to align all R1 reads than would be taken if the system used the second algorithm to perform the first alignment.

9. The method of claim 1, wherein performing the first alignment with a system using the first algorithm uses less system memory to align all R1 reads than would be used if the system used the second algorithm to perform the first alignment.

10. The method of claim 1, wherein said first algorithm is based on Burrows-Wheeler transform.

11. The method of claim 1, wherein said second algorithm is based on Smith-Waterman algorithm or a hash function.

12. The method of claim 1, wherein R1 and R2 sequences are generated for at least 100 different target polynucleotides.

13. The method of claim 1, wherein each barcode differs from every other barcode in a plurality of different barcodes analyzed in parallel.

14. The method of claim 1, wherein the barcode sequence is associated with a single sample in a pool of samples sequenced in a single reaction.

15. The method of claim 1, wherein each of a plurality of barcode sequences is uniquely associated with a single sample in a pool of samples sequenced in a single reaction.

16. The method of claim 1, wherein the barcode sequence is located 5' from sequence D'.

17. The method of claim 1, further comprising grouping sequences from the clusters based on the barcode sequences.

18. The method of claim 17, further comprising discarding all but one of a plurality of R1 sequences having the same sequence and alignment within a barcode sequence grouping.

19. The method of claim 1, wherein sequences A, B, C, and D are at least 5 nucleotides in length.

20. The method of claim 1, wherein sequence G of every cluster is 1 to 1000 nucleotides in length.

21. The method of claim 1, wherein each probe sequence B of a plurality of clusters is complementary to a sequence comprising a causal genetic variant or a sequence within 200 nucleotides of a causal genetic variant.

22. The method of claim 1, wherein an R1 sequence is produced for at least about $10^8$ clusters in a single reaction.

23. The method of claim 1, wherein presence, absence, or allele ratio of one or more causal genetic variants is determined with an accuracy of at least about 90%.

24. The method of claim 1, wherein the consensus sequence identifies an insertion, a deletion, or an insertion and a deletion in a target polynucleotide with an accuracy of at least about 90%.

25. The method of claim 1, wherein each probe sequence B of a plurality of clusters is complementary to a sequence comprising a non-subject sequence or a sequence within 200 nucleotides of a non-subject sequence.

26. The method of claim 1, wherein the presence or absence of one or more non-subject sequences is determined with an accuracy of at least about 90%.

27. A method of detecting genetic variation in a subject's genome comprising:
(a) providing sequencing data for a plurality of clusters of polynucleotides, wherein (i) each cluster comprised multiple copies of a nucleic acid duplex attached to a support; (ii) each duplex in a cluster comprised a first molecule comprising sequences A-B-G'-D'-C' from 5' to 3' and a second molecule comprising sequences C-D-G-B'-A' from 5' to 3'; (iii) sequence A' is complementary to sequence A, sequence B' is complementary to sequence B, sequence C' is complementary to sequence C, sequence D' is complementary to sequence D, and sequence G' is complementary to sequence G; (iv) sequence G is a portion of a target polynucleotide sequence from a subject and is different for each of a plurality of clusters; (v) sequence B' is located 5' with respect to sequence G in the corresponding target polynucleotide sequence; (vi) the sequencing data comprise R1 sequences generated by extension of a first primer comprising sequence D; (vii) the sequencing data comprise R2 sequences generated by extension of a second primer comprising sequence A; (viii) each first molecule comprises a barcode sequence; and (ix) the sequencing data comprise a barcode sequence for each cluster generated by extension of a third primer comprising sequence C;

(b) performing a first alignment using a first algorithm to align all R1 sequences to a first reference sequence;

(c) performing a second alignment using a second algorithm to locally align R1 sequences identified in said first alignment as likely to contain an insertion or deletion with respect to the first reference sequence, to produce a single consensus alignment for each insertion or deletion;

(d) performing an R2 alignment by aligning all R2 sequences to a second reference sequence; and (e) transmitting a report identifying sequence variation identified by steps (b) to (d) to a receiver.

28. The method of claim 27, wherein the first reference sequence comprises a reference genome.

29. The method of claim 27, wherein the second reference sequence consists of every sequence B for every different target polynucleotide.

30. The method of claim 27, wherein R2 sequences are aligned independently of R1 sequences.

31. The method of claim 27, further comprising discarding an R1 sequence that aligns to a first position in the first reference sequence that is more than 10,000 base pairs away from a second position in the first reference sequence to which the R2 sequence for the same cluster aligns.

32. The method of claim 27, further comprising deleting a portion of an R1 sequence for a cluster when the portion of R1 sequence to be deleted is identical to at least a portion of sequence B' for that cluster and sequence G is shorter than the R1 sequence for that cluster.

33. The method of claim 27, further comprising deleting a portion of an R1 sequence for a cluster when the portion of R1 sequence to be deleted is identical to at least a portion of any sequence B', the portion includes either the 5' or 3' nucleotide of R1, and either (i) no R2 sequence was produced for the cluster or (ii) R2 sequence produced is not identical to any sequence B.

34. The method of claim 27, wherein performing the first alignment with a system using the first algorithm takes less time to align all R1 reads than would be taken if the system used the second algorithm to perform the first alignment.

35. The method of claim 27, wherein performing the first alignment with a system using the first algorithm uses less system memory to align all R1 reads than would be used if the system used the second algorithm to perform the first alignment.

36. The method of claim 27, wherein said first algorithm is based on Burrows-Wheeler transform.

37. The method of claim 27, wherein said second algorithm is based on Smith-Waterman algorithm or a hash function.

38. The method of claim 27, wherein the sequencing data comprise R1 and R2 sequences for at least 100 different target polynucleotides.

39. The method of claim 27, wherein each barcode differs from every other barcode in a plurality of different barcodes analyzed in parallel.

40. The method of claim 27, wherein the barcode sequence is associated with a single sample in a pool of samples sequenced in a single reaction and represented in the sequencing data.

41. The method of claim 27, wherein each of a plurality of barcode sequences is uniquely associated with a single sample in a pool of samples sequenced in a single reaction.

42. The method of claim 27, wherein the barcode sequence is located 5' from sequence D'.

43. The method of claim 27, further comprising grouping sequences from the clusters based on the barcode sequences.

44. The method of claim 43, further comprising discarding all but one of a plurality of R1 sequences having the same sequence and alignment within a barcode sequence grouping.

45. The method of claim 27, wherein sequences A, B, C, and D are at least 5 nucleotides in length.

46. The method of claim 27, wherein sequence G of every cluster is 1 to 1000 nucleotides in length.

47. The method of claim 27, wherein each probe sequence B of a plurality of clusters is complementary to a sequence comprising a causal genetic variant or a sequence within 200 nucleotides of a causal genetic variant.

48. The method of claim 27, wherein sequencing data comprise at least about $10^8$ R1 sequences from a single reaction.

49. The method of claim 27, wherein presence, absence, or allele ratio of one or more causal genetic variants is determined with an accuracy of at least about 90%.

50. The method of claim 27, wherein the consensus sequence identifies an insertion, a deletion, or an insertion and a deletion in a target polynucleotide with an accuracy of at least about 90%.

51. The method of claim 27, wherein each probe sequence B of a plurality of clusters is complementary to a sequence comprising a non-subject sequence or a sequence within 200 nucleotides of a non-subject sequence.

52. The method of claim 27, wherein the presence or absence of one or more non-subject sequence is determined with an accuracy of at least about 90%.

53. A method of detecting genetic variation in a subject's genome comprising:

(a) providing a plurality of clusters of polynucleotides, wherein (i) each cluster comprises multiple copies of a nucleic acid duplex attached to a support; (ii) each duplex in a cluster comprises a first molecule comprising sequences A-B-G'-D'-C' from 5' to 3' and a second molecule comprising sequences C-D-G-B'-A' from 5' to 3', (iii) sequence A' is complementary to sequence A, sequence B' is complementary to sequence B, sequence C' is complementary to sequence C, sequence D' is complementary to sequence D, and sequence G' is complementary to sequence G; (iv) sequence G is a portion of a target polynucleotide sequence from a subject and is different for each of a plurality of clusters; (v) sequence B' is located 5' with respect to sequence G in the corresponding target polynucleotide sequence; and (vi) each first molecule comprises a barcode sequence;

(b) sequencing sequence G' by extension of a first primer comprising sequence D to produce an R1 sequence for each cluster;

(c) sequencing sequence B' by extension of a second primer comprising sequence A to produce R2 sequence for each cluster;

(d) performing a first alignment using a first algorithm to align all R1 sequences to a first reference sequence;

(e) performing a second alignment using a second algorithm to locally align R1 sequences identified in said first alignment as likely to contain an insertion or deletion with respect to the first reference sequence, to produce a single consensus alignment for each insertion or deletion;

(f) performing an R2 alignment by aligning all R2 sequences to a second reference sequence;

(g) calculating a plurality of probabilities based on the R1 sequences for the subject and including the probabilities in a report identifying sequence variation identified by steps (d) to (f), wherein each probability is a probability of the subject or a subject's offspring having or developing a disease or trait;
(h) transmitting the report to a receiver; and
(i) hybridizing a third primer to sequence C' and sequencing the barcode sequence by extension of the third primer to produce a barcode sequence for each cluster.

54. The method of claim 53, wherein the first reference sequence comprises a reference genome.

55. The method of claim 53, wherein the second reference sequence consists of every sequence B for every different target polynucleotide.

56. The method of claim 53, wherein R2 sequences are aligned independently of R1 sequences.

57. The method of claim 53, further comprising discarding an R1 sequence that aligns to a first position in the first reference sequence that is more than 10,000 base pairs away from a second position in the first reference sequence to which the R2 sequence for the same cluster aligns.

58. The method of claim 53, further comprising deleting a portion of an R1 sequence for a cluster when the portion of R1 sequence to be deleted is identical to at least a portion of sequence B' for that cluster and sequence G is shorter than the R1 sequence for that cluster.

59. The method of claim 53, further comprising deleting a portion of an R1 sequence for a cluster when the portion of R1 sequence to be deleted is identical to at least a portion of any sequence B', the portion includes either the 5' or 3' nucleotide of R1, and either (i) no R2 sequence was produced for the cluster or (ii) R2 sequence produced is not identical to any sequence B.

60. The method of claim 53, wherein performing the first alignment with a system using the first algorithm takes less time to align all R1 reads than would be taken if the system used the second algorithm to perform the first alignment.

61. The method of claim 53, wherein performing the first alignment with a system using the first algorithm uses less system memory to align all R1 reads than would be used if the system used the second algorithm to perform the first alignment.

62. The method of claim 53, wherein said first algorithm is based on Burrows-Wheeler transform.

63. The method of claim 53, wherein said second algorithm is based on Smith-Waterman algorithm or a hash function.

64. The method of claim 53, wherein R1 and R2 sequences are generated for at least 100 different target polynucleotides.

65. The method of claim 53, wherein each barcode differs from every other barcode in a plurality of different barcodes analyzed in parallel.

66. The method of claim 53, wherein the barcode sequence is associated with a single sample in a pool of samples sequenced in a single reaction.

67. The method of claim 53, wherein each of a plurality of barcode sequences is uniquely associated with a single sample in a pool of samples sequenced in a single reaction.

68. The method of claim 53, wherein the barcode sequence is located 5' from sequence D'.

69. The method of claim 53, wherein sequences A, B, C, and D are at least 5 nucleotides in length.

70. The method of claim 53, wherein sequence G of every cluster is 1 to 1000 nucleotides in length.

71. The method of claim 53, wherein each probe sequence B of a plurality of clusters is complementary to a sequence comprising a causal genetic variant or a sequence within 200 nucleotides of a causal genetic variant.

72. The method of claim 53, wherein an R1 sequence is produced for at least about $10^8$ clusters in a single reaction.

73. The method of claim 53, wherein presence, absence, or allele ratio of one or more causal genetic variants is determined with an accuracy of at least about 90%.

74. The method of claim 53, wherein the consensus sequence identifies an insertion, a deletion, or an insertion and a deletion in a target polynucleotide with an accuracy of at least about 90%.

75. The method of claim 53, wherein each probe sequence B of a plurality of clusters is complementary to a sequence comprising a non-subject sequence or a sequence within 200 nucleotides of a non-subject sequence.

76. The method of claim 53, wherein the presence or absence of one or more non-subject sequences is determined with an accuracy of at least about 90%.

77. A method of detecting genetic variation in a subject's genome comprising:
(a) providing a plurality of clusters of polynucleotides, wherein (i) each cluster comprises multiple copies of a nucleic acid duplex attached to a support; (ii) each duplex in a cluster comprises a first molecule comprising sequences A-B-G'-D'-C' from 5' to 3' and a second molecule comprising sequences C-D-G-B'-A' from 5' to 3'; (iii) sequence A' is complementary to sequence A, sequence B' is complementary to sequence B, sequence C' is complementary to sequence C, sequence D' is complementary to sequence D, and sequence G' is complementary to sequence G; (iv) sequence G is a portion of a target polynucleotide sequence from a subject and is different for each of a plurality of clusters; (v) sequence B' is located 5' with respect to sequence G in the corresponding target polynucleotide sequence; and (vi) each first molecule comprises a barcode sequence;
(b) sequencing sequence G' by extension of a first primer comprising sequence D to produce an R1 sequence for each cluster;
(c) sequencing sequence B' by extension of a second primer comprising sequence A to produce R2 sequence for each cluster;
(d) performing a first alignment using a first algorithm to align all R1 sequences to a first reference sequence;
(e) performing a second alignment using a second algorithm to locally align R1 sequences identified in said first alignment as likely to contain an insertion or deletion with respect to the first reference sequence, to produce a single consensus alignment for each insertion or deletion;
(f) performing an R2 alignment by aligning all R2 sequences to a second reference sequence;
(g) calculating a plurality of probabilities based on the R1 sequences for the subject and including the probabilities in a report identifying sequence variation identified by steps (d) to (f), wherein each probability is a probability of the subject or a subject's offspring having or developing a disease or trait;
(h) transmitting the report to a receiver;
(i) hybridizing a third primer to sequence C' and sequencing the barcode sequence by extension of the third primer to produce a barcode sequence for each cluster; and
(j) grouping sequences from the clusters based on the barcode sequences.

78. A method of detecting genetic variation in a subject's genome comprising:
(a) providing a plurality of clusters of polynucleotides, wherein (i) each cluster comprises multiple copies of a nucleic acid duplex attached to a support; (ii) each duplex in a cluster comprises a first molecule comprising sequences A-B-G'-D'-C' from 5' to 3' and a second molecule comprising sequences C-D-G-B'-A' from 5' to 3'; (iii) sequence A' is complementary to sequence A, sequence B' is complementary to sequence B, sequence C' is complementary to sequence C, sequence D' is complementary to sequence D, and sequence G' is complementary to sequence G; (iv) sequence G is a portion of a target polynucleotide sequence from a subject and is different for each of a plurality of clusters; (v) sequence B' is located 5' with respect to sequence G in the corresponding target polynucleotide sequence; and (vi) each first molecule comprises a barcode sequence;
(b) sequencing sequence G' by extension of a first primer comprising sequence D to produce an R1 sequence for each cluster;
(c) sequencing sequence B' by extension of a second primer comprising sequence A to produce R2 sequence for each cluster;
(d) performing a first alignment using a first algorithm to align all R1 sequences to a first reference sequence;
(e) performing a second alignment using a second algorithm to locally align R1 sequences identified in said first alignment as likely to contain an insertion or deletion with respect to the first reference sequence, to produce a single consensus alignment for each insertion or deletion;
(f) performing an R2 alignment by aligning all R2 sequences to a second reference sequence;
(g) calculating a plurality of probabilities based on the R1 sequences for the subject and including the probabilities in a report identifying sequence variation identified by steps (d) to (f), wherein each probability is a probability of the subject or a subject's offspring having or developing a disease or trait;
(h) transmitting the report to a receiver;
(i) hybridizing a third primer to sequence C' and sequencing the barcode sequence by extension of the third primer to produce a barcode sequence for each cluster
(j) grouping sequences from the clusters based on the barcode sequences; and
(k) discarding all but one of a plurality of R1 sequences having the same sequence and alignment within a barcode sequence grouping.

79. A method of detecting genetic variation in a subject's genome comprising:
(a) providing sequencing data for a plurality of clusters of polynucleotides, wherein (i) each cluster comprised multiple copies of a nucleic acid duplex attached to a support; (ii) each duplex in a cluster comprised a first molecule comprising sequences A-B-G'-D'-C' from 5' to 3' and a second molecule comprising sequences C-D-G-B'-A' from 5' to 3'; (iii) sequence A' is complementary to sequence A, sequence B' is complementary to sequence B, sequence C' is complementary to sequence C, sequence D' is complementary to sequence D, and sequence G' is complementary to sequence G; (iv) sequence G is a portion of a target polynucleotide sequence from a subject and is different for each of a plurality of clusters; (v) sequence B' is located 5' with respect to sequence G in the corresponding target polynucleotide sequence; (vi) the sequencing data comprise R1 sequences generated by extension of a first primer comprising sequence D; (vii) the sequencing data comprise R2 sequences generated by extension of a second primer comprising sequence A, (viii) each first molecule comprises a barcode sequence, and (ix) wherein the sequencing data further comprises a barcode sequence for each cluster generated by extension of a third primer comprising sequence C;
(b) performing a first alignment using a first algorithm to align all R1 sequences to a first reference sequence;
(c) performing a second alignment using a second algorithm to locally align R1 sequences identified in said first alignment as likely to contain an insertion or deletion with respect to the first reference sequence, to produce a single consensus alignment for each insertion or deletion;
(d) performing an R2 alignment by aligning all R2 sequences to a second reference sequence;
(e) calculating a plurality of probabilities based on the R1 sequences for the subject and including the probabilities in a report identifying sequence variation identified by steps (b) to (d), wherein each probability is a probability of the subject or a subject's offspring having or developing a disease or trait; and
(f) transmitting the report to a receiver.

80. The method of claim 79, wherein the first reference sequence comprises a reference genome.

81. The method of claim 79, wherein the second reference sequence consists of every sequence B for every different target polynucleotide.

82. The method of claim 79, wherein R2 sequences are aligned independently of R1 sequences.

83. The method of claim 79, further comprising discarding an R1 sequence that aligns to a first position in the first reference sequence that is more than 10,000 base pairs away from a second position in the first reference sequence to which the R2 sequence for the same cluster aligns.

84. The method of claim 79, further comprising deleting a portion of an R1 sequence for a cluster when the portion of R1 sequence to be deleted is identical to at least a portion of sequence B' for that cluster and sequence G is shorter than the R1 sequence for that cluster.

85. The method of claim 79, further comprising deleting a portion of an R1 sequence for a cluster when the portion of R1 sequence to be deleted is identical to at least a portion of any sequence B', the portion includes either the 5' or 3' nucleotide of R1, and either (i) no R2 sequence was produced for the cluster or (ii) R2 sequence produced is not identical to any sequence B.

86. The method of claim 79, wherein performing the first alignment with a system using the first algorithm takes less time to align all R1 reads than would be taken if the system used the second algorithm to perform the first alignment.

87. The method of claim 79, wherein performing the first alignment with a system using the first algorithm uses less system memory to align all R1 reads than would be used if the system used the second algorithm to perform the first alignment.

88. The method of claim 79, wherein said first algorithm is based on Burrows-Wheeler transform.

89. The method of claim 79, wherein said second algorithm is based on Smith-Waterman algorithm or a hash function.

90. The method of claim 79, wherein the sequencing data comprise R1 and R2 sequences for at least 100 different target polynucleotides.

91. The method of claim 79, wherein each barcode differs from every other barcode in a plurality of different barcodes analyzed in parallel.

92. The method of claim 79, wherein the barcode sequence is associated with a single sample in a pool of samples sequenced in a single reaction and represented in the sequencing data.

93. The method of claim 79, wherein each of a plurality of barcode sequences is uniquely associated with a single sample in a pool of samples sequenced in a single reaction.

94. The method of claim 79, wherein the barcode sequence is located 5' from sequence D'.

95. The method of claim 79, wherein sequences A, B, C, and D are at least 5 nucleotides in length.

96. The method of claim 79, wherein sequence G of every cluster is 1 to 1000 nucleotides in length.

97. The method of claim 79, wherein each probe sequence B of a plurality of clusters is complementary to a sequence comprising a causal genetic variant or a sequence within 200 nucleotides of a causal genetic variant.

98. The method of claim 79, wherein presence, absence, or allele ratio of one or more causal genetic variants is determined with an accuracy of at least about 90%.

99. The method of claim 79, wherein the consensus sequence identifies an insertion, a deletion, or an insertion and a deletion in a target polynucleotide with an accuracy of at least about 90%.

100. The method of claim 79, wherein each probe sequence B of a plurality of clusters is complementary to a sequence comprising a non-subject sequence or a sequence within 200 nucleotides of a non-subject sequence.

101. The method of claim 79, wherein the presence or absence of one or more non-subject sequence is determined with an accuracy of at least about 90%.

102. A method of detecting genetic variation in a subject's genome comprising:
(a) providing sequencing data for a plurality of clusters of polynucleotides, wherein (i) each cluster comprised multiple copies of a nucleic acid duplex attached to a support; (ii) each duplex in a cluster comprised a first molecule comprising sequences A-B-G'-D'-C' from 5' to 3' and a second molecule comprising sequences C-D-G-B'-A' from 5' to 3'; (iii) sequence A' is complementary to sequence A, sequence B' is complementary to sequence B, sequence C' is complementary to sequence C, sequence D' is complementary to sequence D, and sequence G' is complementary to sequence G; (iv) sequence G is a portion of a target polynucleotide sequence from a subject and is different for each of a plurality of clusters; (v) sequence B' is located 5' with respect to sequence G in the corresponding target polynucleotide sequence; (vi) the sequencing data comprise R1 sequences generated by extension of a first primer comprising sequence D; (vii) the sequencing data comprise R2 sequences generated by extension of a second primer comprising sequence A, (viii) each first molecule comprises a barcode sequence, (ix) wherein the sequencing data further comprises a barcode sequence for each cluster generated by extension of a third primer comprising sequence C; and (x) grouping sequences from the clusters based on the barcode sequences;
(b) performing a first alignment using a first algorithm to align all R1 sequences to a first reference sequence;
(c) performing a second alignment using a second algorithm to locally align R1 sequences identified in said first alignment as likely to contain an insertion or deletion with respect to the first reference sequence, to produce a single consensus alignment for each insertion or deletion;
(d) performing an R2 alignment by aligning all R2 sequences to a second reference sequence;
(e) calculating a plurality of probabilities based on the R1 sequences for the subject and including the probabilities in a report identifying sequence variation identified by steps (b) to (d), wherein each probability is a probability of the subject or a subject's offspring having or developing a disease or trait; and
(f) transmitting the report to a receiver.

103. A method of detecting genetic variation in a subject's genome comprising:
(a) providing sequencing data for a plurality of clusters of polynucleotides, wherein (i) each cluster comprised multiple copies of a nucleic acid duplex attached to a support; (ii) each duplex in a cluster comprised a first molecule comprising sequences A-B-G'-D'-C' from 5' to 3' and a second molecule comprising sequences C-D-G-B'-A' from 5' to 3'; (iii) sequence A' is complementary to sequence A, sequence B' is complementary to sequence B, sequence C' is complementary to sequence C, sequence D' is complementary to sequence D, and sequence G' is complementary to sequence G; (iv) sequence G is a portion of a target polynucleotide sequence from a subject and is different for each of a plurality of clusters; (v) sequence B' is located 5' with respect to sequence G in the corresponding target polynucleotide sequence; (vi) the sequencing data comprise R1 sequences generated by extension of a first primer comprising sequence D; (vii) the sequencing data comprise R2 sequences generated by extension of a second primer comprising sequence A, (viii) each first molecule comprises a barcode sequence, (ix) wherein the sequencing data further comprises a barcode sequence for each cluster generated by extension of a third primer comprising sequence C; (x) grouping sequences from the clusters based on the barcode sequences; and (xi) discarding all but one of a plurality of R1 sequences having the same sequence and alignment within a barcode sequence grouping;
(b) performing a first alignment using a first algorithm to align all R1 sequences to a first reference sequence;
(c) performing a second alignment using a second algorithm to locally align R1 sequences identified in said first alignment as likely to contain an insertion or deletion with respect to the first reference sequence, to produce a single consensus alignment for each insertion or deletion;
(d) performing an R2 alignment by aligning all R2 sequences to a second reference sequence;
(e) calculating a plurality of probabilities based on the R1 sequences for the subject and including the probabilities in a report identifying sequence variation identified by steps (b) to (d), wherein each probability is a probability of the subject or a subject's offspring having or developing a disease or trait; and
(f) transmitting the report to a receiver.

* * * * *

SEQUENCE LISTING

<160> NUMBER OF SEQ ID NOS: 123

<210> SEQ ID NO 1
<211> LENGTH: 59
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
cgagatctac acgcctccct cgcgccatca gaggtcacac tcagcagcac gacgatcac        59

<210> SEQ ID NO 2
<211> LENGTH: 59
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
cgagatctac acgcctccct cgcgccatca gcagcagcac tcagcagcac gacgatcac        59

<210> SEQ ID NO 3
<211> LENGTH: 59
<212> TYPE: DNA
<213> ORGANISM: Artificial Sequence
<220> FEATURE:

```
<223> OTHER INFORMATION: Description of Artificial Sequence: Synthetic
      primer

<400> SEQUENCE: 3
cgagatctac acgcctccct cgcgccatca gactgctcac tcagcagcac gacgatcac      59

<210> SEQ ID NO 4
<211> LENGTH: 59
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
cgagatctac acgcctccct cgcgccatca gtaacggcac tcagcagcac gacgatcac      59

<210> SEQ ID NO 5
<211> LENGTH: 59
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
cgagatctac acgcctccct cgcgccatca gggattacac tcagcagcac gacgatcac      59

<210> SEQ ID NO 6
<211> LENGTH: 59
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
cgagatctac acgcctccct cgcgccatca gaacctgcac tcagcagcac gacgatcac      59

<210> SEQ ID NO 7
<211> LENGTH: 59
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
cgagatctac acgcctccct cgcgccatca ggccgttcac tcagcagcac gacgatcac      59

<210> SEQ ID NO 8
<211> LENGTH: 59
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
cgagatctac acgcctccct cgcgccatca gcgttgacac tcagcagcac gacgatcac      59

<210> SEQ ID NO 9
<211> LENGTH: 59
<212> TYPE: DNA
<213> ORGANISM: Artificial Sequence
<220> FEATURE:
<223> OTHER INFORMATION: Description of Artificial Sequence: Synthetic
```

```
                                   primer

<400> SEQUENCE: 9
cgagatctac acgcctccct cgcgccatca ggtaacccac tcagcagcac gacgatcac        59

<210> SEQ ID NO 10
<211> LENGTH: 59
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
cgagatctac acgcctccct cgcgccatca gcttaaccac tcagcagcac gacgatcac        59

<210> SEQ ID NO 11
<211> LENGTH: 59
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
cgagatctac acgcctccct cgcgccatca gtgctaacac tcagcagcac gacgatcac        59

<210> SEQ ID NO 12
<211> LENGTH: 59
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
cgagatctac acgcctccct cgcgccatca ggatccgcac tcagcagcac gacgatcac        59

<210> SEQ ID NO 13
<211> LENGTH: 59
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
cgagatctac acgcctccct cgcgccatca gccaggtcac tcagcagcac gacgatcac        59

<210> SEQ ID NO 14
<211> LENGTH: 59
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
cgagatctac acgcctccct cgcgccatca gttcagccac tcagcagcac gacgatcac        59

<210> SEQ ID NO 15
<211> LENGTH: 59
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 15
cgagatctac acgcctccct cgcgccatca gatgatccac tcagcagcac gacgatcac      59

<210> SEQ ID NO 16
<211> LENGTH: 59
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
cgagatctac acgcctccct cgcgccatca gtcggatcac tcagcagcac gacgatcac      59

<210> SEQ ID NO 17
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
cactcagcag cacgacgatc acagatgtgt ataagagaca gt                        42

<210> SEQ ID NO 18
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
gtgagtcgtc gtgctgctag tgtctacaca tattctctgt c                         41

<210> SEQ ID NO 19
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
cgagatctac acgcctccct cgcgccatca g                                    31

<210> SEQ ID NO 20
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
cactcagcag cacgacgatc acagatgtgt ataagagaca g                         41

<210> SEQ ID NO 21
<211> LENGTH: 59
<212> TYPE: DNA
<213> ORGANISM: Artificial Sequence
<220> FEATURE:
<223> OTHER INFORMATION: Description of Artificial Sequence: Synthetic
      primer
<220> FEATURE:

<221> NAME/KEY: modified_base
<222> LOCATION: (32)..(37)
<223> OTHER INFORMATION: a, c, t, g, unknown, other or absent

<400> SEQUENCE: 21
cgagatctac acgcctccct cgcgccatca gnnnnnncac tcagcagcac gacgatcac   59

<210> SEQ ID NO 22
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
gaggattcag gagtcaatga ctgaggatgg gactccttga                        40

<210> SEQ ID NO 23
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
tgagggcctg gaccaaattc ttcaagcaaa acagaaaaca                        40

<210> SEQ ID NO 24
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
actggaccgc ccctccacg ccctcccacc gcgggcccct                         40

<210> SEQ ID NO 25
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
tcttttttcc gagacaaact tcattctgga aaggctgtca                        40

<210> SEQ ID NO 26
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
ttttgctgag cttacagtgg aaatgctatt aaattctttc                        40

<210> SEQ ID NO 27
<211> LENGTH: 40
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 27
acttagaaag ttaaagtaag aaattattaa tatctcctat                              40

<210> SEQ ID NO 28
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
tcagaagggg caaagcttgc ttcctcctgc atccctcatg                              40

<210> SEQ ID NO 29
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
tttattttgt ctctgctgtt catggcatag tttggtggcg                              40

<210> SEQ ID NO 30
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
aatggcctgc cacctgagaa tctattgttt atggcaagac                              40

<210> SEQ ID NO 31
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
agagcaaaga ggacctggga ggtgcctgca ccccatacca                              40

<210> SEQ ID NO 32
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
caaatagaaa tgctcttata gatgagtatc aaaataaat                               40

<210> SEQ ID NO 33
<211> LENGTH: 40
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 33
tcctccgctc ctcctgcgcg gggtgctgaa acagcccggg       40

<210> SEQ ID NO 34
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
acccgggcct gagccgtcgc tgggcccgtc gccttccccg       40

<210> SEQ ID NO 35
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
ttctacctgt ggaccaggaa tctaggacac agtccctgac       40

<210> SEQ ID NO 36
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
tgccctgctg cagacctaca cgcccccacc atgtgcccac       40

<210> SEQ ID NO 37
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
gggcgtcctg ctgctgggcc tggtgggcta ctacatcttc       40

<210> SEQ ID NO 38
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
gagcgtgatt aggtactgga cacctgccaa gtgctgggct       40

<210> SEQ ID NO 39
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
ctgggatttg agggttttca ttacacttct gctaggataa                   40

<210> SEQ ID NO 40
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
taaaatttaa aaatacagt taaaaatcat ggtcatataa                    40

<210> SEQ ID NO 41
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
ccgctgcact gacttcattt ccttagacaa gacacagtgt                   40

<210> SEQ ID NO 42
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
actgcaacat tttcaaagca aaagaatccc gttgctgtcg                   40

<210> SEQ ID NO 43
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
cttagctcag ctccaggctg tgcagcagaa gtacagggac                   40

<210> SEQ ID NO 44
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
attttagatt caaaattggt agccgattac attttctcaa                   40

<210> SEQ ID NO 45
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
aggcaagctg tcctccaggt ctttatcaga cagtgccccc                            40

<210> SEQ ID NO 46
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
tttaaggttt ctgtgacctt tgttagaaag tttttaaatg                            40

<210> SEQ ID NO 47
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
aatagtaggc tgttggtaca tttctcaact tacttataaa                            40

<210> SEQ ID NO 48
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
aaccagtttc tgcctgtctg taactgccct gtctgccaca                            40

<210> SEQ ID NO 49
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
cctgaaatct cttctcgagg ctgagctgag ggcccttggg                            40

<210> SEQ ID NO 50
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
ctattttctc tctcttattt tcagaattag aaagcaattc                            40

<210> SEQ ID NO 51
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
cacggacata cgcataccgg cccagtgaca cgtcaggcaa                              40

<210> SEQ ID NO 52
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
atgccttatc aacagtaaaa caatgaatca ccatagtaca                              40

<210> SEQ ID NO 53
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
tcctttggaa cagtgtggac cccaggtcat ggctcccaga                              40

<210> SEQ ID NO 54
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
tgtacaggat gttactgtac tggatgttgc aggcaactat                              40

<210> SEQ ID NO 55
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
cactgctgca tgaggagtgg gcctggggcc actaaacccg                              40

<210> SEQ ID NO 56
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
cctgcagtgg gatttcctct gaagagagca cagtgagcag                              40

<210> SEQ ID NO 57
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
aacttattat tttatacctg cttcattgtt gaaaagaaaa          40

<210> SEQ ID NO 58
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
agccactgtg cccggctgca gatattcttt cagtaaatga          40

<210> SEQ ID NO 59
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
cattgcctgt gagtgccctc agtttacata gtgctatctt          40

<210> SEQ ID NO 60
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
taattttatt cgccattagg atgaaatcca tattcacaaa          40

<210> SEQ ID NO 61
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
tcaagccagc ctggaaggga gatggaaaag ctgcgtgcgc          40

<210> SEQ ID NO 62
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
tgctgttaag atgttacttt ctttaaaaaa gatgggttat          40

<210> SEQ ID NO 63
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
aaaaattatg cctattagaa tcaaaatatg atagcaaaac          40

<210> SEQ ID NO 64
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64 gttaatatatt ttatgctaat gcagacaata tatattactg                            40

<210> SEQ ID NO 65
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
gctgtacaga gctatatatc ataattattt ctatactatg                             40

<210> SEQ ID NO 66
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
caggaggatc agtctctgta gaggcaggga ggagctgggg                             40

<210> SEQ ID NO 67
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
tattttcagg tactgaattc tgaaatgata gcattttgtg                             40

<210> SEQ ID NO 68
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
tgttgagttt ttcagtttct ctgaaaagtc atactctaga                             40

<210> SEQ ID NO 69
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
tgtagcccct ttgagcatga ggtatgcata gaacataatg                             40

<210> SEQ ID NO 70
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
cttgcaatca agtaaggtga aatattcata tactggttct                              40

<210> SEQ ID NO 71
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
cggcgggccg cctagggtga ttggctgctg cagcccaccc                              40

<210> SEQ ID NO 72
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
tttcgggagg agggagaggg tggggtggcg ggtgcagact                              40

<210> SEQ ID NO 73
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
cctcagccac aaccattagc tgcaacggtc caggctcgtg                              40

<210> SEQ ID NO 74
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
atctctcgcc atttctgctg aggcctgttc ttttttttctt                             40

<210> SEQ ID NO 75
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
cccgggcagt cctgggcttg aacgtgtgtg tcagccgcgc                              40

<210> SEQ ID NO 76
<211> LENGTH: 40
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 76
ggaacaaggg gtcttccgag cagcccccag ccctcccctc    40

<210> SEQ ID NO 77
<211> LENGTH: 40
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 77
gcaccttccc cgcaggcggt gggtgagccc tgggagctga    40

<210> SEQ ID NO 78
<211> LENGTH: 40
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 78
aaggttttca agaagttaaa ttggaataga aacattttgg    40

<210> SEQ ID NO 79
<211> LENGTH: 40
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 79
aaatcaattt ctgtttctta agtaatttct tcatgagcat    40

<210> SEQ ID NO 80
<211> LENGTH: 40
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 80
taggcacttc cacgtggtgt caatccctga tcactgggag    40

<210> SEQ ID NO 81
<211> LENGTH: 40
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 81
cagaaactta taaatattg ataggcagct tctttgggag    40

<210> SEQ ID NO 82

```
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82
ccagcttggg actatgccca tgagtgcccg gccatgcccg                              40

<210> SEQ ID NO 83
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83 gcgccccag agtcccaggc aaagccagca agggccaggc                               40

<210> SEQ ID NO 84
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 84
gttctggagg aattcgtcct cggggaggca gtgggccagg                              40

<210> SEQ ID NO 85
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
tgtcatcccc agcctcatcc tctcactgtc tcagttttcc                              40

<210> SEQ ID NO 86
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
aggactgtct gtggcattcc ccctgggatc tgaatgatgg                              40

<210> SEQ ID NO 87
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87
ccggaggaaa aaatctctca tcttttgaag ctatttgaag                              40

<210> SEQ ID NO 88
<211> LENGTH: 40
```

<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 88
atatggtgag tattttgaat atctcataca attatgccta                     40

<210> SEQ ID NO 89
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 89
gggctgtggt tgtcacccgt gacgatctgc gtgcatgcca                     40

<210> SEQ ID NO 90
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 90
tactagtgtt ttcattggta ttaagcttga tgtaatattt                     40

<210> SEQ ID NO 91
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91
agccaccacg cctggcccag actcagagaa tgaatacaat                     40

<210> SEQ ID NO 92
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92
gtggcgagaa gcatgaggaa tggagatgga ggaggagcag                     40

<210> SEQ ID NO 93
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 93
tctcagtttg gctgagaagc agggtggggg cctgaaccca                     40

<210> SEQ ID NO 94
<211> LENGTH: 40
<212> TYPE: DNA

```
<213> ORGANISM: Artificial Sequence
<220> FEATURE:
<223> OTHER INFORMATION: Description of Artificial Sequence: Synthetic
      oligonucleotide

<400> SEQUENCE: 94
caacatagca agaccccgtc actataaaaa tgaaaaagcc                              40

<210> SEQ ID NO 95
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95
ccagtgggtg ggagcccggg tggggagggg gcgtgggctc                              40

<210> SEQ ID NO 96
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 96
ttatttttta tggatgtaaa cagcctcttt gtagtttata                              40

<210> SEQ ID NO 97
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 97
tcctgaaaca agcattaaag agggaattaa cttaaataaa                              40

<210> SEQ ID NO 98
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 98
ttattgtatt gaaacatgat tgtgtatcaa atgtgagttt                              40

<210> SEQ ID NO 99
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
cttttctttt ataaaggagg actcttttgc ctgatatctg                              40

<210> SEQ ID NO 100
<211> LENGTH: 40
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 100
cctgaagtct cagtttccat tacattatac cctcactacc                              40

<210> SEQ ID NO 101
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101
cccacccgtg ggtccctggg ggcctgggat cccagatggt                              40

<210> SEQ ID NO 102
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 102
acggggatga ggagggcgtg tggtgctatg tggccgggaa                              40

<210> SEQ ID NO 103
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 103
cctcggattg aagaaagtct ggtactcact ggtggcggta                              40

<210> SEQ ID NO 104
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 104
gtttaaaaaa ttgtccttta ttgtccaaat gtctgccttc                              40

<210> SEQ ID NO 105
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105
taatgtgtaa tgataggtct tgtcaaatag tttaataagt                              40

<210> SEQ ID NO 106
<211> LENGTH: 40
<212> TYPE: DNA
<213> ORGANISM: Artificial Sequence
<220> FEATURE:
```

<223> OTHER INFORMATION: Description of Artificial Sequence: Synthetic
oligonucleotide

<400> SEQUENCE: 106
gagtccgagt gccgctgact gtcactgcca ccattcatcc    40

<210> SEQ ID NO 107
<211> LENGTH: 40
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 107
ctgaatgttg caaatctaaa taaacatgtt ccagaggaga    40

<210> SEQ ID NO 108
<211> LENGTH: 40
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 108
gcctttattc cgtttccact cctccttccc tagttcatcc    40

<210> SEQ ID NO 109
<211> LENGTH: 40
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 109
tcaggaaatc ctacagtcca cactccagtc agccccagga    40

<210> SEQ ID NO 110
<211> LENGTH: 40
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 110
ccttctcgga tctcaaacga gcaagggtta acactcatga    40

<210> SEQ ID NO 111
<211> LENGTH: 40
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 111
ggggcgcggc ccctcaagtc cgaggacctc ccttctgggg    40

<210> SEQ ID NO 112
<211> LENGTH: 40
<212> TYPE: DNA
<213> ORGANISM: Artificial Sequence
<220> FEATURE:
<223> OTHER INFORMATION: Description of Artificial Sequence: Synthetic -continued oligonucleotide

<400> SEQUENCE: 112
agttcctcca gggcgccctg tggcggcgcc gcctgcacct                              40

<210> SEQ ID NO 113
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 113
acgaccctat tactctcata acgatgagtc tagcaagtac                              40

<210> SEQ ID NO 114
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 114
acaaaaaaag gtaactatgt aaagacatat gttaattagc                              40

<210> SEQ ID NO 115
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 115
cttcgagaaa ttctgaaaaa ctgcaaaggt ttgattgtgt                              40

<210> SEQ ID NO 116
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 116
ctatttgaag atttgtcatc aaatattgat gcatgatagg                              40

<210> SEQ ID NO 117
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 117
ttccaggcaa agcagtagcc taagggttta cagctgatga                              40

<210> SEQ ID NO 118
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 118
cccatccaag gaaaatttag aaaagggaag gggatgtgta                              40

<210> SEQ ID NO 119
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 119
gaagtgggag gggtaaaagg gctataaaaa aaaatctaaa                              40

<210> SEQ ID NO 120
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 120
ccaatcattg cacaaacaga aacagctctg acagagaagg                              40

<210> SEQ ID NO 121
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 121
aatttggagg acaccagtgg catcaggtct cctgtgttgc                              40

<210> SEQ ID NO 122
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 122
cagctaccat                                                              10

<210> SEQ ID NO 123
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 123
caggtaccat                                                              10
```